(12) United States Patent
Mcguirk et al.

(10) Patent No.: US 11,117,909 B2
(45) Date of Patent: Sep. 14, 2021

(54) CRYSTALS

(71) Applicant: AEROMICS, INC., New Haven, CT (US)

(72) Inventors: Paul Robert Mcguirk, Spring Hill, FL (US); Robert Zamboni, Beaconsfield (CA); Melanie Bevill, West Lafayette, IN (US); Stephan Parent, West Lafayette, IN (US)

(73) Assignee: AEROMICS, INC., New Haven, CT (US)

( * ) Notice: Subject to any disclaimer, the term of this patent is extended or adjusted under 35 U.S.C. 154(b) by 0 days.

(21) Appl. No.: 16/301,079

(22) PCT Filed: May 12, 2017

(86) PCT No.: PCT/US2017/032563
§ 371 (c)(1),
(2) Date: Nov. 13, 2018

(87) PCT Pub. No.: WO2017/197371
PCT Pub. Date: Nov. 16, 2017

(65) Prior Publication Data
US 2019/0185496 A1   Jun. 20, 2019

Related U.S. Application Data

(60) Provisional application No. 62/336,652, filed on May 14, 2016, provisional application No. 62/336,549, filed on May 13, 2016.

(51) Int. Cl.
*C07F 9/12* (2006.01)
*A61K 31/167* (2006.01)

(52) U.S. Cl.
CPC .............. *C07F 9/12* (2013.01); *A61K 31/167* (2013.01); *C07B 2200/13* (2013.01)

(58) Field of Classification Search
CPC ....................................................... C07F 9/12
See application file for complete search history.

(56) References Cited

U.S. PATENT DOCUMENTS

| | | |
|---|---|---|
| 7,626,042 B2 | 12/2009 | Muto et al. |
| 9,573,885 B2 | 2/2017 | Pelletier et al. |
| 9,827,253 B2 | 11/2017 | Pelletier et al. |
| 9,949,991 B2 | 4/2018 | Pelletier et al. |
| 9,994,514 B2 | 6/2018 | Pelletier et al. |
| 2006/0094718 A1* | 5/2006 | Muto ............... C07D 209/48 514/235.2 |
| 2015/0133405 A1 | 5/2015 | Pelletier et al. |
| 2015/0166589 A1 | 6/2015 | Anderson et al. |
| 2015/0342967 A1 | 12/2015 | Pelletier et al. |
| 2016/0264604 A1 | 9/2016 | Pelletier et al. |
| 2016/0279155 A1 | 9/2016 | Pelletier et al. |
| 2016/0346302 A1 | 12/2016 | Pelletier et al. |
| 2018/0042873 A1 | 2/2018 | Pelletier et al. |
| 2018/0169118 A1 | 6/2018 | Pelletier et al. |
| 2018/0334424 A1 | 11/2018 | Pelletier et al. |

FOREIGN PATENT DOCUMENTS

| | | |
|---|---|---|
| EP | 1 512 397 A1 | 3/2005 |
| WO | WO 2013/169939 A2 | 11/2013 |
| WO | WO 2015/069948 A1 | 5/2015 |
| WO | WO 2015/069956 A2 | 5/2015 |
| WO | WO 2015/069961 A1 | 5/2015 |
| WO | WO 2016/077787 A1 | 5/2016 |

OTHER PUBLICATIONS

Background Information for the October ACPS Meeting, FDA, 2002 (Year: 2002).*
B. Rodriquez-Spong et al. Advanced Drug Delivery Reviews, 2004, 56, pp. 241-274 (Year: 2004).*
Infantes et al. CrystEngComm. 2003, 85, 480-486 (Year: 2003).*
U.S. Appl. No. 14/398,947, filed Nov. 4, 2014 (371(c) Date), Pelletier et al.
U.S. Appl. No. 14/752,839, filed Jun. 27, 2015, Pelletier et al.
U.S. Appl. No. 15/034,274, filed May 4, 2016 (371(c) Date), Pelletier et al.
U.S. Appl. No. 15/034,543, filed May 4, 2016 (371(c) Date), Pelletier et al.
U.S. Appl. No. 15/035,006, filed May 6, 2016 (371(c) Date), Pelletier et al.
U.S. Appl. No. 15/526,706, filed May 12, 2017 (371(c) Date), Pelletier et al.
U.S. Appl. No. 15/792,707, filed Oct. 24, 2017, Pelletier et al.
U.S. Appl. No. 15/982,644, filed May 17, 2018, Pelletier et al.
U.S. Appl. No. 16/236,817, filed Dec. 31, 2018, Pelletier et al.
Farr, G. et al., "Functionalized Phenylbenzamides Inhibit Aquaporin-4 Reducing Cerebral Edema and Improving Outcome in Two Models of CNS Injury," Neuroscience, 2019, accepted manuscript, https://doi.org/10.1016/j.neuroscience.2019.01.034, 46 pages.
International Search Report for International Application No. PCT/US2017/032563, dated Aug. 24, 2017, 3 pages.
Written Opinion of the International Searching Authority for International Application No. PCT/US2017/032563, dated Aug. 24, 2017, 5 pages.
Braga, D. et al., "Dealing with Crystal Forms (The Kingdom of Serendip?)," Chemistry—An Asian Journal, 2011, 6, 2214-2223.
Bučar, D. et al., "Disappearing Polymorphs Revisited," Angewandte Chemie International Edition, 2015, 54, 6972-6993.
Caira, M., "Crystalline Polymorphism of Organic Compounds," Topics in Current Chemistry, 1998, 198, 163-208.

* cited by examiner

*Primary Examiner* — Matthew P Coughlin
(74) *Attorney, Agent, or Firm* — Hoxie & Associates LLC

(57) ABSTRACT

Provided are crystals of 2-{[3,5-bis(trifluoromethyl)phenyl]carbamoyl}-4-chlorophenyl dihydrogen phosphate, compositions comprising the same, and methods of making and using such crystals.

30 Claims, 59 Drawing Sheets

CRYSTALS

CROSS REFERENCE TO RELATED APPLICATIONS

This application is the National Stage Entry under 35 U.S.C. § 371 of International Application No. PCT/US2017/032563 filed May 12, 2017, which claims priority to U.S. Provisional Application No. 62/336,549 filed May 13, 2016, and U.S. Provisional Application No. 62/336,652 filed May 14, 2016, all of which are incorporated herein by reference in their entirety.

FIELD

Provided are crystals comprising 2-{[3,5-bis(trifluoromethyl)phenyl]carbamoyl}-4-chlorophenyl dihydrogen phosphate (also known as 5-chloro-2-phosphonooxy-N-[3,5-bis(trifluoromethyl)phenyl]benzamide), compositions comprising the same, and methods of making and using such crystals.

BACKGROUND

2-{[3,5-bis(trifluoromethyl)phenyl]carbamoyl}-4-chlorophenyl dihydrogen phosphate is disclosed in International Publication No. WO 2013/169939 (U.S. national stage application published as U.S. Patent Publication No. 2015/0133405). The compound may be used for the prophylaxis, treatment, and control of aquaporin-mediated conditions, e.g., diseases of water imbalance, for example, cerebral edema consequent to head trauma and ischemic stroke.

Active pharmaceutical ingredients can exist in different physical forms (e.g., liquid or solid in different crystalline, amorphous, hydrate, or solvate forms), which can vary the processability, stability, solubility, bioavailability, or pharmacokinetics (absorption, distribution, metabolism, excretion, or the like) and/or bioequivalency of the active pharmaceutical ingredient and pharmaceutical compositions comprising it.

Thus, there is a need to identify active pharmaceutical ingredients having an advantageous physical form (e.g., in solid, liquid, crystalline, hydrate, solvate, or amorphous forms).

SUMMARY

2-{[3,5-bis(trifluoromethyl)phenyl]carbamoyl}-4-chlorophenyl dihydrogen phosphate is shown as Formula I below Formula I

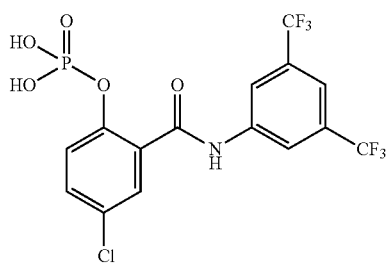

In stroke or other severely debilitating diseases or conditions, for example where the patient may be unconscious or unable to swallow, an IV infusion or IV bolus may be preferred. In addition, when a patient has suffered a stroke, or traumatic brain or spinal cord injury, rapid achievement of therapeutically effective amounts of a therapeutic agent may be important to a successful therapeutic outcome. In the acute care settings in the hospital, particularly for stroke, traumatic brain injury, and myocardial infarction, best practices are to administer drugs via IV. However, a therapeutic agent with only a limited solubility in water and/or physiological media and/or limited stability may make parenteral administration, e.g., intravenous, intramuscular, intraperitoneal, subcutaneous, epidural, sublingual, or intracerebral, of the therapeutic agent challenging. While N-[3,5-bis(trifluoromethyl)phenyl]-5-chloro-2-hydroxybenzamide is an aquaporin inhibitor, its solubility in water is 3 µg/ml. Alanine and di-alanine prodrugs of N-[3,5-bis(trifluoromethyl)phenyl]-5-chloro-2-hydroxybenzamide are insoluble in water and pH 7.4 water. A prodrug salt form of N-[3,5-bis(trifluoromethyl)phenyl]-5-chloro-2-hydroxybenzamide does show improved solubility—specifically, the solubility of 2-{[3,5-bis(trifluoromethyl)phenyl]carbamoyl}-4-chlorophenyl phosphate disodium salt in pH 8.5 water is 20 mg/ml. However, prodrug salt forms of N-[3,5-bis(trifluoromethyl)phenyl]-5-chloro-2-hydroxybenzamide may revert to N-[3,5-bis(trifluoromethyl)phenyl]-5-chloro-2-hydroxybenzamide even in the solid state. For instance, 2-((3,5-bis(trifluoromethyl)phenyl)carbamoyl)-4-chlorophenyl hydrogen phosphate mono sodium salt ("mono sodium salt"), 2-((3,5-bis(trifluoromethyl)phenyl)carbamoyl)-4-chlorophenyl phosphate bis sodium salt ("bis sodium salt"), and 2-((3,5-bis(trifluoromethyl)phenyl)carbamoyl)-4-chlorophenyl phosphate bis ethanolamine salt ("bis ethanolamine salt") show hydrolysis in the solid state at 1% per day. Thus, stable pharmaceutical compositions which allow rapid achievement of therapeutically effective amounts of N-[3,5-bis(trifluoromethyl)phenyl]-5-chloro-2-hydroxybenzamide are needed.

International Publication No. WO 2015/069956, which is hereby incorporated by reference in its entirety, describes formulations of 2-{[3,5-bis(trifluoromethyl)phenyl]carbamoyl}-4-chlorophenyl dihydrogen phosphate which may allow rapid achievement of therapeutically effective amounts of N-[3,5-bis(trifluoromethyl)phenyl]-5-chloro-2-hydroxybenzamide. For instance, International Publication No. WO 2015/069956 describes pharmaceutical compositions comprising 2-{[3,5-bis(trifluoromethyl)phenyl]carbamoyl}-4-chlorophenyl dihydrogen phosphate, wherein the composition is a solid.

It has been found that 2-{[3,5-bis(trifluoromethyl)phenyl]carbamoyl}-4-chlorophenyl dihydrogen phosphate (Formula I) exhibits a high propensity to exist as multiple polymorphic/solvated forms, for instance, as an ethyl acetate solvate (Form A), a hydrate (Form N), and an anhydrous/non-solvated form (Form B). Interconversion of Forms A, B, and N is shown in FIG. 30. The forms differ from each other with respect to their physical properties, spectral data, stability, and methods of preparation. The preparation of Form A allows for a final finish filtration, which is a sterilization as well. However, the ethyl acetate makes the form less desirable pharmaceutically, and Form A shows significant hygroscopicity (~6% weight gain from 5-95% RH). Further, in a larger scale synthesis of Form A, it was found that extraction with ethyl acetate was not able to remove trifluoroacetic acid and acetic acid impurities. Compared to Form A, Form B is more desirable pharmaceutically because of the lack of solvent content and low hygroscopicity (~0.6% weight gain from 5-95% RH). Form N is also more desirable pharmaceutically compared to Form A because of lack of organic solvent content and because it has shown less hygroscopicity by DVS (~3% weight gain from 5-95% RH).

Provided herein is 2-{[3,5-bis(trifluoromethyl)phenyl]carbamoyl}-4-chlorophenyl dihydrogen phosphate (Formula I) in crystalline form which may be used in the pharmaceutical compositions, methods, or kits described in International Publication No. WO 2015/069956.

Accordingly, provided is a hemi-solvate (e.g., hemi-ethyl acetate, hemi-acetonitrile, hemi-p-dioxane, or hemi-methanol solvate) of 2-{[3,5-bis(trifluoromethyl)phenyl]carbamoyl}-4-chlorophenyl dihydrogen phosphate, e.g, as described in Crystalline Forms 1-4 below.

Further provided is an ethyl acetate solvate of

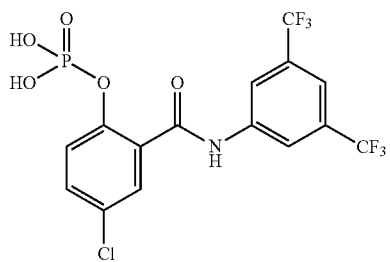

Formula I (Crystalline Form 1, also referred to herein as Form A). Further provided is Crystalline Form 1 as follows:

1.1 Crystalline Form 1 wherein the molar ratio of ethyl acetate to Formula I is 0.5 moles ethyl acetate maximum (i.e., up to 0.5 moles ethyl acetate) to 1 mole Formula I, e.g., 0.4-0.5 moles ethyl acetate to 1 mole Formula I.

1.2 Crystalline Form 1 or 1.1 wherein the molar ratio of ethyl acetate to Formula I is 0.5:1.

1.3 Any of Crystalline Form 1 et seq. wherein the crystalline form is a variable ethyl acetate solvate.

1.4 Any of Crystalline Form 1 et seq. wherein the crystalline form is a hemi-ethyl acetate solvate, i.e., wherein the asymmetric unit contains two molecules of Formula I and one ethyl acetate molecule.

1.5 Any of Crystalline Form 1 et seq. wherein the crystalline form crystallizes in the monoclinic crystal system, belongs to the C2/c space group, and has the following unit cell parameters: a=26.2223(3) Å, b=9.10581(10) Å, c=34.9080(4) Å, β=97.3256(11)°, α=γ=90°.

1.6 Crystalline Form 1.5 wherein the crystalline form has a calculated volume of V=8267.13(16)Å$^3$.

1.7 Crystalline Form 1.5 or 1.6 wherein the crystal structure is obtained with a crystal having approximate dimensions of 0.563×0.089×0.039 mm$^3$, e.g., a colorless needle having approximate dimensions of 0.563×0.089×0.039 mm$^3$.

1.8 Any of Crystalline Form 1.5-1.7 wherein the crystal structure is obtained with Cu Kα radiation, e.g., Cu Kα radiation having λ=1.54184 Å.

1.9 Any of Crystalline Form 1.5-1.8 wherein the crystal structure is obtained at 150 K, e.g., 150.00(10) K.

1.10 Any of Crystalline Form 1 et seq. having a calculated XRPD pattern as shown in FIG. 8.

1.11 Any of Crystalline Form 1 et seq. exhibiting an XRPD pattern comprising at least three, e.g., at least five, 2-theta (°) values selected from the group consisting of 5.1, 6.6, 8.0, 13.8, 14.5, 16.1, 16.5, 17.4, 19.3, 20.9, 21.2, 22.0, 23.2, and 23.8, wherein the XRPD is measured using an incident beam of Cu Kα radiation, e.g., wherein the XRPD is measured using radiation of wavelength 1.54059 Å.

1.12 Any of Crystalline Form 1 et seq. exhibiting an XRPD pattern comprising 2-theta (°) values of 5.1, 6.6, 8.0, 13.8, 14.5, 16.1, 16.5, 17.4, 19.3, 20.9, 21.2, 22.0, 23.2, and 23.8, wherein the XRPD is measured using an incident beam of Cu Kα radiation, e.g., wherein the XRPD is measured using radiation of wavelength 1.54059 Å.

1.13 Any of Crystalline Form 1 et seq. exhibiting an XRPD pattern comprising at least three, e.g., at least five, 2-theta (°) values selected from the group consisting of 5.07, 6.61, 7.99, 13.80, 14.46, 16.05, 16.52, 17.40, 19.29, 20.93, 21.18, 21.99, 23.17 and 23.82, wherein the XRPD is measured using an incident beam of Cu Kα radiation, e.g., wherein the XRPD is measured using radiation of wavelength 1.54059 Å.

1.14 Any of Crystalline Form 1 et seq. exhibiting an XRPD pattern comprising 2-theta (°) values of 5.07, 6.61, 7.99, 13.80, 14.46, 16.05, 16.52, 17.40, 19.29, 20.93, 21.18, 21.99, 23.17 and 23.82, wherein the XRPD is measured using an incident beam of Cu Kα radiation, e.g., wherein the XRPD is measured using radiation of wavelength 1.54059 Å.

1.15 Any of Crystalline Form 1 et seq. exhibiting an XRPD pattern comprising at least three, e.g., at least five, 2-theta (°) values selected from those set forth in Table A below:

TABLE A

| °2θ | d space (Å) | Intensity (%) |
|---|---|---|
| 5.07 ± 0.20 | 17.430 ± 0.688 | 22 |
| 6.61 ± 0.20 | 13.364 ± 0.404 | 100 |
| 7.99 ± 0.20 | 11.055 ± 0.276 | 41 |
| 13.80 ± 0.20 | 6.410 ± 0.092 | 33 |
| 14.46 ± 0.20 | 6.121 ± 0.084 | 37 |
| 16.05 ± 0.20 | 5.518 ± 0.068 | 41 |
| 16.52 ± 0.20 | 5.363 ± 0.064 | 33 |
| 17.40 ± 0.20 | 5.093 ± 0.058 | 36 |
| 19.29 ± 0.20 | 4.597 ± 0.047 | 86 |
| 20.93 ± 0.20 | 4.241 ± 0.040 | 55 |
| 21.18 ± 0.20 | 4.192 ± 0.039 | 50 |
| 21.99 ± 0.20 | 4.039 ± 0.036 | 50 |
| 23.17 ± 0.20 | 3.835 ± 0.033 | 89 |
| 23.82 ± 0.20 | 3.732 ± 0.031 | 77 | wherein the XRPD is measured using an incident beam of Cu Kα radiation, e.g., wherein the XRPD is measured using radiation of wavelength 1.54059 Å.

1.16 Any of Crystalline Form 1 et seq. exhibiting an XRPD pattern having the 2-theta (°) values set forth in Table A of Crystalline Form 1.15, wherein the XRPD is measured using an incident beam of Cu Kα radiation, e.g., wherein the XRPD is measured using radiation of wavelength 1.54059 Å.

1.17 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, 2-theta (°) values selected from the group consisting of 5.1, 6.6, 8.0, 8.7, 10.2, 11.3, 11.5, 12.6, 13.3, 13.8, 14.2, 14.5, 14.6, 15.4, 16.1, 16.5, 17.2, 17.4, 17.7, 18.3, 19.3, 20.0, 20.2, 20.7, 20.9, 21.2, 21.7, 22.0, 23.2, 23.8, 24.3, 24.7, 25.0, 25.2, 25.9, 26.2, 26.8, 27.0, 27.5, 27.9, 28.2, 28.6, and 29.4, wherein the XRPD is measured using an incident beam of Cu Kα radiation, e.g., wherein the XRPD is measured using radiation of wavelength 1.54059 Å.

1.18 Any of Crystalline Form 1 et seq. exhibiting an XRPD pattern having the following 2-theta (°) values: 5.1, 6.6, 8.0, 8.7, 10.2, 11.3, 11.5, 12.6, 13.3, 13.8, 14.2, 14.5, 14.6, 15.4, 16.1, 16.5, 17.2, 17.4, 17.7, 18.3, 19.3, 20.0, 20.2, 20.7, 20.9, 21.2, 21.7, 22.0, 23.2, 23.8, 24.3, 24.7, 25.0, 25.2, 25.9, 26.2, 26.8, 27.0, 27.5, 27.9, 28.2, 28.6, and 29.4,
wherein the XRPD is measured using an incident beam of Cu Kα radiation, e.g., wherein the XRPD is measured using radiation of wavelength 1.54059 Å.

1.19 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, 2-theta (°) values selected from the group consisting of 5.07, 6.61, 7.99, 8.67, 10.15, 11.25, 11.49, 12.58, 13.27, 13.80, 14.21, 14.46, 14.58, 15.39, 16.05, 16.52, 17.16, 17.40, 17.68, 18.26, 19.29, 19.96, 20.18, 20.65, 20.93, 21.18, 21.65, 21.99, 23.17, 23.82, 24.28, 24.70, 24.95, 25.23, 25.93, 26.21, 26.79, 26.98, 27.46, 27.86, 28.22, 28.63, and 29.43, wherein the XRPD is measured using an incident beam of Cu Kα radiation, e.g., wherein the XRPD is measured using radiation of wavelength 1.54059 Å.

1.20 Any of Crystalline Form 1 et seq. exhibiting an XRPD pattern having the following 2-theta (°) values: 5.07, 6.61, 7.99, 8.67, 10.15, 11.25, 11.49, 12.58, 13.27, 13.80, 14.21, 14.46, 14.58, 15.39, 16.05, 16.52, 17.16, 17.40, 17.68, 18.26, 19.29, 19.96, 20.18, 20.65, 20.93, 21.18, 21.65, 21.99, 23.17, 23.82, 24.28, 24.70, 24.95, 25.23, 25.93, 26.21, 26.79, 26.98, 27.46, 27.86, 28.22, 28.63, and 29.43, wherein the XRPD is measured using an incident beam of Cu Kα radiation, e.g., wherein the XRPD is measured using radiation of wavelength 1.54059 Å.

1.21 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, 2-theta (°) values selected from those set forth in Table B below:

TABLE B

| °2θ | d space (Å) | Intensity (%) |
|---|---|---|
| 5.07 ± 0.20 | 17.430 ± 0.688 | 22 |
| 6.61 ± 0.20 | 13.364 ± 0.404 | 100 |
| 7.99 ± 0.20 | 11.055 ± 0.276 | 41 |
| 8.67 ± 0.20 | 10.190 ± 0.235 | 6 |
| 10.15 ± 0.20 | 8.705 ± 0.171 | 9 |
| 11.25 ± 0.20 | 7.862 ± 0.139 | 7 |
| 11.49 ± 0.20 | 7.695 ± 0.133 | 18 |
| 12.58 ± 0.20 | 7.029 ± 0.111 | 14 |
| 13.27 ± 0.20 | 6.669 ± 0.100 | 4 |
| 13.80 ± 0.20 | 6.410 ± 0.092 | 33 |
| 14.21 ± 0.20 | 6.228 ± 0.087 | 7 |
| 14.46 ± 0.20 | 6.121 ± 0.084 | 37 |
| 14.58 ± 0.20 | 6.070 ± 0.083 | 22 |
| 15.39 ± 0.20 | 5.753 ± 0.074 | 5 |
| 16.05 ± 0.20 | 5.518 ± 0.068 | 41 |
| 16.52 ± 0.20 | 5.363 ± 0.064 | 33 |
| 17.16 ± 0.20 | 5.162 ± 0.060 | 15 |
| 17.40 ± 0.20 | 5.093 ± 0.058 | 36 |
| 17.68 ± 0.20 | 5.013 ± 0.056 | 7 |
| 18.26 ± 0.20 | 4.856 ± 0.053 | 19 |
| 19.29 ± 0.20 | 4.597 ± 0.047 | 86 |
| 19.96 ± 0.20 | 4.444 ± 0.044 | 28 |
| 20.18 ± 0.20 | 4.397 ± 0.043 | 22 |
| 20.65 ± 0.20 | 4.298 ± 0.041 | 13 |
| 20.93 ± 0.20 | 4.241 ± 0.040 | 55 |
| 21.18 ± 0.20 | 4.192 ± 0.039 | 50 |
| 21.65 ± 0.20 | 4.101 ± 0.037 | 22 |
| 21.99 ± 0.20 | 4.039 ± 0.036 | 50 |
| 23.17 ± 0.20 | 3.835 ± 0.033 | 89 |
| 23.82 ± 0.20 | 3.732 ± 0.031 | 77 |
| 24.28 ± 0.20 | 3.663 ± 0.030 | 22 |
| 24.70 ± 0.20 | 3.601 ± 0.029 | 14 |
| 24.95 ± 0.20 | 3.566 ± 0.028 | 20 |
| 25.23 ± 0.20 | 3.527 ± 0.028 | 29 |
| 25.93 ± 0.20 | 3.433 ± 0.026 | 27 |
| 26.21 ± 0.20 | 3.397 ± 0.025 | 26 |
| 26.79 ± 0.20 | 3.325 ± 0.024 | 21 |
| 26.98 ± 0.20 | 3.302 ± 0.024 | 14 |
| 27.46 ± 0.20 | 3.246 ± 0.023 | 13 |
| 27.86 ± 0.20 | 3.199 ± 0.023 | 9 |
| 28.22 ± 0.20 | 3.160 ± 0.022 | 10 |
| 28.63 ± 0.20 | 3.115 ± 0.021 | 20 |
| 29.43 ± 0.20 | 3.033 ± 0.020 | 12 | wherein the XRPD is measured using an incident beam of Cu Kα radiation, e.g., wherein the XRPD is measured using radiation of wavelength 1.54059 Å.

1.22 Any of Crystalline Form 1 et seq. exhibiting an XRPD pattern having the 2-theta (°) values set forth in Table B of Crystalline Form 1.21, wherein the XRPD is measured using an incident beam of Cu Kα radiation, e.g., wherein the XRPD is measured using radiation of wavelength 1.54059 Å.

1.23 Any of Crystalline Form 1 et seq. exhibiting an XRPD pattern comprising at least three, e.g., at least five, d-spacing (Å) values selected from the group consisting of 17.4, 13.4, 11.1, 6.4, 6.1, 5.5, 5.4, 5.1, 4.6, 4.2, 4.0, 3.8, and 3.7.

1.24 Any of Crystalline Form 1 et seq. exhibiting an XRPD pattern comprising the d-spacing (Å) values below:
17.4, 13.4, 11.1, 6.4, 6.1, 5.5, 5.4, 5.1, 4.6, 4.2, 4.0, 3.8, and 3.7.

1.25 Any of Crystalline Form 1 et seq. exhibiting an XRPD pattern comprising at least three, e.g., at least five, d-spacing (Å) values selected from the group consisting of 17.43, 13.36, 11.06, 6.41, 6.12, 5.52, 5.36, 5.09, 4.60, 4.24, 4.19, 4.04, 3.84, and 3.73

1.26 Any of Crystalline Form 1 et seq. wherein the crystal exhibits an XRPD pattern comprising the d-spacing (Å) values below:
17.43, 13.36, 11.06, 6.41, 6.12, 5.52, 5.36, 5.09, 4.60, 4.24, 4.19, 4.04, 3.84, and 3.73

1.27 Any of Crystalline Form 1 et seq. exhibiting an XRPD pattern comprising at least three, e.g., at least five, d-spacing (Å) values selected from the group consisting of 17.430, 13.364, 11.055, 6.410, 6.121, 5.518, 5.363, 5.093, 4.597, 4.241, 4.192, 4.039, 3.835, and 3.732.

1.28 Any of Crystalline Form 1 et seq. exhibiting an XRPD pattern comprising the d-spacing (Å) values below:
17.430, 13.364, 11.055, 6.410, 6.121, 5.518, 5.363, 5.093, 4.597, 4.241, 4.192, 4.039, 3.835, and 3.732.

1.29 Any of Crystalline Form 1 et seq. exhibiting an XRPD pattern comprising at least three, e.g., at least five, d-spacing (Å) values selected from those set forth in Table A of Crystalline Form 1.15.

1.30 Any of Crystalline Form 1 et seq. exhibiting an XRPD pattern comprising the d-spacing (Å) values set forth in Table A of Crystalline Form 1.15.

1.31 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, d-spacing (Å) values selected from the group consisting of 17.4, 13.4, 11.1, 10.2, 8.7, 7.9, 7.7, 7.0, 6.7, 6.4, 6.2, 6.1, 5.8, 5.5, 5.4, 5.2, 5.1, 5.0, 4.9, 4.6, 4.4, 4.3, 4.2, 4.1, 4.0, 3.8, 3.7, 3.6, 3.5, 3.4, 3.3, 3.2, 3.1, and 3.0.

1.32 Any of Crystalline Form 1 et seq. exhibiting an XRPD pattern having the d-spacing (Å) values below: 17.4, 13.4, 11.1, 10.2, 8.7, 7.9, 7.7, 7.0, 6.7, 6.4, 6.2, 6.1, 5.8, 5.5, 5.4, 5.2, 5.1, 5.0, 4.9, 4.6, 4.4, 4.3, 4.2, 4.1, 4.0, 3.8, 3.7, 3.6, 3.5, 3.4, 3.3, 3.2, 3.1, and 3.0.

1.33 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, d-spacing (Å) values selected from the group consisting of 17.43, 13.36, 11.06, 10.19, 8.71, 7.86, 7.70, 7.03, 6.67, 6.41, 6.23, 6.12, 6.07, 5.75, 5.52, 5.36, 5.16, 5.09, 5.01, 4.86, 4.60, 4.44, 4.40, 4.30, 4.24, 4.19, 4.10, 4.04, 3.84, 3.73, 3.66, 3.60, 3.57, 3.53, 3.43, 3.40, 3.33, 3.30, 3.25, 3.20, 3.16, 3.12, and 3.03.

1.34 Any of Crystalline Form 1 et seq. exhibiting an XRPD pattern having the d-spacing (Å) values below: 17.43, 13.36, 11.06, 10.19, 8.71, 7.86, 7.70, 7.03, 6.67, 6.41, 6.23, 6.12, 6.07, 5.75, 5.52, 5.36, 5.16, 5.09, 5.01, 4.86, 4.60, 4.44, 4.40, 4.30, 4.24, 4.19, 4.10, 4.04, 3.84, 3.73, 3.66, 3.60, 3.57, 3.53, 3.43, 3.40, 3.33, 3.30, 3.25, 3.20, 3.16, 3.12, and 3.03.

1.35 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, d-spacing (Å) values selected from the group consisting of 17.430, 13.364, 11.055, 10.190, 8.705, 7.862, 7.695, 7.029, 6.669, 6.410, 6.228, 6.121, 6.070, 5.753, 5.518, 5.363, 5.162, 5.093, 5.013, 4.856, 4.597, 4.444, 4.397, 4.298, 4.241, 4.192, 4.101, 4.039, 3.835, 3.732, 3.663, 3.601, 3.566, 3.527, 3.433, 3.397, 3.325, 3.302, 3.246, 3.199, 3.160, 3.115, and 3.033.

1.36 Any of Crystalline Form 1 et seq. exhibiting an XRPD pattern having the d-spacing (Å) values below: 17.430, 13.364, 11.055, 10.190, 8.705, 7.862, 7.695, 7.029, 6.669, 6.410, 6.228, 6.121, 6.070, 5.753, 5.518, 5.363, 5.162, 5.093, 5.013, 4.856, 4.597, 4.444, 4.397, 4.298, 4.241, 4.192, 4.101, 4.039, 3.835, 3.732, 3.663, 3.601, 3.566, 3.527, 3.433, 3.397, 3.325, 3.302, 3.246, 3.199, 3.160, 3.115, and 3.033.

1.37 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, d-spacing (Å) values selected from the group consisting of those set forth in Table B of Crystalline Form 1.21.

1.38 Any of Crystalline Form 1 et seq. exhibiting an XRPD pattern having the d-spacing (Å) values set forth in Table B of Crystalline Form 1.21.

1.39 Any of Crystalline Form 1 et seq. exhibiting an XRPD pattern comprising at least three, e.g., at least five, 2-theta (°) values selected from the group consisting of 5.1, 6.7, 14.6, 16.6, 19.3, 21.2, 22.1, 23.2, and 23.9, wherein the XRPD is measured using an incident beam of Cu Kα radiation, e.g., wherein the XRPD is measured using radiation of wavelength 1.54059 Å.

1.40 Any of Crystalline Form 1 et seq. exhibiting an XRPD pattern comprising 2-theta (°) values of 5.1, 6.7, 14.6, 16.6, 19.3, 21.2, 22.1, 23.2, and 23.9, wherein the XRPD is measured using an incident beam of Cu Kα radiation, e.g., wherein the XRPD is measured using radiation of wavelength 1.54059 Å.

1.41 Any of Crystalline Form 1 et seq. exhibiting an XRPD pattern comprising at least three, e.g., at least five, 2-theta (°) values selected from the group consisting of 5.10, 6.65, 14.60, 16.56, 19.29, 21.19, 22.07, 23.23, and 23.94, wherein the XRPD is measured using an incident beam of Cu Kα radiation, e.g., wherein the XRPD is measured using radiation of wavelength 1.54059 Å.

1.42 Any of Crystalline Form 1 et seq. exhibiting an XRPD pattern comprising 2-theta (°) values of 5.10, 6.65, 14.60, 16.56, 19.29, 21.19, 22.07, 23.23, and 23.94, wherein the XRPD is measured using an incident beam of Cu Kα radiation, e.g., wherein the XRPD is measured using radiation of wavelength 1.54059 Å.

1.43 Any of Crystalline Form 1 et seq. exhibiting an XRPD pattern comprising at least three, e.g., at least five, 2-theta (°) values selected from those set forth in Table AA below:

TABLE AA

| °2θ | d space (Å) | Intensity (%) |
|---|---|---|
| 5.10 ± 0.20 | 17.299 ± 0.677 | 25 |
| 6.65 ± 0.20 | 13.276 ± 0.399 | 28 |
| 14.60 ± 0.20 | 6.064 ± 0.083 | 19 |
| 16.56 ± 0.20 | 5.348 ± 0.064 | 24 |
| 19.29 ± 0.20 | 4.597 ± 0.047 | 100 |
| 21.19 ± 0.20 | 4.189 ± 0.039 | 40 |
| 22.07 ± 0.20 | 4.024 ± 0.036 | 23 |
| 23.23 ± 0.20 | 3.827 ± 0.032 | 64 |
| 23.94 ± 0.20 | 3.714 ± 0.031 | 58 | wherein the XRPD is measured using an incident beam of Cu Kα radiation, e.g., wherein the XRPD is measured using radiation of wavelength 1.54059 Å.

1.44 Any of Crystalline Form 1 et seq. exhibiting an XRPD pattern having the 2-theta (°) values set forth in Table AA of Crystalline Form 1.43, wherein the XRPD is measured using an incident beam of Cu Kα radiation, e.g., wherein the XRPD is measured using radiation of wavelength 1.54059 Å.

1.45 Any of Crystalline Form 1 et seq. exhibiting an XRPD pattern comprising at least three, e.g., at least five, e.g., at least nine, e.g., at least ten, e.g., at least fifteen, e.g., at least twenty, e.g., at least twenty-five, e.g., at least thirty, e.g., at least thirty-five, e.g., at least forty, 2-theta (°) values selected from the group consisting of 5.1, 6.7, 8.1, 8.7, 10.2, 10.4, 11.3, 11.5, 12.6, 14.0, 14.3, 14.6, 16.3, 16.6, 16.9, 17.2, 17.4, 17.7, 18.3, 18.5, 19.3, 19.7, 20.1, 20.5, 20.7, 21.0, 21.2, 21.7, 22.1, 22.2, 23.2, 23.9, 24.3, 24.8, 25.2, 25.4, 25.7, 26.0, 26.2, 26.5, 27.1, 27.6, 28.4, 28.8, and 29.5, wherein the XRPD is measured using an incident beam of Cu Kα radiation, e.g., wherein the XRPD is measured using radiation of wavelength 1.54059 Å.

1.46 Any of Crystalline Form 1 et seq. exhibiting an XRPD pattern having the following 2-theta (°) values: 5.1, 6.7, 8.1, 8.7, 10.2, 10.4, 11.3, 11.5, 12.6, 14.0, 14.3, 14.6, 16.3, 16.6, 16.9, 17.2, 17.4, 17.7, 18.3, 18.5, 19.3, 19.7, 20.1, 20.5, 20.7, 21.0, 21.2, 21.7, 22.1, 22.2, 23.2, 23.9, 24.3, 24.8, 25.2, 25.4, 25.7, 26.0, 26.2, 26.5, 27.1, 27.6, 28.4, 28.8, and 29.5, wherein the XRPD is measured using an incident beam of Cu Kα radiation, e.g., wherein the XRPD is measured using radiation of wavelength 1.54059 Å.

1.47 Any of Crystalline Form 1 et seq. exhibiting an XRPD pattern comprising at least three, e.g., at least five, e.g., at least nine, e.g., at least ten, e.g., at least fifteen, e.g., at least twenty, e.g., at least twenty-five, e.g., at least thirty, e.g., at least thirty-five, e.g., at least forty, 2-theta (°) values selected from the group consisting of 5.10, 6.65, 8.11, 8.68, 10.23, 10.43, 11.30, 11.49, 12.60, 13.98, 14.29, 14.60, 16.29, 16.56, 16.88, 17.20, 17.40, 17.69, 18.29, 18.46, 19.29, 19.72, 20.09, 20.51, 20.65, 20.96, 21.19, 21.69, 22.07, 22.24, 23.23, 23.94, 24.30, 24.78, 25.15, 25.38, 25.71, 25.96, 26.22, 26.51, 27.11, 27.60, 28.35, 28.81, and 29.48, wherein the XRPD is measured using an incident beam of Cu Kα radiation, e.g., wherein the XRPD is measured using radiation of wavelength 1.54059 Å.

1.48 Any of Crystalline Form 1 et seq. exhibiting an XRPD pattern having the following 2-theta (°) values: 5.10, 6.65, 8.11, 8.68, 10.23, 10.43, 11.30, 11.49, 12.60, 13.98, 14.29, 14.60, 16.29, 16.56, 16.88, 17.20, 17.40, 17.69, 18.29, 18.46, 19.29, 19.72, 20.09, 20.51, 20.65, 20.96, 21.19, 21.69, 22.07, 22.24, 23.23, 23.94, 24.30, 24.78, 25.15, 25.38, 25.71, 25.96, 26.22, 26.51, 27.11, 27.60, 28.35, 28.81, and 29.48, wherein the XRPD is measured using an incident beam of Cu Kα radiation, e.g., wherein the XRPD is measured using radiation of wavelength 1.54059 Å.

1.49 Any of Crystalline Form 1 et seq. exhibiting an XRPD pattern comprising at least three, e.g., at least five, e.g., at least nine, e.g., at least ten, e.g., at least fifteen, e.g., at least twenty, e.g., at least twenty-five, e.g., at least thirty, e.g., at least thirty-five, e.g., at least forty, 2-theta (°) values selected from those set forth in Table BB below:

TABLE BB

| °2θ | d space (Å) | Intensity (%) |
|---|---|---|
| 5.10 ± 0.20 | 17.299 ± 0.677 | 25 |
| 6.65 ± 0.20 | 13.276 ± 0.399 | 28 |
| 8.11 ± 0.20 | 10.892 ± 0.268 | 16 |
| 8.68 ± 0.20 | 10.183 ± 0.234 | 7 |
| 10.23 ± 0.20 | 8.640 ± 0.168 | 10 |
| 10.43 ± 0.20 | 8.472 ± 0.162 | 7 |
| 11.30 ± 0.20 | 7.827 ± 0.138 | 8 |
| 11.49 ± 0.20 | 7.698 ± 0.134 | 17 |
| 12.60 ± 0.20 | 7.020 ± 0.111 | 9 |
| 13.98 ± 0.20 | 6.330 ± 0.090 | 9 |
| 14.29 ± 0.20 | 6.194 ± 0.086 | 5 |
| 14.60 ± 0.20 | 6.064 ± 0.083 | 19 |
| 16.29 ± 0.20 | 5.438 ± 0.066 | 13 |
| 16.56 ± 0.20 | 5.348 ± 0.064 | 24 |
| 16.88 ± 0.20 | 5.249 ± 0.062 | 4 |
| 17.20 ± 0.20 | 5.152 ± 0.059 | 10 |
| 17.40 ± 0.20 | 5.091 ± 0.058 | 16 |
| 17.69 ± 0.20 | 5.009 ± 0.056 | 4 |

TABLE BB-continued

| °2θ | d space (Å) | Intensity (%) |
|---|---|---|
| 18.29 ± 0.20 | 4.847 ± 0.053 | 5 |
| 18.46 ± 0.20 | 4.801 ± 0.052 | 8 |
| 19.29 ± 0.20 | 4.597 ± 0.047 | 100 |
| 19.72 ± 0.20 | 4.498 ± 0.045 | 9 |
| 20.09 ± 0.20 | 4.417 ± 0.044 | 8 |
| 20.51 ± 0.20 | 4.327 ± 0.042 | 11 |
| 20.65 ± 0.20 | 4.298 ± 0.041 | 12 |
| 20.96 ± 0.20 | 4.234 ± 0.040 | 18 |
| 21.19 ± 0.20 | 4.189 ± 0.039 | 40 |
| 21.69 ± 0.20 | 4.093 ± 0.037 | 6 |
| 22.07 ± 0.20 | 4.024 ± 0.036 | 23 |
| 22.24 ± 0.20 | 3.995 ± 0.035 | 16 |
| 23.23 ± 0.20 | 3.827 ± 0.032 | 64 |
| 23.94 ± 0.20 | 3.714 ± 0.031 | 58 |
| 24.30 ± 0.20 | 3.660 ± 0.030 | 8 |
| 24.78 ± 0.20 | 3.591 ± 0.029 | 10 |
| 25.15 ± 0.20 | 3.538 ± 0.028 | 16 |
| 25.38 ± 0.20 | 3.507 ± 0.027 | 14 |
| 25.71 ± 0.20 | 3.463 ± 0.026 | 7 |
| 25.96 ± 0.20 | 3.430 ± 0.026 | 14 |
| 26.22 ± 0.20 | 3.396 ± 0.025 | 12 |
| 26.51 ± 0.20 | 3.359 ± 0.025 | 8 |
| 27.11 ± 0.20 | 3.287 ± 0.024 | 12 |
| 27.60 ± 0.20 | 3.229 ± 0.023 | 7 |
| 28.35 ± 0.20 | 3.146 ± 0.022 | 7 |
| 28.81 ± 0.20 | 3.096 ± 0.021 | 16 |
| 29.48 ± 0.20 | 3.028 ± 0.020 | 10 | wherein the XRPD is measured using an incident beam of Cu Kα radiation, e.g., wherein the XRPD is measured using radiation of wavelength 1.54059 Å.

1.50 Any of Crystalline Form 1 et seq. exhibiting an XRPD pattern having the 2-theta (°) values set forth in Table BB of Crystalline Form 1.49, wherein the XRPD is measured using an incident beam of Cu Kα radiation, e.g., wherein the XRPD is measured using radiation of wavelength 1.54059 Å.

1.51 Any of Crystalline Form 1 et seq. exhibiting an XRPD pattern comprising at least three, e.g., at least five, d-spacing (Å) values selected from the group consisting of 17.3, 13.3, 6.1, 5.3, 4.6, 4.2, 4.0, 3.8, and 3.7.

1.52 Any of Crystalline Form 1 et seq. exhibiting an XRPD pattern comprising the d-spacing (Å) values below:
17.3, 13.3, 6.1, 5.3, 4.6, 4.2, 4.0, 3.8, and 3.7.

1.53 Any of Crystalline Form 1 et seq. exhibiting an XRPD pattern comprising at least three, e.g., at least five, d-spacing (Å) values selected from the group consisting of 17.30, 13.28, 6.06, 5.35, 4.60, 4.19, 4.02, 3.83, and 3.71.

1.54 Any of Crystalline Form 1 et seq. wherein the crystal exhibits an XRPD pattern comprising the d-spacing (Å) values below:
17.30, 13.28, 6.06, 5.35, 4.60, 4.19, 4.02, 3.83, and 3.71.

1.55 Any of Crystalline Form 1 et seq. exhibiting an XRPD pattern comprising at least three, e.g., at least five, d-spacing (Å) values selected from the group consisting of 17.299, 13.276, 6.064, 5.348, 4.597, 4.189, 4.024, 3.827, and 3.714.

1.56 Any of Crystalline Form 1 et seq. exhibiting an XRPD pattern comprising the d-spacing (Å) values below:
17.299, 13.276, 6.064, 5.348, 4.597, 4.189, 4.024, 3.827, and 3.714.

1.57 Any of Crystalline Form 1 et seq. exhibiting an XRPD pattern comprising at least three, e.g., at least five, d-spacing (Å) values selected from those set forth in Table AA of Crystalline Form 1.43.

1.58 Any of Crystalline Form 1 et seq. exhibiting an XRPD pattern comprising the d-spacing (Å) values set forth in Table AA of Crystalline Form 1.43.

1.59 Any of Crystalline Form 1 et seq. exhibiting an XRPD pattern comprising at least three, e.g., at least five, e.g., at least nine, e.g., at least ten, e.g., at least fifteen, e.g., at least twenty, e.g., at least twenty-five, e.g., at least thirty, d-spacing (Å) values selected from the group consisting of 17.3, 13.3, 10.9, 10.2, 8.6, 8.5, 7.8, 7.7, 7.0, 6.3, 6.2, 6.1, 5.4, 5.3, 5.2, 5.1, 5.0, 4.8, 4.6, 4.5, 4.4, 4.3, 4.2, 4.1, 4.0, 3.8, 3.7, 3.6, 3.5, 3.4, 3.3, 3.2, 3.1, and 3.0.

1.60 Any of Crystalline Form 1 et seq. exhibiting an XRPD pattern having the d-spacing (Å) values below: 17.3, 13.3, 10.9, 10.2, 8.6, 8.5, 7.8, 7.7, 7.0, 6.3, 6.2, 6.1, 5.4, 5.3, 5.2, 5.1, 5.0, 4.8, 4.6, 4.5, 4.4, 4.3, 4.2, 4.1, 4.0, 3.8, 3.7, 3.6, 3.5, 3.4, 3.3, 3.2, 3.1, and 3.0.

1.61 Any of Crystalline Form 1 et seq. exhibiting an XRPD pattern comprising at least three, e.g., at least five, e.g., at least nine, e.g., at least ten, e.g., at least fifteen, e.g., at least twenty, e.g., at least twenty-five, e.g., at least thirty, e.g., at least thirty-five, e.g., at least forty, d-spacing (Å) values selected from the group consisting of 17.30, 13.28, 10.89, 10.18, 8.64, 8.47, 7.83, 7.70, 7.02, 6.33, 6.19, 6.06, 5.44, 5.35, 5.25, 5.15, 5.09, 5.01, 4.85, 4.80, 4.60, 4.50, 4.42, 4.33, 4.30, 4.23, 4.19, 4.09, 4.02, 4.00, 3.83, 3.71, 3.66, 3.59, 3.54, 3.51, 3.46, 3.43, 3.40, 3.36, 3.29, 3.23, 3.15, 3.10, and 3.03.

1.62 Any of Crystalline Form 1 et seq. exhibiting an XRPD pattern having the d-spacing (Å) values below: 17.30, 13.28, 10.89, 10.18, 8.64, 8.47, 7.83, 7.70, 7.02, 6.33, 6.19, 6.06, 5.44, 5.35, 5.25, 5.15, 5.09, 5.01, 4.85, 4.80, 4.60, 4.50, 4.42, 4.33, 4.30, 4.23, 4.19, 4.09, 4.02, 4.00, 3.83, 3.71, 3.66, 3.59, 3.54, 3.51, 3.46, 3.43, 3.40, 3.36, 3.29, 3.23, 3.15, 3.10, and 3.03.

1.63 Any of Crystalline Form 1 et seq. exhibiting an XRPD pattern comprising at least three, e.g., at least five, e.g., at least nine, e.g., at least ten, e.g., at least fifteen, e.g., at least twenty, e.g., at least twenty-five, e.g., at least thirty, e.g., at least thirty-five, e.g., at least forty, d-spacing (Å) values selected from the group consisting of 17.299, 13.276, 10.892, 10.183, 8.640, 8.472, 7.827, 7.698, 7.020, 6.330, 6.194, 6.064, 5.438, 5.348, 5.249, 5.152, 5.091, 5.009, 4.847, 4.801, 4.597, 4.498, 4.417, 4.327, 4.298, 4.234, 4.189, 4.093, 4.024, 3.995, 3.827, 3.714, 3.660, 3.591, 3.538, 3.507, 3.463, 3.430, 3.396, 3.359, 3.287, 3.229, 3.146, 3.096, and 3.028.

1.64 Any of Crystalline Form 1 et seq. exhibiting an XRPD pattern having the d-spacing (Å) values below: 17.299, 13.276, 10.892, 10.183, 8.640, 8.472, 7.827, 7.698, 7.020, 6.330, 6.194, 6.064, 5.438, 5.348, 5.249, 5.152, 5.091, 5.009, 4.847, 4.801, 4.597, 4.498, 4.417, 4.327, 4.298, 4.234, 4.189, 4.093, 4.024, 3.995, 3.827, 3.714, 3.660, 3.591, 3.538, 3.507, 3.463, 3.430, 3.396, 3.359, 3.287, 3.229, 3.146, 3.096, and 3.028.

1.65 Any of Crystalline Form 1 et seq. exhibiting an XRPD pattern comprising at least three, e.g., at least five, e.g., at least nine, e.g., at least ten, e.g., at least fifteen, e.g., at least twenty, e.g., at least twenty-five, e.g., at least thirty, e.g., at least thirty-five, e.g., at least forty, d-spacing (Å) values selected from the group consisting of those set forth in Table BB of Crystalline Form 1.49.

1.66 Any of Crystalline Form 1 et seq. exhibiting an XRPD pattern having the d-spacing (Å) values set forth in Table BB of Crystalline Form 1.49.

1.67 Any of Crystalline Form 1 et seq. exhibiting an XRPD pattern comprising at least three, e.g., at least five, e.g., at least ten, 2-theta (°) values selected from the group consisting of 5.1, 6.6, 8.0, 11.5, 13.9, 14.5, 16.2, 16.5, 17.4, 19.3, 20.9, 21.1, 22.0, 23.2, and 23.9, wherein the XRPD is measured using an incident beam of Cu Kα radiation, e.g., wherein the XRPD is measured using radiation of wavelength 1.54059 Å.

1.68 Any of Crystalline Form 1 et seq. exhibiting an XRPD pattern comprising 2-theta (°) values of 5.1, 6.6, 8.0, 11.5, 13.9, 14.5, 16.2, 16.5, 17.4, 19.3, 20.9, 21.1, 22.0, 23.2, and 23.9, wherein the XRPD is measured using an incident beam of Cu Kα radiation, e.g., wherein the XRPD is measured using radiation of wavelength 1.54059 Å.

1.69 Any of Crystalline Form 1 et seq. exhibiting an XRPD pattern comprising at least three, e.g., at least five, e.g., at least ten, 2-theta (°) values selected from the group consisting of 5.08, 6.62, 8.03, 11.47, 13.86, 14.53, 16.15, 16.53, 17.36, 19.26, 20.93, 21.13, 22.03, 23.17, and 23.88, wherein the XRPD is measured using an incident beam of Cu Kα radiation, e.g., wherein the XRPD is measured using radiation of wavelength 1.54059 Å.

1.70 Any of Crystalline Form 1 et seq. exhibiting an XRPD pattern comprising 2-theta (°) values of 5.08, 6.62, 8.03, 11.47, 13.86, 14.53, 16.15, 16.53, 17.36, 19.26, 20.93, 21.13, 22.03, 23.17, and 23.88, wherein the XRPD is measured using an incident beam of Cu Kα radiation, e.g., wherein the XRPD is measured using radiation of wavelength 1.54059 Å.

1.71 Any of Crystalline Form 1 et seq. exhibiting an XRPD pattern comprising at least three, e.g., at least five, e.g., at least ten, 2-theta (°) values selected from those set forth in Table CC below:

TABLE CC

| °2θ | d space (Å) | Intensity (%) |
| --- | --- | --- |
| 5.08 ± 0.20 | 17.372 ± 0.683 | 20 |
| 6.62 ± 0.20 | 13.349 ± 0.403 | 100 |
| 8.03 ± 0.20 | 10.998 ± 0.273 | 29 |
| 11.47 ± 0.20 | 7.710 ± 0.134 | 18 |
| 13.86 ± 0.20 | 6.385 ± 0.092 | 20 |
| 14.53 ± 0.20 | 6.091 ± 0.083 | 27 |
| 16.15 ± 0.20 | 5.483 ± 0.067 | 23 |
| 16.53 ± 0.20 | 5.359 ± 0.064 | 28 |
| 17.36 ± 0.20 | 5.103 ± 0.058 | 34 |
| 19.26 ± 0.20 | 4.606 ± 0.047 | 81 |
| 20.93 ± 0.20 | 4.240 ± 0.040 | 36 |
| 21.13 ± 0.20 | 4.201 ± 0.039 | 49 |
| 22.03 ± 0.20 | 4.031 ± 0.036 | 32 |
| 23.17 ± 0.20 | 3.835 ± 0.033 | 72 |
| 23.88 ± 0.20 | 3.723 ± 0.031 | 53 | wherein the XRPD is measured using an incident beam of Cu Kα radiation, e.g., wherein the XRPD is measured using radiation of wavelength 1.54059 Å.

1.72 Any of Crystalline Form 1 et seq. exhibiting an XRPD pattern having the 2-theta (°) values set forth in Table CC of Crystalline Form 1.71, wherein the XRPD is measured using an incident beam of Cu Kα radiation, e.g., wherein the XRPD is measured using radiation of wavelength 1.54059 Å.

1.73 Any of Crystalline Form 1 et seq. exhibiting an XRPD pattern comprising at least three, e.g., at least five, e.g., at least ten, e.g., at least fifteen, e.g., at least twenty, e.g., at least twenty-five, 2-theta (°) values selected from the group consisting of 5.1, 6.6, 8.0, 8.6, 10.2, 11.3, 11.5, 12.6, 13.9, 14.5, 16.2, 16.5, 17.4, 17.7, 18.3, 19.3, 20.0, 20.6, 20.9, 21.1, 22.0, 23.2, 23.9, 24.2, 24.7, 25.3, 26.0, and 26.2, wherein the XRPD is measured using an incident beam of Cu Kα radiation, e.g., wherein the XRPD is measured using radiation of wavelength 1.54059 Å.

1.74 Any of Crystalline Form 1 et seq. exhibiting an XRPD pattern having the following 2-theta (°) values: 5.1, 6.6, 8.0, 8.6, 10.2, 11.3, 11.5, 12.6, 13.9, 14.5, 16.2, 16.5, 17.4, 17.7, 18.3, 19.3, 20.0, 20.6, 20.9, 21.1, 22.0, 23.2, 23.9, 24.2, 24.7, 25.3, 26.0, and 26.2, wherein the XRPD is measured using an incident beam of Cu Kα radiation, e.g., wherein the XRPD is measured using radiation of wavelength 1.54059 Å.

1.75 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, 2-theta (°) values selected from the group consisting of 5.08, 6.62, 8.03, 8.64, 10.18, 11.28, 11.47, 12.58, 13.86, 14.53, 16.15, 16.53, 17.36, 17.67, 18.32, 19.26, 19.97, 20.58, 20.93, 21.13, 22.03, 23.17, 23.88, 24.24, 24.74, 25.28, 25.95, and 26.17, wherein the XRPD is measured using an incident beam of Cu Kα radiation, e.g., wherein the XRPD is measured using radiation of wavelength 1.54059 Å.

1.76 Any of Crystalline Form 1 et seq. exhibiting an XRPD pattern having the following 2-theta (°) values: 5.08, 6.62, 8.03, 8.64, 10.18, 11.28, 11.47, 12.58, 13.86, 14.53, 16.15, 16.53, 17.36, 17.67, 18.32, 19.26, 19.97, 20.58, 20.93, 21.13, 22.03, 23.17, 23.88, 24.24, 24.74, 25.28, 25.95, and 26.17, wherein the XRPD is measured using an incident beam of Cu Kα radiation, e.g., wherein the XRPD is measured using radiation of wavelength 1.54059 Å.

1.77 Any of Crystalline Form 1 et seq. exhibiting an XRPD pattern comprising at least three, e.g., at least five, e.g., at least ten, e.g., at least fifteen, e.g., at least twenty, e.g., at least twenty-five, 2-theta (°) values selected from those set forth in Table DD below:

TABLE DD

| °2θ | d space (Å) | Intensity (%) |
|---|---|---|
| 5.08 ± 0.20 | 17.372 ± 0.683 | 20 |
| 6.62 ± 0.20 | 13.349 ± 0.403 | 100 |
| 8.03 ± 0.20 | 10.998 ± 0.273 | 29 |
| 8.64 ± 0.20 | 10.223 ± 0.236 | 7 |
| 10.18 ± 0.20 | 8.682 ± 0.170 | 7 |
| 11.28 ± 0.20 | 7.837 ± 0.138 | 7 |
| 11.47 ± 0.20 | 7.710 ± 0.134 | 18 |
| 12.58 ± 0.20 | 7.029 ± 0.111 | 12 |
| 13.86 ± 0.20 | 6.385 ± 0.092 | 20 |
| 14.53 ± 0.20 | 6.091 ± 0.083 | 27 |
| 16.15 ± 0.20 | 5.483 ± 0.067 | 23 |
| 16.53 ± 0.20 | 5.359 ± 0.064 | 28 |
| 17.36 ± 0.20 | 5.103 ± 0.058 | 34 |
| 17.67 ± 0.20 | 5.015 ± 0.056 | 6 |
| 18.32 ± 0.20 | 4.839 ± 0.052 | 11 |
| 19.26 ± 0.20 | 4.606 ± 0.047 | 81 |
| 19.97 ± 0.20 | 4.442 ± 0.044 | 24 |
| 20.58 ± 0.20 | 4.311 ± 0.041 | 18 |
| 20.93 ± 0.20 | 4.240 ± 0.040 | 36 |
| 21.13 ± 0.20 | 4.201 ± 0.039 | 49 |
| 22.03 ± 0.20 | 4.031 ± 0.036 | 32 |
| 23.17 ± 0.20 | 3.835 ± 0.033 | 72 |
| 23.88 ± 0.20 | 3.723 ± 0.031 | 53 |
| 24.24 ± 0.20 | 3.669 ± 0.030 | 18 |
| 24.74 ± 0.20 | 3.596 ± 0.029 | 12 |
| 25.28 ± 0.20 | 3.521 ± 0.027 | 24 |
| 25.95 ± 0.20 | 3.430 ± 0.026 | 22 |
| 26.17 ± 0.20 | 3.402 ± 0.026 | 20 | wherein the XRPD is measured using an incident beam of Cu Kα radiation, e.g., wherein the XRPD is measured using radiation of wavelength 1.54059 Å.

1.78 Any of Crystalline Form 1 et seq. exhibiting an XRPD pattern having the 2-theta (°) values set forth in Table DD of Crystalline Form 1.77, wherein the XRPD is measured using an incident beam of Cu Kα radiation, e.g., wherein the XRPD is measured using radiation of wavelength 1.54059 Å.

1.79 Any of Crystalline Form 1 et seq. exhibiting an XRPD pattern comprising at least three, e.g., at least five, e.g., at least ten, d-spacing (Å) values selected from the group consisting of 17.4, 13.3, 11.0, 7.7, 6.4, 6.1, 5.5, 5.4, 5.1, 4.6, 4.2, 4.0, 3.8, and 3.7.

1.80 Any of Crystalline Form 1 et seq. exhibiting an XRPD pattern comprising the d-spacing (Å) values below:
17.4, 13.3, 11.0, 7.7, 6.4, 6.1, 5.5, 5.4, 5.1, 4.6, 4.2, 4.0, 3.8, and 3.7.

1.81 Any of Crystalline Form 1 et seq. exhibiting an XRPD pattern comprising at least three, e.g., at least five, e.g., at least ten, d-spacing (Å) values selected from the group consisting of 17.37, 13.35, 11.00, 7.71, 6.39, 6.09, 5.48, 5.36, 5.10, 4.61, 4.24, 4.20, 4.03, 3.84, and 3.72.

1.82 Any of Crystalline Form 1 et seq. wherein the crystal exhibits an XRPD pattern comprising the d-spacing (Å) values below:
17.37, 13.35, 11.00, 7.71, 6.39, 6.09, 5.48, 5.36, 5.10, 4.61, 4.24, 4.20, 4.03, 3.84, and 3.72.

1.83 Any of Crystalline Form 1 et seq. exhibiting an XRPD pattern comprising at least three, e.g., at least five, e.g., at least ten, d-spacing (Å) values selected from the group consisting of 17.372, 13.349, 10.998, 7.710, 6.385, 6.091, 5.483, 5.359, 5.103, 4.606, 4.240, 4.201, 4.031, 3.835, and 3.723.

1.84 Any of Crystalline Form 1 et seq. exhibiting an XRPD pattern comprising the d-spacing (Å) values below:
17.372, 13.349, 10.998, 7.710, 6.385, 6.091, 5.483, 5.359, 5.103, 4.606, 4.240, 4.201, 4.031, 3.835, and 3.723.

1.85 Any of Crystalline Form 1 et seq. exhibiting an XRPD pattern comprising at least three, e.g., at least five, d-spacing (Å) values selected from those set forth in Table CC of Crystalline Form 1.71.

1.86 Any of Crystalline Form 1 et seq. exhibiting an XRPD pattern comprising the d-spacing (Å) values set forth in Table CC of Crystalline Form 1.71.

1.87 Any of Crystalline Form 1 et seq. exhibiting an XRPD pattern comprising at least three, e.g., at least five, e.g., at least ten, e.g., at least fifteen, e.g., at least twenty, d-spacing (Å) values selected from the group consisting of 17.4, 13.3, 11.0, 10.2, 8.7, 7.8, 7.7, 7.0, 6.4, 6.1, 5.5, 5.4, 5.1, 5.0, 4.8, 4.6, 4.4, 4.3, 4.2, 4.0, 3.8, 3.7, 3.6, 3.5, and 3.4.

1.88 Any of Crystalline Form 1 et seq. exhibiting an XRPD pattern having the d-spacing (Å) values below: 17.4, 13.3, 11.0, 10.2, 8.7, 7.8, 7.7, 7.0, 6.4, 6.1, 5.5, 5.4, 5.1, 5.0, 4.8, 4.6, 4.4, 4.3, 4.2, 4.0, 3.8, 3.7, 3.6, 3.5, and 3.4.

1.89 Any of Crystalline Form 1 et seq. exhibiting an XRPD pattern comprising at least three, e.g., at least five, e.g., at least ten, e.g., at least fifteen, e.g., at least twenty, e.g., at least twenty-five, d-spacing (Å) values selected from the group consisting of 17.37, 13.35, 11.00, 10.22, 8.68, 7.84, 7.71, 7.03, 6.39, 6.09, 5.48, 5.36, 5.10, 5.02, 4.84, 4.61, 4.44, 4.31, 4.24, 4.20, 4.03, 3.84, 3.72, 3.67, 3.60, 3.52, 3.43, and 3.40.

1.90 Any of Crystalline Form 1 et seq. exhibiting an XRPD pattern having the d-spacing (Å) values below: 17.37, 13.35, 11.00, 10.22, 8.68, 7.84, 7.71, 7.03, 6.39, 6.09, 5.48, 5.36, 5.10, 5.02, 4.84, 4.61, 4.44, 4.31, 4.24, 4.20, 4.03, 3.84, 3.72, 3.67, 3.60, 3.52, 3.43, and 3.40.

1.91 Any of Crystalline Form 1 et seq. exhibiting an XRPD pattern comprising at least three, e.g., at least five, e.g., at least ten, e.g., at least fifteen, e.g., at least twenty, e.g., at least twenty-five, d-spacing (Å) values selected from the group consisting of 17.372, 13.349, 10.998, 10.223, 8.682, 7.837, 7.710, 7.029, 6.385, 6.091, 5.483, 5.359, 5.103, 5.015, 4.839, 4.606, 4.442, 4.311, 4.240, 4.201, 4.031, 3.835, 3.723, 3.669, 3.596, 3.521, 3.430, and 3.402.

1.92 Any of Crystalline Form 1 et seq. exhibiting an XRPD pattern having the d-spacing (Å) values below: 17.372, 13.349, 10.998, 10.223, 8.682, 7.837, 7.710, 7.029, 6.385, 6.091, 5.483, 5.359, 5.103, 5.015, 4.839, 4.606, 4.442, 4.311, 4.240, 4.201, 4.031, 3.835, 3.723, 3.669, 3.596, 3.521, 3.430, and 3.402.

1.93 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, d-spacing (Å) values selected from the group consisting of those set forth in Table DD of Crystalline Form 1.77.

1.94 Any of Crystalline Form 1 et seq. exhibiting an XRPD pattern having the d-spacing (Å) values set forth in Table DD of Crystalline Form 1.77.

1.95 Any of Crystalline Form 1 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, e.g., all of the peaks, of the XRPD shown in FIG. 10, wherein the XRPD is obtained using Cu Kα radiation, e.g., wherein the XRPD is measured using radiation of wavelength 1.54059 Å.

1.96 Any of Crystalline Form 1 et seq. comprising characteristic peaks of the XRPD pattern shown in FIG. 10, wherein the XRPD is obtained using Cu Kα radiation, e.g., wherein the XRPD is measured using radiation of wavelength 1.54059 Å.

1.97 Any of Crystalline Form 1 et seq. comprising representative peaks of the XRPD pattern shown in FIG. 10, wherein the XRPD is obtained using Cu Kα radiation, e.g., wherein the XRPD is measured using radiation of wavelength 1.54059 Å.

1.98 Any of Crystalline Form 1 et seq. exhibiting an XRPD pattern as shown in FIG. 10, wherein the XRPD is obtained using Cu Kα radiation, e.g., wherein the XRPD is measured using radiation of wavelength 1.54059 Å.

1.99 Any of Crystalline Form 1 et seq. exhibiting an XRPD pattern comprising at least three, e.g., at least five, e.g., at least nine, e.g., at least ten, e.g., at least fourteen, e.g., at least fifteen, e.g., at least twenty, e.g., at least twenty-five, e.g., at least thirty, e.g., at least thirty-five, e.g., at least forty, e.g., all of the peaks, of the XRPD shown in FIG. 11, wherein the XRPD is obtained using Cu Kα radiation, e.g., wherein the XRPD is measured using radiation of wavelength 1.54059 Å.

1.100 Any of Crystalline Form 1 et seq. comprising the characteristic peaks of the XRPD pattern shown in FIG. 11, wherein the XRPD is obtained using Cu Kα radiation, e.g., wherein the XRPD is measured using radiation of wavelength 1.54059 Å.

1.101 Any of Crystalline Form 1 et seq. comprising the representative peaks of the XRPD pattern shown in FIG. 11, wherein the XRPD is obtained using Cu Kα radiation, e.g., wherein the XRPD is measured using radiation of wavelength 1.54059 Å.

1.102 Any of Crystalline Form 1 et seq. exhibiting an XRPD pattern as shown in FIG. 11, wherein the XRPD is obtained using Cu Kα radiation, e.g., wherein the XRPD is measured using radiation of wavelength 1.54059 Å.

1.103 Any of Crystalline Form 1 et seq. exhibiting an XRPD pattern comprising at least five peaks, e.g., all of the peaks, of the XRPD shown in FIG. 12a, wherein the XRPD is obtained using a copper source, e.g., obtained using Cu Kα radiation.

1.104 Any of Crystalline Form 1 et seq. comprising the characteristic peaks of the XRPD pattern shown in FIG. 12a, wherein the XRPD is obtained using a copper source, e.g., obtained using Cu Kα radiation.

1.105 Any of Crystalline Form 1 et seq. comprising the representative peaks of the XRPD pattern shown in FIG. 12a, wherein the XRPD is obtained using a copper source, e.g., obtained using Cu Kα radiation.

1.106 Any of Crystalline Form 1 et seq. exhibiting an XRPD pattern as shown in FIG. 12a, wherein the XRPD is obtained using a copper source, e.g., obtained using Cu Kα radiation.

1.107 Any of Crystalline Form 1 et seq. exhibiting an XRPD pattern comprising at least five peaks, e.g., all of the peaks, of the XRPD pattern shown in FIG. 12b, wherein the XRPD is obtained using a copper source, e.g., obtained using Cu Kα radiation.

1.108 Any of Crystalline Form 1 et seq. comprising the characteristic peaks of the XRPD pattern shown in FIG. 12b, wherein the XRPD is obtained using a copper source, e.g., obtained using Cu Kα radiation.

1.109 Any of Crystalline Form 1 et seq. comprising the representative peaks of the XRPD pattern shown in FIG. 12b, wherein the XRPD is obtained using a copper source, e.g., obtained using Cu Kα radiation.

1.110 Any of Crystalline Form 1 et seq. exhibiting an XRPD pattern as shown in FIG. 12b, wherein the XRPD is obtained using a copper source, e.g., obtained using Cu Kα radiation.

1.111 Any of Crystalline Form 1 et seq. exhibiting an XRPD pattern comprising at least three, e.g., at least five, e.g., at least ten, e.g., e.g., at least fifteen, e.g., at least twenty, e.g., at least twenty-five, e.g., at least thirty, e.g., at least thirty-five, e.g., at least forty, e.g., all of the peaks, of the XRPD shown in FIG. 10, 11, 12*a*, 12*b*, 31, 32, 33, 35, 36, 38, 39, 58, or 59, e.g., shown in FIG. 10 or 11 or 12*a* or 12*b* or 31 or 32 or 33 or 35 or 36 or 38 or 39 or 58 or 59, wherein the XRPD is obtained using Cu Kα radiation, e.g., wherein the XRPD is measured using radiation of wavelength 1.54059 Å.

1.112 Any of Crystalline Form 1 et seq. comprising characteristic peak(s) of the XRPD pattern shown in FIG. 10, 11, 12*a*, 12*b*, 31, 32, 33, 35, 36, 38, 39, 58, or 59, e.g., shown in FIG. 10 or 11 or 12*a* or 12*b* or 31 or 32 or 33 or 35 or 36 or 38 or 39 or 58 or 59, wherein the XRPD is obtained using Cu Kα radiation, e.g., wherein the XRPD is measured using radiation of wavelength 1.54059 Å.

1.113 Any of Crystalline Form 1 et seq. comprising representative peak(s) of the XRPD pattern shown in FIG. 10, 11, 12*a*, 12*b*, 31, 32, 33, 35, 36, 38, 39, 58, or 59, e.g., shown in FIG. 10 or 11 or 12*a* or 12*b* or 31 or 32 or 33 or 35 or 36 or 38 or 39 or 58 or 59, wherein the XRPD is obtained using Cu Kα radiation, e.g., wherein the XRPD is measured using radiation of wavelength 1.54059 Å.

1.114 Any of Crystalline Form 1 et seq. exhibiting an XRPD pattern substantially as shown in FIG. 10, 11, 12*a*, 12*b*, 31, 32, 33, 35, 36, 38, 39, 58, or 59, e.g., substantially as shown in FIG. 10 or 11 or 12*a* or 12*b* or 31 or 32 or 33 or 35 or 36 or 38 or 39 or 58 or 59, e.g., substantially as shown in any XRPD for Crystalline Form A pictured herein, wherein the XRPD is obtained using Cu Kα radiation, e.g., wherein the XRPD is measured using radiation of wavelength 1.54059 Å.

1.115 Any of Crystalline Form 1 et seq. exhibiting a thermogravimetric analysis (TGA) thermogram comprising weight loss between 90° C. and 165° C., e.g., a weight loss of 6-9 weight %, e.g., a weight loss of 7-9 weight %, e.g., a weight loss of 7-8 weight %, e.g., a weight loss of 7.8 weight %.

1.116 Any of Crystalline Form 1 et seq. exhibiting a thermogravimetric analysis (TGA) thermogram as shown in FIG. 25.

1.117 Any of Crystalline Form 1 et seq. exhibiting a differential scanning calorimetry (DSC) thermogram comprising an endotherm at 113° C.

1.118 Any of Crystalline Form 1 et seq. exhibiting a differential scanning calorimetry (DSC) thermogram comprising an endotherm at 123° C.

1.119 Any of Crystalline Form 1 et seq. exhibiting a differential scanning calorimetry (DSC) thermogram comprising an endotherm at 131° C.

1.120 Any of Crystalline Form 1 et seq. exhibiting a differential scanning calorimetry (DSC) thermogram comprising an endotherm at 176° C., e.g., an endotherm at 176° C. with an onset at 170° C.

1.121 Any of Crystalline Form 1 et seq. exhibiting a differential scanning calorimetry (DSC) thermogram as shown in FIG. 25.

1.122 Any of Crystalline Form 1 et seq. exhibiting a dynamic (water) vapor sorption (DVS) isotherm comprising 7% or less weight gain upon increasing the relative humidity (RH) from 5% to 95%, e.g., 6.5% or less weight gain, e.g., 6-7% weight gain, e.g., 2% or less weight gain between 5%-75% relative humidity and 5% or less weight gain between 75%-95% relative humidity, e.g., 1-2% weight gain between 5%-75% relative humidity and 4-5% weight gain between 75%-95% relative humidity.

1.123 Any of Crystalline Form 1 et seq. exhibiting a dynamic (water) vapor sorption (DVS) isotherm as shown in FIG. 34.

1.124 Any of Crystalline Form 1 et seq. wherein the preparation of the crystal comprises acidifying, e.g., to a pH less than 2, e.g., to pH 1, e.g., with HCl, e.g., to pH 1 with HCl, an aqueous solution comprising one or more of 2-{[3,5-bis(trifluoromethyl)phenyl]carbamoyl}-4-chlorophenyl dihydrogen phosphate, 2 {[3,5-bis(trifluoromethyl)phenyl]carbamoyl}-4-chlorophenyl hydrogen phosphate monoanion, and 2-{[3,5-bis(trifluoromethyl)phenyl]carbamoyl}-4-chlorophenyl phosphate dianion.

1.125 Crystalline Form 1.124 further comprising extracting 2-{[3,5-bis(trifluoromethyl)phenyl]carbamoyl}-4-chlorophenyl dihydrogen phosphate with an organic solvent, e.g., ethyl acetate, to generate an aqueous fraction and an organic fraction.

1.126 Crystalline Form 1.125 further comprising separating the organic fraction.

1.127 Crystalline Form 1.126 further comprising drying the organic fraction, e.g., with sodium sulphate.

1.128 Crystalline Form 1.127 further comprising evaporating the organic solvent.

1.129 Any of Crystalline Form 1.124-1.128 further comprising isolating the crystal.

1.130 Any of Crystalline Form 1.124-1.128 further comprising concentrating the organic solvent under reduced pressure to provide an oil.

1.131 Crystalline Form 1.130 further comprising dissolving the oil in an organic solvent (e.g., ethyl acetate) optionally with stirring.

1.132 Crystalline Form 1.131 further comprising adding an anti-solvent, e.g., an organic anti-solvent (e.g., n-heptane), optionally with stirring, e.g., adding an excess of anti-solvent, e.g., 2.5:1 or greater of the anti-solvent to the organic solvent, 5:1 or greater of the anti-solvent to the organic solvent, e.g., 12:1 or greater of the anti-solvent to the organic solvent, e.g., 2.5:1 to 12:1 of the anti-solvent to the organic solvent.

1.133 Crystalline Form 1.132 further comprising isolating a solid, e.g., by filtering.

1.134 Crystalline Form 1.133 further comprising washing the solid with an anti-solvent, e.g., an organic anti-solvent (e.g., n-heptane).

1.135 Crystalline Form 1.134 further comprising drying the solid under vacuum.

1.136 Any of Crystalline Form 1.124-1.135 further comprising isolating the crystal.

1.137 Any of Crystalline Form 1 et seq. wherein the preparation of the crystal comprises dissolving 2-{[3,5-bis(trifluoromethyl)phenyl]carbamoyl}-4-chlorophenyl dihydrogen phosphate in an organic solvent (e.g., ethyl acetate or a mixture comprising ethyl acetate), e.g., optionally at room temperature and/or optionally with stirring.

1.138 Crystalline Form 1.137 further comprising adding an anti-solvent, e.g., an organic anti-solvent (e.g., n-heptane) optionally with stirring, e.g., adding an excess of anti-solvent, e.g., 2.5:1 or greater of the anti-solvent to the organic solvent, 5:1 or greater of the anti-solvent to the organic solvent, e.g., 12:1 or greater of the anti-solvent to the organic solvent, e.g., 2.5:1 to 12:1 of the anti-solvent to the organic solvent.

1.139 Crystalline Form 1.138 further comprising isolating a solid, e.g., by filtering.
1.140 Crystalline Form 1.139 further comprising washing the solid with an anti-solvent, e.g., an organic anti-solvent (e.g., n-heptane).
1.141 Crystalline Form 1.140 further comprising drying the solid under vacuum.
1.142 Any of Crystalline Form 1.124-1.141 further comprising isolating the crystal.
1.143 Any of Crystalline Form 1 et seq. wherein the crystal is made by any of Process 1 et seq., vide infra.
1.144 Any of Crystalline Form 1 et seq. wherein the crystal is made as described in any of the examples that produce Form A.
1.145 Any of Crystalline Form 1 et seq. wherein the 2-theta (°) values of the XRPD pattern have an acceptable deviation of ±0.2°.

Further provided is a crystalline hemi-sodium salt of

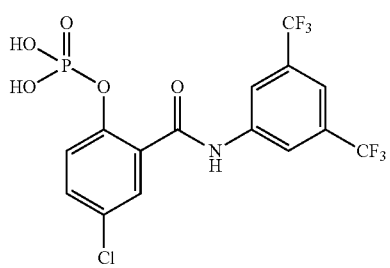

Formula I (Crystalline Form 2a).

Further provided is an acetonitrile solvate of

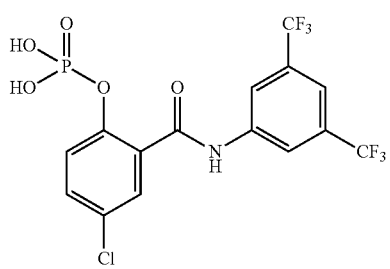

Formula I (Crystalline Form 2b).

Further provided are Crystalline Form 2a and Crystalline Form 2b as follows:

2.1 Any of Crystalline Form 2a or Crystalline Form 2b wherein the crystalline form is a hemi-sodium hemi-acetonitrile solvate, e.g., wherein the asymmetric unit contains four molecules of Formula I (two neutral molecules of Formula I and two mono-deprotonated molecules of Formula I), two sodium cations, and two acetonitrile molecules. Na replaces one proton on the PO₄ group of half the molecules.
2.2 Any of Crystalline Form 2a, 2b, or 2.1 wherein the molar ratio of acetonitrile to Formula I is 0.5:1.
2.3 Any of Crystalline Form 2a, 2b, et seq. wherein the molar ratio of sodium to Formula I is 0.5:1.
2.4 Any of Crystalline Form 2a, 2b, et seq. wherein the molar ratio of acetonitrile to sodium to Formula I is 0.5:0.5:1.
2.5 Any of Crystalline Form 2a, 2b, et seq. wherein the crystalline form crystallizes in the monoclinic crystal system, belongs to the P2₁ space group, and has the following unit cell parameters: a=9.0319(2) Å, b=15.4685(4) Å, c=27.7447(5) Å, β=96.9157(15°), α=γ=90°.
2.6 Crystalline Form 2.5 wherein the crystalline form has a calculated volume of V=3848.01(15) Å³.
2.7 Crystalline Form 2.5 or 2.6 wherein the crystal structure is obtained with a crystal having approximate dimensions of 0.25×0.10×0.09 mm³, e.g., a colorless rod having approximate dimensions of 0.25×0.10×0.09 mm³.
2.8 Any of Crystalline Form 2.5-2.7 wherein the crystal structure is obtained with Cu Kα radiation, e.g., Cu Kα radiation having λ=1.54178 Å.
2.9 Any of Crystalline Form 2.5-2.8 wherein the crystal structure is obtained at 100 K, e.g., 100(2) K.
2.10 Any of Crystalline Form 2a, 2b, et seq. having a calculated XRPD as shown in FIG. 20.
2.11 Any of Crystalline Form 2a, 2b, et seq. wherein the crystal is made as described in Example 5.
2.12 Any of Crystalline Form 2 et seq. wherein the crystal is made by any of Process 1 et seq., vide infra.
2.13 Any of Crystalline Form 2 et seq. wherein the 2-theta (°) values of the XRPD pattern have an acceptable deviation of ±0.2°.

Further provided is a p-dioxane solvate of

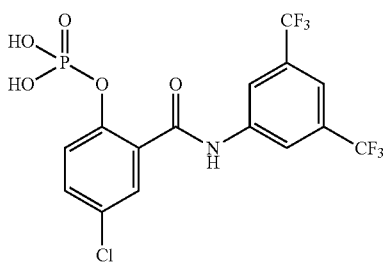

Formula I (Crystalline Form 3, also referred to herein as Form I).
Further provided is Crystalline Form 3 as follows:

3.1 Crystalline Form 3 wherein the crystalline form is a hemi-p-dioxane solvate, i.e., wherein the molar ratio of p-dioxane to Formula I is 0.5:1.
3.2 Crystalline Form 3 or 3.1 exhibiting an XRPD pattern comprising at least three, e.g., at least five, 2-theta (°) values selected from the group consisting of 6.4, 8.5, 16.3, 17.1, 19.3, 20.1, 21.6, and 23.7, wherein the XRPD is measured using an incident beam of Cu Kα radiation, e.g., wherein the XRPD is measured using radiation of wavelength 1.54059 Å.
3.3 Any of Crystalline Form 3 et seq. exhibiting an XRPD pattern comprising 2-theta (°) values of 6.4, 8.5, 16.3, 17.1, 19.3, 20.1, 21.6, and 23.7, wherein the XRPD is measured using an incident beam of Cu Kα radiation, e.g., wherein the XRPD is measured using radiation of wavelength 1.54059 Å.
3.4 Any of Crystalline Form 3 et seq. exhibiting an XRPD pattern comprising at least three, e.g., at least five, 2-theta (°) values selected from the group consisting of 6.37, 8.49, 16.33, 17.06, 19.28, 20.14, 21.61, and 23.65, wherein the XRPD is measured using an incident beam of Cu Kα radiation, e.g., wherein the XRPD is measured using radiation of wavelength 1.54059 Å.

3.5 Any of Crystalline Form 3 et seq. exhibiting an XRPD pattern comprising 2-theta (°) values of 6.37, 8.49, 16.33, 17.06, 19.28, 20.14, 21.61, and 23.65, wherein the XRPD is measured using an incident beam of Cu Kα radiation, e.g., wherein the XRPD is measured using radiation of wavelength 1.54059 Å.

3.6 Any of Crystalline Form 3 et seq. exhibiting an XRPD pattern comprising at least three, e.g., at least five, 2-theta (°) values selected from those set forth in Table E below:

TABLE E

| °2θ | d space (Å) | Intensity (%) |
|---|---|---|
| 6.37 ± 0.20 | 13.870 ± 0.435 | 58 |
| 8.49 ± 0.20 | 10.402 ± 0.244 | 20 |
| 16.33 ± 0.20 | 5.422 ± 0.066 | 18 |
| 17.06 ± 0.20 | 5.194 ± 0.060 | 33 |
| 19.28 ± 0.20 | 4.600 ± 0.047 | 49 |
| 20.14 ± 0.20 | 4.405 ± 0.043 | 30 |
| 21.61 ± 0.20 | 4.108 ± 0.038 | 26 |
| 23.65 ± 0.20 | 3.758 ± 0.031 | 100 | wherein the XRPD is measured using an incident beam of Cu Kα radiation, e.g., wherein the XRPD is measured using radiation of wavelength 1.54059 Å.

3.7 Any of Crystalline Form 3 et seq. exhibiting an XRPD pattern having the 2-theta (°) values set forth in Table E of Crystalline Form 3.6, wherein the XRPD is measured using an incident beam of Cu Kα radiation, e.g., wherein the XRPD is measured using radiation of wavelength 1.54059 Å.

3.8 Any of Crystalline Form 3 et seq. exhibiting an XRPD pattern comprising at least three, e.g., at least five, e.g., at least eight, e.g., at least ten, e.g., at least fifteen, e.g., at least twenty, e.g., at least twenty-five, e.g., at least thirty, 2-theta (°) values selected from the group consisting of 6.4, 8.5, 10.7, 12.2, 12.8, 13.6, 14.1, 16.1, 16.3, 17.1, 17.6, 19.3, 19.7, 20.1, 21.0, 21.6, 21.9, 22.2, 22.5, 22.7, 23.7, 24.1, 24.6, 25.2, 25.4, 26.5, 27.5, 28.0, 28.4, 29.0, 29.2, 29.4, 29.9, and 30.2, wherein the XRPD is measured using an incident beam of Cu Kα radiation, e.g., wherein the XRPD is measured using radiation of wavelength 1.54059 Å.

3.9 Any of Crystalline Form 3 et seq. exhibiting an XRPD pattern having the following 2-theta (°) values:
6.4, 8.5, 10.7, 12.2, 12.8, 13.6, 14.1, 16.1, 16.3, 17.1, 17.6, 19.3, 19.7, 20.1, 21.0, 21.6, 21.9, 22.2, 22.5, 22.7, 23.7, 24.1, 24.6, 25.2, 25.4, 26.5, 27.5, 28.0, 28.4, 29.0, 29.2, 29.4, 29.9, and 30.2,
wherein the XRPD is measured using an incident beam of Cu Kα radiation, e.g., wherein the XRPD is measured using radiation of wavelength 1.54059 Å.

3.10 Any of Crystalline Form 3 et seq. exhibiting an XRPD pattern comprising at least three, e.g., at least five, e.g., at least eight, e.g., at least ten, e.g., at least fifteen, e.g., at least twenty, e.g., at least twenty-five, e.g., at least thirty, 2-theta (°) values selected from the group consisting of 6.37, 8.49, 10.70, 12.22, 12.77, 13.63, 14.07, 16.10, 16.33, 17.06, 17.58, 19.28, 19.73, 20.14, 21.04, 21.61, 21.92, 22.19, 22.47, 22.72, 23.65, 24.13, 24.61, 25.15, 25.40, 26.53, 27.47, 28.04, 28.35, 28.95, 29.17, 29.44, 29.88, and 30.19, wherein the XRPD is measured using an incident beam of Cu Kα radiation, e.g., wherein the XRPD is measured using radiation of wavelength 1.54059 Å.

3.11 Any of Crystalline Form 3 et seq. exhibiting an XRPD pattern having the following 2-theta (°) values:
6.37, 8.49, 10.70, 12.22, 12.77, 13.63, 14.07, 16.10, 16.33, 17.06, 17.58, 19.28, 19.73, 20.14, 21.04, 21.61, 21.92, 22.19, 22.47, 22.72, 23.65, 24.13, 24.61, 25.15, 25.40, 26.53, 27.47, 28.04, 28.35, 28.95, 29.17, 29.44, 29.88, and 30.19,
wherein the XRPD is measured using an incident beam of Cu Kα radiation, e.g., wherein the XRPD is measured using radiation of wavelength 1.54059 Å.

3.12 Any of Crystalline Form 3 et seq. exhibiting an XRPD pattern comprising at least three, e.g., at least five, e.g., at least eight, e.g., at least ten, e.g., at least fifteen, e.g., at least twenty, e.g., at least twenty-five, e.g., at least thirty, 2-theta (°) values selected from those set forth in Table F below:

TABLE F

| °2θ | d space (Å) | Intensity (%) |
|---|---|---|
| 6.37 ± 0.20 | 13.870 ± 0.435 | 58 |
| 8.49 ± 0.20 | 10.402 ± 0.244 | 20 |
| 10.70 ± 0.20 | 8.263 ± 0.154 | 8 |
| 12.22 ± 0.20 | 7.235 ± 0.118 | 10 |
| 12.77 ± 0.20 | 6.928 ± 0.108 | 9 |
| 13.63 ± 0.20 | 6.489 ± 0.095 | 6 |
| 14.07 ± 0.20 | 6.290 ± 0.089 | 13 |
| 16.10 ± 0.20 | 5.502 ± 0.068 | 7 |
| 16.33 ± 0.20 | 5.422 ± 0.066 | 18 |
| 17.06 ± 0.20 | 5.194 ± 0.060 | 33 |
| 17.58 ± 0.20 | 5.041 ± 0.057 | 7 |
| 19.28 ± 0.20 | 4.600 ± 0.047 | 49 |
| 19.73 ± 0.20 | 4.497 ± 0.045 | 10 |
| 20.14 ± 0.20 | 4.405 ± 0.043 | 30 |
| 21.04 ± 0.20 | 4.219 ± 0.040 | 17 |
| 21.61 ± 0.20 | 4.108 ± 0.038 | 26 |
| 21.92 ± 0.20 | 4.051 ± 0.036 | 13 |
| 22.19 ± 0.20 | 4.003 ± 0.036 | 21 |
| 22.47 ± 0.20 | 3.954 ± 0.035 | 15 |
| 22.72 ± 0.20 | 3.910 ± 0.034 | 25 |
| 23.65 ± 0.20 | 3.758 ± 0.031 | 100 |
| 24.13 ± 0.20 | 3.685 ± 0.030 | 16 |
| 24.61 ± 0.20 | 3.614 ± 0.029 | 21 |
| 25.15 ± 0.20 | 3.539 ± 0.028 | 18 |
| 25.40 ± 0.20 | 3.504 ± 0.027 | 13 |
| 26.53 ± 0.20 | 3.357 ± 0.025 | 11 |
| 27.47 ± 0.20 | 3.244 ± 0.023 | 6 |
| 28.04 ± 0.20 | 3.180 ± 0.022 | 5 |
| 28.35 ± 0.20 | 3.145 ± 0.022 | 5 |
| 28.95 ± 0.20 | 3.082 ± 0.021 | 9 |
| 29.17 ± 0.20 | 3.059 ± 0.021 | 8 |
| 29.44 ± 0.20 | 3.031 ± 0.020 | 6 |
| 29.88 ± 0.20 | 2.988 ± 0.020 | 7 |
| 30.19 ± 0.20 | 2.958 ± 0.019 | 8 | wherein the XRPD is measured using an incident beam of Cu Kα radiation, e.g., wherein the XRPD is measured using radiation of wavelength 1.54059 Å.

3.13 Any of Crystalline Form 3 et seq. exhibiting an XRPD pattern having the 2-theta (°) values set forth in Table F of Crystalline Form 3.12, wherein the XRPD is measured using an incident beam of Cu Kα radiation, e.g., wherein the XRPD is measured using radiation of wavelength 1.54059 Å.

3.14 Any of Crystalline Form 3 et seq. exhibiting an XRPD pattern comprising at least three, e.g., at least five, d-spacing (Å) values selected from the group consisting of 13.9, 10.4, 5.4, 5.2, 4.6, 4.4, 4.1, and 3.8.

3.15 Any of Crystalline Form 3 et seq. exhibiting an XRPD pattern comprising the d-spacing (Å) values below:
13.9, 10.4, 5.4, 5.2, 4.6, 4.4, 4.1, and 3.8.

3.16 Any of Crystalline Form 3 et seq. exhibiting an XRPD pattern comprising at least three, e.g., at least five, d-spacing (Å) values selected from the group consisting of 13.87, 10.40, 5.42, 5.19, 4.60, 4.41, 4.11, and 3.76.

3.17 Any of Crystalline Form 3 et seq. wherein the crystal exhibits an XRPD pattern comprising the d-spacing (Å) values below:
13.87, 10.40, 5.42, 5.19, 4.60, 4.41, 4.11, and 3.76.

3.18 Any of Crystalline Form 3 et seq. exhibiting an XRPD pattern comprising at least three, e.g., at least five, d-spacing (Å) values selected from the group consisting of 13.870, 10.402, 5.422, 5.194, 4.600, 4.405, 4.108, and 3.758.

3.19 Any of Crystalline Form 3 et seq. exhibiting an XRPD pattern comprising the d-spacing (Å) values below:
13.870, 10.402, 5.422, 5.194, 4.600, 4.405, 4.108, and 3.758.

3.20 Any of Crystalline Form 3 et seq. exhibiting an XRPD pattern comprising at least three, e.g., at least five, d-spacing (Å) values selected from those set forth in Table E of Crystalline Form 3.6.

3.21 Any of Crystalline Form 3 et seq. exhibiting an XRPD pattern comprising the d-spacing (Å) values set forth in Table E of Crystalline Form 3.6.

3.22 Any of Crystalline Form 3 et seq. exhibiting an XRPD pattern comprising at least three, e.g., at least five, e.g., at least eight, e.g., at least ten, e.g., at least fifteen, e.g., at least twenty, e.g., at least twenty-five, d-spacing (Å) values selected from the group consisting of 13.9, 10.4, 8.3, 7.2, 6.9, 6.5, 6.3, 5.5, 5.4, 5.2, 5.0, 4.6, 4.5, 4.4, 4.2, 4.1, 4.0, 3.9, 3.8, 3.7, 3.6, 3.5, 3.4, 3.2, 3.1, and 3.0.

3.23 Any of Crystalline Form 3 et seq. exhibiting an XRPD pattern having the d-spacing (Å) values below:
13.9, 10.4, 8.3, 7.2, 6.9, 6.5, 6.3, 5.5, 5.4, 5.2, 5.0, 4.6, 4.5, 4.4, 4.2, 4.1, 4.0, 3.9, 3.8, 3.7, 3.6, 3.5, 3.4, 3.2, 3.1, and 3.0.

3.24 Any of Crystalline Form 3 et seq. exhibiting an XRPD pattern comprising at least three, e.g., at least five, e.g., at least eight, e.g., at least ten, e.g., at least fifteen, e.g., at least twenty, e.g., at least twenty-five, e.g., at least thirty, d-spacing (Å) values selected from the group consisting of 13.87, 10.40, 8.26, 7.24, 6.93, 6.49, 6.29, 5.50, 5.42, 5.19, 5.04, 4.60, 4.50, 4.41, 4.22, 4.11, 4.05, 4.00, 3.95, 3.91, 3.76, 3.69, 3.61, 3.54, 3.50, 3.36, 3.24, 3.18, 3.15, 3.08, 3.06, 3.03, 2.99, and 2.96.

3.25 Any of Crystalline Form 3 et seq. exhibiting an XRPD pattern having the d-spacing (Å) values below:
13.87, 10.40, 8.26, 7.24, 6.93, 6.49, 6.29, 5.50, 5.42, 5.19, 5.04, 4.60, 4.50, 4.41, 4.22, 4.11, 4.05, 4.00, 3.95, 3.91, 3.76, 3.69, 3.61, 3.54, 3.50, 3.36, 3.24, 3.18, 3.15, 3.08, 3.06, 3.03, 2.99, and 2.96.

3.26 Any of Crystalline Form 3 et seq. exhibiting an XRPD pattern comprising at least three, e.g., at least five, e.g., at least eight, e.g., at least ten, e.g., at least fifteen, e.g., at least twenty, e.g., at least twenty-five, e.g., at least thirty, d-spacing (Å) values selected from the group consisting of 13.870, 10.402, 8.263, 7.235, 6.928, 6.489, 6.290, 5.502, 5.422, 5.194, 5.041, 4.600, 4.497, 4.405, 4.219, 4.108, 4.051, 4.003, 3.954, 3.910, 3.758, 3.685, 3.614, 3.539, 3.504, 3.357, 3.244, 3.180, 3.145, 3.082, 3.059, 3.031, 2.988, and 2.958.

3.27 Any of Crystalline Form 3 et seq. exhibiting an XRPD pattern having the d-spacing (Å) values below:
13.870, 10.402, 8.263, 7.235, 6.928, 6.489, 6.290, 5.502, 5.422, 5.194, 5.041, 4.600, 4.497, 4.405, 4.219, 4.108, 4.051, 4.003, 3.954, 3.910, 3.758, 3.685, 3.614, 3.539, 3.504, 3.357, 3.244, 3.180, 3.145, 3.082, 3.059, 3.031, 2.988, and 2.958.

3.28 Any of Crystalline Form 3 et seq. exhibiting an XRPD pattern comprising at least three, e.g., at least five, e.g., at least eight, e.g., at least ten, e.g., at least fifteen, e.g., at least twenty, e.g., at least twenty-five, e.g., at least thirty, d-spacing (Å) values selected from the group consisting of those set forth in Table F of Crystalline Form 3.12.

3.29 Any of Crystalline Form 3 et seq. exhibiting an XRPD pattern having the d-spacing (Å) values set forth in Table F of Crystalline Form 3.12.

3.30 Any of Crystalline Form 3 et seq. exhibiting an XRPD pattern comprising at least three, e.g., at least five, e.g., at least eight, e.g., at least ten, e.g., at least fifteen, e.g., at least twenty, e.g., at least twenty-five, e.g., at least thirty, e.g., all of the peaks, of the XRPD shown in FIG. 22, wherein the XRPD is obtained using Cu Kα radiation, e.g., wherein the XRPD is measured using radiation of wavelength 1.54059 Å.

3.31 Any of Crystalline Form 3 et seq. comprising the characteristic peaks of the XRPD pattern shown in FIG. 22, wherein the XRPD is obtained using Cu Kα radiation, e.g., wherein the XRPD is measured using radiation of wavelength 1.54059 Å.

3.32 Any of Crystalline Form 3 et seq. comprising the representative peaks of the XRPD pattern shown in FIG. 22, wherein the XRPD is obtained using Cu Kα radiation, e.g., wherein the XRPD is measured using radiation of wavelength 1.54059 Å.

3.33 Any of Crystalline Form 3 et seq. exhibiting an XRPD pattern as shown in FIG. 22, wherein the XRPD is obtained using Cu Kα radiation, e.g., wherein the XRPD is measured using radiation of wavelength 1.54059 Å.

3.34 Any of Crystalline Form 3 et seq. wherein the preparation of the crystal comprises dissolving Formula I in a solvent comprising p-dioxane, optionally with sonication.

3.35 Crystalline Form 3.34 further comprising isolating a solid, e.g., by filtering.

3.36 Crystalline Form 3.35 further comprising drying the solid under vacuum.

3.37 Any of Crystalline Form 3.34-3.36 further comprising isolating the crystal.

3.38 Any of Crystalline Form 3 et seq. wherein the crystal is made as described in Example 6.

3.39 Any of Crystalline Form 3 et seq. wherein the 2-theta (°) values of the XRPD pattern have an acceptable deviation of ±0.2°.

3.40 Any of Crystalline Form 3 et seq. wherein the crystal is made by any of Process 1 et seq., vide infra.

Further provided is a methanol solvate of

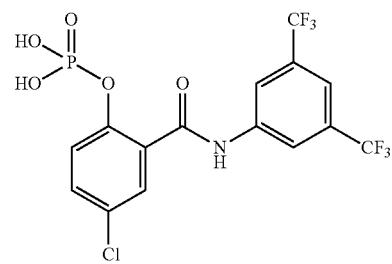

(Crystalline Form 4, also referred to herein as Form L). Further provided is Crystalline Form 4 as follows:

4.1 Crystalline Form 4 wherein the molar ratio of methanol to Formula I is 0.6 moles methanol maximum (i.e., up to 0.6 moles methanol) to 1 mole Formula I.

4.2 Crystalline Form 4 or 4.1 wherein the crystalline form is a hemi-methanol solvate, i.e., wherein the molar ratio of methanol to Formula I is 0.5:1.

4.3 Any of Crystalline Form 4 et seq. exhibiting an XRPD pattern comprising 2-theta (°) values of 19.0, 20.3, 21.8, 22.0, and 26.0, wherein the XRPD is measured using an incident beam of Cu Kα radiation, e.g., wherein the XRPD is measured using radiation of wavelength 1.54059 Å.

4.4 Any of Crystalline Form 4 et seq. exhibiting an XRPD pattern comprising 2-theta (°) values of 18.98, 20.27, 21.75, 21.97, and 25.96, wherein the XRPD is measured using an incident beam of Cu Kα radiation, e.g., wherein the XRPD is measured using radiation of wavelength 1.54059 Å.

4.5 Any of Crystalline Form 4 et seq. exhibiting an XRPD pattern having the 2-theta (°) values set forth in Table G below:

TABLE G

| °2θ | d space (Å) | Intensity (%) |
|---|---|---|
| 18.98 ± 0.20 | 4.671 ± 0.049 | 32 |
| 20.27 ± 0.20 | 4.377 ± 0.043 | 48 |
| 21.75 ± 0.20 | 4.083 ± 0.037 | 35 |
| 21.97 ± 0.20 | 4.042 ± 0.036 | 38 |
| 25.96 ± 0.20 | 3.429 ± 0.026 | 100 | wherein the XRPD is measured using an incident beam of Cu Kα radiation, e.g., wherein the XRPD is measured using radiation of wavelength 1.54059 Å.

4.6 Any of Crystalline Form 4 et seq. exhibiting an XRPD pattern comprising at least three, e.g., at least five, e.g., at least ten, e.g., at least fifteen, e.g., at least twenty, e.g., at least twenty-five, e.g., at least thirty, 2-theta (°) values selected from the group consisting of 6.3, 8.8, 9.5, 11.3, 12.6, 14.2, 14.4, 16.4, 17.6, 18.2, 19.0, 20.3, 20.8, 21.8, 22.0, 22.2, 22.7, 23.1, 23.7, 24.0, 24.8, 25.0, 25.2, 26.0, 26.6, 27.0, 27.2, 27.8, 28.6, 29.0, 29.3, 29.7, and 29.9, wherein the XRPD is measured using an incident beam of Cu Kα radiation, e.g., wherein the XRPD is measured using radiation of wavelength 1.54059 Å.

4.7 Any of Crystalline Form 4 et seq. exhibiting an XRPD pattern having the following 2-theta (°) values:
6.3, 8.8, 9.5, 11.3, 12.6, 14.2, 14.4, 16.4, 17.6, 18.2, 19.0, 20.3, 20.8, 21.8, 22.0, 22.2, 22.7, 23.1, 23.7, 24.0, 24.8, 25.0, 25.2, 26.0, 26.6, 27.0, 27.2, 27.8, 28.6, 29.0, 29.3, 29.7, and 29.9,
wherein the XRPD is measured using an incident beam of Cu Kα radiation, e.g., wherein the XRPD is measured using radiation of wavelength 1.54059 Å.

4.8 Any of Crystalline Form 4 et seq. exhibiting an XRPD pattern comprising at least three, e.g., at least five, e.g., at least ten, e.g., at least fifteen, e.g., at least twenty, e.g., at least twenty-five, e.g., at least thirty, 2-theta (°) values selected from the group consisting of 6.29, 8.76, 9.45, 11.26, 12.60, 14.15, 14.44, 16.38, 17.57, 18.17, 18.98, 20.27, 20.75, 21.75, 21.97, 22.21, 22.67, 23.08, 23.73, 23.95, 24.81, 24.95, 25.16, 25.96, 26.55, 26.97, 27.19, 27.76, 28.64, 29.00, 29.32, 29.73, and 29.91, wherein the XRPD is measured using an incident beam of Cu Kα radiation, e.g., wherein the XRPD is measured using radiation of wavelength 1.54059 Å.

4.9 Any of Crystalline Form 4 et seq. exhibiting an XRPD pattern having the following 2-theta (°) values:
6.29, 8.76, 9.45, 11.26, 12.60, 14.15, 14.44, 16.38, 17.57, 18.17, 18.98, 20.27, 20.75, 21.75, 21.97, 22.21, 22.67, 23.08, 23.73, 23.95, 24.81, 24.95, 25.16, 25.96, 26.55, 26.97, 27.19, 27.76, 28.64, 29.00, 29.32, 29.73, and 29.91,
wherein the XRPD is measured using an incident beam of Cu Kα radiation, e.g., wherein the XRPD is measured using radiation of wavelength 1.54059 Å.

4.10 Any of Crystalline Form 4 et seq. exhibiting an XRPD pattern comprising at least three, e.g., at least five, e.g., at least ten, e.g., at least fifteen, e.g., at least twenty, e.g., at least twenty-five, e.g., at least thirty, 2-theta (°) values selected from those set forth in Table H below:

TABLE H

| °2θ | d space (Å) | Intensity (%) |
|---|---|---|
| 6.29 ± 0.20 | 14.039 ± 0.446 | 14 |
| 8.76 ± 0.20 | 10.081 ± 0.230 | 12 |
| 9.45 ± 0.20 | 9.347 ± 0.197 | 9 |
| 11.26 ± 0.20 | 7.848 ± 0.139 | 11 |
| 12.60 ± 0.20 | 7.019 ± 0.111 | 16 |
| 14.15 ± 0.20 | 6.256 ± 0.088 | 9 |
| 14.44 ± 0.20 | 6.131 ± 0.084 | 11 |
| 16.38 ± 0.20 | 5.409 ± 0.066 | 7 |
| 17.57 ± 0.20 | 5.042 ± 0.057 | 6 |
| 18.17 ± 0.20 | 4.877 ± 0.053 | 6 |
| 18.98 ± 0.20 | 4.671 ± 0.049 | 32 |
| 20.27 ± 0.20 | 4.377 ± 0.043 | 48 |
| 20.75 ± 0.20 | 4.276 ± 0.041 | 13 |
| 21.75 ± 0.20 | 4.083 ± 0.037 | 35 |
| 21.97 ± 0.20 | 4.042 ± 0.036 | 38 |
| 22.21 ± 0.20 | 3.998 ± 0.036 | 5 |
| 22.67 ± 0.20 | 3.920 ± 0.034 | 7 |
| 23.08 ± 0.20 | 3.851 ± 0.033 | 17 |
| 23.73 ± 0.20 | 3.747 ± 0.031 | 11 |
| 23.95 ± 0.20 | 3.713 ± 0.031 | 9 |
| 24.81 ± 0.20 | 3.586 ± 0.028 | 16 |
| 24.95 ± 0.20 | 3.566 ± 0.028 | 17 |
| 25.16 ± 0.20 | 3.537 ± 0.028 | 6 |
| 25.96 ± 0.20 | 3.429 ± 0.026 | 100 |
| 26.55 ± 0.20 | 3.355 ± 0.025 | 9 |
| 26.97 ± 0.20 | 3.303 ± 0.024 | 6 |
| 27.19 ± 0.20 | 3.277 ± 0.024 | 4 |
| 27.76 ± 0.20 | 3.211 ± 0.023 | 7 |
| 28.64 ± 0.20 | 3.114 ± 0.021 | 7 |
| 29.00 ± 0.20 | 3.076 ± 0.021 | 4 |
| 29.32 ± 0.20 | 3.043 ± 0.020 | 7 |
| 29.73 ± 0.20 | 3.002 ± 0.020 | 4 |
| 29.91 ± 0.20 | 2.985 ± 0.020 | 10 | wherein the XRPD is measured using an incident beam of Cu Kα radiation, e.g., wherein the XRPD is measured using radiation of wavelength 1.54059 Å.

4.11 Any of Crystalline Form 4 et seq. exhibiting an XRPD pattern having the 2-theta (°) values set forth in Table H of Crystalline Form 4.10, wherein the XRPD is measured using an incident beam of Cu Kα radiation, e.g., wherein the XRPD is measured using radiation of wavelength 1.54059 Å.

4.12 Any of Crystalline Form 4 et seq. exhibiting an XRPD pattern comprising the d-spacing (Å) values below:
4.7, 4.4, 4.1, 4.0, and 3.4.

4.13 Any of Crystalline Form 4 et seq. wherein the crystal exhibits an XRPD pattern comprising the d-spacing (Å) values below:

4.67, 4.38, 4.08, 4.04, and 3.43.

4.14 Any of Crystalline Form 4 et seq. exhibiting an XRPD pattern comprising the d-spacing (Å) values below:
4.671, 4.377, 4.083, 4.042, and 3.429.

4.15 Any of Crystalline Form 4 et seq. exhibiting an XRPD pattern comprising the d-spacing (Å) values set forth in Table G of Crystalline Form 4.5.

4.16 Any of Crystalline Form 4 et seq. exhibiting an XRPD pattern comprising at least three, e.g., at least five, e.g., at least ten, e.g., at least fifteen, e.g., at least twenty, d-spacing (Å) values selected from the group consisting of 14.0, 10.1, 9.3, 7.8, 7.0, 6.3, 6.1, 5.4, 5.0, 4.9, 4.7, 4.4, 4.3, 4.1, 4.0, 3.9, 3.7, 3.6, 3.5, 3.4, 3.3, 3.2, 3.1, and 3.0.

4.17 Any of Crystalline Form 4 et seq. exhibiting an XRPD pattern having the d-spacing (Å) values below:
14.0, 10.1, 9.3, 7.8, 7.0, 6.3, 6.1, 5.4, 5.0, 4.9, 4.7, 4.4, 4.3, 4.1, 4.0, 3.9, 3.7, 3.6, 3.5, 3.4, 3.3, 3.2, 3.1, and 3.0.

4.18 Any of Crystalline Form 4 et seq. exhibiting an XRPD pattern comprising at least three, e.g., at least five, e.g., at least ten, e.g., at least fourteen, e.g., at least twenty, e.g., at least twenty-five, e.g., at least thirty, d-spacing (Å) values selected from the group consisting of 14.04, 10.08, 9.35, 7.85, 7.02, 6.26, 6.13, 5.41, 5.04, 4.88, 4.67, 4.38, 4.28, 4.08, 4.04, 4.00, 3.92, 3.85, 3.75, 3.71, 3.59, 3.57, 3.54, 3.43, 3.36, 3.30, 3.28, 3.21, 3.11, 3.08, 3.04, 3.00, and 2.99.

4.19 Any of Crystalline Form 4 et seq. exhibiting an XRPD pattern having the d-spacing (Å) values below:
14.04, 10.08, 9.35, 7.85, 7.02, 6.26, 6.13, 5.41, 5.04, 4.88, 4.67, 4.38, 4.28, 4.08, 4.04, 4.00, 3.92, 3.85, 3.75, 3.71, 3.59, 3.57, 3.54, 3.43, 3.36, 3.30, 3.28, 3.21, 3.11, 3.08, 3.04, 3.00, and 2.99.

4.20 Any of Crystalline Form 4 et seq. exhibiting an XRPD pattern comprising at least three, e.g., at least five, e.g., at least ten, e.g., at least fifteen, e.g., at least twenty, e.g., at least twenty-five, e.g., at least thirty, d-spacing (Å) values selected from the group consisting of 14.039, 10.081, 9.347, 7.848, 7.019, 6.256, 6.131, 5.409, 5.042, 4.877, 4.671, 4.377, 4.276, 4.083, 4.042, 3.998, 3.920, 3.851, 3.747, 3.713, 3.586, 3.566, 3.537, 3.429, 3.355, 3.303, 3.277, 3.211, 3.114, 3.076, 3.043, 3.002, and 2.985.

4.21 Any of Crystalline Form 4 et seq. exhibiting an XRPD pattern having the d-spacing (Å) values below:
14.039, 10.081, 9.347, 7.848, 7.019, 6.256, 6.131, 5.409, 5.042, 4.877, 4.671, 4.377, 4.276, 4.083, 4.042, 3.998, 3.920, 3.851, 3.747, 3.713, 3.586, 3.566, 3.537, 3.429, 3.355, 3.303, 3.277, 3.211, 3.114, 3.076, 3.043, 3.002, and 2.985.

4.22 Any of Crystalline Form 4 et seq. exhibiting an XRPD pattern comprising at least three, e.g., at least five, e.g., at least ten, e.g., at least fifteen, e.g., at least twenty, e.g., at least twenty-five, e.g., at least thirty, d-spacing (Å) values selected from the group consisting of those set forth in Table H of Crystalline Form 4.10.

4.23 Any of Crystalline Form 4 et seq. exhibiting an XRPD pattern having the d-spacing (Å) values set forth in Table H of Crystalline Form 4.10.

4.24 Any of Crystalline Form 4 et seq. exhibiting an XRPD pattern comprising at least three, e.g., at least five, e.g., at least ten, e.g., at least fifteen, e.g., at least twenty, e.g., at least twenty-five, e.g., at least thirty, e.g., all of the peaks, of the XRPD shown in FIG. 23, wherein the XRPD is obtained using Cu Kα radiation, e.g., wherein the XRPD is measured using radiation of wavelength 1.54059 Å.

4.25 Any of Crystalline Form 4 et seq. comprising the characteristic peaks of the XRPD shown in FIG. 23, wherein the XRPD is obtained using Cu Kα radiation, e.g., wherein the XRPD is measured using radiation of wavelength 1.54059 Å.

4.26 Any of Crystalline Form 4 et seq. comprising the representative peaks of the XRPD shown in FIG. 23, wherein the XRPD is obtained using Cu Kα radiation, e.g., wherein the XRPD is measured using radiation of wavelength 1.54059 Å.

4.27 Any of Crystalline Form 4 et seq. exhibiting an XRPD as shown in FIG. 23, wherein the XRPD is obtained using Cu Kα radiation, e.g., wherein the XRPD is measured using radiation of wavelength 1.54059 Å.

4.28 Any of Crystalline Form 4 et seq. exhibiting a thermogravimetric analysis (TGA) thermogram comprising stepwise weight loss between 90° C. and 150° C., e.g., a weight loss of 3-5 weight %, e.g., a weight loss of 4-5 weight %, e.g., a weight loss of 4.2 weight %.

4.29 Any of Crystalline Form 4 et seq. exhibiting a thermogravimetric analysis (TGA) thermogram as shown in FIG. 29.

4.30 Any of Crystalline Form 4 et seq. wherein the preparation of the crystal comprises dissolving, optionally with heating, Formula I in a solvent comprising methanol, e.g., a mixture comprising methanol and water, e.g., a mixture comprising methanol and water wherein the solvent mixture has lower water activity ($a_w$), e.g., wherein $a_w$ is less than 0.9.

4.31 Crystalline Form 4.30 further comprising slow cooling and optionally allowing the solution to stand at room temperature.

4.32 Crystalline Form 4.30 or 4.31 further comprising keeping the solution in the freezer and optionally warming to room temperature.

4.33 Crystalline Form 4.32 further comprising isolating a solid, e.g., by filtering.

4.34 Crystalline Form 4.33 further comprising drying the solid under vacuum.

4.35 Any of Crystalline Form 4.30-4.34 further comprising isolating the crystal.

4.36 Any of Crystalline Form 4 et seq. wherein the crystal is made as described in Example 7.

4.37 Any of Crystalline Form 4 et seq. wherein the 2-theta (°) values of the XRPD pattern have an acceptable deviation of ±0.2°.

4.38 Any of Crystalline Form 4 et seq. wherein the crystal is made by any of Process 1 et seq., vide infra.

Further provided is a hydrate of

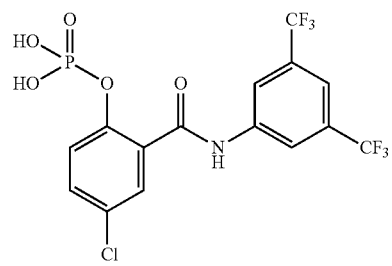 [SMILES: O=C(Nc1cc(C(F)(F)F)cc(C(F)(F)F)c1)c1cc(Cl)ccc1OP(=O)(O)O]

Formula I (Crystalline Form 5, also referred to herein as Form N). Further provided is Crystalline Form 5 as follows:

5.1 Crystalline Form 5 wherein the molar ratio of water to Formula I is 3:1 to 4:1.

5.2 Crystalline Form 5 wherein the molar ratio of water to Formula I is 4.5:1 or less, e.g., 4.2:1 or less, e.g., 4.2:1, e.g., wherein the molar ratio of water to Formula I is 4:1 or less, e.g., 3:1 or less, e.g., 2:1 or less, e.g., 4:1, e.g., 3:1, e.g., 2:1.

5.3 Any of Crystalline Form 5 et seq. wherein the crystalline form is a stoichiometric hydrate.

5.4 Any of Crystalline Form 5 et seq. exhibiting an XRPD pattern comprising at least three, e.g., at least five, 2-theta (°) values selected from the group consisting of 8.8, 9.5, 11.1, 15.2, 15.5, 16.4, 20.2, 20.6, 23.6, 24.0, 24.9, and 27.2, wherein the XRPD is measured using an incident beam of Cu Kα radiation, e.g., wherein the XRPD is measured using radiation of wavelength 1.54059 Å.

5.5 Any of Crystalline Form 5 et seq. exhibiting an XRPD pattern comprising 2-theta (°) values of 8.8, 9.5, 11.1, 15.2, 15.5, 16.4, 20.2, 20.6, 23.6, 24.0, 24.9, and 27.2, wherein the XRPD is measured using an incident beam of Cu Kα radiation, e.g., wherein the XRPD is measured using radiation of wavelength 1.54059 Å.

5.6 Any of Crystalline Form 5 et seq. exhibiting an XRPD pattern comprising at least three, e.g., at least five, 2-theta (°) values selected from the group consisting of 8.82, 9.49, 11.12, 15.23, 15.53, 16.35, 20.20, 20.62, 23.63, 23.95, 24.89, and 27.16, wherein the XRPD is measured using an incident beam of Cu Kα radiation, e.g., wherein the XRPD is measured using radiation of wavelength 1.54059 Å.

5.7 Any of Crystalline Form 5 et seq. exhibiting an XRPD pattern comprising 2-theta (°) values of 8.82, 9.49, 11.12, 15.23, 15.53, 16.35, 20.20, 20.62, 23.63, 23.95, 24.89, and 27.16, wherein the XRPD is measured using an incident beam of Cu Kα radiation, e.g., wherein the XRPD is measured using radiation of wavelength 1.54059 Å.

5.8 Any of Crystalline Form 5 et seq. exhibiting an XRPD pattern comprising at least five 2-theta (°) values selected from those set forth in Table I below:

TABLE I

| °2θ | d space (Å) | Intensity (%) |
|---|---|---|
| 8.82 ± 0.20 | 10.019 ± 0.227 | 25 |
| 9.49 ± 0.20 | 9.311 ± 0.196 | 21 |
| 11.12 ± 0.20 | 7.952 ± 0.143 | 33 |
| 15.23 ± 0.20 | 5.813 ± 0.076 | 100 |
| 15.53 ± 0.20 | 5.700 ± 0.073 | 31 |
| 16.35 ± 0.20 | 5.417 ± 0.066 | 69 |
| 20.20 ± 0.20 | 4.392 ± 0.043 | 43 |
| 20.62 ± 0.20 | 4.305 ± 0.041 | 39 |
| 23.63 ± 0.20 | 3.763 ± 0.031 | 67 |
| 23.95 ± 0.20 | 3.713 ± 0.031 | 38 |
| 24.89 ± 0.20 | 3.574 ± 0.028 | 40 |
| 27.16 ± 0.20 | 3.280 ± 0.024 | 35 | wherein the XRPD is measured using an incident beam of Cu Kα radiation, e.g., wherein the XRPD is measured using radiation of wavelength 1.54059 Å.

5.9 Any of Crystalline Form 5 et seq. exhibiting an XRPD pattern having the 2-theta (°) values set forth in Table I of Crystalline Form 5.8, wherein the XRPD is measured using an incident beam of Cu Kα radiation, e.g., wherein the XRPD is measured using radiation of wavelength 1.54059 Å.

5.10 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, e.g., at least thirty, e.g., at least thirty-five, e.g., at least forty, 2-theta (°) values selected from the group consisting of 4.7, 5.4, 5.6, 8.8, 9.5, 9.9, 10.8, 11.1, 13.1, 14.0, 14.9, 15.2, 15.5, 16.4, 16.5, 17.6, 17.7, 18.8, 19.1, 19.3, 19.5, 19.8, 20.0, 20.2, 20.6, 20.9, 21.2, 21.7, 21.9, 22.4, 22.7, 22.8, 23.2, 23.3, 23.6, 24.0, 24.9, 25.5, 25.8, 26.3, 26.5, 27.0, 27.2, and 27.4, wherein the XRPD is measured using an incident beam of Cu Kα radiation, e.g., wherein the XRPD is measured using radiation of wavelength 1.54059 Å.

5.11 Any of Crystalline Form 5 et seq. exhibiting an XRPD pattern having the following 2-theta (°) values: 4.7, 5.4, 5.6, 8.8, 9.5, 9.9, 10.8, 11.1, 13.1, 14.0, 14.9, 15.2, 15.5, 16.4, 16.5, 17.6, 17.7, 18.8, 19.1, 19.3, 19.5, 19.8, 20.0, 20.2, 20.6, 20.9, 21.2, 21.7, 21.9, 22.4, 22.7, 22.8, 23.2, 23.3, 23.6, 24.0, 24.9, 25.5, 25.8, 26.3, 26.5, 27.0, 27.2, and 27.4,
wherein the XRPD is measured using an incident beam of Cu Kα radiation, e.g., wherein the XRPD is measured using radiation of wavelength 1.54059 Å.

5.12 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, e.g., at least thirty, e.g., at least thirty-five, e.g., at least forty, 2-theta (°) values selected from the group consisting of 4.73, 5.36, 5.55, 8.82, 9.49, 9.85, 10.77, 11.12, 13.05, 13.99, 14.91, 15.23, 15.53, 16.35, 16.53, 17.59, 17.70, 18.78, 19.07, 19.30, 19.47, 19.75, 19.99, 20.20, 20.62, 20.91, 21.16, 21.65, 21.89, 22.39, 22.68, 22.83, 23.17, 23.31, 23.63, 23.95, 24.89, 25.54, 25.83, 26.32, 26.52, 27.00, 27.16, and 27.42, wherein the XRPD is measured using an incident beam of Cu Kα radiation, e.g., wherein the XRPD is measured using radiation of wavelength 1.54059 Å.

5.13 Any of Crystalline Form 5 et seq. exhibiting an XRPD pattern having the following 2-theta (°) values: 4.73, 5.36, 5.55, 8.82, 9.49, 9.85, 10.77, 11.12, 13.05, 13.99, 14.91, 15.23, 15.53, 16.35, 16.53, 17.59, 17.70, 18.78, 19.07, 19.30, 19.47, 19.75, 19.99, 20.20, 20.62, 20.91, 21.16, 21.65, 21.89, 22.39, 22.68, 22.83, 23.17, 23.31, 23.63, 23.95, 24.89, 25.54, 25.83, 26.32, 26.52, 27.00, 27.16, and 27.42, wherein the XRPD is measured using an incident beam of Cu Kα radiation, e.g., wherein the XRPD is measured using radiation of wavelength 1.54059 Å.

5.14 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, e.g., at least thirty, e.g., at least thirty-five, e.g., at least 40, 2-theta (°) values selected from those set forth in Table J below:

TABLE J

| °2θ | d space (Å) | Intensity (%) |
|---|---|---|
| 4.73 ± 0.20 | 18.682 ± 0.790 | 13 |
| 5.36 ± 0.20 | 16.479 ± 0.615 | 10 |
| 5.55 ± 0.20 | 15.916 ± 0.573 | 10 |
| 8.82 ± 0.20 | 10.019 ± 0.227 | 25 |
| 9.49 ± 0.20 | 9.311 ± 0.196 | 21 |

TABLE J-continued

| °2θ | d space (Å) | Intensity (%) |
|---|---|---|
| 9.85 ± 0.20 | 8.969 ± 0.182 | 10 |
| 10.77 ± 0.20 | 8.206 ± 0.152 | 8 |
| 11.12 ± 0.20 | 7.952 ± 0.143 | 33 |
| 13.05 ± 0.20 | 6.779 ± 0.103 | 7 |
| 13.99 ± 0.20 | 6.327 ± 0.090 | 7 |
| 14.91 ± 0.20 | 5.937 ± 0.079 | 9 |
| 15.23 ± 0.20 | 5.813 ± 0.076 | 100 |
| 15.53 ± 0.20 | 5.700 ± 0.073 | 31 |
| 16.35 ± 0.20 | 5.417 ± 0.066 | 69 |
| 16.53 ± 0.20 | 5.359 ± 0.064 | 21 |
| 17.59 ± 0.20 | 5.038 ± 0.057 | 19 |
| 17.70 ± 0.20 | 5.006 ± 0.056 | 15 |
| 18.78 ± 0.20 | 4.722 ± 0.050 | 26 |
| 19.07 ± 0.20 | 4.649 ± 0.048 | 10 |
| 19.30 ± 0.20 | 4.596 ± 0.047 | 23 |
| 19.47 ± 0.20 | 4.555 ± 0.046 | 12 |
| 19.75 ± 0.20 | 4.492 ± 0.045 | 24 |
| 19.99 ± 0.20 | 4.438 ± 0.044 | 17 |
| 20.20 ± 0.20 | 4.392 ± 0.043 | 43 |
| 20.62 ± 0.20 | 4.305 ± 0.041 | 39 |
| 20.91 ± 0.20 | 4.245 ± 0.040 | 13 |
| 21.16 ± 0.20 | 4.194 ± 0.039 | 20 |
| 21.65 ± 0.20 | 4.101 ± 0.037 | 23 |
| 21.89 ± 0.20 | 4.056 ± 0.037 | 15 |
| 22.39 ± 0.20 | 3.968 ± 0.035 | 18 |
| 22.68 ± 0.20 | 3.917 ± 0.034 | 30 |
| 22.83 ± 0.20 | 3.892 ± 0.034 | 19 |
| 23.17 ± 0.20 | 3.836 ± 0.033 | 27 |
| 23.31 ± 0.20 | 3.813 ± 0.032 | 34 |
| 23.63 ± 0.20 | 3.763 ± 0.031 | 67 |
| 23.95 ± 0.20 | 3.713 ± 0.031 | 38 |
| 24.89 ± 0.20 | 3.574 ± 0.028 | 40 |
| 25.54 ± 0.20 | 3.485 ± 0.027 | 21 |
| 25.83 ± 0.20 | 3.446 ± 0.026 | 15 |
| 26.32 ± 0.20 | 3.384 ± 0.025 | 23 |
| 26.52 ± 0.20 | 3.358 ± 0.025 | 19 |
| 27.00 ± 0.20 | 3.300 ± 0.024 | 25 |
| 27.16 ± 0.20 | 3.280 ± 0.024 | 35 |
| 27.42 ± 0.20 | 3.250 ± 0.023 | 20 | wherein the XRPD is measured using an incident beam of Cu Kα radiation, e.g., wherein the XRPD is measured using radiation of wavelength 1.54059 Å.

5.15 Any of Crystalline Form 5 et seq. exhibiting an XRPD pattern having the 2-theta (°) values set forth in Table J of Crystalline Form 5.14, wherein the XRPD is measured using an incident beam of Cu Kα radiation, e.g., wherein the XRPD is measured using radiation of wavelength 1.54059 Å.

5.16 Any of Crystalline Form 5 et seq. exhibiting an XRPD pattern comprising at least three, e.g., at least five, d-spacing (Å) values selected from the group consisting of 10.0, 9.3, 8.0, 5.8, 5.7, 5.4, 4.4, 4.3, 3.8, 3.7, 3.6, and 3.3.

5.17 Any of Crystalline Form 5 et seq. exhibiting an XRPD pattern comprising the d-spacing (Å) values below:
10.0, 9.3, 8.0, 5.8, 5.7, 5.4, 4.4, 4.3, 3.8, 3.7, 3.6, and 3.3.

5.18 Any of Crystalline Form 5 et seq. exhibiting an XRPD pattern comprising at least three, e.g., at least five, d-spacing (Å) values selected from the group consisting of 10.02, 9.31, 7.95, 5.81, 5.70, 5.42, 4.39, 4.31, 3.76, 3.71, 3.57, and 3.28.

5.19 Any of Crystalline Form 5 et seq. wherein the crystal exhibits an XRPD pattern comprising the d-spacing (Å) values below:
10.02, 9.31, 7.95, 5.81, 5.70, 5.42, 4.39, 4.31, 3.76, 3.71, 3.57, and 3.28.

5.20 Any of Crystalline Form 5 et seq. exhibiting an XRPD pattern comprising at least three, e.g., at least five, d-spacing (Å) values selected from the group consisting of 10.019, 9.311, 7.952, 5.813, 5.700, 5.417, 4.392, 4.305, 3.763, 3.713, 3.574, and 3.280.

5.21 Any of Crystalline Form 5 et seq. exhibiting an XRPD pattern comprising the d-spacing (Å) values below:
10.019, 9.311, 7.952, 5.813, 5.700, 5.417, 4.392, 4.305, 3.763, 3.713, 3.574, and 3.280.

5.22 Any of Crystalline Form 5 et seq. exhibiting an XRPD pattern comprising at least three, e.g., at least five, d-spacing (Å) values selected from those set forth in Table I of Crystalline Form 5.8.

5.23 Any of Crystalline Form 5 et seq. exhibiting an XRPD pattern comprising the d-spacing (Å) values set forth in Table I of Crystalline Form 5.8.

5.24 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, d-spacing (Å) values selected from the group consisting of 18.7, 16.5, 15.9, 10.0, 9.3, 9.0, 8.2, 8.0, 6.8, 6.3, 5.9, 5.8, 5.7, 5.4, 5.0, 4.7, 4.6, 4.5, 4.4, 4.3, 4.2, 4.1, 4.0, 3.9, 3.8, 3.7, 3.6, 3.5, 3.4, and 3.3.

5.25 Any of Crystalline Form 5 et seq. exhibiting an XRPD pattern having the d-spacing (Å) values below:
18.7, 16.5, 15.9, 10.0, 9.3, 9.0, 8.2, 8.0, 6.8, 6.3, 5.9, 5.8, 5.7, 5.4, 5.0, 4.7, 4.6, 4.5, 4.4, 4.3, 4.2, 4.1, 4.0, 3.9, 3.8, 3.7, 3.6, 3.5, 3.4, and 3.3.

5.26 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, e.g., at least thirty, e.g., at least thirty-five, e.g., at least forty, d-spacing (Å) values selected from the group consisting of 18.68, 16.48, 15.92, 10.02, 9.31, 8.97, 8.21, 7.95, 6.78, 6.33, 5.94, 5.81, 5.70, 5.42, 5.36, 5.04, 5.01, 4.72, 4.65, 4.60, 4.56, 4.49, 4.44, 4.39, 4.31, 4.25, 4.19, 4.10, 4.06, 3.97, 3.92, 3.89, 3.84, 3.81, 3.76, 3.71, 3.57, 3.49, 3.45, 3.38, 3.36, 3.30, 3.28, and 3.25.

5.27 Any of Crystalline Form 5 et seq. exhibiting an XRPD pattern having the d-spacing (Å) values below:
18.68, 16.48, 15.92, 10.02, 9.31, 8.97, 8.21, 7.95, 6.78, 6.33, 5.94, 5.81, 5.70, 5.42, 5.36, 5.04, 5.01, 4.72, 4.65, 4.60, 4.56, 4.49, 4.44, 4.39, 4.31, 4.25, 4.19, 4.10, 4.06, 3.97, 3.92, 3.89, 3.84, 3.81, 3.76, 3.71, 3.57, 3.49, 3.45, 3.38, 3.36, 3.30, 3.28, and 3.25.

5.28 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, e.g., at least thirty, e.g., at least thirty-five, e.g., at least forty, d-spacing (Å) values selected from the group consisting of 18.682, 16.479, 15.916, 10.019, 9.311, 8.969, 8.206, 7.952, 6.779, 6.327, 5.937, 5.813, 5.700, 5.417, 5.359, 5.038, 5.006, 4.722, 4.649, 4.596, 4.555, 4.492, 4.438, 4.392, 4.305, 4.245, 4.194, 4.101, 4.056, 3.968, 3.917, 3.892, 3.836, 3.813, 3.763, 3.713, 3.574, 3.485, 3.446, 3.384, 3.358, 3.300, 3.280, and 3.250.

5.29 Any of Crystalline Form 5 et seq. exhibiting an XRPD pattern having the d-spacing (Å) values below:
18.682, 16.479, 15.916, 10.019, 9.311, 8.969, 8.206, 7.952, 6.779, 6.327, 5.937, 5.813, 5.700, 5.417, 5.359, 5.038, 5.006, 4.722, 4.649, 4.596, 4.555, 4.492, 4.438, 4.392, 4.305, 4.245, 4.194, 4.101, 4.056, 3.968, 3.917, 3.892, 3.836, 3.813, 3.763, 3.713, 3.574, 3.485, 3.446, 3.384, 3.358, 3.300, 3.280, and 3.250.

5.30 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, e.g., at least thirty, e.g., at least thirty-five, e.g., at least forty, d-spacing (Å) values selected from the group consisting of those set forth in Table J of Crystalline Form 5.14.

5.31 Any of Crystalline Form 5 et seq. exhibiting an XRPD pattern having the d-spacing (Å) values set forth in Table J of Crystalline Form 5.14.

5.32 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, e.g., at least thirty, e.g., at least thirty-five, e.g., at least forty, e.g., all of the peaks, of the XRPD shown in FIG. 24, wherein the XRPD is obtained using Cu Kα radiation, e.g., wherein the XRPD is measured using radiation of wavelength 1.54059 Å.

5.33 Any of Crystalline Form 5 et seq. comprising the characteristic peaks of the XRPD shown in FIG. 24, wherein the XRPD is obtained using Cu Kα radiation, e.g., wherein the XRPD is measured using radiation of wavelength 1.54059 Å.

5.34 Any of Crystalline Form 5 et seq. comprising the representative peaks of the XRPD shown in FIG. 24, wherein the XRPD is obtained using Cu Kα radiation, e.g., wherein the XRPD is measured using radiation of wavelength 1.54059 Å.

5.35 Any of Crystalline Form 5 et seq. exhibiting an XRPD as shown in FIG. 24, wherein the XRPD is obtained using Cu Kα radiation, e.g., wherein the XRPD is measured using radiation of wavelength 1.54059 Å.

5.36 Any of Crystalline Form 5 et seq. exhibiting an XRPD pattern comprising at least three, e.g., at least five, e.g., at least ten, e.g., at least twelve, e.g., at least fifteen, e.g., at least twenty, e.g., at least twenty-five, e.g., at least thirty, e.g., at least thirty-five, e.g., at least forty, e.g., all of the peaks, of the XRPD shown in FIG. 24, 44, 45, 46, 48, 50, 51, 52, 54, or 57, e.g., shown in FIG. 24 or 44 or 45 or 46 or 48 or 50 or 51 or 52 or 54 or 57, wherein the XRPD is obtained using Cu Kα radiation, e.g., wherein the XRPD is measured using radiation of wavelength 1.54059 Å.

5.37 Any of Crystalline Form 5 et seq. comprising characteristic peak(s) of the XRPD shown in FIG. 24, 44, 45, 46, 48, 50, 51, 52, 54, or 57, e.g., shown in FIG. 24 or 44 or 45 or 46 or 48 or 50 or 51 or 52 or 54 or 57, wherein the XRPD is obtained using Cu Kα radiation, e.g., wherein the XRPD is measured using radiation of wavelength 1.54059 Å.

5.38 Any of Crystalline Form 5 et seq. comprising representative peak(s) of the XRPD shown in FIG. 24, 44, 45, 46, 48, 50, 51, 52, 54, or 57, e.g., shown in FIG. 24 or 44 or 45 or 46 or 48 or 50 or 51 or 52 or 54 or 57, wherein the XRPD is obtained using Cu Kα radiation, e.g., wherein the XRPD is measured using radiation of wavelength 1.54059 Å.

5.39 Any of Crystalline Form 5 et seq. exhibiting an XRPD substantially as shown in FIG. 24, 44, 45, 46, 48, 50, 51, 52, 54, or 57, e.g., substantially as shown in FIG. 24 or 44 or 45 or 46 or 48 or 50 or 51 or 52 or 54 or 57, e.g., substantially as shown in any XRPD for Crystalline Form N pictured herein, wherein the XRPD is obtained using Cu Kα radiation, e.g., wherein the XRPD is measured using radiation of wavelength 1.54059 Å.

5.40 Any of Crystalline Form 5 et seq. exhibiting a thermogravimetric analysis (TGA) thermogram comprising weight loss between 20° C. and 80° C., e.g., between 23° C. and 70° C., e.g., between 23° C. and 70° C., e.g., a weight loss of 3-4 weight %, e.g., a weight loss of 3.5 weight %, e.g., a weight loss of 3.7 weight %.

5.41 Any of Crystalline Form 5 et seq. exhibiting a thermogravimetric analysis (TGA) thermogram comprising weight loss between 60° C. and 110° C., e.g., between 70° C. and 105° C., e.g., a weight loss of 3-4 weight %, e.g., a weight loss of 3.6 weight %, e.g., a weight loss of 3.7 weight %.

5.42 Any of Crystalline Form 5 exhibiting a thermogravimetric analysis (TGA) thermogram comprising weight loss between 100° C. and 170° C., e.g., between 105° C. and 160° C., e.g., a weight loss of 0.1-2 weight %, e.g., a weight loss of 0.6 weight %, e.g., a weight loss of 1.3 weight %.

5.43 Any of Crystalline Form 5 et seq. exhibiting a thermogravimetric analysis (TGA) thermogram as shown in FIG. 26.

5.44 Any of Crystalline Form 5 et seq. exhibiting a differential scanning calorimetry (DSC) thermogram comprising an endotherm at 85° C.

5.45 Any of Crystalline Form 5 et seq. exhibiting a differential scanning calorimetry (DSC) thermogram comprising an endotherm at 91° C.

5.46 Any of Crystalline Form 5 et seq. exhibiting a differential scanning calorimetry (DSC) thermogram comprising an endotherm at 95° C.

5.47 Any of Crystalline Form 5 et seq. exhibiting a differential scanning calorimetry (DSC) thermogram comprising an endotherm at 118° C.

5.48 Any of Crystalline Form 5 et seq. exhibiting a differential scanning calorimetry (DSC) thermogram comprising an endotherm at 178° C., e.g., an endotherm at 178° C. with an onset at 169° C.

5.49 Any of Crystalline Form 5 et seq. exhibiting a differential scanning calorimetry (DSC) thermogram as shown in FIG. 26.

5.50 Any of Crystalline Form 5 et seq. exhibiting a dynamic (water) vapor sorption (DVS) isotherm comprising 30% weight loss upon equilibration to 5% relative humidity.

5.51 Any of Crystalline Form 5 et seq. exhibiting a dynamic (water) vapor sorption (DVS) isotherm comprising 4% or less weight gain upon increasing the relative humidity from 5% to 95%, e.g., 3% or less weight gain upon increasing the relative humidity from 5% to 95%, e.g., 3% weight gain upon increasing the relative humidity from 5% to 95%.

5.52 Any of Crystalline Form 5 et seq. exhibiting a dynamic (water) vapor sorption (DVS) isotherm as shown in FIG. 27.

5.53 Any of Crystalline Form 5 et seq. containing 14% water by Karl Fischer analysis (equivalent to 4 moles), e.g., 14.2% water by Karl Fischer (KF) analysis (equivalent to 4.2 moles water).

5.54 Any of Crystalline Form 5 et seq. wherein the preparation of the crystal comprises mixing, optionally with stirring, 2-{[3,5-bis(trifluoromethyl)phenyl]carbamoyl}-4-chlorophenyl dihydrogen phosphate with water (e.g., comprising mixing with water alone or comprising mixing with a mixture comprising water (e.g., wherein the mixture has high water activity ($a_w$), e.g., wherein $a_w$ is 0.9 or greater).

5.55 Crystalline Form 5.54 further comprising isolating a solid, e.g., by filtering.

5.56 Crystalline Form 5.55 further comprising drying the solid under vacuum.

5.57 Any of Crystalline Form 5.54-5.56 further comprising isolating the crystal.

5.58 Any of Crystalline Form 5 et seq. wherein the crystal is made as described in any of the examples that produce Form N.

5.59 Any of Crystalline Form 5 et seq. wherein the crystal is made by any of Process 1 et seq., vide infra.

5.60 Any of Crystalline Form 5 et seq. wherein the crystal is made by any of Process 2 et seq., 3 et seq., or 4 et seq., vide infra.

5.61 Any of Crystalline Form 5 et seq. wherein the 2-theta (°) values of the XRPD pattern have an acceptable deviation of ±0.2°.

Further provided is a non-solvate non-hydrate crystalline form of

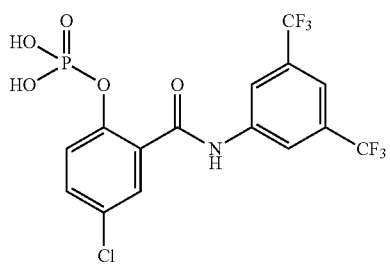

Formula I (Crystalline Form 6, also referred to herein as Form B). Further provided is Crystalline Form 6 as follows:

6.1 Crystalline Form 6 exhibiting an XRPD pattern comprising at least three, e.g., at least five, 2-theta (°) values selected from the group consisting of 6.6, 11.0, 12.6, 14.5, 14.6, 18.0, 19.7, 20.1, 21.0, 21.6, 22.0, 22.4, 23.8, 24.5, 24.8, and 27.4, wherein the XRPD is measured using an incident beam of Cu Kα radiation, e.g., wherein the XRPD is measured using radiation of wavelength 1.54059 Å.

6.2 Crystalline Form 6 or 6.1 exhibiting an XRPD pattern comprising 2-theta (°) values of 6.6, 11.0, 12.6, 14.5, 14.6, 18.0, 19.7, 20.1, 21.0, 21.6, 22.0, 22.4, 23.8, 24.5, 24.8, and 27.4, wherein the XRPD is measured using an incident beam of Cu Kα radiation, e.g., wherein the XRPD is measured using radiation of wavelength 1.54059 Å.

6.3 Any of Crystalline Form 6 et seq. exhibiting an XRPD pattern comprising at least three, e.g., at least five, 2-theta (°) values selected from the group consisting of 6.64, 10.95, 12.55, 14.48, 14.61, 17.99, 19.74, 20.07, 20.97, 21.63, 22.02, 22.40, 23.80, 24.50, 24.78, and 27.42, wherein the XRPD is measured using an incident beam of Cu Kα radiation, e.g., wherein the XRPD is measured using radiation of wavelength 1.54059 Å.

6.4 Any of Crystalline Form 6 et seq. exhibiting an XRPD pattern comprising 2-theta (°) values of 6.64, 10.95, 12.55, 14.48, 14.61, 17.99, 19.74, 20.07, 20.97, 21.63, 22.02, 22.40, 23.80, 24.50, 24.78, and 27.42, wherein the XRPD is measured using an incident beam of Cu Kα radiation, e.g., wherein the XRPD is measured using radiation of wavelength 1.54059 Å.

6.5 Any of Crystalline Form 6 et seq. exhibiting an XRPD pattern comprising at least three, e.g., at least five, 2-theta (°) values selected from those set forth in Table C below:

TABLE C

| °2θ | d space (Å) | Intensity (%) |
|---|---|---|
| 6.64 ± 0.20 | 13.298 ± 0.400 | 48 |
| 10.95 ± 0.20 | 8.075 ± 0.147 | 52 |
| 12.55 ± 0.20 | 7.049 ± 0.112 | 40 |
| 14.48 ± 0.20 | 6.110 ± 0.084 | 46 |
| 14.61 ± 0.20 | 6.060 ± 0.083 | 63 |
| 17.99 ± 0.20 | 4.926 ± 0.054 | 52 |
| 19.74 ± 0.20 | 4.495 ± 0.045 | 41 |
| 20.07 ± 0.20 | 4.421 ± 0.044 | 61 |
| 20.97 ± 0.20 | 4.233 ± 0.040 | 73 |
| 21.63 ± 0.20 | 4.106 ± 0.038 | 51 |
| 22.02 ± 0.20 | 4.033 ± 0.036 | 95 |
| 22.40 ± 0.20 | 3.965 ± 0.035 | 36 |
| 23.80 ± 0.20 | 3.735 ± 0.031 | 100 |
| 24.50 ± 0.20 | 3.630 ± 0.029 | 87 |
| 24.78 ± 0.20 | 3.590 ± 0.029 | 50 |
| 27.42 ± 0.20 | 3.251 ± 0.023 | 38 | wherein the XRPD is measured using an incident beam of Cu Kα radiation, e.g., wherein the XRPD is measured using radiation of wavelength 1.54059 Å.

6.6 Any of Crystalline Form 6 et seq. exhibiting an XRPD pattern having the 2-theta (°) values set forth in Table C of Crystalline Form 6.5, wherein the XRPD is measured using an incident beam of Cu Kα radiation, e.g., wherein the XRPD is measured using radiation of wavelength 1.54059 Å.

6.7 Any of Crystalline Form 6 et seq. exhibiting an XRPD pattern comprising at least three, e.g., at least five, e.g., at least ten, e.g., at least fifteen, e.g., at least sixteen, e.g., at least twenty, 2-theta (°) values selected from the group consisting of 6.6, 11.0, 11.1, 12.6, 14.5, 14.6, 15.3, 16.4, 17.1, 18.0, 19.7, 20.1, 21.0, 21.4, 21.6, 22.0, 22.4, 22.8, 23.8, 24.5, 24.8, 25.8, 27.4, and 29.0, wherein the XRPD is measured using an incident beam of Cu Kα radiation, e.g., wherein the XRPD is measured using radiation of wavelength 1.54059 Å.

6.8 Any of Crystalline Form 6 et seq. exhibiting an XRPD pattern having the following 2-theta (°) values:
6.6, 11.0, 11.1, 12.6, 14.5, 14.6, 15.3, 16.4, 17.1, 18.0, 19.7, 20.1, 21.0, 21.4, 21.6, 22.0, 22.4, 22.8, 23.8, 24.5, 24.8, 25.8, 27.4, and 29.0,
wherein the XRPD is measured using an incident beam of Cu Kα radiation, e.g., wherein the XRPD is measured using radiation of wavelength 1.54059 Å.

6.9 Any of Crystalline Form 6 et seq. exhibiting an XRPD pattern comprising at least three, e.g., at least five, e.g., at least ten, e.g., at least fifteen, e.g., at least sixteen, e.g., at least twenty, 2-theta (°) values selected from the group consisting of 6.64, 10.95, 11.13, 12.55, 14.48, 14.61, 15.28, 16.35, 17.09, 17.99, 19.74, 20.07, 20.97, 21.36, 21.63, 22.02, 22.40, 22.77, 23.80, 24.50, 24.78, 25.76, 27.42, and 29.01,
wherein the XRPD is measured using an incident beam of Cu Kα radiation, e.g., wherein the XRPD is measured using radiation of wavelength 1.54059 Å.

6.10 Any of Crystalline Form 6 et seq. exhibiting an XRPD pattern having the following 2-theta (°) values:
6.64, 10.95, 11.13, 12.55, 14.48, 14.61, 15.28, 16.35, 17.09, 17.99, 19.74, 20.07, 20.97, 21.36, 21.63, 22.02, 22.40, 22.77, 23.80, 24.50, 24.78, 25.76, 27.42, and 29.01, wherein the XRPD is measured using an incident beam of Cu Kα radiation, e.g., wherein the XRPD is measured using radiation of wavelength 1.54059 Å.

6.11 Any of Crystalline Form 6 et seq. exhibiting an XRPD pattern comprising at least three, e.g., at least five, e.g., at least ten, e.g., at least fifteen, e.g., at least sixteen, e.g., at least twenty, 2-theta (°) values selected from those set forth in Table D below:

TABLE D

| °2θ | d space (Å) | Intensity (%) |
|---|---|---|
| 6.64 ± 0.20 | 13.298 ± 0.400 | 48 |
| 10.95 ± 0.20 | 8.075 ± 0.147 | 52 |
| 11.13 ± 0.20 | 7.944 ± 0.142 | 26 |
| 12.55 ± 0.20 | 7.049 ± 0.112 | 40 |
| 14.48 ± 0.20 | 6.110 ± 0.084 | 46 |
| 14.61 ± 0.20 | 6.060 ± 0.083 | 63 |
| 15.28 ± 0.20 | 5.793 ± 0.075 | 21 |
| 16.35 ± 0.20 | 5.417 ± 0.066 | 22 |
| 17.09 ± 0.20 | 5.185 ± 0.060 | 27 |
| 17.99 ± 0.20 | 4.926 ± 0.054 | 52 |
| 19.74 ± 0.20 | 4.495 ± 0.045 | 41 |
| 20.07 ± 0.20 | 4.421 ± 0.044 | 61 |
| 20.97 ± 0.20 | 4.233 ± 0.040 | 73 |
| 21.36 ± 0.20 | 4.157 ± 0.038 | 18 |
| 21.63 ± 0.20 | 4.106 ± 0.038 | 51 |
| 22.02 ± 0.20 | 4.033 ± 0.036 | 95 |
| 22.40 ± 0.20 | 3.965 ± 0.035 | 36 |
| 22.77 ± 0.20 | 3.901 ± 0.034 | 23 |
| 23.80 ± 0.20 | 3.735 ± 0.031 | 100 |
| 24.50 ± 0.20 | 3.630 ± 0.029 | 87 |
| 24.78 ± 0.20 | 3.590 ± 0.029 | 50 |
| 25.76 ± 0.20 | 3.456 ± 0.026 | 20 |
| 27.42 ± 0.20 | 3.251 ± 0.023 | 38 |
| 29.01 ± 0.20 | 3.075 ± 0.021 | 14 | wherein the XRPD is measured using an incident beam of Cu Kα radiation, e.g., wherein the XRPD is measured using radiation of wavelength 1.54059 Å.

6.12 Any of Crystalline Form 6 et seq. exhibiting an XRPD pattern having the 2-theta (°) values set forth in Table D of Crystalline Form 6.11, wherein the XRPD is measured using an incident beam of Cu Kα radiation, e.g., wherein the XRPD is measured using radiation of wavelength 1.54059 Å.

6.13 Any of Crystalline Form 6 et seq. exhibiting an XRPD pattern comprising at least three, e.g., at least five, d-spacing (Å) values selected from the group consisting of 13.3, 8.1, 7.0, 6.1, 4.9, 4.5, 4.4, 4.2, 4.1, 4.0, 3.7, 3.6, and 3.3.

6.14 Any of Crystalline Form 6 et seq. exhibiting an XRPD pattern comprising the d-spacing (Å) values below:
13.3, 8.1, 7.0, 6.1, 4.9, 4.5, 4.4, 4.2, 4.1, 4.0, 3.7, 3.6, and 3.3.

6.15 Any of Crystalline Form 6 et seq. exhibiting an XRPD pattern comprising at least three, e.g., at least five, d-spacing (Å) values selected from the group consisting of 13.30, 8.08, 7.05, 6.11, 6.06, 4.93, 4.50, 4.42, 4.23, 4.11, 4.03, 3.97, 3.74, 3.63, 3.59, and 3.25.

6.16 Any of Crystalline Form 6 et seq. wherein the crystal exhibits an XRPD pattern comprising the d-spacing (Å) values below:
13.30, 8.08, 7.05, 6.11, 6.06, 4.93, 4.50, 4.42, 4.23, 4.11, 4.03, 3.97, 3.74, 3.63, 3.59, and 3.25.

6.17 Any of Crystalline Form 6 et seq. exhibiting an XRPD pattern comprising at least three, e.g., at least five, d-spacing (Å) values selected from the group consisting of 13.298, 8.075, 7.049, 6.110, 6.060, 4.926, 4.495, 4.421, 4.233, 4.106, 4.033, 3.965, 3.735, 3.630, 3.590, and 3.251.

6.18 Any of Crystalline Form 6 et seq. exhibiting an XRPD pattern comprising the d-spacing (Å) values below:
13.298, 8.075, 7.049, 6.110, 6.060, 4.926, 4.495, 4.421, 4.233, 4.106, 4.033, 3.965, 3.735, 3.630, 3.590, and 3.251.

6.19 Any of Crystalline Form 6 et seq. exhibiting an XRPD pattern comprising at least three, e.g., at least five, d-spacing (Å) values selected from those set forth in Table C of Crystalline Form 6.5.

6.20 Any of Crystalline Form 6 et seq. exhibiting an XRPD pattern comprising the d-spacing (Å) values set forth in Table C of Crystalline Form 6.5.

6.21 Any of Crystalline Form 6 et seq. exhibiting an XRPD pattern comprising at least three, e.g., at least five, e.g., at least ten, e.g., at least fifteen, e.g., at least sixteen, d-spacing (Å) values selected from the group consisting of 13.3, 8.1, 7.9, 7.0, 6.1, 5.8, 5.4, 5.2, 4.9, 4.5, 4.4, 4.2, 4.1, 4.0, 3.9, 3.7, 3.6, 3.5, 3.3, and 3.1.

6.22 Any of Crystalline Form 6 et seq. exhibiting an XRPD pattern having the d-spacing (Å) values below:
13.3, 8.1, 7.9, 7.0, 6.1, 5.8, 5.4, 5.2, 4.9, 4.5, 4.4, 4.2, 4.1, 4.0, 3.9, 3.7, 3.6, 3.5, 3.3, and 3.1.

6.23 Any of Crystalline Form 6 et seq. exhibiting an XRPD pattern comprising at least three, e.g., at least five, e.g., at least ten, e.g., at least fifteen, e.g., at least sixteen, e.g., at least twenty, d-spacing (Å) values selected from the group consisting of 13.30, 8.08, 7.94, 7.05, 6.11, 6.06, 5.79, 5.42, 5.19, 4.93, 4.50, 4.42, 4.23, 4.16, 4.11, 4.03, 3.97, 3.90, 3.74, 3.63, 3.59, 3.46, 3.25, and 3.08.

6.24 Any of Crystalline Form 6 et seq. exhibiting an XRPD pattern having the d-spacing (Å) values below:
13.30, 8.08, 7.94, 7.05, 6.11, 6.06, 5.79, 5.42, 5.19, 4.93, 4.50, 4.42, 4.23, 4.16, 4.11, 4.03, 3.97, 3.90, 3.74, 3.63, 3.59, 3.46, 3.25, and 3.08.

6.25 Any of Crystalline Form 6 et seq. exhibiting an XRPD pattern comprising at least three, e.g., at least five, e.g., at least ten, e.g., at least sixteen, e.g., at least twenty, d-spacing (Å) values selected from the group consisting of 13.298, 8.075, 7.944, 7.049, 6.110, 6.060, 5.793, 5.417, 5.185, 4.926, 4.495, 4.421, 4.233, 4.157, 4.106, 4.033, 3.965, 3.901, 3.735, 3.630, 3.590, 3.456, 3.251, and 3.075.

6.26 Any of Crystalline Form 6 et seq. exhibiting an XRPD pattern having the d-spacing (Å) values below:
13.298, 8.075, 7.944, 7.049, 6.110, 6.060, 5.793, 5.417, 5.185, 4.926, 4.495, 4.421, 4.233, 4.157, 4.106, 4.033, 3.965, 3.901, 3.735, 3.630, 3.590, 3.456, 3.251, and 3.075.

6.27 Any of Crystalline Form 6 et seq. exhibiting an XRPD pattern comprising at least three, e.g., at least five, e.g., at least ten, e.g., at least sixteen, e.g., at least twenty, d-spacing (Å) values selected from the group consisting of those set forth in Table D of Crystalline Form 6.11.

6.28 Any of Crystalline Form 6 et seq. exhibiting an XRPD pattern having the d-spacing (Å) values set forth in Table D of Crystalline Form 6.11.

6.29 Any of Crystalline Form 6 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, e.g., all of the peaks, of the XRPD shown in FIG. 21, wherein the XRPD is obtained using Cu Kα radiation, e.g., wherein the XRPD is measured using radiation of wavelength 1.54059 Å.

6.30 Any of Crystalline Form 6 et seq. comprising the characteristic peaks of the XRPD shown in FIG. 21, wherein the XRPD is obtained using Cu Kα radiation, e.g., wherein the XRPD is measured using radiation of wavelength 1.54059 Å.

6.31 Any of Crystalline Form 6 et seq. comprising the representative peaks of the XRPD shown in FIG. 21, wherein the XRPD is obtained using Cu Kα radiation, e.g., wherein the XRPD is measured using radiation of wavelength 1.54059 Å.

6.32 Any of Crystalline Form 6 et seq. exhibiting an XRPD as shown in FIG. 21, wherein the XRPD is obtained using Cu Kα radiation, e.g., wherein the XRPD is measured using radiation of wavelength 1.54059 Å.

6.33 Any of Crystalline Form 6 et seq. exhibiting an XRPD pattern comprising at least three, e.g., at least five, e.g., at least ten, e.g., at least fourteen, e.g., at least fifteen, e.g., at least twenty, e.g., at least twenty-five, e.g., at least thirty, e.g., at least thirty-five, e.g., at least forty, e.g., all of the peaks, of the XRPD shown in Figure FIG. 21, 37, 41, 42, 43, 49, 53, or 55, e.g., shown in FIG. 21 or 37 or 41 or 42 or 43 or 49 or 53 or 55, wherein the XRPD is obtained using Cu Kα radiation, e.g., wherein the XRPD is measured using radiation of wavelength 1.54059 Å.

6.34 Any of Crystalline Form 6 et seq. comprising characteristic peak(s) of the XRPD shown in FIG. 21, 37, 41, 42, 43, 49, 53, or 55, e.g., shown in FIG. 21 or 37 or 41 or 42 or 43 or 49 or 53 or 55, wherein the XRPD is obtained using Cu Kα radiation, e.g., wherein the XRPD is measured using radiation of wavelength 1.54059 Å.

6.35 Any of Crystalline Form 6 et seq. comprising representative peak(s) of the XRPD shown in FIG. 21, 37, 41, 42, 43, 49, 53, or 55, e.g., shown in FIG. 21 or 37 or 41 or 42 or 43 or 49 or 53 or 55, wherein the XRPD is obtained using Cu Kα radiation, e.g., wherein the XRPD is measured using radiation of wavelength 1.54059 Å.

6.36 Any of Crystalline Form 6 et seq. exhibiting an XRPD substantially as shown in FIG. 21, 37, 41, 42, 43, 49, 53, or 55, e.g., substantially as shown in FIG. 21 or 37 or 41 or 42 or 43 or 49 or 53 or 55, e.g., substantially as shown in any XRPD for Crystalline Form B pictured herein, wherein the XRPD is obtained using Cu Kα radiation, e.g., wherein the XRPD is measured using radiation of wavelength 1.54059 Å.

6.37 Any of Crystalline Form 6 et seq. exhibiting a dynamic (water) vapor sorption (DVS) isotherm comprising 0.6 weight % water vapor sorption from 5% to 95% relative humidity.

6.38 Any of Crystalline Form 6 exhibiting a dynamic (water) vapor sorption (DVS) isotherm as shown in FIG. 28.

6.39 Any of Crystalline Form 6 et seq. exhibiting a differential scanning calorimetry (DSC) thermogram comprising an endotherm at 177° C., e.g., an endotherm at 177° C. having an onset at 173° C.

6.40 Any of Crystalline Form 6 et seq. exhibiting a differential scanning calorimetry (DSC) thermogram as shown in FIG. 40.

6.41 Any of Crystalline Form 6 et seq. exhibiting a thermogravimetric analysis (TGA) thermogram comprising weight loss of 0.1-1 weight %, e.g., 0.7 weight %, between 23° C. to 150° C.

6.42 Any of Crystalline Form 6 et seq. exhibiting a thermogravimetric analysis (TGA) thermogram as shown in FIG. 40.

6.43 Any of Crystalline Form 6 et seq. wherein the preparation of the crystal comprises mixing, optionally with stirring, 2-{[3,5-bis(trifluoromethyl)phenyl]carbamoyl}-4-chlorophenyl dihydrogen phosphate with an organic solvent, e.g., a halogenated organic solvent, e.g., a fluorinated organic solvent (e.g., hexafluoroisopropanol (HFIPA), 2,2,2-trifluoroethanol (TFE), and/or chloroform) and/or toluene.

6.44 Crystalline Form 6.43 further comprising cooling the mixture.

6.45 Crystalline Form 6.43 or 6.44 further comprising isolating a solid, e.g., by filtering.

6.46 Crystalline Form 6.45 further comprising drying the solid under vacuum.

6.47 Any of Crystalline Form 6.43-6.46 further comprising isolating the crystal.

6.48 Any of Crystalline Form 6 et seq. wherein the crystal is made by any of Process 1 et seq., vide infra.

6.49 Any of Crystalline Form 6 et seq. wherein the crystal is made by any of Process 5 et seq., vide infra.

6.50 Any of Crystalline Form 6 et seq. wherein the crystal is made as described in any of the examples that produce Form B.

6.51 Any of Crystalline Form 6 et seq. wherein the 2-theta (°) values of the XRPD pattern have an acceptable deviation of ±0.2°.

Further provided is a process (Process 1) for making 2-{[3,5-bis(trifluoromethyl)phenyl]carbamoyl}-4-chlorophenyl dihydrogen phosphate (Formula I) in crystalline form, e.g., for making any of Crystalline Form 1 et seq., Crystalline Form 2 et seq., Crystalline Form 3 et seq., Crystalline Form 4 et seq., Crystalline Form 5 et seq., and Crystalline Form 6 et seq., e.g., Crystalline Form 1. Further provided is Process 1 as follows:

1.1 Process 1 comprising acidifying e.g., to a pH less than 2, e.g., to pH 1, e.g., with HCl, e.g., to pH 1 with HCl, an aqueous solution comprising one or more of 2-{[3,5-bis(trifluoromethyl)phenyl]carbamoyl}-4-chlorophenyl dihydrogen phosphate, 2-{[3,5-bis(trifluoromethyl)phenyl]carbamoyl}-4-chlorophenyl hydrogen phosphate monoanion, and 2-{[3,5-bis(trifluoromethyl)phenyl]carbamoyl}-4-chlorophenyl phosphate dianion.

1.2 Process 1.1 further comprising extracting with an organic solvent, e.g., ethyl acetate, to generate an aqueous fraction and an organic fraction 1.3 Process 1.2 further comprising separating the organic fraction.

1.4 Process 1.3 further comprising drying the organic fraction, e.g., with sodium sulphate.

1.5 Process 1.4 further comprising evaporating the organic solvent.

1.6 Process 1.5 further comprising isolating the crystal.

1.7 Process 1.4 further comprising concentrating the organic solvent under reduced pressure to provide an oil.

1.8 Process 1.7 further comprising dissolving the oil in an organic solvent (e.g., ethyl acetate) optionally with stirring.

1.9 Process 1.8 further comprising adding an anti-solvent, e.g., an organic anti-solvent (e.g., n-heptane), optionally with stirring.

1.10 Process 1.9 further comprising isolating a solid, e.g., by filtering.

1.11 Process 1.10 further comprising washing the solid with an anti-solvent, e.g., an organic anti-solvent (e.g., n-heptane).

1.12 Process 1.11 further comprising drying the solid under vacuum.

1.13 Process 1.11 or 1.12 further comprising isolating the crystal.

1.14 Any of Process 1 et seq. further comprising dissolving 2-{[3,5-bis(trifluoromethyl)phenyl]carbamoyl}-4-chlorophenyl dihydrogen phosphate in an organic solvent (e.g., ethyl acetate) at room temperature optionally with stirring.

1.15 Process 1.14 further comprising adding an anti-solvent, e.g., an organic anti-solvent (e.g., n-heptane), optionally with stirring.

1.16 Process 1.15 further comprising isolating a solid, e.g., by filtering.

1.17 Process 1.16 further comprising washing the solid with an anti-solvent, e.g., an organic anti-solvent (e.g., n-heptane).

1.18 Process 1.17 further comprising drying under vacuum.

1.19 Process 1.17 or 1.18 further comprising isolating the crystal.

1.20 Process 1 et seq. comprising admixing Formula I with an organic solvent and optionally with an anti-solvent, e.g., admixing Formula I with one or more of ethyl acetate, heptane, acetonitrile, toluene, methanol, and p-dioxane. The mixture may optionally be stirred and/or cooled.

1.21 Any of Process 1 et seq. further comprising isolating the crystal.

1.22 A crystal comprising 2-{[3,5-bis(trifluoromethyl) phenyl]carbamoyl}-4-chlorophenyl dihydrogen phosphate made by any of Process 1 et seq.

1.23 Any of Crystalline Form 1 et seq., Crystalline Form 2 et seq., Crystalline Form 3 et seq., Crystalline Form 4 et seq., Crystalline Form 5 et seq., and Crystalline Form 6 et seq., e.g., any of Crystalline Form 1 et seq., wherein the crystal is made by any of Process 1 et seq.

Further provided is a crystal made by any of Process 1 et seq.

Further provided is a process (Process 2) for making 2-{[3,5-bis(trifluoromethyl)phenyl]carbamoyl}-4-chlorophenyl dihydrogen phosphate (Formula I) comprising crystallizing 2-{[3,5-bis(trifluoromethyl)phenyl]carbamoyl}-4-chlorophenyl dihydrogen phosphate from an organic solvent (e.g., from one or more of ethyl acetate, heptane, acetonitrile, methanol, toluene, e.g., ethyl acetate/heptane) to obtain a solvate, and stirring and/or washing the solvate with water to obtain 2-{[3,5-bis(trifluoromethyl)phenyl]carbamoyl}-4-chlorophenyl dihydrogen phosphate free of the organic solvent. Further provided is Process 2 as follows:

2.1 Process 2 wherein the organic solvent is one or more of ethyl acetate, heptane, acetonitrile, methanol, and toluene, e.g., ethyl acetate, e.g., ethyl acetate/heptane.

2.2 Process 2 or 2.1 comprising stirring the solvate with water, e.g., stirring the solvate with water at room temperature, e.g., stirring the solvate with water at room temperature for 2 hours.

2.3 Process 2.2 further comprising collecting the solid, e.g., by filtering.

2.4 Process 2.3 further comprising washing the solid with water.

2.5 Process 2.4 further comprising drying the solid, e.g., drying the solid under vacuum, e.g., drying the solid under vacuum for 1 hour.

2.6 Any of Process 2 et seq. further comprising isolating the solid, optionally in crystalline form.

2.7 Any of Process 2 et seq. wherein the final product is a crystal comprising 2-{[3,5-bis(trifluoromethyl)phenyl]carbamoyl}-4-chlorophenyl dihydrogen phosphate, e.g., a hydrate of 2-{[3,5-bis(trifluoromethyl) phenyl]carbamoyl}-4-chlorophenyl dihydrogen phosphate, e.g. any of Crystalline Form 5 et seq.

Further provided is a crystal made by any of Process 2 et seq.

Further provided is a process (Process 3) for making a hydrate of 2-{[3,5-bis(trifluoromethyl)phenyl]carbamoyl}-4-chlorophenyl dihydrogen phosphate (Formula I) (e.g., any of Crystalline Form 5 et seq.) comprising mixing 2-{[3,5-bis(trifluoromethyl)phenyl]carbamoyl}-4-chlorophenyl dihydrogen phosphate (e.g., any of Crystalline Form 1 et seq., e.g., Form A,) and water optionally with stirring. Further provided is Process 3 as follows:

3.1 Process 3 further comprising mixing 2-{[3,5-bis(trifluoromethyl)phenyl]carbamoyl}-4-chlorophenyl dihydrogen phosphate (e.g., any of Crystalline Form 1 et seq.) and water with anti-solvent (e.g., toluene) optionally with stirring.

3.2 Process 3 or 3.1 further comprising collecting the solid by filtration.

3.3 Process 3.2 further comprising vacuum drying the solid.

3.4 Any of Process 3 et seq. further comprising isolating the crystal.

Further provided is a crystal made by any of Process 3 et seq.

Further provided is a process (Process 4) for making a hydrate of 2-{[3,5-bis(trifluoromethyl)phenyl]carbamoyl}-4-chlorophenyl dihydrogen phosphate (Formula I) (e.g., any of Crystalline Form 5 et seq.) comprising mixing 2-{[3,5-bis(trifluoromethyl)phenyl]carbamoyl}-4-chlorophenyl dihydrogen phosphate with water optionally with stirring. Further provided is Process 4 as follows:

4.1 Process 4 comprising mixing 2-{[3,5-bis(trifluoromethyl)phenyl]carbamoyl}-4-chlorophenyl dihydrogen phosphate with water and an organic solvent, e.g., an anti-solvent, optionally with stirring.

4.2 Process 4 or 4.1 comprising mixing 2-{[3,5-bis(trifluoromethyl)phenyl]carbamoyl}-4-chlorophenyl dihydrogen phosphate in a solvent mixture comprising water wherein the solvent mixture has high water activity ($a_w$), e.g., wherein $a_w$ is 0.9 or greater.

4.3 Any of Process 4 et seq. further comprising collecting the solid by filtration.

4.4 Any of Process 4 et seq. further comprising vacuum drying the solid.

4.5 Any of Process 4 et seq. further comprising isolating the crystal.

Further provided is a crystal made by any of Process 4 et seq.

Further provided is a process (Process 5) for making a non-solvate non-hydrate crystalline form of 2-{[3,5-bis(trifluoromethyl)phenyl]carbamoyl}-4-chlorophenyl dihydrogen phosphate (Formula I) (e.g., any of Crystalline Form 6 et seq.) comprising mixing, optionally with stirring, 2-{[3, 5-bis(trifluoromethyl)phenyl]carbamoyl}-4-chlorophenyl dihydrogen phosphate with an organic solvent (e.g., a halogenated organic solvent, e.g., a fluorinated organic solvent (e.g., hexafluoroisopropanol (HFIPA), 2,2,2-trifluoroethanol (TFE), and/or chloroform) and/or toluene). Further provided is Process 4 as follows:

5.1 Process 5 wherein the organic solvent is a halogenated organic solvent, e.g., a fluorinated organic solvent (e.g., hexafluoroisopropanol (HFIPA), 2,2,2-trifluoroethanol (TFE), and/or chloroform).

5.2 Process 5 or 5.1 wherein the organic solvent is toluene.

5.3 Any of Process 5 et seq. further comprising cooling the mixture.

5.4 Any of Process 5 et seq. further comprising isolating a solid, e.g., by filtering.

5.5 Process 5.4 further comprising drying the solid under vacuum.

5.6 Any of Process 5 et seq. further comprising isolating the crystal

Further provided is a pharmaceutical composition (Composition 1), e.g., a pharmaceutical composition as described in International Publication No. WO 2015/069956, which is hereby incorporated by reference in its entirety, comprising 2-{[3,5-bis(trifluoromethyl)phenyl]carbamoyl}-4-chlorophenyl dihydrogen phosphate (Formula I) in crystalline form, e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq., e.g., any of Crystalline Form 6 et seq.

Further provided is a pharmaceutical composition (Composition 1) comprising a crystal comprising 2-{[3,5-bis(trifluoromethyl)phenyl]carbamoyl}-4-chlorophenyl dihydrogen phosphate (Crystalline Formula I), e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq. Further provided is Composition 1 as follows:

1.1 Composition 1 wherein the composition comprises 25 to 500 mg, e.g., from 25 to 300 or 350 mg, e.g., from 25 to 200 mg, e.g., from 15, 20, 30, 35, 50, or 100 to 150, 200, 300, 350, 400, 450, 500, 550, or 600 mg, e.g., 35 mg, e.g., 350 mg, of Crystalline Formula I.

1.2 Composition 1 or 1.1 wherein the composition comprises Crystalline Formula I in an amount sufficient to provide a dose of 0.01 or 0.1 or 0.5 mg/kg to 1 or 5 or 10 or 15 mg/kg of N-[3,5-bis(trifluoromethyl)phenyl]-5-chloro-2-hydroxybenzamide, e.g., a dose of 0.05 to 1 or 5 mg/kg, e.g., a dose of 0.05 to 0.1, 0.2, 0.3, 0.4, 0.5, 1, 5, 10 or 20 mg/kg, e.g., a dose of 0.5 to 1, 2, 3, 4, 5 or 10 or 20 mg/kg, e.g, a dose of 1 to 2, 3, 4, 5, 10, 20 or 50 mg/kg.

1.3 Any of Composition 1 et seq. wherein the composition comprises a base, e.g., a base wherein upon dissolution of the composition in a solvent, e.g., an aqueous solution, the composition has a pH between 7, 7.5, or 8 and 10.5, e.g., between 7, 7.5, or 8 and 9.5, e.g., between 7 or 7.5 and 8, e.g., between 7.5 and 8.5, e.g., 7.5, e.g., 8.5, e.g., between 8 and 8.5, e.g., 8.2, e.g., a base wherein a conjugate acid of the base has a pKa between 6, 7, 8, 9, or 10 and 11, e.g., between 6, 7, 8, or 9 and 10, e.g., between 7 and 9, e.g., between 8 and 9, e.g., wherein the base is:

a) a $C_{1-8}$-alkyl mono-, di-, or tri-carboxylic acid salt, e.g., a citrate salt, e.g, a metal citrate salt (e.g., an alkali and/or alkaline citrate salt, e.g., an alkali citrate salt, sodium citrate and/or potassium citrate), e.g., a tartrate salt (e.g., a metal tartrate salt, an alkali tartrate, e.g., sodium tartrate), e.g., a succinate salt (e.g., a metal succinate salt, e.g., an alkali succinate, e.g., disodium succinate), and/or e.g., a lactate salt (e.g., a metal lactate salt, e.g., an alkali lactate, e.g., sodium lactate), b) a phosphate salt, e.g., a metal phosphate salt (e.g., an alkali and/or alkaline phosphate salt, e.g., an alkali phosphate salt, e.g., sodium phosphate (e.g., $NaH_2PO_4$ and/or $Na_2HPO_4$) and/or potassium phosphate (e.g., $KH_2PO_4$ and/or $K_2HPO_4$)), c) an amine and/or a salt thereof (e.g., morpholine, piperazine, benethamine, benzathine, trimethylglycine, chloroprocaine, hydrabamine, an amino acid (e.g., arginine and/or lysine), a mono- and/or poly-hydroxyalkylamine, and/or a salt thereof, e.g., $(HO)_nR^8NH_2$, $[(HO)_nR^8]_2NH$, $[(HO)_nR^8]_3N$, and/or a salt thereof wherein each $R^8$ is independently $C_{1-8}$alkyl (e.g., $C_{1-6}$-alkyl, e.g., $C_{1-4}$-alkyl, e.g., $-CH_2CH_3$, e.g., $-CH_3$) and n is 0 or $C_{1-8}$-alkylene (e.g., $C_{1-6}$-alkylene, e.g., $C_{1-4}$-alkylene, e.g., $-CH_2-CH_2-$, e.g., $-C(CH_2)_3-$, e.g., one $R^8$ is $-CH_3$ and another $R^8$ is $-(CH_2)_6-$) and each n is independently 1-8 (e.g., 1, 2, 3, 4, 5, or 6), e.g., tris(hydroxymethyl)aminomethane (also known as tris base) and/or a salt thereof (e.g., tris(hydroxymethyl)aminomethane acetate (also known as tris acetate), meglumine, dimethylethanolamine, diethylamine, diethylethanolamine, and/or diethanolamine), e.g., any of the preceding wherein a conjugate acid of the amine and/or salt thereof has a pKa between 6, 7, 8, 9, or 10 and 11, e.g., between 6, 7, 8, or 9 and 10, e.g., between 7 and 9, e.g., between 8 and 9, d) an acetate salt, e.g., a metal acetate salt (e.g., an alkali and/or alkaline acetate salt, e.g., an alkali acetate salt, e.g., sodium acetate and/or potassium acetate), e) a hydroxide and/or alkoxide salt, e.g., a metal hydroxide and/or metal alkoxide salt (e.g., a quarternary ammonium hydroxide, e.g., ammonium hydroxide and/or choline hydroxide, lithium hydroxide, aluminum hydroxide, e.g., an alkali and/or alkaline hydroxide salt, e.g., sodium hydroxide, potassium hydroxide, calcium hydroxide, magnesium hydroxide, and/or magnesium ethoxide, e.g., sodium hydroxide), f) a carbonate and/or bicarbonate salt, e.g., a metal carbonate and/or metal bicarbonate salt (e.g., an alkali and/or alkaline carbonate salt, e.g., an alkali and/or alkaline bicarbonate salt, e.g., sodium bicarbonate), or g) a borate salt, e.g., a metal borate salt (e.g., an alkali borate salt, e.g., sodium borate), or any combination thereof, e.g., one or more of sodium citrate, $Na_2HPO_4$, tris(hydroxymethyl)aminomethane, and a tris(hydroxymethyl)aminomethane salt (e.g., tris acetate), e.g., one or more of sodium citrate, $Na_2HPO_4$, and tris(hydroxymethyl)aminomethane, e.g., one or more of sodium citrate and $Na_2HPO_4$, e.g., $Na_2HPO_4$, e.g., tris(hydroxymethyl)aminomethane.

1.4 Composition 1.3 wherein the composition comprises 1 or 5 mg to 200 or 500 mg of the base, e.g., from 1 or 5 or 10 mg to 15, 20, 25, 30, 40, 50, 75, 100, 150, 200, 250, 300, 350, 400, 450, 500, 1000, or 1500 mg, e.g., from 15, 20, 30, 50, or 100 to 200, 250, 400, 450, 500, 600, 700, 800, 1000, or 1500 mg.

1.5 Composition 1.3 or 1.4 wherein the base is an amine and/or a salt thereof (e.g., morpholine, an amino acid (e.g., arginine), a mono- and/or poly-hydroxyalkylamine, and/or a salt thereof e.g., $H_2NR^{20}$, $HNR^{20}R^{21}$, $NR^{20}R^{21}R^{22}$, and/or a salt thereof wherein each $R^{20}$, $R^{21}$, and $R^{22}$ are independently $C_{1-8}$-alkyl (e.g., $C_{1-6}$-alkyl, e.g. $C_{1-4}$-alkyl, e.g., $C_2$-alkyl, e.g., $-CH_3$) optionally substituted with one or more —OH (e.g., optionally substituted with 1-8 —OH, e.g., 1, 2, 3, 4, 5, or 6), e.g., tris(hydroxymethyl)aminomethane (also known as tris base) and/or a salt thereof (e.g., tris (hydroxymethyl)aminomethane acetate (also known as tris acetate), meglumine, and/or diethanolamine), e.g., any of the preceding wherein a conjugate acid of the amine and/or salt thereof has a pKa between 6, 7, 8, 9, or 10 and 11, e.g., between 6, 7, 8, or 9 and 10, e.g., between 7 and 9, e.g., between 8 and 9.

1.6 Any of Composition 1.3-1.5 wherein the base is tris base.

1.7 Any of Composition 1.3-1.6 wherein a conjugate acid of the base, e.g., an amine and/or a salt thereof, has a pKa between 6, 7, 8, 9, or 10 and 11, e.g., between 6, 7, 8, or 9 and 10, e.g., between 7 and 9, e.g., between 8 and 9.

1.8 Any of Composition 1.3-1.7 wherein a molar ratio of 2-{[3,5-bis(trifluoromethyl)phenyl]carbamoyl}-4-chlorophenyl dihydrogen phosphate to the base is at least 1:1, e.g., wherein the molar ratio of 2-{[3,5-bis (trifluoromethyl)phenyl]carbamoyl}-4-chlorophenyl dihydrogen phosphate to the base is at least 2:1.

1.9 Any of Composition 1.3-1.7 wherein the molar ratio of 2-{[3,5-bis(trifluoromethyl)phenyl]carbamoyl}-4-chlorophenyl dihydrogen phosphate to the base is at least 1:2, e.g., at least 1:2, 1:3, 1:4, or 1:5 to 1:6, 1:7, 1:8, 1:10, 1:15, 1:20, or 1:30, e.g., at least 1:2.5 to 1:5, 1:6, 1:7, 1:8, 1:9, 1:10, 1:15, 1:20, or 1:30, e.g., at least 1:2.5, e.g., at least 1:5, e.g. at least 1:10.

1.10 Any of Composition 1 et seq. wherein the composition comprises a bulking agent, e.g., one or more of mannitol, lactose, sucrose, trehalose, sorbitol, glucose, raffinose, arginine, glycine, histidine, dextran (e.g., dextran 40), polyvinylpyrrolidone, polyethylene glycol, and polypropylene glycol, e.g., one or more of mannitol, glucose, sucrose, lactose, trehalose, and dextran (e.g., dextran 40), e.g., dextran (e.g., dextran 40).

1.11 Any of Composition 1 et seq. wherein the composition comprises 5 or 10 or 50 mg to 2 or 5 g of the bulking agent, e.g., from 50 or 100 mg to 200, 300, 500, or 800 mg, or 1, 1.5, 2, 3, 4, or 5 g of the bulking agent.

1.12 Any of Composition 1 et seq. wherein the composition is a solid, e.g., the pharmaceutically acceptable excipient, e.g, the one or more bases, is a solid.

1.13 Any of Composition 1 et seq., which is suitable for admixture with an aqueous solution into a pharmaceutically acceptable liquid (e.g., a solution or suspension, e.g., a solution).

1.14 Any of Composition 1 et seq. wherein the composition is for injection, e.g., subcutaneously, intramuscularly, intravenously, or intrathecally, e.g., intramuscularly or intravenously, e.g., a bolus injected subcutaneously, intramuscularly, intravenously, or intrathecally.

1.15 Composition 1.14 wherein the composition is for injection intravenously, e.g., IV bolus and/or IV infusion, e.g., IV bolus followed by IV infusion.

1.16 Composition 1.14 wherein the composition is for injection intramuscularly, e.g., IM bolus and/or IM infusion, e.g., IM bolus followed by IM infusion.

1.17 Any of Composition 1.3-1.16 wherein the Crystalline Formula I and the base are milled together.

1.18 Composition 1 wherein the composition comprises between 20 and 500 mg Crystalline Formula I, e.g., between 25 and 450 mg, e.g., between 30 and 400 mg, e.g., between 35 and 350 mg, and a base, e.g., one or more of tris(hydroxymethyl)aminomethane, $Na_2HPO_4$, meglumine, and sodium citrate, e.g., between 15 and 1000 mg of the base, e.g., between 20 and 600 mg, e.g., between 50 and 200 mg, e.g., between 50 and 150 mg, e.g., between 10 and 1500 mg of the base, e.g., between 15 and 1000 mg, e.g., between 20 and 600 mg, e.g., between 50 and 200 mg, e.g., between 50 and 150 mg.

1.19 Composition 1.18 wherein the composition comprises between 20 and 500 mg Crystalline Formula I, e.g., between 25 and 450 mg, e.g., between 30 and 400 mg, e.g., between 35 and 350 mg, and tris(hydroxymethyl)aminomethane, e.g., between 10 and 600 mg tris(hydroxymethyl)aminomethane, e.g., between 20 and 500, e.g., between 40 and 500 mg.

1.20 Any of Composition 1 et seq. wherein the composition is stable for at least one week at room temperature, e.g., for at least 1, 2, 4, 6, 8, or 12 months, e.g., the composition has <20% N-[3,5-bis(trifluoromethyl) phenyl]-5-chloro-2-hydroxybenzamide, <15% N-[3,5-bis(trifluoromethyl)phenyl]-5-chloro-2-hydroxybenzamide, <10% N-[3,5-bis(trifluoromethyl)phenyl]-5-chloro-2-hydroxybenzamide, <5% N-[3,5-bis (trifluoromethyl)phenyl]-5-chloro-2-hydroxybenzamide, <2% N-[3,5-bis(trifluoromethyl) phenyl]-5-chloro-2-hydroxybenzamide, 1% N-[3,5-bis (trifluoromethyl)phenyl]-5-chloro-2-hydroxybenzamide, or <1% N-[3,5-bis (trifluoromethyl)phenyl]-5-chloro-2-hydroxybenzamide.

1.21 Any of Composition 1 et seq. wherein the composition comprises less than 10%, 15%, or 20% of N-[3,5-bis(trifluoromethyl)phenyl]-5-chloro-2-hydroxybenzamide, e.g., less than 5, 4, 3, or 2% of N-[3,5-bis (trifluoromethyl)phenyl]-5-chloro-2-hydroxybenzamide for at least one week, e.g., for at least 1, 2, 4, 6, 8, or 12 months.

1.22 Any of Composition 1 et seq. wherein Crystalline Formula I is any of Crystalline Form 1 et seq.

1.23 Any of Composition 1 et seq. wherein Crystalline Formula I is any of Crystalline Form 2 et seq.

1.24 Any of Composition 1 et seq. wherein Crystalline Formula I is any of Crystalline Form 5 et seq.

1.25 Any of Composition 1 et seq. wherein Crystalline Formula I is any of Crystalline Form 6 et seq.

1.26 Any of Composition 1 et seq. wherein the composition is for use in any of the methods described herein, e.g., for use in any of Method 1 et seq. and Method 2 et seq., vide infra.

1.27 Any of Composition 1 et seq. exhibiting an XRPD pattern substantially as shown in the top pattern in FIG. 47 (or as shown in FIG. 56), wherein the XRPD is obtained using Cu Kα radiation, e.g., wherein the XRPD is measured using radiation of wavelength 1.54059 Å.

1.28 Any of Composition 1 et seq. wherein an XRPD pattern of the composition comprises any of the 2-theta (°) values and/or d-spacing (Å) values (e.g., characteristic, representative, and/or major peaks) as set forth in any of Crystalline Form 1 et seq., 2 et seq., 5 et seq., or 6 et seq.

Further provided is a process (Process 4) for preparing a pharmaceutical composition comprising a mono or di-anion of 2-{[3,5-bis(trifluoromethyl)phenyl]carbamoyl}-4-chlorophenyl dihydrogen phosphate (Formula I) comprising admixing Crystalline Formula I, e.g., any of Crystalline Form 1 et seq., 2 et seq., 5 et seq., or 6 et seq., and a pharmaceutically acceptable liquid, e.g., an aqueous solution, e.g., a sterile solution. Further provided is Process 4 as follows:

4.1 Process 4.1 rein the mono-anion of Formula I is

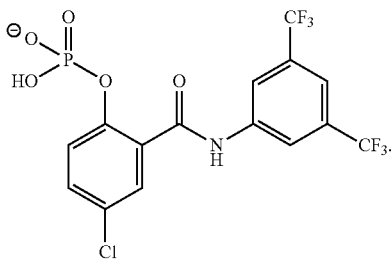 [SMILES: O=C(Nc1cc(C(F)(F)F)cc(C(F)(F)F)c1)c1cc(Cl)ccc1OP(=O)([O-])O]

4.2 Process 4 wherein the di-anion of Formula I is

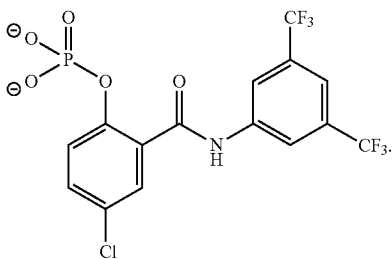 [SMILES: O=C(Nc1cc(C(F)(F)F)cc(C(F)(F)F)c1)c1cc(Cl)ccc1OP(=O)([O-])[O-]]

4.3 Any of Process 4 et seq. comprising admixing any of Composition 1 et seq. and the liquid, e.g., the aqueous solution.
4.4 Any of Process 4 et seq. wherein the concentration of the mono or di-anion is 0.01 or 0.02 or 0.05 or 0.1 or 0.5 or 1 or 2 to 250 mM, e.g., from 0.01 or 0.1 or 0.5 to 1, 2, 5, 10, 15, 20, 25, 40, 50, 60, 75, 100, 125, 150, 175, 200, 250 mM, or 1000 mM, e.g. from 1 to 2, 5, 10, 15, 20, 25, 40, 50 or 60 mM, e.g., from 5, 10, 15, 20, 25, or 50 to 100, 200, 250, 300, 400, 500, or 1000 mM, e.g., 2, 20, or 200 mM, e.g., 5, 10, 50, 500, 500, or 1000 mM.
4.5 Any of Process 4 et seq. wherein the liquid, e.g., the aqueous solution, comprises a base.
4.6 Process 4.5 wherein the base and amount thereof is as described in any of Composition 1.3-1.9, 1.12, 1.18, and 1.19, vide supra,
4.7 Any of Process 4 et seq. wherein the liquid comprises sterile water for injection optionally comprising a base as in Process 4.5 or 4.6.
4.8 Any of Process 4 et seq. wherein the liquid is a sterile solution comprising dextrose (e.g., dextrose injection 5%) optionally comprising a base as in Process 4.5 or 4.6.
4.9 Any of Process 4 et seq. wherein the liquid is a sterile solution comprising sodium chloride (e.g., 0.9% sodium chloride injection) optionally comprising a base as in Process 4.5 or 4.6.
4.10 Any of Process 4 et seq. wherein the liquid is a sterile solution comprising benzyl alcohol (e.g., bacteriostatic water for injection with benzyl alcohol or bacteriostatic sodium chloride for injection with benzyl alcohol) optionally comprising a base as in Process 4.5 or 4.6.
4.11 Any of Process 4 et seq. wherein the liquid comprises Lactated Ringer's optionally comprising a base as in Process 4.5 or 4.6.
4.12 Any of Process 4 et seq. wherein Crystalline Formula I is admixed with 0.5 to 500 mL of the liquid, e.g., the aqueous solution, e.g., any of the liquids set forth in any of Process 4.5-4.11, e.g., from 1 or 2 mL to 500 mL, e.g., from 1 or 2 mL to 5, 10, 25, 30, 35, 50, 75, 100, 150, 200, 300 or 500 mL, e.g., from 1 or 2 mL to 5, 10, 25, 50, 75, 100, or 200 mL, e.g., from 3.5 or 5 to 10, 25, 50, or 100 mL, e.g., 3.5 or 35 mL.
4.13 Any of Process 4 et seq. wherein the pharmaceutical composition has a pH between 7, 7.5, or 8 and 10.5, e.g., between 7, 7.5, or 8 and 9.5, e.g., between 7 or 7.5 and 8, e.g., between 7.5 and 8.5, e.g., 7.5, e.g., 8.5, e.g., between 8 and 8.5, e.g., 8.2.
4.14 Any of Process 4 et seq. wherein the pharmaceutical composition is for injection, e.g., subcutaneously, intramuscularly, intravenously, or intrathecally, e.g., intramuscularly or intravenously, e.g., a bolus injected subcutaneously, intramuscularly, intravenously, or intrathecally.
4.15 Any of Process 4 et seq. wherein the pharmaceutical composition is for injection intravenously, e.g., IV bolus and/or IV infusion, e.g., IV bolus followed by IV infusion.
4.16 Any of Process 4 et seq. wherein the pharmaceutical composition is for injection intramuscularly, e.g., IM bolus and/or IM infusion, e.g., IM bolus followed by IM infusion.
4.17 Any of Process 4.14-4.16 further comprising filtering the pharmaceutical composition to remove particles and microbes prior to injection.
4.18 Any of Process 4 et seq. wherein Crystalline Formula I is any of Crystalline Form 1 et seq.
4.19 Any of Process 4 et seq. wherein Crystalline Formula I is any of Crystalline Form 2 et seq.
4.20 Any of Process 4 et seq. wherein Crystalline Formula I is any of Crystalline Form 5 et seq.
4.21 Any of Process 4 et seq. wherein Crystalline Formula I is any of Crystalline Form 6 et seq.
4.22 Any of Process 4 et seq. wherein the pharmaceutical composition is prepared, e.g., admixing Crystalline Formula I and the pharmaceutically acceptable liquid, immediately or shortly before administration to a patient in need thereof.
4.23 Any of Process 4 et seq. wherein the pharmaceutical composition is prepared 24 hours or less, e.g., 12 hours or less, e.g., 10 hours or less, e.g., 8 hours or less, e.g., 2 hours or less, e.g., 1 hour or less, e.g., 30 minutes or less, e.g., 20 minutes or less, e.g., 15 minutes or less, e.g, 10 minutes or less, e.g., 5 minutes or less, e.g., 3 minutes or less, e.g., 2 minutes or less, e.g., 1 minute or less before administration to a patient in need thereof
4.24 Any of Process 4 et seq. wherein Crystalline Formula I and the base are admixed (e.g., in solid form, e.g., milled together) prior to admixture with the liquid.
4.25 Any of Process 4 or 4.1-4.23 wherein Crystalline Formula I is admixed with the liquid and wherein the liquid comprises the base.

The pH of the pharmaceutical compositions disclosed herein, e.g., any of Composition 1 et seq. when dissolved in a pharmaceutically acceptable liquid, may be adjusted to achieve the desired pH by addition of a metal hydroxide salt (e.g., NaOH and/or KOH, e.g., NaOH) to the composition.

Further provided is a kit (Kit 1) comprising a crystal comprising 2-{[3,5-bis(trifluoromethyl)phenyl]carbamoyl}-4-chlorophenyl dihydrogen phosphate (Crystalline Formula I), e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq. Further provided is Kit 1 as follows:

1.1 Kit 1 wherein the kit comprises 25 to 500 mg, e.g., from 25 to 300 or 350 mg, e.g., from 25 to 200 mg, e.g., from 15, 20, 30, 35, 50, or 100 to 150, 200, 300, 350, 400, 450, 500, 550, or 600 mg, e.g., 35 mg, e.g., 350 mg, of Crystalline Formula I.

1.2 Kit 1 or 1.1 wherein the composition comprises Crystalline Formula I in an amount sufficient to provide a dose of 0.01 or 0.1 or 0.5 mg/kg to 1 or 5 or 10 or 15 mg/kg of N-[3,5-bis(trifluoromethyl)phenyl]-5-chloro-2-hydroxybenzamide, e.g., a dose of 0.05 to 1 or 5 mg/kg, e.g., a dose of 0.05 to 0.1, 0.2, 0.3, 0.4, 0.5, 1, 5, 10 or 20 mg/kg, e.g., a dose of 0.5 to 1, 2, 3, 4, 5 or 10 or 20 mg/kg, e.g., a dose of 1 to 2, 3, 4, 5, 10, 20 or 50 mg/kg.

1.3 Kit 1 or 1.1 wherein the kit further comprises a base, e.g., wherein the base and amount thereof is as described in any of Composition 1.3-1.9, 1.12, 1.18, and 1.19, vide supra.

1.4 Kit 1.3 wherein the kit comprises 1 or 5 mg to 200 or 500 mg of the base, e.g., from 1 or 5 or 10 mg to 15, 20, 25, 30, 40, 50, 75, 100, 150, 200, 250, 300, 350, 400, 450, 500, 1000, or 1500 mg, e.g., from 15, 20, 30, 50, or 100 to 200, 250, 400, 450, 500, 600, 700, 800, 1000, or 1500 mg.

1.5 Kit 1.3 or 1.4 wherein the concentration of the base is 0.01 or 0.1 or 0.5 or 1 or 2 to 250 mM, e.g., from 0.01 or 0.1 or 0.5 to 1, 2, 5, 10, 15, 20, 25, 40, 50, 60, 75, 100, 125, 150, 175, 200, 250, or 1000 mM, e.g. from 1 to 2, 5, 10, 15, 20, 25, 40, 50 or 60 mM, e.g., from 5 to 50 mM, e.g., from 5, 10, 15, 20, 25, or 50 to 100, 200, 250, 300, 400, 500, or 1000 mM, e.g., 2, 20, or 200 mM, e.g., 5, 10, 50, 500, 500, or 1000 mM, e.g., from 5, 10, 15, 20, 25, or 50 to 100, 200, 250, 300, 400, 500, or 1000 mM.

1.6 Any of Kit 1.3-1.5 wherein the base is an amine and/or a salt thereof (e.g., morpholine, an amino acid (e.g., arginine), a mono- and/or poly-hydroxyalkylamine, and/or a salt thereof, e.g., $H_2NR^{20}$, $HNR^{20}R^{21}$, $NR^{20}R^{21}R^{22}$, and/or a salt thereof wherein each $R^{20}$, $R^{21}$, and $R^{22}$ are independently $C_{1-8}$-alkyl (e.g., $C_{1-6}$-alkyl, e.g. $C_{1-4}$-alkyl, e.g., $C_2$-alkyl, e.g., —$CH_3$) optionally substituted with one or more —OH (e.g., optionally substituted with 1-8 —OH, e.g., 1, 2, 3, 4, 5, or 6), e.g., tris(hydroxymethyl)aminomethane (also known as tris base) and/or a salt thereof (e.g., tris(hydroxymethyl)aminomethane acetate (also known as tris acetate), meglumine, and/or diethanolamine), e.g., any of the preceding wherein a conjugate acid of the amine and/or salt thereof has a pKa between 6, 7, 8, 9, or 10 and 11, e.g., between 6, 7, 8, or 9 and 10, e.g., between 7 and 9, e.g., between 8 and 9.

1.7 Any of Kit 1.3-1.6 wherein the base is tris base.

1.8 Any of Kit 1.3-1.7 wherein a conjugate acid of the base, e.g., an amine and/or a salt thereof, has a pKa between 6, 7, 8, 9, or 10 and 11, e.g., between 6, 7, 8, or 9 and 10, e.g., between 7 and 9, e.g., between 8 and 9.

1.9 Any of Kit 1.3-1.8 wherein the kit comprises a molar ratio of 2-{[3,5-bis(trifluoromethyl)phenyl]carbamoyl}-4-chlorophenyl dihydrogen phosphate to the base of at least 1:1, e.g., wherein the molar ratio of 2-{[3,5-bis(trifluoromethyl)phenyl]carbamoyl}-4-chlorophenyl dihydrogen phosphate to the base is at least 2:1.

1.10 Any of Kit 1.3-1.8 wherein the kit comprises a molar ratio of 2-{[3,5-bis(trifluoromethyl)phenyl]carbamoyl}-4-chlorophenyl dihydrogen phosphate to the one or more bases of at least 1:2, e.g., at least 1:2, 1:3, 1:4, or 1:5 to 1:6, 1:7, 1:8 to 1:10, 1:15, 1:20, or 1:30, e.g., at least 1:2.5 to 1:5, 1:6, 1:7, 1:8, 1:9, 1:10, 1:15, 1:20, or 1:30, e.g., at least 1:2.5, e.g., at least 1:5, e.g. at least 1:10.

1.11 Any of Kit 1 et seq. wherein the kit further comprises a pharmaceutically acceptable excipient, e.g., a bulking agent, e.g., one or more of mannitol, lactose, sucrose, trehalose, sorbitol, glucose, raffinose, arginine, glycine, histidine, dextran (e.g., dextran 40), polyvinylpyrrolidone, polyethylene glycol, and polypropylene glycol, e.g., one or more of mannitol, glucose, sucrose, lactose, trehalose, and dextran (e.g., dextran 40).

1.12 Kit 1.11 wherein the kit comprises 5 or 10 or 50 mg to 2 or 5 g of the bulking agent, e.g., from 50 or 100 mg to 200, 300, 500, or 800 mg, or 1, 1.5, 2, 3, 4, or 5 g of the bulking agent.

1.13 Kit 1 wherein the kit comprises between 20 and 500 mg Crystalline Formula I, e.g., between 25 and 450 mg, e.g., between 30 and 400 mg, e.g., between 35 and 350 mg, and a base, e.g., one or more of tris(hydroxymethyl)aminomethane, $Na_2HPO_4$, meglumine, and sodium citrate, e.g., between 15 and 1000 mg of the base, e.g., between 20 and 600 mg, e.g., between 50 and 200 mg, e.g., between 50 and 150 mg, e.g., between 10 and 1500 mg of the base, e.g., between 15 and 1000 mg, e.g., between 20 and 600 mg, e.g., between 50 and 200 mg, e.g., between 50 and 150 mg.

1.14 Kit 1.13 wherein the kit comprises between 20 and 500 mg Crystalline Formula I, e.g., between 25 and 450 mg, e.g., between 30 and 400 mg, e.g., between 35 and 350 mg, and tris(hydroxymethyl)aminomethane, e.g., between 10 and 600 mg tris(hydroxymethyl)aminomethane, e.g., between 20 and 500, e.g., between 40 and 500 mg.

1.15 Any of Kit 1 et seq. wherein Crystalline Formula I is suitable for admixture with an aqueous solution into a pharmaceutically acceptable liquid (e.g., a solution or suspension, e.g., a solution).

1.16 Any of Kit 1 et seq. wherein the kit comprises a pharmaceutically acceptable liquid, e.g., a sterile solution, e.g., an aqueous solution, optionally comprising a base, e.g., a base and amount thereof as described in any of Composition 1.3-1.9, 1.12, 1.18, and 1.19, vide supra, e.g., a base or amount thereof as described in any of Kit 1.3-1.10, 1.13, or 1.14.

1.17 Kit 1.16 wherein the liquid comprises sterile water for injection.

1.18 Kit 1.16 or 1.17 wherein the liquid is a sterile solution comprising dextrose (e.g., dextrose injection 5%).

1.19 Any of Kit 1.16-1.18 wherein the liquid is a sterile solution comprising sodium chloride (e.g., 0.9% sodium chloride injection).

1.20 Any of Kit 1.16-1.19 wherein the liquid is a sterile solution comprising benzyl alcohol (e.g., bacteriostatic water for injection with benzyl alcohol or bacteriostatic sodium chloride for injection with benzyl alcohol).

1.21 Any of Kit 1.16-1.20 wherein the liquid comprises Lactated Ringer's.

1.22 Any of Kit 1.16-1.21 wherein the kit comprises 0.5 to 500 mL of the liquid, e.g., an aqueous solution, e.g., from 1 or 2 mL to 500 mL, e.g., from 1 or 2 mL to 5, 10, 25, 30, 35, 50, 75, 100, 150, 200, 300 or 500 mL, e.g., from 1 or 2 mL to 5, 10, 25, 50, 75, 100, or 200 mL, e.g., from 3.5 or 5 to 10, 25, 50, or 100 mL, e.g., 3.5 or 35 mL.

1.23 Any of Kit 1 et seq. wherein the kit comprises a pharmaceutical composition comprising Crystalline Formula I, e.g., any of Composition 1 et seq.

1.24 Any of Kit 1 et seq. wherein the components of the kit are present in the same container or one or more different containers.

1.25 Kit 1.24 wherein Crystalline Formula I and the base are in the same container (Container 1) and the liquid is in a different container (Container 2).

1.26 Kit 1.24 wherein the liquid and the base are in the same container (Container 1) and Crystalline Formula I is in a different container (Container 2).

1.27 Kit 1.24 wherein Crystalline Formula I is in a container (Container 1), the base is in a different container (Container 2), and the liquid is in a further different container (Container 3).

1.28 Any of Kit 1.25-1.27 wherein the pharmaceutically acceptable excipient is in Container 1.

1.29 Any of Kit 1.25-1.27 wherein the pharmaceutically acceptable excipient is in Container 2.

1.30 Kit 1.27 wherein the pharmaceutically acceptable excipient is in Container 3.

1.31 Kit 1.24 wherein each of Crystalline Formula I, the base, the liquid, and the pharmaceutically acceptable excipient are in separate containers.

1.32 Any of Kit 1 et seq. wherein Crystalline Formula I is any of Crystalline Form 1 et seq.

1.33 Any of Kit 1 et seq. wherein Crystalline Formula I is any of Crystalline Form 2 et seq.

1.34 Any of Kit 1 et seq. wherein Crystalline Formula I is any of Crystalline Form 5 et seq.

1.35 Any of Kit 1 et seq. wherein Crystalline Formula I is any of Crystalline Form 6 et seq.

1.36 Any of Kit 1 et seq. wherein the kit comprises instructions, e.g., instructions for using 2-{[3,5-bis(trifluoromethyl)phenyl]carbamoyl}-4-chlorophenyl dihydrogen phosphate to treat or control a disease or condition mediated by an aquaporin (e.g., to treat any of the diseases or conditions described herein, e.g., for use in any of Method 1 et seq. and Method 2 et seq., vide infra), e.g., instructions for administering 2-{[3,5-bis(trifluoromethyl)phenyl]carbamoyl}-4-chlorophenyl dihydrogen phosphate to a patient in need thereof, e.g., instructions for mixing Crystalline Formula I with the base and/or the liquid, e.g., instructions for using the pharmaceutical composition of Kit 1.23 to treat or control a disease or condition mediated by an aquaporin (e.g., to treat any of the diseases or conditions described herein, e.g., for use in any of Method 1 et seq. and Method 2 et seq., vide infra), e.g., instructions for administering the pharmaceutical composition of Kit 1.23 to a patient in need thereof, e.g., instructions for preparing the pharmaceutical composition of Kit 1.23.

1.37 Any of Kit 1 et seq. wherein the kit is for use in any of the methods described herein, e.g., for use in any of Method 1 et seq. and Method 2 et seq., vide infra.

Further provided is a method (Method 1) of treating or controlling a disease or condition mediated by an aquaporin, e.g., diseases or conditions of water imbalance and other diseases, in a patient in need thereof comprising administering to the patient an effective amount (or a pharmaceutical composition comprising an effective amount) of a crystal comprising 2-{[3,5-bis(trifluoromethyl)phenyl]carbamoyl}-4-chlorophenyl dihydrogen phosphate, e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq. Further provided is Method 1 as follows:

1.1 Method 1 wherein the disease or condition is selected from edema, epilepsy, neuromyelitis optica, a migraine, hyponatremia, retinal ischemia or other diseases of the eye associated with abnormalities in intraocular pressure and/or tissue hydration, excessive fluid retention, myocardial ischemia, myocardial infarction, myocardial hypoxia, congestive heart failure, and sepsis.

1.2 Method 1 or 1.1 wherein the disease or condition is edema, e.g., edema of the brain or spinal cord.

1.3 Method 1.2 wherein the disease or condition is cerebral edema, e.g., cerebral edema consequent to ischemic stroke, e.g., cytotoxic cerebral edema, e.g., cytotoxic cerebral edema consequent to ischemic stroke.

1.4 Method 1.3 wherein the disease or condition is cerebral edema, e.g., cytotoxic cerebral edema, consequent to trauma (e.g., head trauma), a stroke (e.g., an ischemic stroke), a traumatic brain injury, glioma, meningitis, acute mountain sickness, an epileptic seizure, an infection, a metabolic disorder, hypoxia (including general systemic hypoxia and hypoxia due to cardiac arrest or other interruption of blood perfusion to the brain), water intoxication, hepatic failure, hepatic encephalopathy, or diabetic ketoacidosis, e.g., consequent to head trauma, e.g., consequent to a stroke (e.g., an ischemic stroke), e.g., consequent to a traumatic brain injury, e.g., consequent to hypoxia due to cardiac arrest or other interruption of blood perfusion to the brain.

1.5 Method 1.3 wherein the disease or condition is cerebral edema, e.g., cytotoxic cerebral edema, consequent to microgravity exposure, radiation exposure, an invasive central nervous system procedure (e.g., neurosurgery, endovascular clot removal, spinal tap, aneurysm repair, or deep brain stimulation), an abscess, eclampsia, Creutzfeldt-Jakob disease, or lupus cerebritis.

1.6 Method 1.2 wherein the disease or condition is spinal cord edema, e.g., spinal cord edema consequent to spinal cord trauma, e.g., spinal cord compression.

1.7 Method 1.2 wherein the disease or condition is retinal edema, optic nerve edema consequent to microgravity or radiation exposure, edema consequent to hypoxia, or cardiac edema (e.g., cardiac edema consequent to cardiac ischemia or other interruption of blood flow to the heart).

1.8 Method 1 or 1.1 wherein the disease or condition is selected from hyponatremia and excessive fluid retention, e.g., hyponatremia or excessive fluid retention consequent to heart failure, liver cirrhosis, nephrotic disorder, or syndrome of inappropriate antidiuretic hormone secretion (SIADH).

1.9 Method 1 wherein the disease or condition is selected from glioblastoma, ovarian hyperstimulation syndrome, pulmonary edema, fibromyalgia, and multiple sclerosis.

1.10 Any of Method 1 et seq., wherein the disease or condition is described in International Publication No. WO 2013/169939 (U.S. national stage application published as U.S. Patent Publication No. 2015/0133405) or International Publication Nos. WO 2015/069948 (U.S. National Stage application Ser. No. 15/034,543), WO 2015/069956 (U.S. National Stage application Ser. No. 15/035,006), WO 2015/069961 (U.S. National Stage application Ser. No. 15/034,274), or WO 2016/077787, each of which is hereby incorporated by reference in its entirety.

Further provided is a method (Method 2) for treatment or prophylaxis of transplant rejection, inhibiting rejection of transplanted biological material, or prophylaxis, treatment, or control of edema consequent to a transplant, in a patient in need thereof comprising administering to the patient an effective amount (or a pharmaceutical composition comprising an effective amount) of a crystal comprising 2-{[3,5-bis(trifluoromethyl)phenyl]carbamoyl}-4-chlorophenyl dihydrogen phosphate, e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq. Further provided is Method 2 as follows:

2.1 Method 2 comprising treatment or prophylaxis of transplant rejection.

2.2 Method 2 comprising inhibiting rejection of transplanted biological material.

2.3 Method 2 comprising prophylaxis, treatment, or control of edema consequent to a transplant.

2.4 Any of Method 2 et seq. wherein the rejection or edema, e.g., transplant rejection, e.g., edema, is consequent to transplant of an organ (e.g., a kidney, the liver, the pancreas, a lung, the heart, the thymus, the intestine, the uterus, e.g., the heart) or a portion thereof 2.5 Any of Method 2 or 2.1-2.3 wherein the rejection or edema, e.g., transplant rejection, e.g., edema, is consequent to a face, limb (e.g., hand), eye, trachea, muscle, or esophagus transplant.

2.6 Any of Method 2 et seq. wherein the transplant rejection is hyperacute or accelerated rejection, e.g., hyperacute rejection, e.g., accelerated rejection.

2.7 Any of Method 2 or 2.1-2.5 wherein the transplant rejection is acute rejection.

2.8 Any of Method 2 or 2.1-2.5 wherein the transplant rejection is chronic rejection.

2.9 Any of Method 2 et seq., wherein the transplant rejection, inhibiting rejection of transplanted biological material, or prophylaxis, treatment, or control of edema consequent to a transplant is as described in International Application No. PCT/US2015/060731, which is hereby incorporated by reference in its entirety.

Further provided is a method for protection of a heart during heart surgery, e.g., open heart surgery, in a patient in need thereof comprising administering to the patient an effective amount (or a pharmaceutical composition comprising an effective amount) of a crystal comprising 2-{[3,5-bis(trifluoromethyl)phenyl]carbamoyl}-4-chlorophenyl dihydrogen phosphate, e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq.

Further provided is (i) a crystal comprising 2-{[3,5-bis(trifluoromethyl)phenyl]carbamoyl}-4-chlorophenyl dihydrogen phosphate (Formula I) as described herein, e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq., for use in any method or in the treatment of any disease or condition as described herein, (ii) a crystal comprising 2-{[3,5-bis(trifluoromethyl)phenyl]carbamoyl}-4-chlorophenyl dihydrogen phosphate (Formula I) as described herein, e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq., (in the manufacture of a medicament) for treating any disease or condition as described herein, (iii) a pharmaceutical composition comprising a crystal comprising 2-{[3,5-bis(trifluoromethyl)phenyl]carbamoyl}-4-chlorophenyl dihydrogen phosphate as described herein, e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq., in combination or association with a pharmaceutically acceptable diluent or carrier, e.g., any of Composition 1 et seq., and (iv) a pharmaceutical composition comprising a crystal comprising 2-{[3,5-bis(trifluoromethyl)phenyl]carbamoyl}-4-chlorophenyl dihydrogen phosphate (Formula I) as described herein, e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq., in combination or association with a pharmaceutically acceptable diluent or carrier, e.g., any of Composition 1 et seq. for use in the treatment of any disease or condition as described herein.

DETAILED DESCRIPTION

Figure 1:
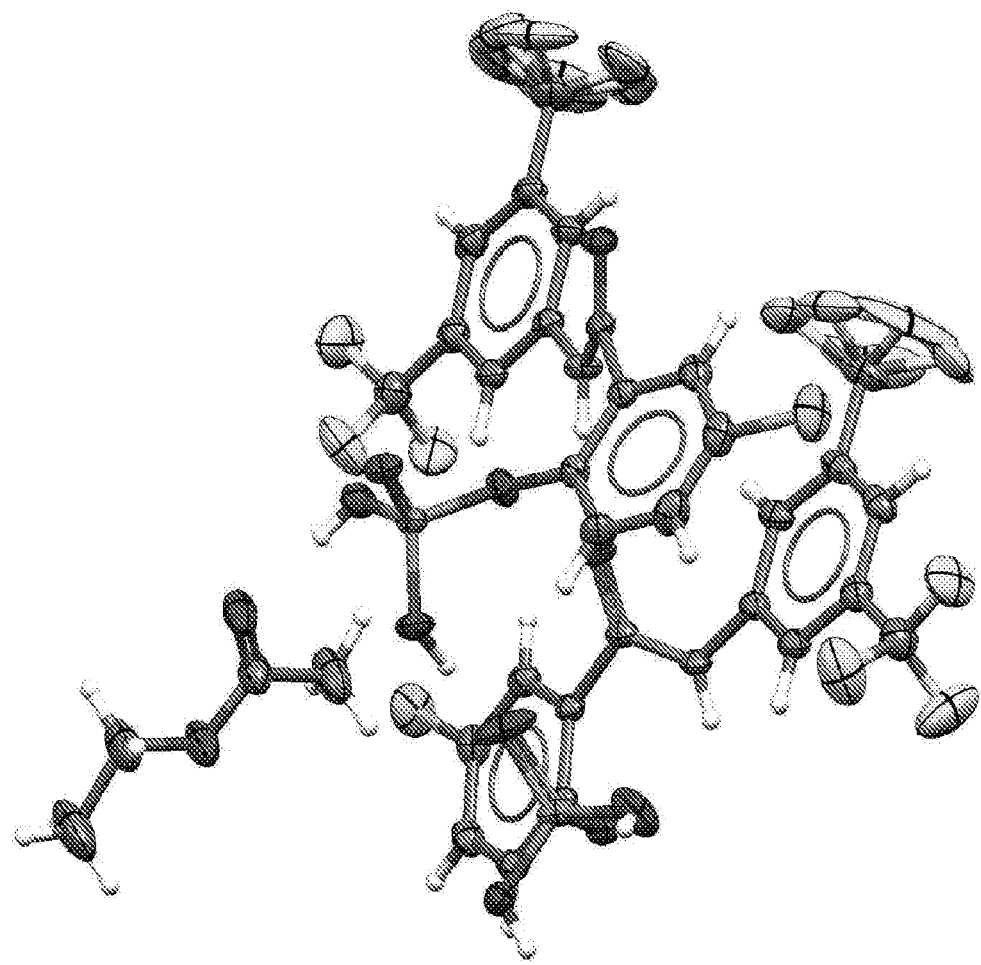
FIG. 1 depicts an atomic displacement ellipsoid drawing of the asymmetric unit of Form A. Atoms are represented by 50% probability anisotropic thermal ellipsoids.

The crystallinity, morphology, and properties of the crystals described herein, e.g., any of Crystalline Form 1 et seq., Crystalline Form 2 et seq., Crystalline Form 3 et seq., Crystalline Form 4 et seq., Crystalline Form 5 et seq., and Crystalline Form 6 et seq., may be determined by a number of methods, including, but not limited to single crystal X-ray diffraction, X-ray powder diffraction, polarizing optical microscopy, thermal microscopy, differential scanning calorimetry (DSC), thermogravimetric analysis (TGA), dynamic (water) vapor sorption, infrared absorption spectroscopy, and Raman spectroscopy.

It is to be understood that an XRPD pattern of a given sample may vary (standard deviation) depending on the instrument used, the time and temperature of the sample when measured, and standard experimental errors. Therefore, the 2-theta values (° 2θ), d-spacing values, heights and relative intensity of the peaks will have an acceptable level of deviation. For example, the values may have an acceptable deviation of e.g., 20%, 15%, 10%, 5%, 3%, 2% or 1%. In a particular embodiment, the 2-theta (°) values or the d-spacing (Å) values of the XRPD patterns of the crystalline forms described herein may have an acceptable deviation of ±0.2° and/or ±0.2 Å. Further, the XRPD patterns of the crystalline forms described herein may be identified by characteristic peak(s) as recognized by one skilled in the art. For example, the crystalline forms disclosed herein, e.g., any of Crystalline Form 1 et seq., 2 et seq., 3 et seq., 4 et seq., or 5 et seq. may be identified by, e.g., two characteristic peaks, in some instances, three characteristic peaks, in another instance, five characteristic peaks. Therefore, the term "substantially as" shown in a particular figure refers to any crystal which has an XRPD having the major and/or characteristic and/or representative peaks as recognized by one skilled in the art.

It is also to be understood that the differential scanning calorimetry and thermogravimetric analysis thermograms of a given sample may vary (standard deviation) depending on the instrument used, the time and temperature of the sample when measured, and standard experimental errors. The temperature value itself may deviate by ±10° C., preferably ±5° C., preferably ±3° C. of the reference temperature.

Per USP guidelines, variable hydrates and solvates may display peak variances greater than ±0.2° 2θ. Accordingly, peak variances of ±0.2° 2θ may not be applicable to these materials.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "representative peaks." In general, the more data collected to determine representative peaks, the more confident one can be of the classification of those peaks.

"Characteristic peaks," to the extent they exist, are a subset of representative peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2 °2θ. Not all crystalline polymorphs of a compound necessarily have at least one characteristic peak.

As used herein, "XRPD" means X-ray powder diffraction.

As used herein, "patient" includes human and non-human. In one embodiment, the patient is a human. In another embodiment, the patient is a non-human.

As used herein, "bolus" refers to administration of a therapeutic agent in a single injection that lasts for a relatively short period of time, e.g., 60 minutes or less, 30 minutes or less, 20 minutes or less, 10 minutes or less, 5 minutes or less, e.g., 3 minutes or less, e.g., 1 minute or less. A bolus may rapidly deliver a therapeutically effective amount of a therapeutic agent to the blood.

As used herein, the term "solvate" refers to a crystal containing either stoichiometric or nonstoichiometric amounts of a solvent incorporated within the crystal structure.

As used herein, the term "non-solvate" refers to a crystal that is free or substantially free of solvent molecules within the crystal structure.

As used herein, the term "hydrate" refers to a crystal containing either stoichiometric or nonstoichiometric amounts of water incorporated within the crystal structure.

As used herein, the term "non-hydrate" refers to a crystal that is free or substantially free of water molecules within the crystal structure.

As used herein, "stoichiometric hydrate" refers to a crystalline material with a defined water content over an extended relative humidity (RH) range.

As used herein, "variable hydrate" refers to a crystalline material with variable water content over an extended relative humidity (RH) range, yet with no phase change.

As used herein, the term "amorphous" refers to solids of disordered arrangements of molecules and do not possess a distinguishable crystal lattice.

As used herein, "anti-solvent" means a solvent in which 2-{[3,5-bis(trifluoromethyl)phenyl]carbamoyl}-4-chlorophenyl dihydrogen phosphate (Formula I) has low solubility or is insoluble. For instance, an anti-solvent includes a solvent in which 2-{[3,5-bis(trifluoromethyl)phenyl]carbamoyl}-4-chlorophenyl dihydrogen phosphate (Formula I) has a solubility of less than 35 mg/ml, e.g., a solubility of 10-30 mg/ml, e.g., a solubility of 1-10 mg/ml, e.g., a solubility of less than 1 mg/ml.

As used herein, "Crystalline Formula I" means a crystal comprising 2-{[3,5-bis(trifluoromethyl)phenyl]carbamoyl}-4-chlorophenyl dihydrogen phosphate (Formula I), e.g., any of Crystalline Form 1 et seq., Crystalline Form 2 et seq., Crystalline Form 5 et seq., and Crystalline Form 6 et seq., e.g., any of Crystalline Form 1 et seq., e.g., any of Crystalline Form 5 et seq.

In some embodiments, the base used herein is a solid.

In some embodiments, "base" as used herein is any inorganic or organic Bronsted base.

The wavelength used to calculate the d-spacing (Å) values herein is 1.5405929 Å, the Cu—$K_{\alpha 1}$ wavelength (Holzer, G. et al., E. *Phys. Rev.*, 1997, A56 (6), 4554-4568). Variability associated with d-spacing estimates is calculated from the USP recommendation, at each d-spacing, and provided in the respective data tables.

EXAMPLES

Example 1—General Procedures

Example 1A—General XRPD Procedure

XRPD patterns are collected with a PANalytical X'Pert PRO MPD diffractometer using an incident beam of Cu radiation produced using an Optix long, fine focus source. An elliptically graded multilayer mirror is used to focus Cu Kα X-rays through the specimen and onto the detector. Prior to the analysis, a silicon specimen (NIST SRM 640e) is analyzed to verify the Si 111 peak position. A specimen of the sample is sandwiched between 3-μm-thick films and analyzed in transmission geometry. A beam stop, short anti-scatter extension, and an anti-scatter knife edge are used to minimize the background generated by air. Soller slits for the incident and diffracted beams are used to minimize broadening from axial divergence. Diffraction patterns are collected using a scanning position-sensitive detector (X'Celerator) located 240 mm from the specimen and Data Collector software v. 2.2b.

Peaks within a range of up to about 30° 2θ are selected. Rounding algorithms are used to round each peak to the nearest 0.1° or 0.01° 2θ, depending on the instrument used to collect the data and/or the inherent peak resolution. Peak position variabilities are given to within ±0.2° 2θ. Third party measurements on independently prepared samples on different instruments may lead to variability which is greater than ±0.2° 2θ.

Prominent peaks are selected from observed peaks by identifying preferably non-overlapping, low-angle peaks, with strong intensity.

Example 1B—XRPD Indexing

Within the figure referenced for a given indexed XRPD pattern, agreement between the allowed peak positions, marked with bars, and the observed peaks indicates a consistent unit cell determination. Successful indexing of a pattern indicates that the sample is composed primarily of a single crystalline phase unless otherwise stated. To confirm the tentative indexing solution, the molecular packing motifs within the crystallographic unit cells must be determined. No attempts at molecular packing are performed.

Example 1C—Differential Scanning Calorimetry (DSC)

a. Standard DSC

DSC is performed using a TA Instruments 2920 differential scanning calorimeter. Temperature calibration is performed using NIST-traceable indium metal. The sample is placed into an aluminum DSC pan, covered with a lid, and the weight is accurately recorded. A weighed aluminum pan configured as the sample pan is placed on the reference side of the cell. The method code for a thermogram is an abbreviation for the start and end temperature as well as the heating rate; e.g., (−30)-250-10 means "from −30° C. to 250° C., at 10° C./min." The abbreviation TOC indicates use of a Tzero crimped pan.

b. Modulated DSC

Modulated DSC data are obtained on a TA Instruments Q2000 differential scanning calorimeter equipped with a refrigerated cooling system (RCS). Temperature calibration is performed using NIST-traceable indium metal. The sample is placed into an aluminum DSC pan, and the weight is accurately recorded. The pan is covered with a lid and the lid is crimped. A weighed, crimped aluminum pan is placed on the reference side of the cell. Data are obtained using a modulation amplitude of ±1.00° C. and a 60 second period with an underlying heating rate of 2° C./minute from 2 to 200° C. The reported glass transition temperatures are obtained from the inflection point of the step change in the reversing heat flow versus temperature curve.

Example 1D—Dynamic Vapor Sorption (DVS)

Dynamic vapor sorption (DVS) data are collected on a VTI SGA-100 Vapor Sorption Analyzer. NaCl and PVP are used as calibration standards. Samples are not dried prior to analysis. Sorption and desorption data are collected over a range from 5% to 95% relative humidity (RH) at 10% RH increments under a nitrogen purge. The equilibrium criterion used for analysis is less than 0.0100% weight change in 5 minutes with a maximum equilibration time of 3 hours. Data are not corrected for the initial moisture content of the samples.

Example 1E—Thermogravimetry (TGA)

TG analyses are performed using a TA Instruments Discovery or Q5000 IR thermogravimetric analyzer. Temperature calibration is performed using nickel and Alumel™. Each sample is placed in an aluminum pan. The sample is hermetically sealed, the lid pierced, then inserted into the TG furnace. The furnace is heated under nitrogen. The data are collected at a ramp rate of 10° C./min.

Example 1F—Energy-Dispersive X-Ray Spectroscopy (EDX)

EDX is performed using an EDAX™ Sapphire X-ray detector mounted on an FEI Quanta 200 SEM. Data are collected and analysed using EDAX Genesis software (v. 3.5). The detector is calibrated using NIST-traceable aluminum and copper. Samples are prepared for analysis by placing a small amount on a carbon adhesive tab supported on an aluminum mount. Analysis time, recorded in detector live time, is 200 seconds and uses a 10 μs amp time and a 15 kV beam voltage.

Example 1G—Karl Fischer Coulometric Titration Analysis (KF)

Coulometric Karl Fischer analysis for water determination is performed using a Mettler Toledo DL39 Karl Fischer titrator with a Stromboli oven attachment. Two replicates of the sample are placed into the drying oven set at a temperature of approximately 130-140° C. The drying oven is purged into the titrator vessel with dry nitrogen. The samples are then titrated by means of a generator electrode, which produces iodine by electrochemical oxidation: $2I-\rightarrow I_2+2e-$. A NIST-traceable water standard (Hydranal Water Standard 10.0) is analyzed to check the operation of the coulometer.

Example 1H—Crash Cool (CC)

A concentrated solution of Formula I is prepared in a solvent at an elevated temperature. The solution is optionally filtered warm through a 0.2-μm nylon filter into a warm vial. The solution is capped and placed directly in the freezer for crash cooling. The solution is allowed to remain in the freezer for a period of time and any solids present are collected.

Example 1I—Crash Precipitation (CP)

A solution of Formula I is prepared in a solvent. The solution is optionally filtered through a 0.2-μm nylon filter. An aliquot of an anti-solvent is dispensed with stirring until precipitation occurs. Solids are isolated.

Example 1J—Fast Cool (FC)

A concentrated solution of Formula I is prepared in a solvent at an elevated temperature. The solution is optionally filtered warm through a 0.2-μm nylon filter into a warm vial. The solution is capped and placed directly on a lab bench to quickly cool to room temperature. The solution is allowed to remain at ambient conditions for a period of time and any solids present are collected.

Example 1K—Slow Evaporation (SE)

A solution of Formula I is prepared in a solvent. The solution is optionally filtered through a 0.2-μm nylon filter. The solution is allowed to evaporate under conditions conducive to slow evaporation, such as a loosely capped vial or a vial covered with perforated aluminum foil. The solution is allowed to evaporate to dryness unless the procedure is a partial slow evaporation (solid present with a small amount of solvent remaining). Solids are isolated.

Example 2A—2-{[3,5-bis(trifluoromethyl)phenyl] carbamoyl}-4-chlorophenyl Dihydrogen Phosphate Ethyl Acetate Solvate (Form A)

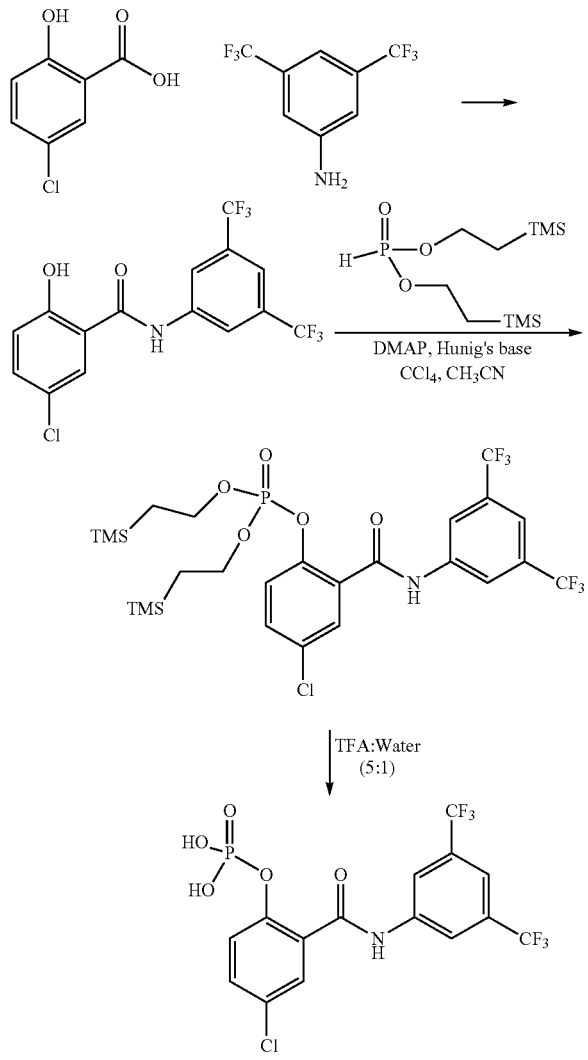

Step 1:

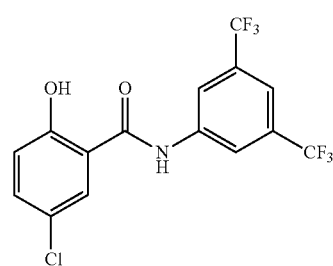 [SMILES: O=C(Nc1cc(C(F)(F)F)cc(C(F)(F)F)c1)c1cc(Cl)ccc1O]

5-chloro salicylic acid (43.7 g, 300 mmol, 1 eq) is dissolved in toluene (1500 mL) under N₂ atmosphere, then phosphorus trichloride (10.5 mL, 150 mmol, 0.5 eq) is added dropwise followed by 3,5-bis(trifluoromethyl)aniline (50 g, 228 mmol, 0.87 eq). The reaction mixture is stirred under reflux for 12 h then cooled to room temperature. Another 0.1 eq of phosphorous trichloride (2 ml) is added and the reaction is heated for 4 more hours, cooled, and 1 L ethyl acetate is added. The reaction mixture is poured onto 1 kg column of silica gel and the silica gel column is eluted with 3 L ethyl acetate to give 70 g of product after evaporation of solvent. $^1$H NMR (400 MHz, CDCl$_3$): δ 11.35 (bs, 1H), 10.85 (bs, 1H), 8.40 (s, 2H), 7.80-7.79 (m, 2H), 7.50 (dd, 1H), 7.00 (d, 1H).

Step 2:

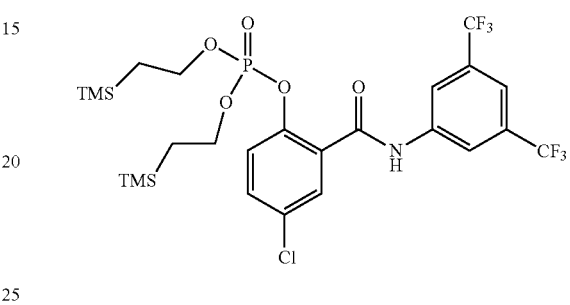

N-(3,5-bis(trifluoromethyl)phenyl)-5-chloro-2-hydroxy-benzamide (40.0 g, 0.1 mol, 1 eq) is dissolved in CH$_3$CN (400 mL) then DMAP (0.8 g, 0.001 mol, 0.06 eq), Hunig's base (34 mL, 0.21 mol, 2 eq), and CCl$_4$ (82.02 g, 0.52 mol, 5 eq) are added in this order. The solution is cooled to 0° C. and ((CH$_3$)$_3$SiCH$_2$CH$_2$O)$_2$P(O)H (46 g, 0.16 mol, 1.5 eq) in CH$_3$CN (50 mL) is added dropwise. The reaction mixture is stirred at room temperature for 20 h, then water is added (6 L) and extracted twice with EtOAc (2 L). The combined organic layers are washed with a saturated solution of NaCl, dried over Na$_2$SO$_4$, filtered, and the solvent is concentrated in vacuo to give the crude material which is used as such for next step. $^1$H NMR (200 MHz, CDCl$_3$): δ 10.20 (bs, 1H), 8.32 (s, 2H), 7.90 (s, 1H), 7.62 (s, 1H), 7.45-7.40 (m, 1H), 7.30-7.28 (m, 1H), 4.40-4.30 (m, 4H), 1.20-1.00 (m, 4H), 0.0 (s, 18H).

Step 3:

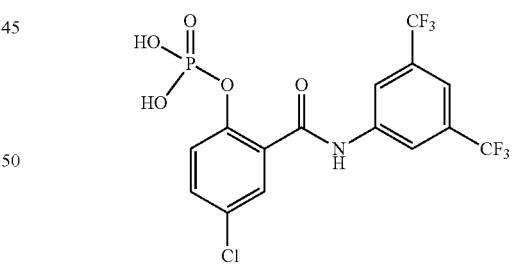

2-((3,5-bis(trifluoromethyl)phenyl)carbamoyl)-4-chloro-phenyl bis(2-(trimethylsilyl)ethyl) phosphate (64 g, 0.1 mol, 1 eq) is dissolved in a mixture TFA:water (5:1, 500 mL). The reaction mixture is stirred at room temperature for 2 h, then solvent is concentrated. The crude oil is dissolved in 1 L of water containing 0.4 moles of NaOH (16 g). The cloudy solution is extracted twice with 1 L of ethyl acetate. The aqueous phase is acidified to pH 1 with concentrated HCl and extracted twice with 1.5 L of ethyl acetate. Combined ethyl acetate fractions are dried with sodium sulphate and evaporated to give 24 grams of off white solid which is crystalline by XRPD. Mass spec M+1=463.9946, calc for C15H10ClF6NO5P=463.9889. $^1$H NMR (400 MHz, CD$_3$OD): δ 8.38 (s, 2H), 7.78 (s, 1H), 7.70 (s, 1H), 7.55-7.50 (m, 1H), 7.45-7.43 (m, 1H). $^1$H NMR (600 MHZ, DMSO d6): δ 11.2 (s, 1H), 8.07 (s, 2H), 7.8 (s, 1H), 7.75 (s, 1H), 7.70 (d, 1H), 7.4 (d, 1H).

Elemental analysis: 39.67% C, 2.23% H, 2.87% N, 7.15% Cl, 20.49% F, 6.28% P

Ion chromatography (IC) and inductively coupled plasma-optical emission spectrometry (ICP-OES) (Na$^+$ analysis): 0.18% Na$^+$ by IC, 0.19% Na$^+$ by ICP-OES (acid digestion)

Figure 12:
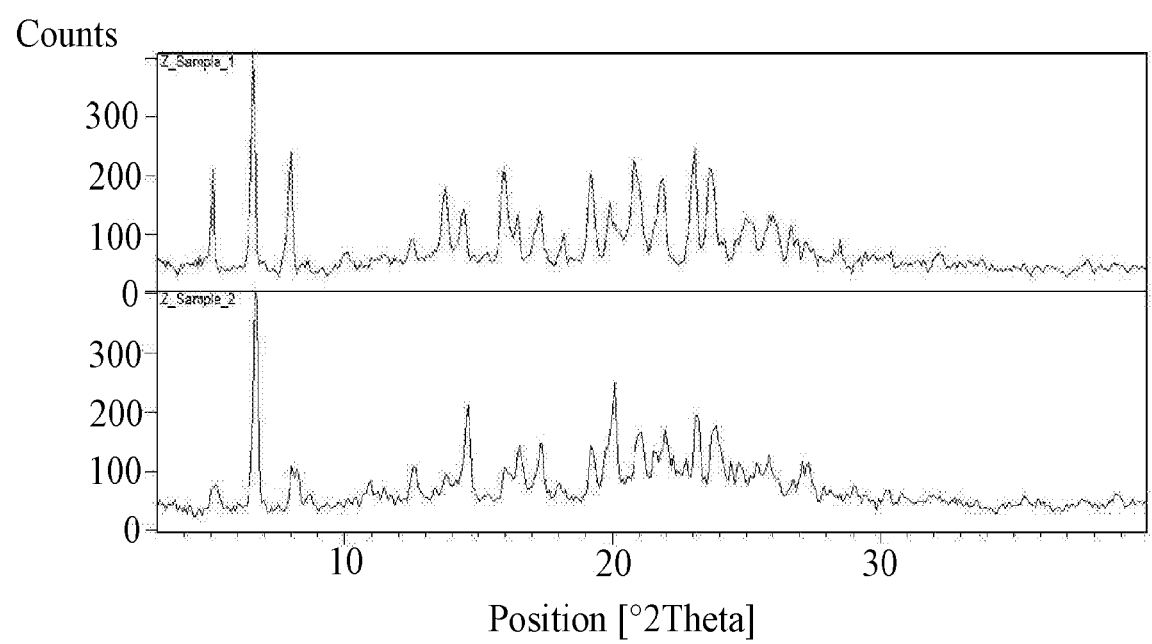
FIGS. 12a (top) and 12b (bottom) depict XRPD patterns of Form A collected using a copper source.

XRPD patterns of 2-{[3,5-bis(trifluoromethyl)phenyl]carbamoyl}-4-chlorophenyl dihydrogen phosphate ethyl acetate solvate prepared as described in this example are shown in FIGS. 12a and 12b. The XRPDs are obtained with a Bruker D2 phaser using a copper source.

Figure 10:
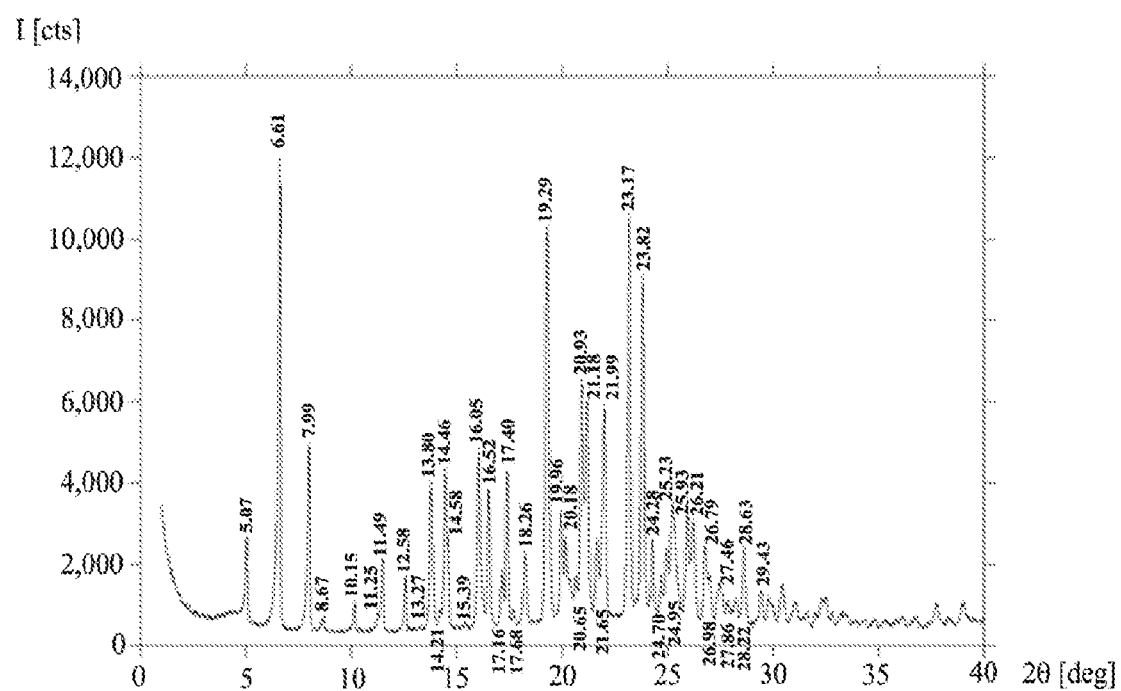
FIG. 10 depicts an XRPD pattern of Form A collected with Cu Kα radiation.
Figure 31:
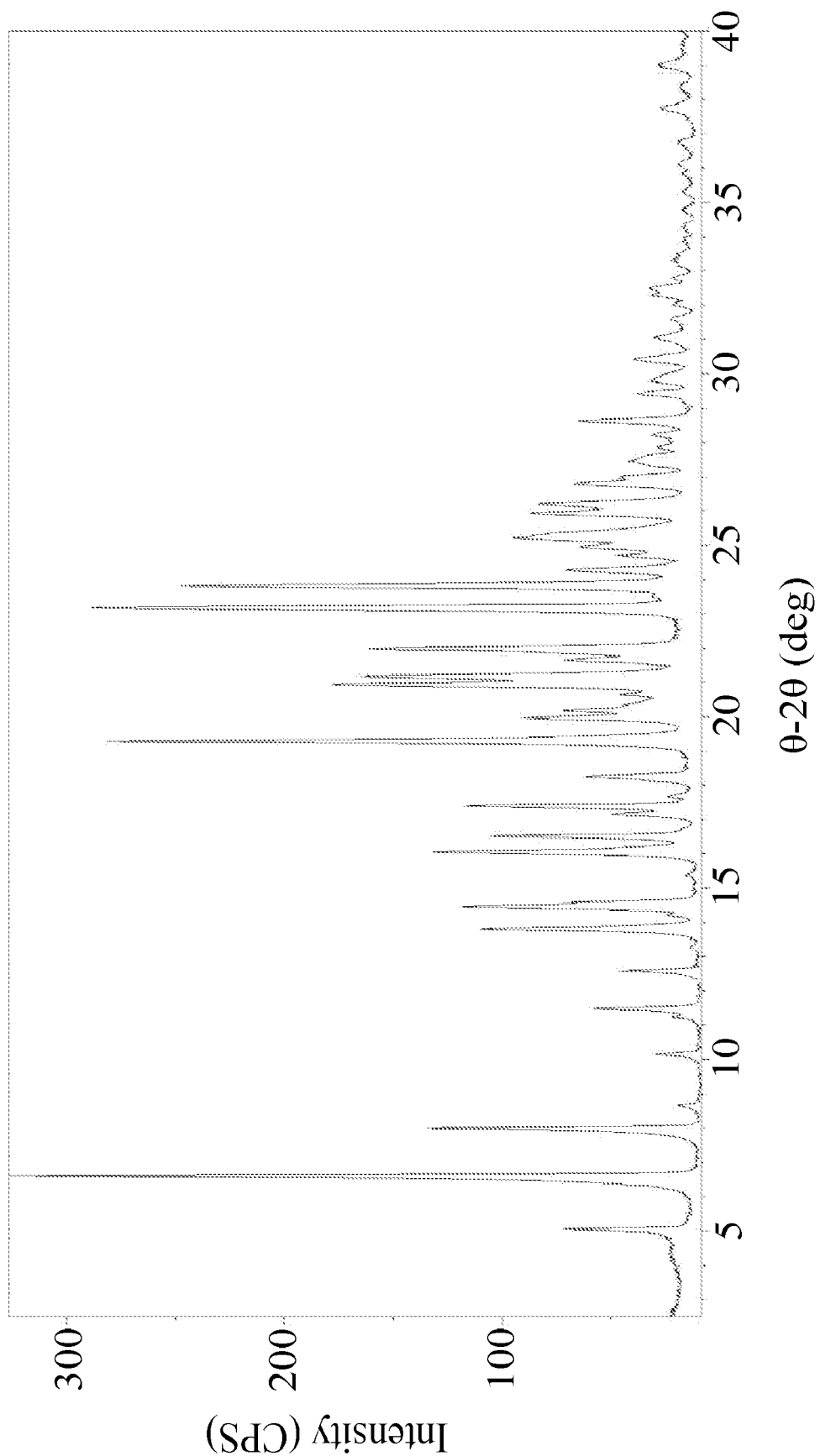
FIG. 31 depicts an XRPD pattern of Form A collected with Cu Kα radiation.

An XRPD pattern of 2-{[3,5-bis(trifluoromethyl)phenyl]carbamoyl}-4-chlorophenyl dihydrogen phosphate ethyl acetate solvate prepared as described in this example is shown in FIG. 10. The XRPD pattern is also shown in FIG. 31. The XRPD pattern is obtained as described in the general XRPD procedure in Example 1. 2-theta values, d-spacings, and peak intensities for the XRPD pattern shown in FIGS. 10 and 31 are provided above in Table B in Crystalline Form 1.21. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.01-39.98° 2θ, Step Size: 0.017° 2θ, Collection Time: 717 s, Scan Speed 3.3°/min, Slit: DS: ½°, SS: null, Revolution Time: 1.0 s, Mode: Transmission.

The XRPD pattern in FIG. 10 (also shown in FIG. 31) is successfully indexed indicating that the material consists primarily or exclusively of a single crystalline phase. The unit cell volume obtained from the indexing solution can accommodate Formula I with up to ~0.5 mole EtOAc per mole of Formula I.

$^1$H NMR shows 0.4 moles EtOAc per mole of 2-{[3,5-bis(trifluoromethyl)phenyl]carbamoyl}-4-chlorophenyl dihydrogen phosphate.

Figure 25:
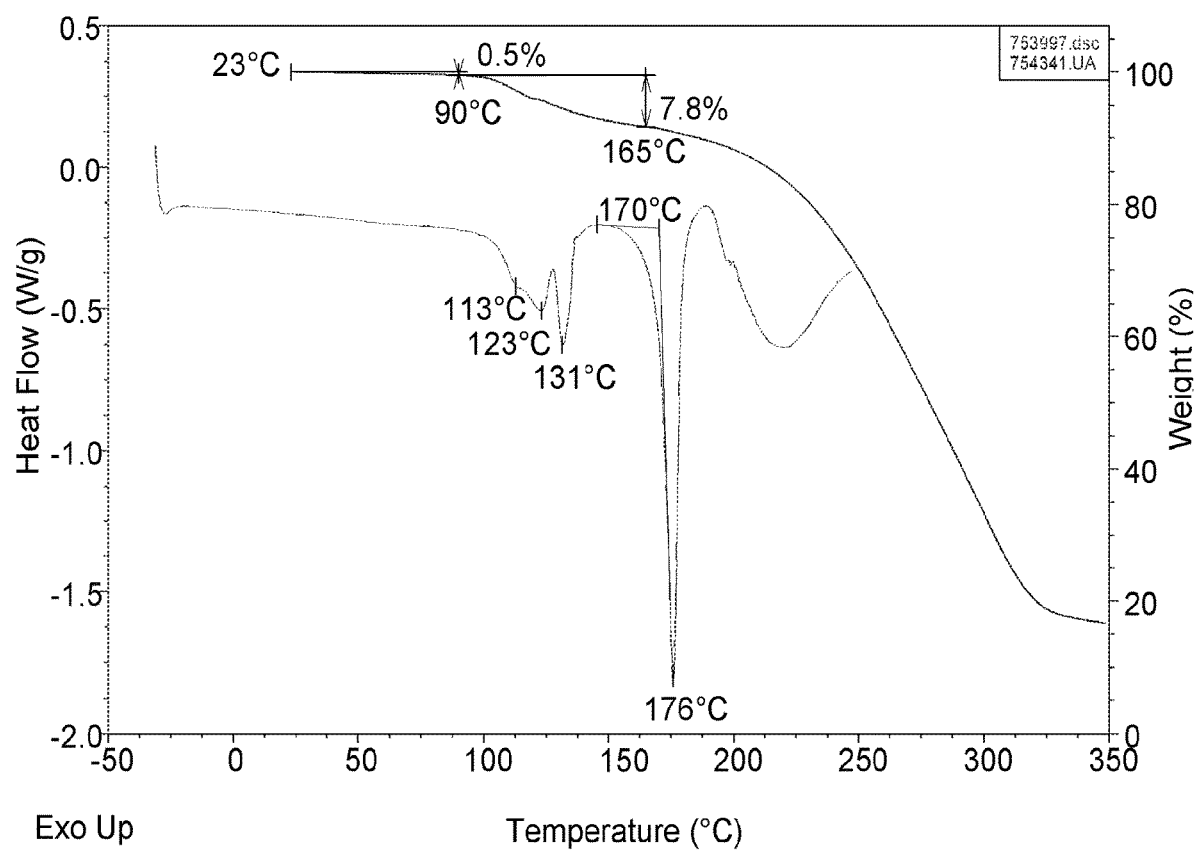
FIG. 25 depicts a DSC and TGA overlay for Form A.

An overlay of DSC and TGA thermograms are shown in FIG. 25 (DSC Parameters: Size: 2.5900 mg, Method: (−30)-250-10, TOC, Instrument: 2920 MDSC V2.6A, TGA: 12.8974 mg). Weight loss of 0.5 weight % is observed between 23° C. to 90° C. Weight loss of 7.8 weight % is observed between 90° C. and 165° C. Assuming EtOAc is the only volatile during this weight loss, the weight loss is equivalent to 0.4 moles EtOAc. Overlapping endothermic events occur with peak maxima at 113° C., 123° C., and 131° C., likely corresponding with desolvation. A sharp endotherm is observed at 176° C. (onset 170° C.), possibly corresponding with the melt. Decomposition likely follows the melt, evidenced by the steep drop in the TGA thermogram.

The kinetic and thermodynamic hygroscopicity of Form A is assessed by DVS and stressing at elevated RH, respectively. Stressing of a sample of Form A at ~97% RH for 7 days induces a form change to a mixture of materials with a minor Form N (hydrate) component.

Figure 34:
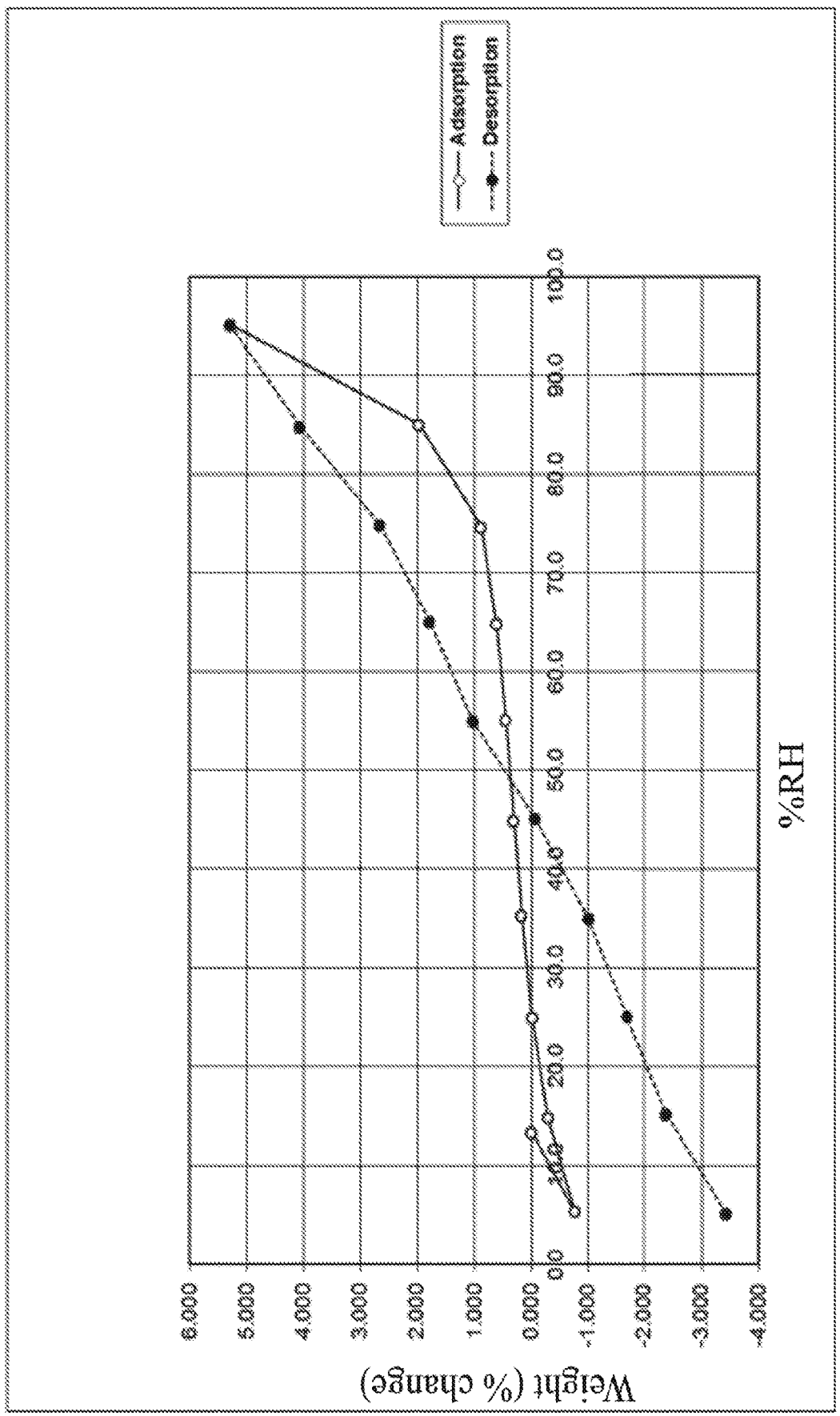
FIG. 34 depicts a DVS isotherm of Form A.

The DVS isotherm is shown in FIG. 34. Initially, the sample loses 0.76 wt % upon equilibration at 5% RH, likely corresponding to loss of moisture from sorption upon ambient storage and/or a portion of bound EtOAc. The material exhibits significant hygroscopicity, taking up 6.07 wt % moisture between 5% and 95% RH (1.65% weight gain 5%-75% RH, 4.42% weight gain 75%-95% RH). The vast majority of water sorption (4.42%) occurs between 75% and 95% RH. Significant hysteresis is noted in the isotherm upon desorption, with a steady weight loss of 8.73% occurring between 95% and 5% RH. The larger weight loss on desorption indicates a concurrent loss of bound EtOAc and water from sorption. To be noted, two steps in the experiment reach the maximum equilibration time: 85%-95% on sorption and 85%-75% RH on desorption. It is possible that the sample may experience additional vapor sorption or desorption at the corresponding RH conditions if allowed a longer equilibration time.

XRPD of the post-DVS sample indicates a change to a disordered unknown material.

As described in Example 5, a single crystal structure for a crystal grown using this lot of Form A is solved. The crystal structure is consistent with a hemi-ACN hemi-Na salt of Formula I. To investigate whether the single crystal is representative of this entire lot of Form A, the material is analysed by elemental analysis (EA), ion chromatography (IC), inductively coupled plasma-optical emission spectrometry (ICP-OES), and energy dispersive X-ray spectroscopy (EDX), and comparison of the resulting measurements with theoretical composition percentages are presented in Table 1.

TABLE 1

| | Theoretical (EtOAc hemi-solvate) | Theoretical (hemi Na salt, EtOAc hemi-solvate) | Measured |
|---|---|---|---|
| EA | 40.2% C | 39.4% C | 39.67% C |
| | 2.6% H | 2.4% H | 2.23% H |
| | 2.8% N | 2.7% N | 2.87% N |
| | 7.0% Cl | 6.8% Cl | 7.15% Cl |
| | 22.5% F | 22.0% F | 20.49% F |
| | 6.1% P | 6.0% P | 6.28% P |
| IC and ICP-OES (Na$^+$ analysis) | Theoretical (hemi Na salt, EtOAc hemi-solvate): 2.2% Na$^+$ Measured: 0.18% Na$^+$ by IC 0.19% Na$^+$ by ICP-OES (acid digestion) | | |
| | Na$^+$ not present above 0.1% Approximate quantitation: | | |
| | Preparation 1: | Preparation 2: | |
| EDX | 51.7% C | 52.7% C | |
| | 19.4% O | 18.7% O | |
| | 20.5% F | 19.4% F | |
| | 0.0% Na | 0.1% Na | |
| | 4.4% P | 4.8% P | |
| | 3.9% Cl | 4.5% Cl | |

The EA test is relatively inclusive because the measured values for C, H, N, Cl, F, and P cannot distinguish between the hemi-sodium salt versus the free acid. Analysis by IC, ICP OES (with acid digestion), and EDX all indicate negligible sodium content, confirming that the this lot of Form A consists of Formula I (free acid). The hemi-Na salt analyzed by SCXRD may have resulted from a minor Na impurity in the material that crystallized out of solution as the hemi-Na salt.

Crash precipitation, slow evaporation, crash cooling, and fast cooling of Formula I in EtOAc/heptane mixtures all result in Form A.

Example 2B—Reworked 2-{[3,5-bis(trifluoromethyl)phenyl]carbamoyl}-4-chlorophenyl Dihydrogen Phosphate Ethyl Acetate Solvate (Form A)

An EtOAc solution of a portion of 2-{[3,5-bis(trifluoromethyl)phenyl]carbamoyl}-4-chlorophenyl dihydrogen phosphate from Example 2A is mixed with 1N HCl. White solid is isolated by evaporation. 600 MHz NMR shows ~0.28 moles EtOAc. The material is analysed by EDX, and the results are in Table 2.

TABLE 2

| | Na+ not present above 0.1% Approximate quantitation: | |
|---|---|---|
| | Preparation 1: | Preparation 2: |
| EDX | 51.3% C | 55.6% C |
| | 19.0% O | 18.5% O |
| | 20.2% F | 17.5% F |
| | 0.0% Na | 0.0% Na |
| | 4.9% P | 4.6% P |
| | 4.6% Cl | 3.9% Cl |

Figure 35:
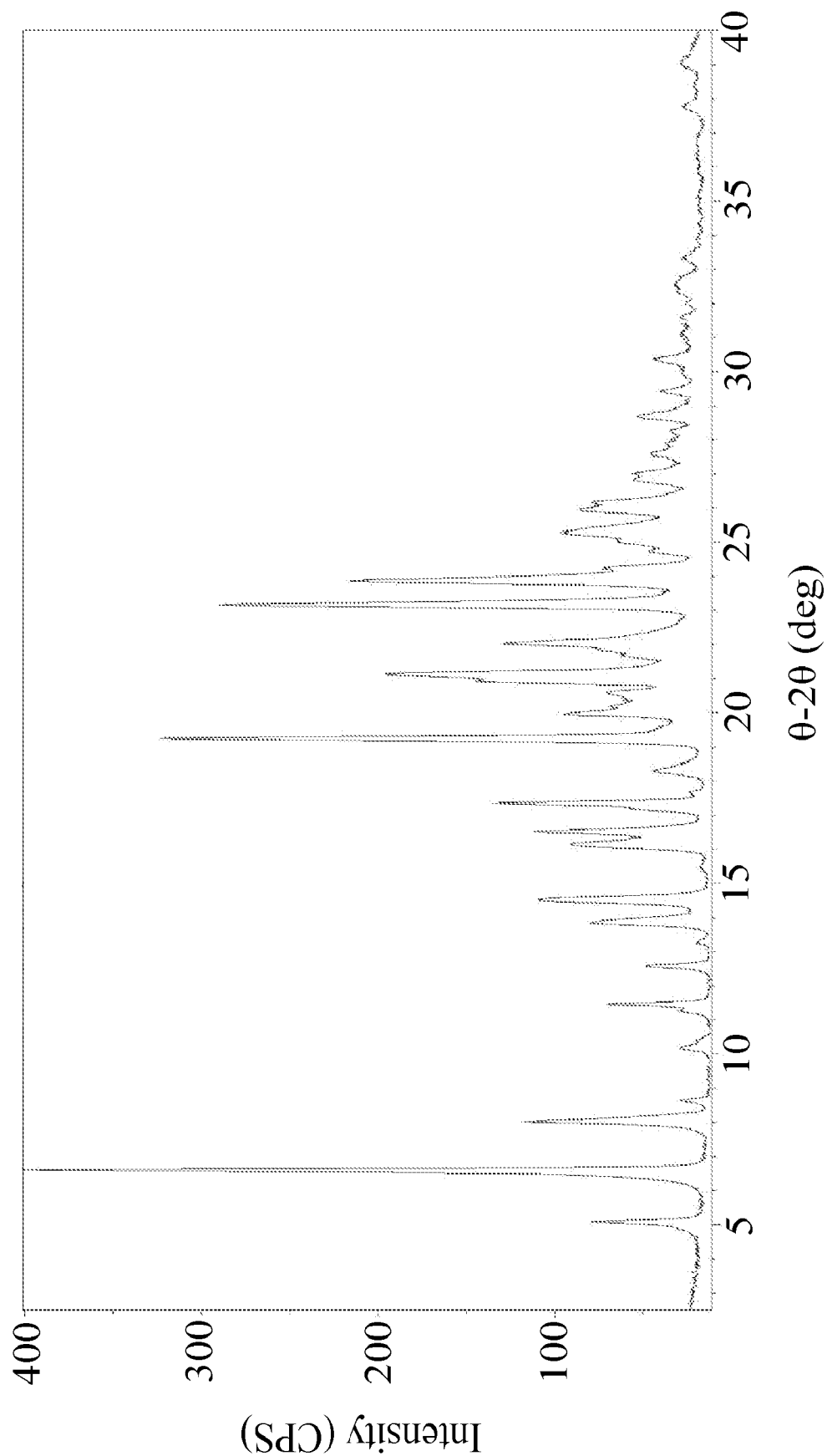
FIG. 35 depicts an XRPD pattern of Form A collected with Cu Kα radiation.
Figure 36:
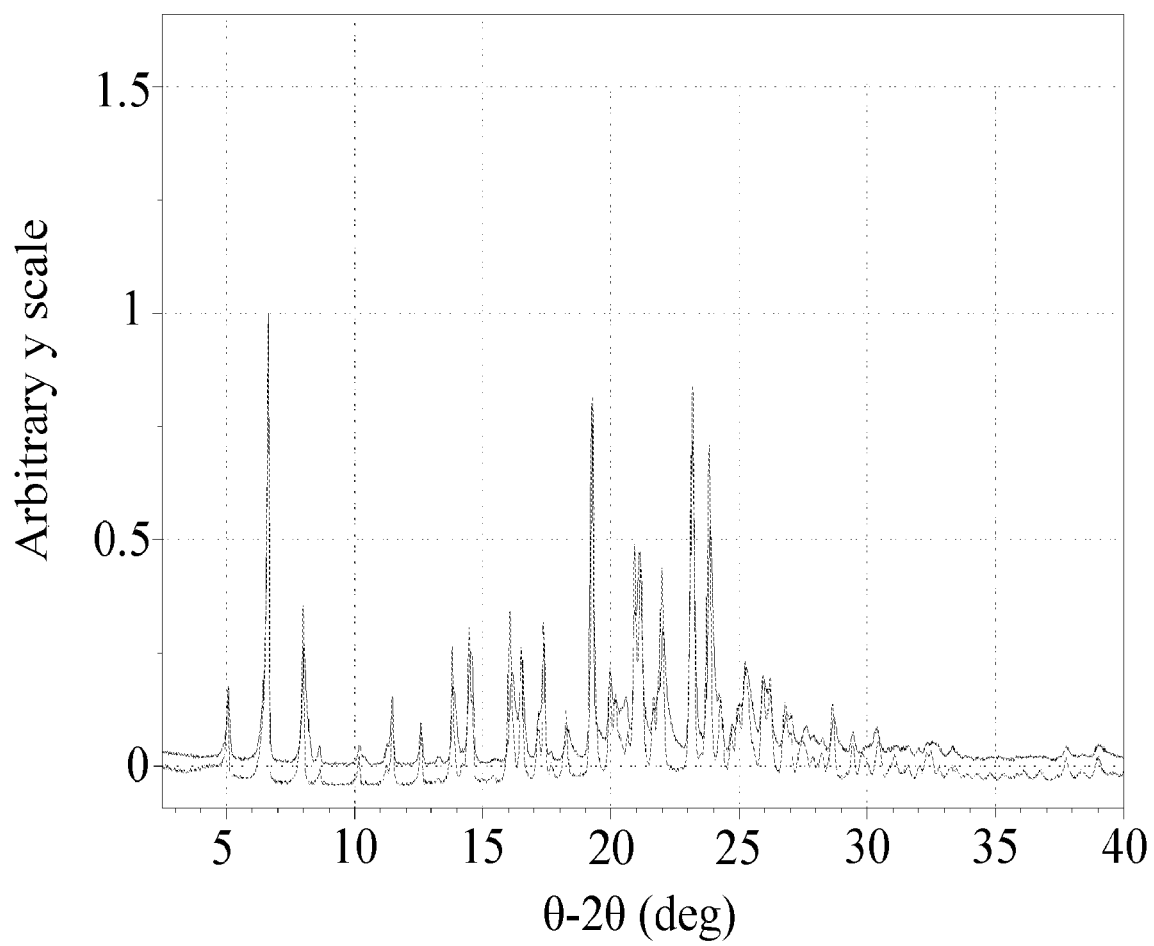
FIG. 36 depicts an overlay of Form A XRPD patterns. Top XRPD pattern is Form A from Example 2B (XRPD pattern shown in FIG. 35). Bottom XRPD pattern is Form A from Example 2A (XRPD patterns shown in FIGS. 10 and 31).

An XRPD pattern of 2-{[3,5-bis(trifluoromethyl)phenyl]carbamoyl}-4-chlorophenyl dihydrogen phosphate ethyl acetate solvate prepared as described in this example is shown in FIG. 35. The XRPD pattern is obtained as described in the general XRPD procedure in Example 1. 2-theta values, d-spacings, and peak intensities for the XRPD pattern shown in FIG. 35 are provided above in Table DD in Crystalline Form 1.77. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 716 s, Scan Speed 3.3°/min, Slit: DS: ½°, SS: null, Revolution Time: 1.0 s, Mode: Transmission.

The XRPD pattern shows the sample is Form A plus possible minor unknown component.

Example 3—2-{[3,5-bis(trifluoromethyl)phenyl]carbamoyl}-4-chlorophenyl Dihydrogen Phosphate Ethyl Acetate Solvate (Form A)

2-{[3,5-bis(trifluoromethyl)phenyl]carbamoyl}-4-chlorophenyl dihydrogen phosphate is stirred in EtOAc with 1 N HCl and evaporated. The solid is then crash precipitated with EtOAc/heptane and vacuum filtered.

Additional experimental details for the synthesis are set forth in this paragraph. 2-{[3,5-bis(trifluoromethyl)phenyl]carbamoyl}-4-chlorophenyl dihydrogen phosphate from Example 2B (28.1 mg) is dissolved in EtOAc (0.1 mL) with sonication, resulting in a clear solution. Aliquots of heptane (4×0.1 mL) are added with stirring, causing precipitation. An opaque white suspension is observed. The resulting solids are isolated by vacuum filtration and air dried on the filter under reduced pressure for 2 minutes.

Figure 11:
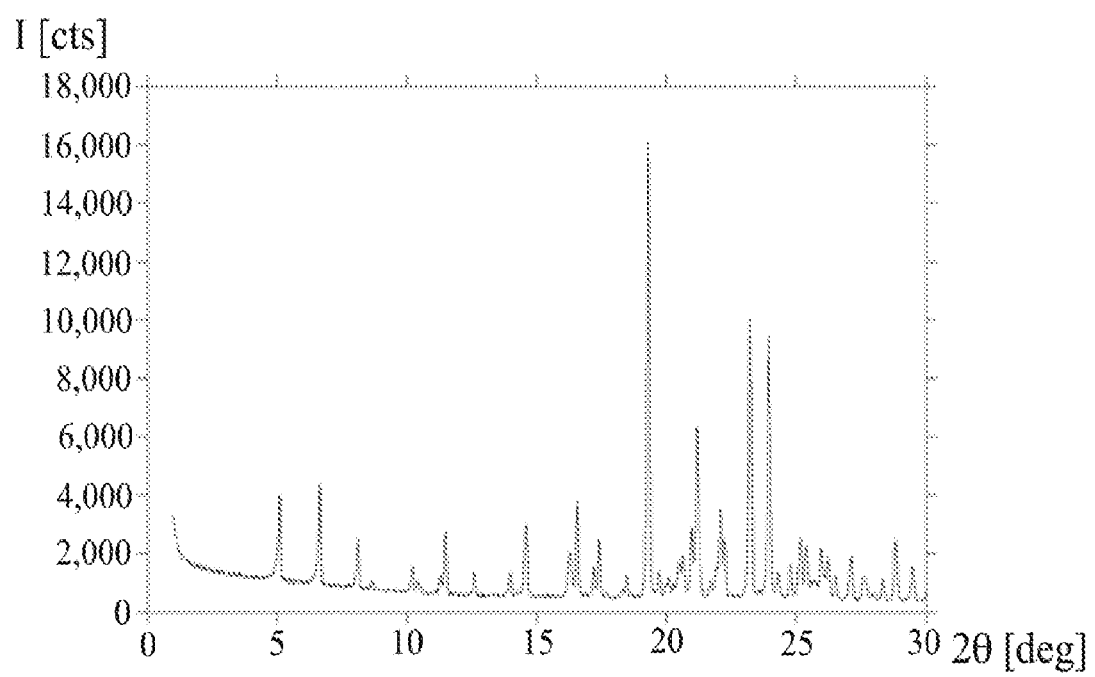
FIG. 11 depicts an XRPD pattern of Form A collected with Cu Kα radiation.
Figure 32:
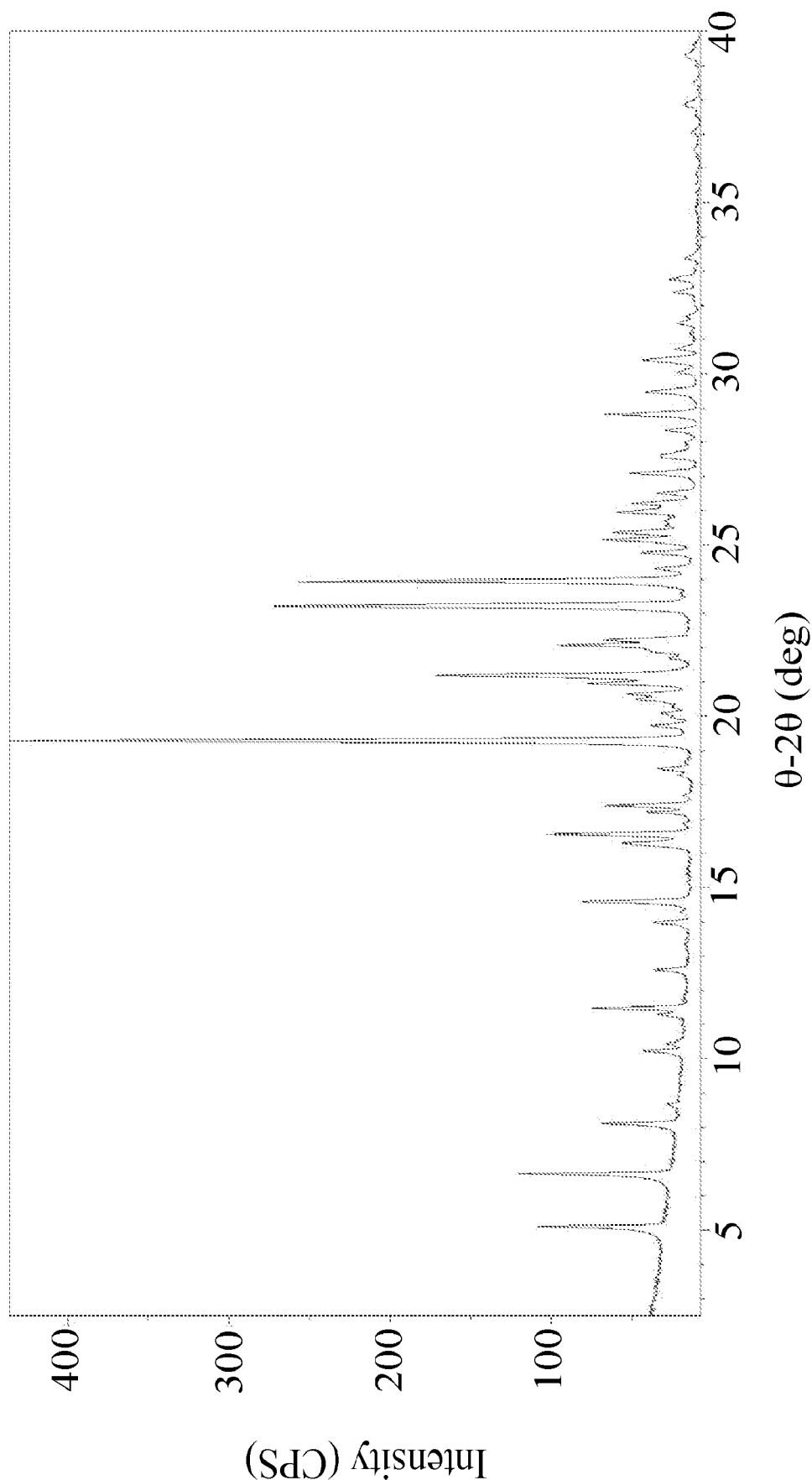
FIG. 32 depicts an XRPD pattern of Form A collected with Cu Kα radiation.

An XRPD pattern of the product (2-{[3,5-bis(trifluoromethyl)phenyl]carbamoyl}-4-chlorophenyl dihydrogen phosphate ethyl acetate solvate) is shown in FIG. 11. The XRPD pattern is also shown in FIG. 32. The XRPD pattern is obtained as described in the general XRPD procedure in Example 1. 2-theta values, d-spacings, and peak intensities for the XRPD pattern shown in FIGS. 11 and 32 are provided above in Table BB in Crystalline Form 1.49. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 721 s, Scan Speed 3.2°/min, Slit: DS: ½°, SS: null, Revolution Time: 1.0 s, Mode: Transmission.

Peak shifting is noted among Form A XRPD patterns, likely caused by variable EtOAc content, which can cause expansion or contraction of the crystal lattice.

Figure 33:
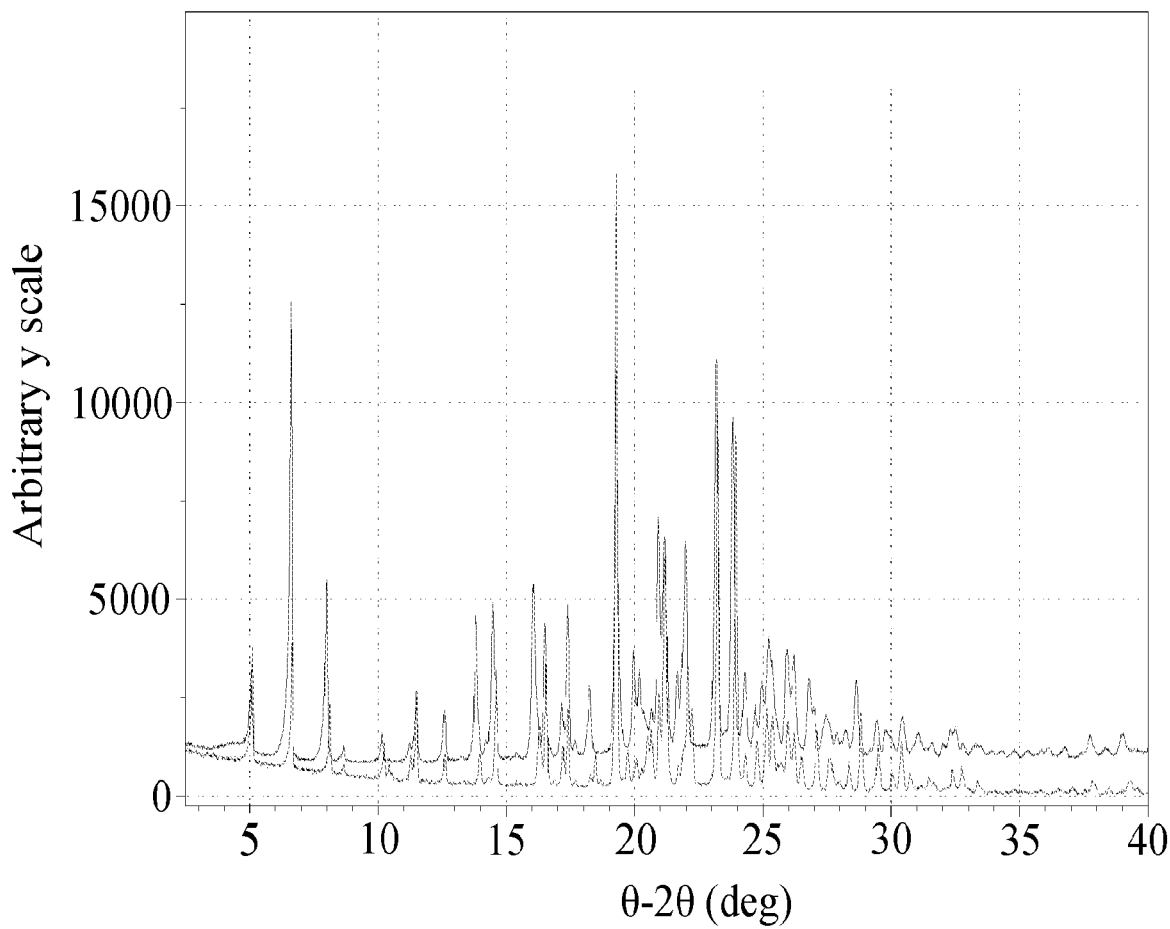
FIG. 33 depicts an overlay of Form A XRPD patterns. Top XRPD pattern is Form A from Example 2A (XRPD patterns shown in FIGS. 10 and 31). Bottom XRPD pattern is Form A from Example 3 (XRPD patterns shown in FIGS. 11 and 32).

For comparison purposes, the XRPD pattern of FIG. 11 (also shown in FIG. 32) is indexed. The unit cell volume for this material can also accommodate up to ~0.5 mole EtOAc per mole of Formula I, although the volume is slightly smaller than that of Form A from Example 2A. An XRPD overlay illustrating the observed peak shifting between the XRPD patterns of FIGS. 10 and 31 and of FIGS. 11 and 32 is presented in FIG. 33. The indexing results suggest that a fairly small difference in EtOAc content (and, consequently, unit cell volume) can cause relatively significant peak shifts by XRPD.

Example 4—Preparation and Single Crystal Structure Determination of 2-{[3,5-bis(trifluoromethyl)phenyl]carbamoyl}-4-chlorophenyl Dihydrogen Phosphate Hemi-Ethyl Acetate Solvate (Form A)

Introduction

The structure of the single crystal is determined by single crystal X-ray diffraction. The single crystal data collection, structure solution, and refinement are not performed according to cGMP specifications.

Results and Discussion

The monoclinic cell parameters and calculated volume are: a=26.2223(3) Å, b=9.10581(10) Å, c=34.9080(4) Å, β=97.3256(11)° (α=γ=90°), V=8267.13(16) Å3. The formula weight of the asymmetric unit in the crystal structure of Form A is 1015.41 g mol$^{-1}$ with Z=8, resulting in a calculated density of 1.632 g cm$^{-3}$. The space group is determined to be C2/c (no. 15). A summary of the crystal data and crystallographic data collection parameters are provided in Table 3.

The fit residual (R) is 0.0388 (3.88%).

Figure 2:
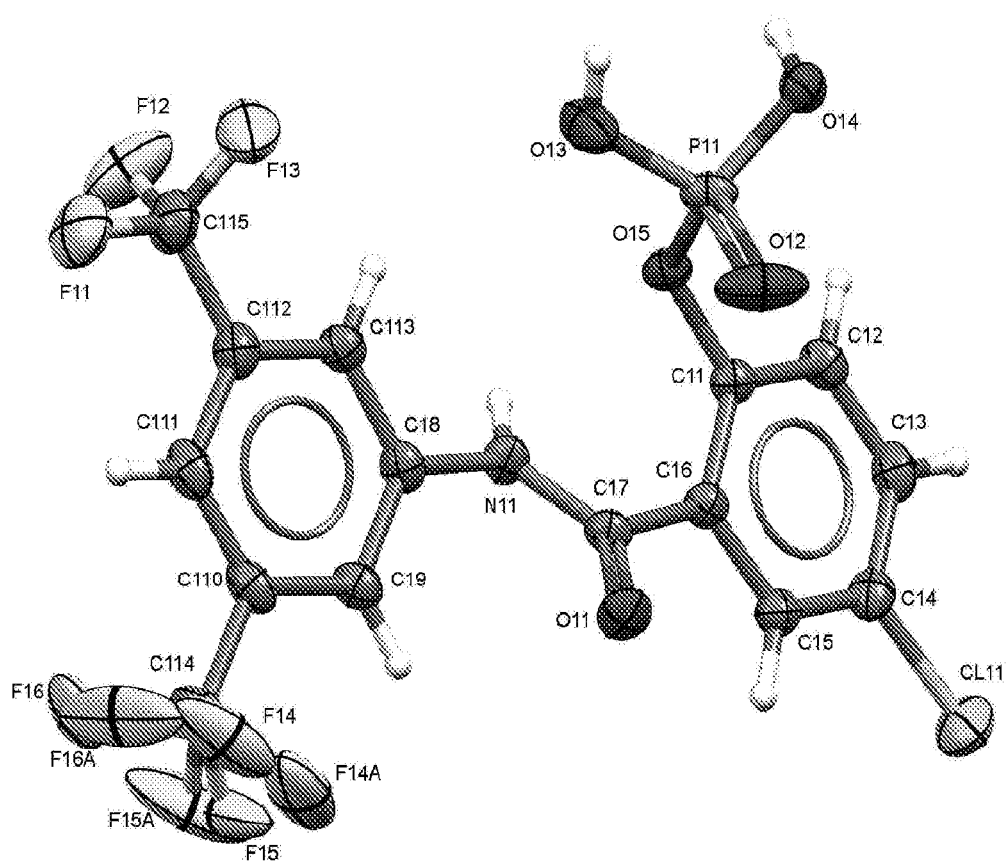
FIG. 2 depicts an atomic displacement ellipsoid drawing of Form A. Atoms are represented by 50% probability anisotropic thermal ellipsoids. One of the two molecules of Formula I is shown with atomic labeling.

An atomic displacement ellipsoid drawing of the asymmetric unit of Form A is shown in FIG. 1 and the atomic labeling is shown in FIG. 2.

The asymmetric unit shown in FIG. 1 contains two molecules of Formula I and one ethyl acetate molecule, indicating that Form A is a hemi-ethyl acetate solvate.

One of the —CF$_3$ moieties on each of the molecules of Formula I is modeled as disordered.

Figure 3:
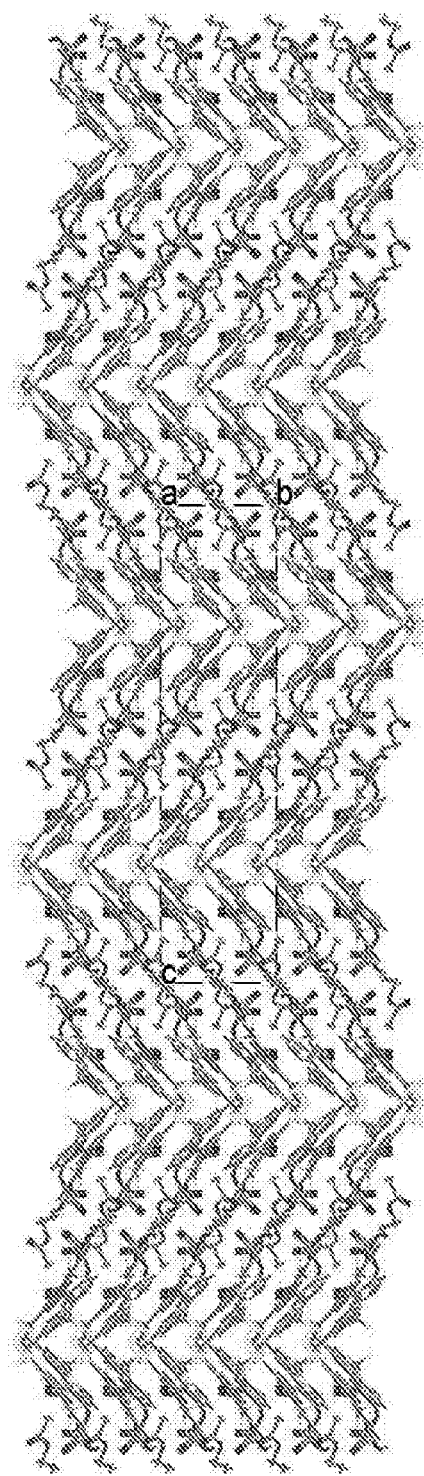
FIG. 3 depicts a packing diagram of Form A viewed along the crystallographic a axis.
Figure 4:
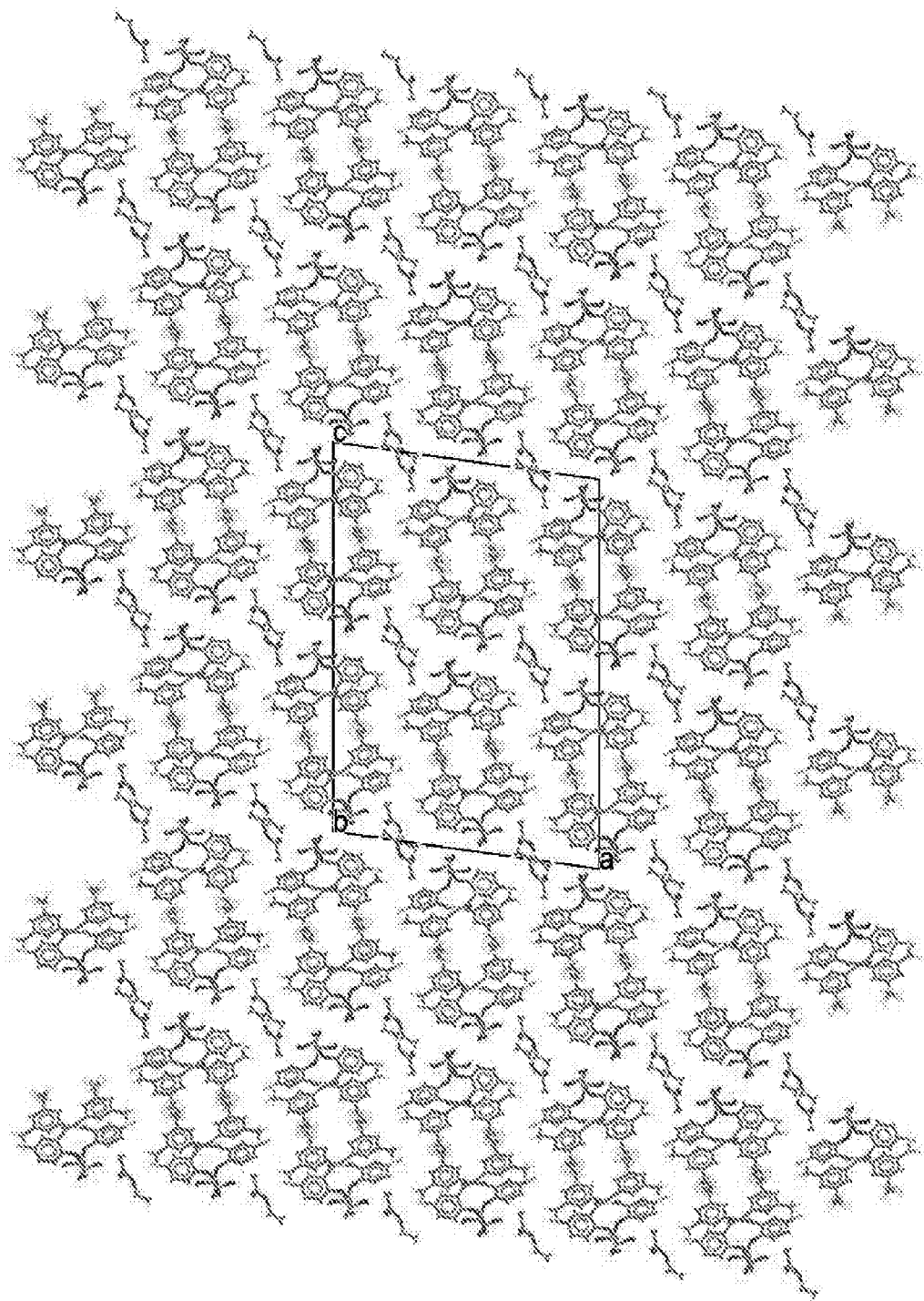
FIG. 4 depicts a packing diagram of Form A viewed along the crystallographic b axis.
Figure 5:
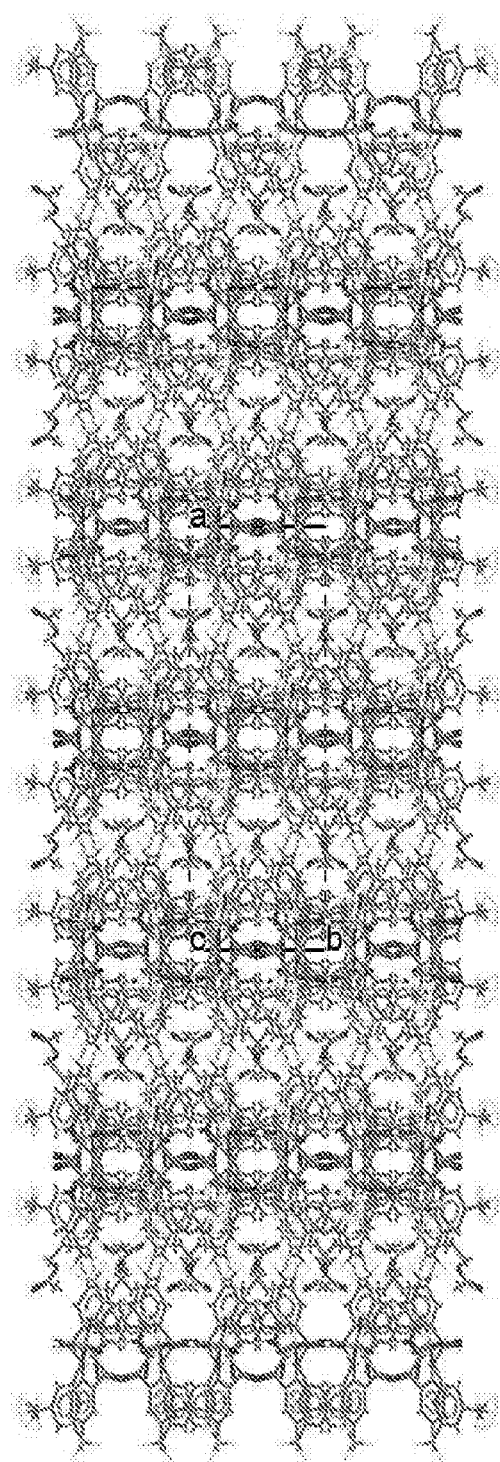
FIG. 5 depicts a packing diagram of Form A viewed along the crystallographic c axis.
Figure 6:
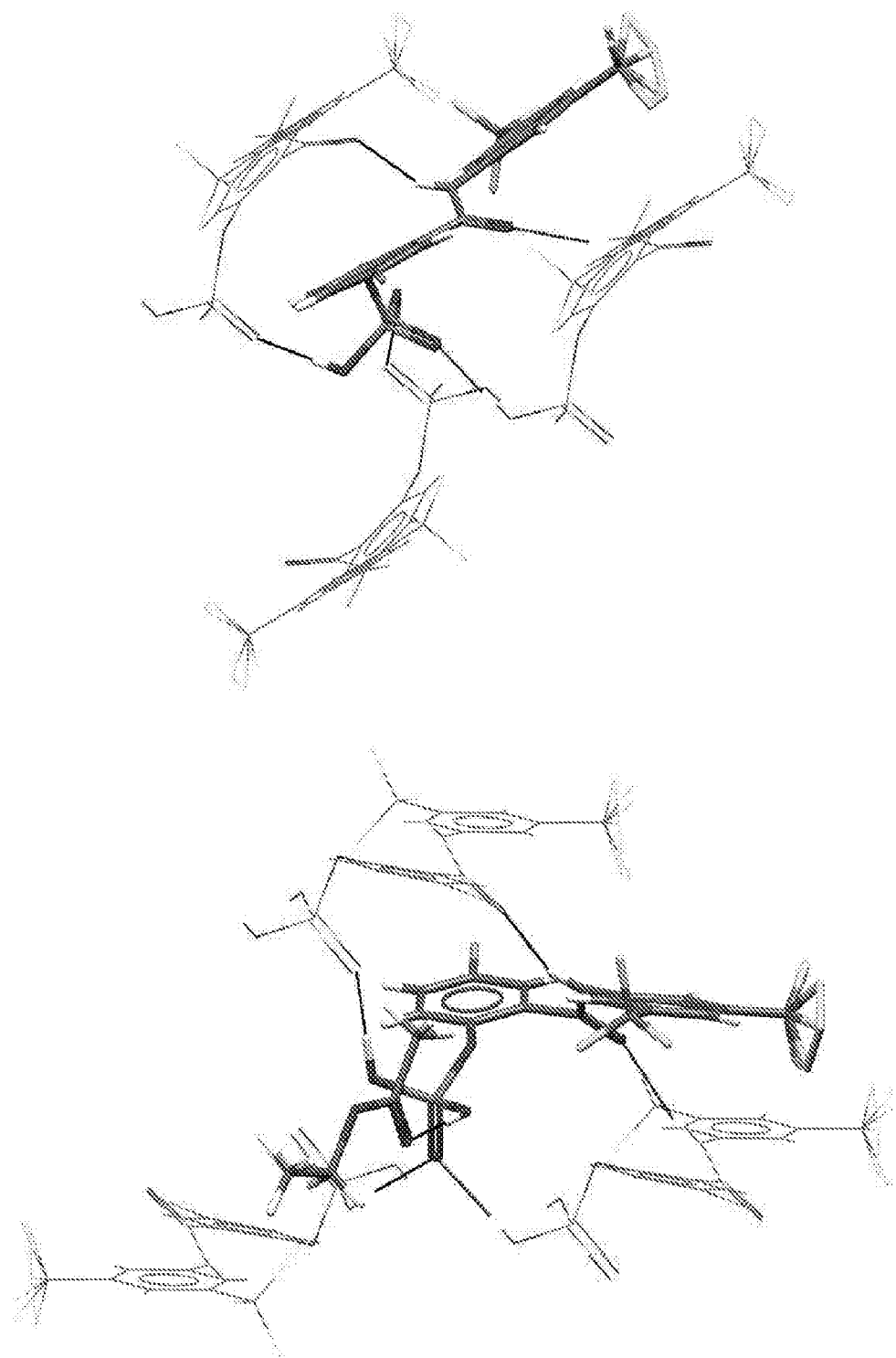
FIG. 6 depicts hydrogen bonding environments around the two molecules in the asymmetric unit of Form A.
Figure 7:
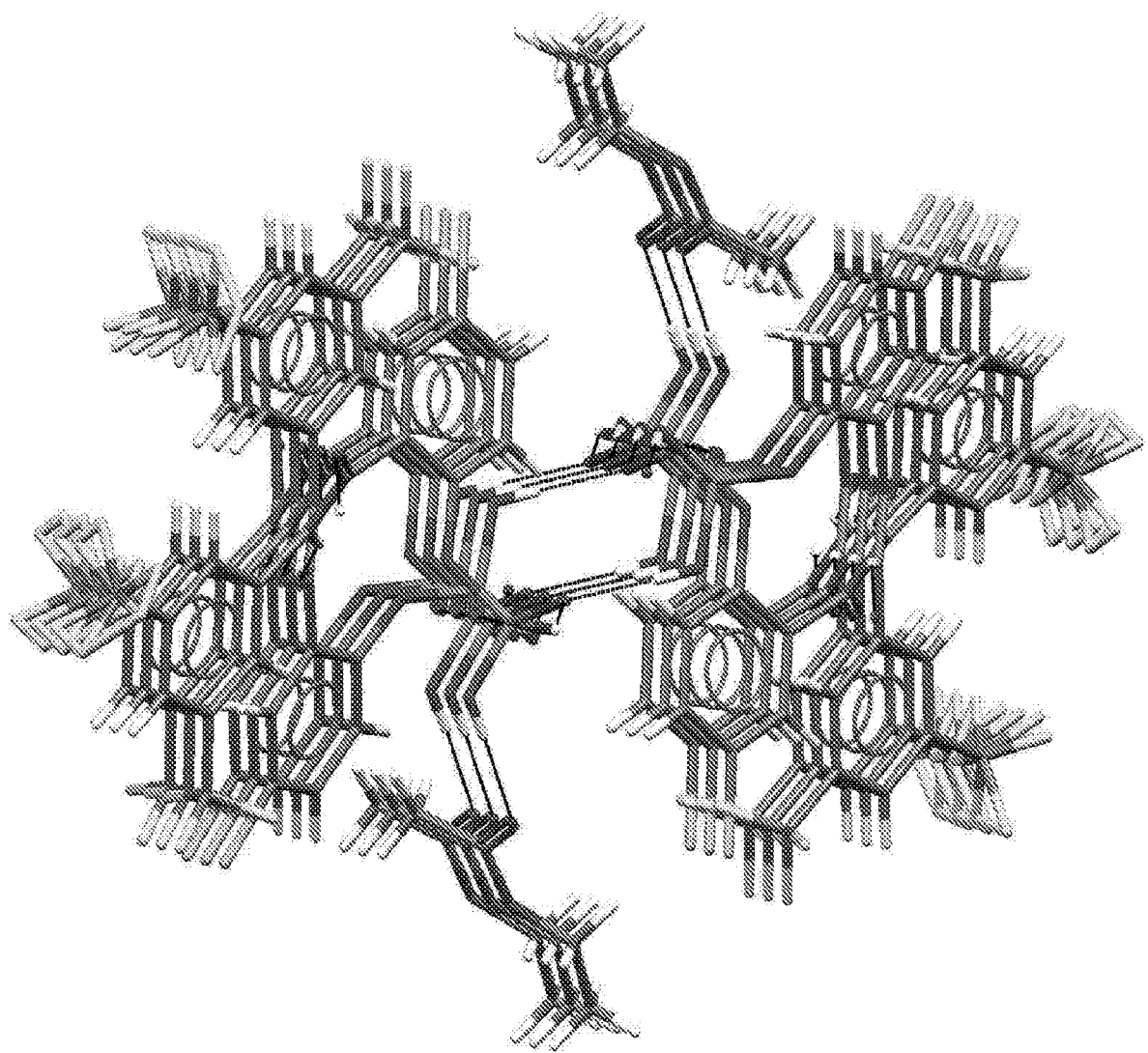
FIG. 7 depicts a hydrogen bonded chain along the b axis of Form A.

Packing diagrams viewed along the a, b, and c crystallographic axes are shown in FIGS. 3-5 respectively. The hydrogen bonding environment around both 2-{[3,5-bis(trifluoromethyl)phenyl]carbamoyl}-4-chlorophenyl dihydrogen phosphate molecules in the asymmetric unit is shown in FIG. 6. Hydrogen bonding occurs from the amide nitrogen to the amide oxygen of an adjacent molecule and between phosphate moieties of adjacent molecules forming one-dimensional chains down the b axis (FIG. 7). The ethyl acetate molecules are hydrogen bonded to alternating phosphate molecules down the chain.

Figure 8:
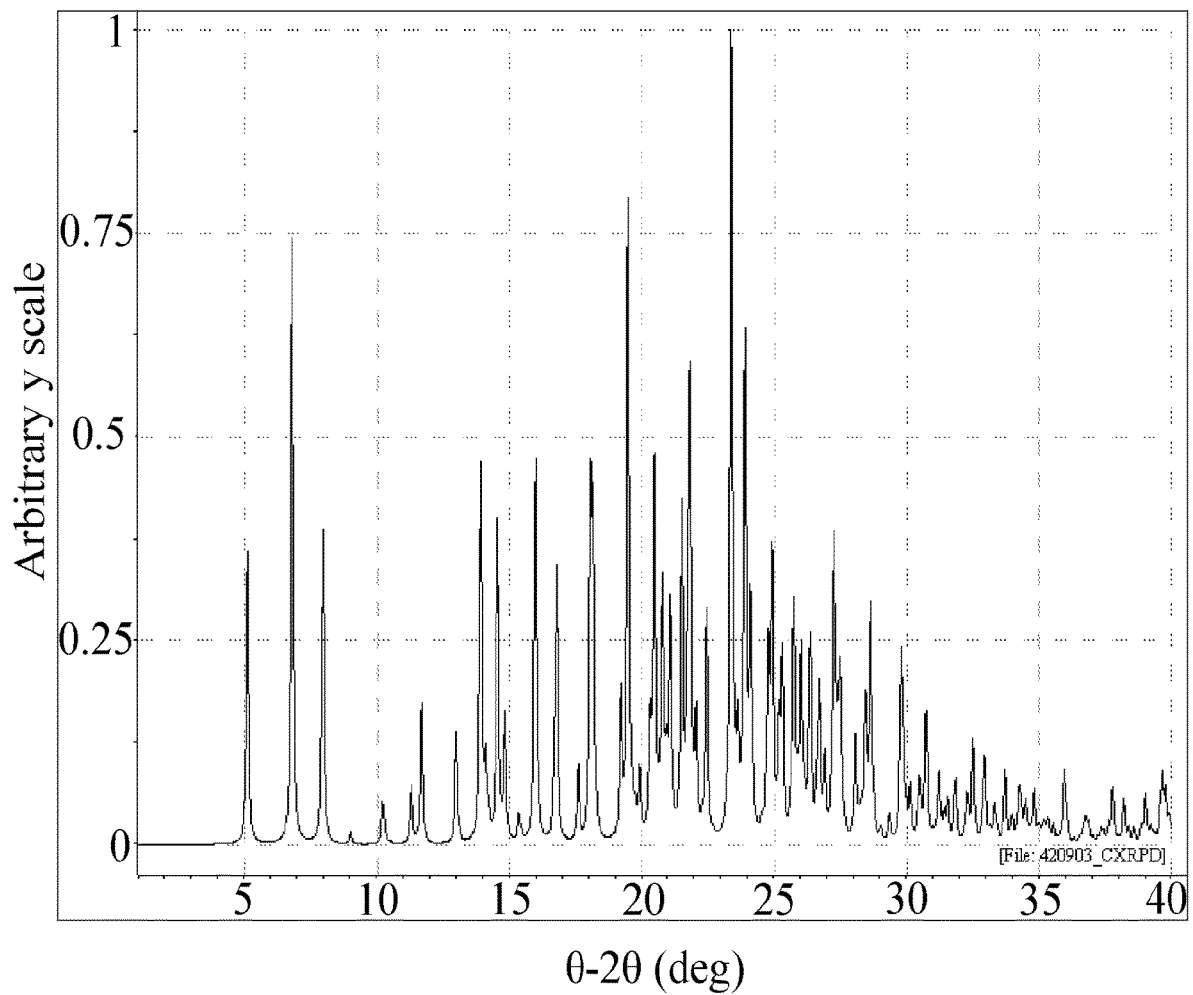
FIG. 8 depicts a calculated XRPD pattern of Form A.
Figure 9:
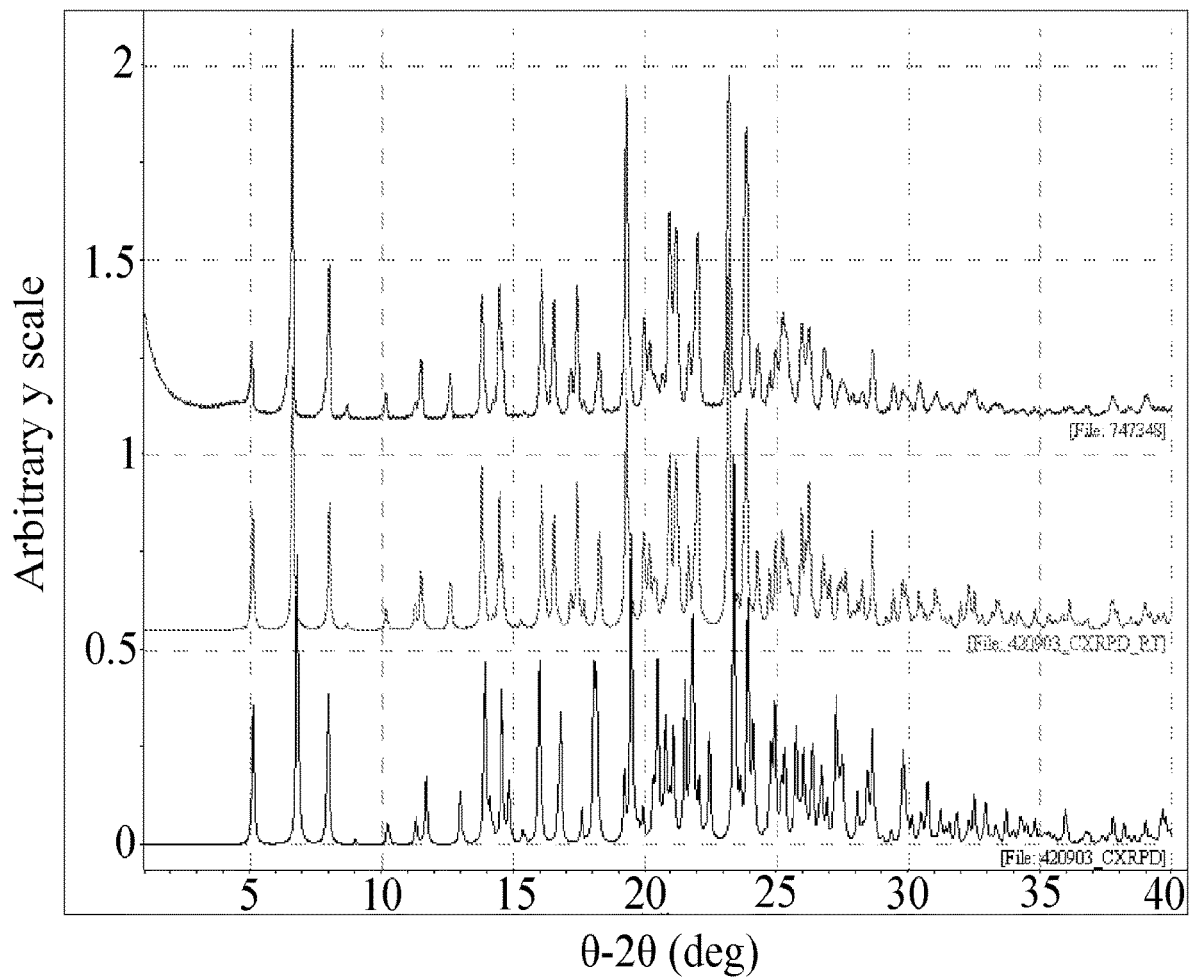
FIG. 9 depicts experimental and calculated XRPD patterns of Form A. Top XRPD pattern is an experimental XRPD pattern at room temperature. Middle XRPD pattern is the calculated XRPD pattern adjusted to room temperature. Bottom XRPD pattern is the calculated XRPD pattern at 150 K.

FIG. 8 shows a calculated XRPD pattern of Form A, generated from the single crystal structure. An experimental XRPD pattern of Form A is shown overlaid with calculated XRPD patterns in FIG. 9. All peaks in the experimental pattern are represented in the calculated XRPD patterns.

Differences in intensities between calculated and experimental powder diffraction patterns often are due to preferred orientation. Preferred orientation is the tendency for crystals to align themselves with some degree of order. This preferred orientation of the sample can significantly affect peak intensities, but not peak positions, in the experimental powder diffraction pattern. Furthermore, some shift in peak position between the calculated and experimental powder diffraction patterns may be expected because the experimental powder pattern is collected at ambient temperature and the single crystal data is collected at 150 K. Low temperatures are used in single crystal analysis to improve the quality of the structure but can contract the crystal resulting in a change in the unit cell parameters which is reflected in the calculated powder diffraction pattern. These shifts are particularly evident at high diffraction angles. The unit cell parameters from XRPD indexing are used to adjust the calculated pattern to room temperature.

TABLE 3

Crystal Data and Data Collection Parameters for Form A

| | |
|---|---|
| Empirical formula | $C_{34}H_{26}N_2O_{12}F_{12}P_2Cl_2$ |
| Formula weight | 1015.41 |
| Temperature/K | 150.00(10) |
| Crystal system | monoclinic |
| Space group | C2/c |
| a/Å | 26.2223(3) |
| b/Å | 9.10581(10) |
| c/Å | 34.9080(4) |
| α/° | 90 |
| β/° | 97.3256(11) |
| γ/° | 90 |
| Volume/Å$^3$ | 8267.13(16) |
| Z | 8 |
| $\rho_{calc}$g/cm$^3$ | 1.632 |
| μ/mm$^{-1}$ | 3.221 |
| F (000) | 4096.0 |
| Crystal size/mm$^3$ | 0.563 × 0.089 × 0.039 |
| Radiation | CuKα (λ = 1.54184) |
| 2Θ range for data collection/° | 6.798 to 154.67 |
| Index ranges | −33 ≤ h ≤ 32, −11 ≤ k ≤ 8, −44 ≤ l ≤ 39 |
| Reflections collected | 21801 |
| Independent reflections | 8486 [$R_{int}$ = 0.0292, $R_{sigma}$ = 0.0307] |
| Data/restraints/parameters | 8486/0/660 |
| Goodness-of-fit on F$^2$ | 1.039 |
| Final R indexes [I >= 2σ (I)] | $R_1$ = 0.0388, $wR_2$ = 0.1068 |
| Final R indexes [all data] | $R_1$ = 0.0441, $wR_2$ = 0.1110 |
| Largest diff. peak/hole/e Å$^{-3}$ | 0.79/−0.54 |

Experimental
Preparation

Single crystals are grown by temperature cycling in heptane/EtOAc 81:19 (v/v).

2-{[3,5-bis(trifluoromethyl)phenyl]carbamoyl}-4-chlorophenyl dihydrogen phosphate is stirred in EtOAc with 1 N HCl and evaporated. The solid is then slow cooled in heptane/EtOAc 81:19 (v/v) from 74° C. to room temperature and allowed to stand at room temperature for 1 day. The solution is reheated to 71° C. with occasional swirling (no stirring), slow cooled from 71° C. to room temperature, and allowed to stand at room temperature for 3 days. The solution is reheated to 71° C. with orbital shaking, slow cooled from 71° C. to room temperature over 5 hours (no shaking), and allowed to stand at room temperature for 1 day. The solution is reheated to 72° C. with orbital shaking, slow cooled from 72° C. to room temperature over 5 hours (no shaking), and allowed to stand at room temperature for 1 day. Thin needles are observed.

Additional experimental details for the synthesis are set forth in this paragraph. A solution of 2-{[3,5-bis(trifluoromethyl)phenyl]carbamoyl}-4-chlorophenyl dihydrogen phosphate from Example 2B (31.2 mg) in heptane/EtOAc 81:19 (v/v, 2.35 mL) is heated with stirring at 74° C., resulting in a clear solution. The solution is left in the heater block on the hot plate, and the heat source is turned off, allowing the sample to slowly cool to ambient temperature. After standing at ambient temperature for 1 day, the sample is observed to consist of a clear liquid phase with a large mass of white solids. The sample is reheated with occasional manual swirling to 71° C. until a small amount of undissolved solids remain. The sample is again left to slowly cool to ambient temperature in the heater block on the hot plate with no stirring. After standing at ambient temperature for 3 days, white solids and a clear liquid phase are observed. The sample is reheated to 71° C. using an orbital shaker with shaking until a small amount of undissolved solids remain. The orbital shaker is set to incrementally cool by 5° C. every 30 minutes to ambient temperature with no shaking. After standing at ambient temperature for 1 day, white solids and a clear liquid phase are observed. The sample is reheated to 72° C. with orbital shaking until a small amount of undissolved solids remain, and the orbital shaker is set to cool with the same parameters. After standing at ambient temperature for 1 day, the sample is observed to contain a clear liquid phase with white solids consisting of birefringent thin needles. A single crystal is harvested and analysed by Single Crystal X-ray Diffraction.

Data Collection

A colorless needle of $C_{34}H_{26}Cl_2F_{12}N_2O_{12}P_2$ [2($C_{15}H_9ClF_6NO_5P$), $C_4H_8O_2$] having approximate dimensions of 0.563×0.089×0.039 mm$^3$, is mounted on a fiber in random orientation. Preliminary examination and data collection are performed with Cu Kα radiation (λ=1.54184 Å) on a Rigaku SuperNova diffractometer, equipped with a copper anode microfocus sealed X-ray tube and a Dectris Pilatus3 R 200K hybrid pixel array detector. Refinements are performed using SHELXL-2014 (Sheldrick, G. M., *Acta Cryst.*, 2008, A64, 112-122). Cell constants and an orientation matrix for data collection are obtained from least-squares refinement using the setting angles of 13054 reflections in the range 4°<θ<77°. The space group is determined by the program CrysAlisPro (CrysAlisPro 1.171.38.41r (Rigaku Oxford Diffraction, 2015)) to be C2/c (no. 15). The data are collected to a maximum diffraction angle (2θ) of 154.67°, at a temperature of 150 K.

Data Reduction

Frames are integrated with CrysAlisPro (CrysAlisPro 1.171.38.41r (Rigaku Oxford Diffraction, 2015)). A total of 21801 reflections are collected, of which 8486 are unique. Lorentz and polarization corrections are applied to the data. The linear absorption coefficient is 3.221 mm$^{-1}$ for Cu Kα radiation. A numerical absorption correction using CrysAlisPro (CrysAlisPro 1.171.38.41r (Rigaku Oxford Diffraction, 2015)) is applied. Transmission coefficients range from 0.424 to 0.888. A secondary extinction correction is applied. The final coefficient, refined in least squares, is 0.000093 (13) (in absolute units). Intensities of equivalent reflections are averaged. The agreement factor for the averaging is 2.92% based on intensity.

Structure Solution and Refinement

Using Olex2 (Dolomanov, O. V. et al., *J. Appl. Cryst.*, 2009, 42, 339-341), the structure is solved by direct methods using SHELXT (Sheldrick, G. M., *Acta Cryst.*, 2015, A71, 3-8). The remaining atoms are located in succeeding difference Fourier syntheses. Refinements are performed using SHELXL-2014 (Sheldrick, G. M., *Acta Cryst.*, 2008, A64, 112-122). Hydrogen atoms located on oxygen or nitrogen are refined independently. All other hydrogen atoms are included in the refinement but restrained to ride on the atom to which they are bonded. The structure is refined in full-matrix least-squares by minimizing the function:

$$\Sigma w(|F_o|^2 - |F_c|^2)^2$$

The weight w is defined as:
$1/[\sigma^2(F_o^2)+(0.0619P)^2+(7.7432P)]$, where $P=(F_o^2+2F_c^2)/3$.

Scattering factors are taken from the "International Tables for Crystallography" (International Tables for Crystallography, Vol. C, Kluwer Academic Publishers: Dordrecht, The Netherlands, 1992, Tables 4.2.6.8 and 6.1.14). Of the 8486 reflections used in the refinements, only the reflections with $F_o^2 > 2\sigma(F_o^2)$ are used in calculating the fit residual, R. A total of 7442 reflections are used in the calculation. The final cycle of refinement included 660 variable parameters and converged with unweighted and weighted agreement factors of:

$$R = \Sigma |F_o - F_c| / \Sigma F_o = 0.0388$$

$$R_w = \sqrt{(\Sigma w (F_o^2 - F_c^2)^2 / \Sigma w (F_o^2)^2)} = 0.1068$$

The standard deviation of an observation of unit weight (goodness of fit) is 1.039. The highest peak in the final difference Fourier has a height of 0.793 e/Å$^3$. The minimum negative peak has a height of −0.537 e/Å$^3$.

Calculated X-Ray Powder Diffraction (XRPD) Pattern

A calculated XRPD pattern is generated for Cu radiation using Mercury (Macrae, C. F. et al., *J. Appl. Cryst.*, 2006, 39, 453-457) and the atomic coordinates, space group, and unit cell parameters from the single crystal structure. Because the single crystal data are collected at low temperatures (150 K), peak shifts may be evident between the pattern calculated from low temperature data and the room temperature experimental powder diffraction pattern, particularly at high diffraction angles. The unit cell obtained from XRPD indexing is used to adjust the calculated XRPD pattern to room temperature.

Atomic Displacement Ellipsoid and Packing Diagrams

The atomic displacement ellipsoid diagram is prepared using Mercury (Macrae, C. F., *J. Appl. Cryst.*, 2006, 39, 453-457). Atoms are represented by 50% probability anisotropic thermal ellipsoids. Packing diagrams and additional figures are also prepared using Mercury. Hydrogen bonding is represented as dashed lines.

Example 5—Preparation and Single Crystal Structure Determination of 2-{[3,5-bis(trifluoromethyl) phenyl]carbamoyl}-4-chlorophenyl Dihydrogen Phosphate Hemi-Sodium Hemi-Acetonitrile Solvate (Hemi-Sodium Hemi-Acetonitrile Solvate)

Introduction

The structure of the single crystal is determined by single crystal X-ray diffraction. The single crystal data collection, structure solution, and refinement are not performed according to cGMP specifications.

Results and Discussion

The monoclinic cell parameters and calculated volume are: a=9.0319(2) Å, b=15.4685(4) Å, c=27.7447(5) Å, β=96.9157(15)° (α=γ=90°), V=3848.01(15) Å$^3$. The formula weight of the asymmetric unit in the crystal structure of the hemi-sodium hemi-acetonitrile solvate is 990.34 g mol$^{-1}$ with Z=4, resulting in a calculated density of 1.709 g cm$^{-3}$. The space group is determined to be P2$_1$ (no. 4). A summary of the crystal data and crystallographic data collection parameters are provided in Table 4.

The fit residual (R) is 0.0509 (5.09%).

Figure 13:
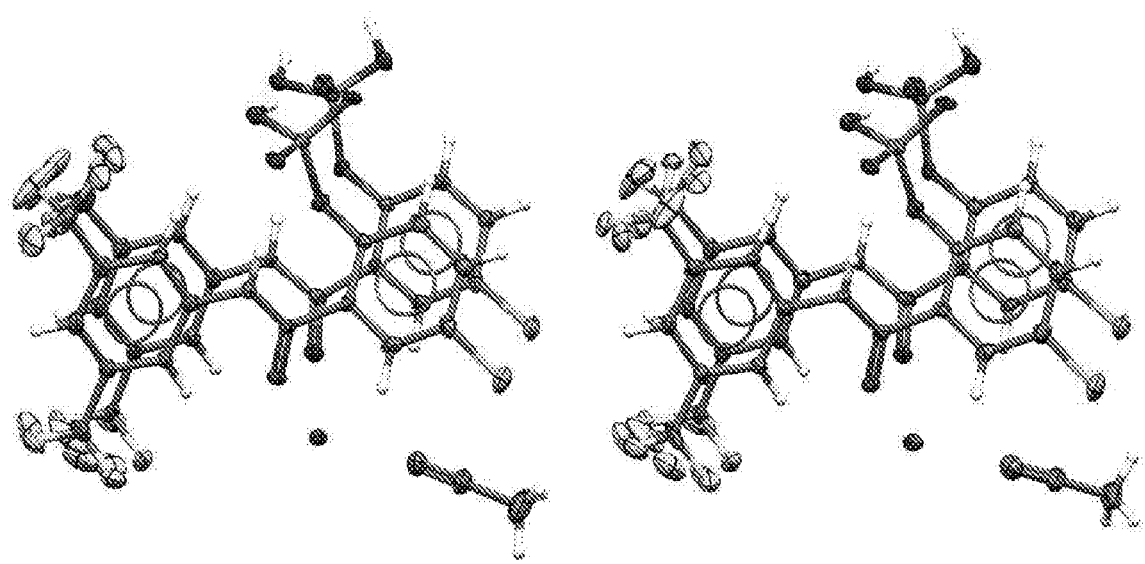
FIG. 13 depicts an atomic displacement ellipsoid drawing of hemi-sodium hemi-acetonitrile solvate. Atoms are represented by 50% probability anisotropic thermal ellipsoids.
Figure 14:
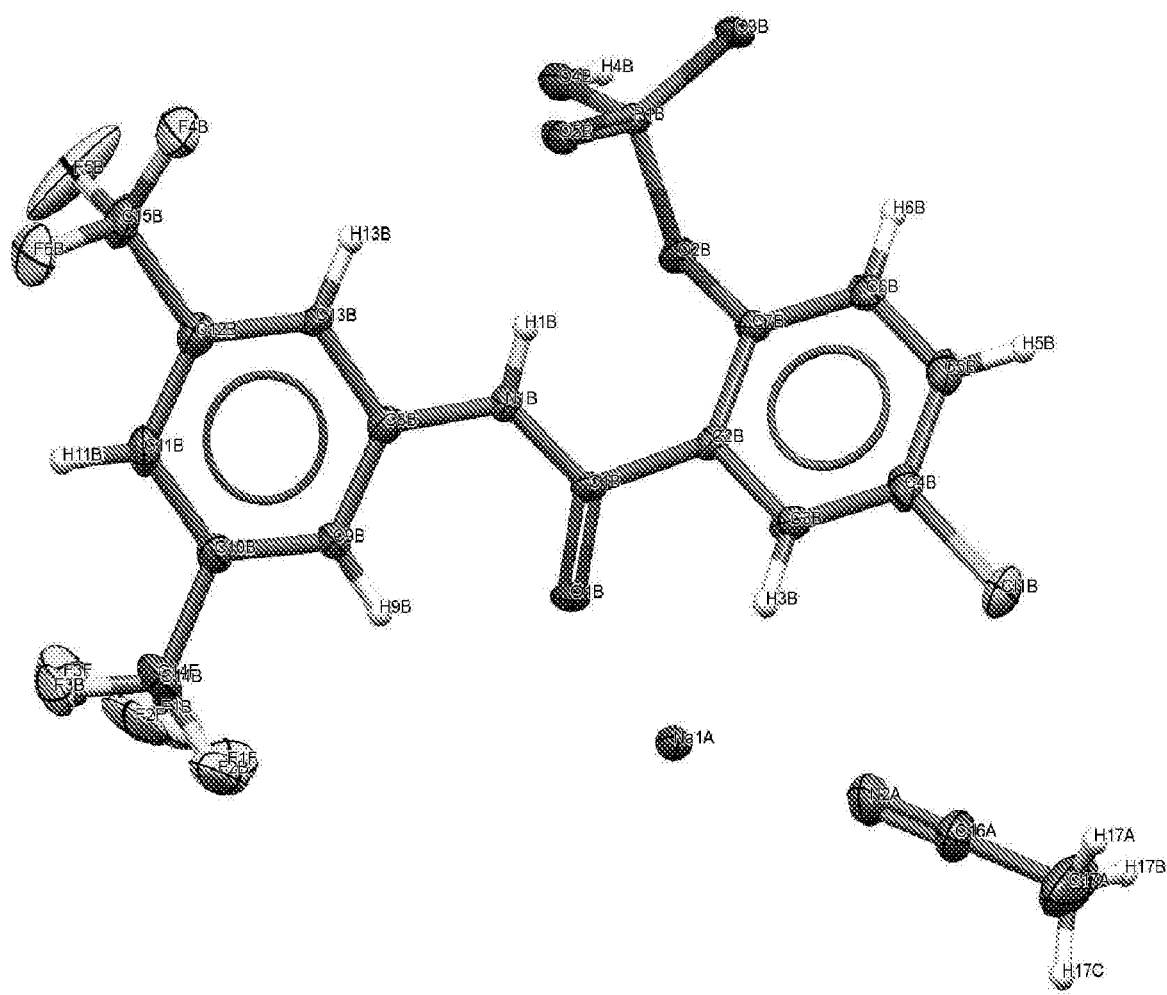
FIG. 14 depicts an atomic displacement ellipsoid drawing of hemi-sodium hemi-acetonitrile solvate. Atoms are represented by 50% probability anisotropic thermal ellipsoids.
Figure 15:
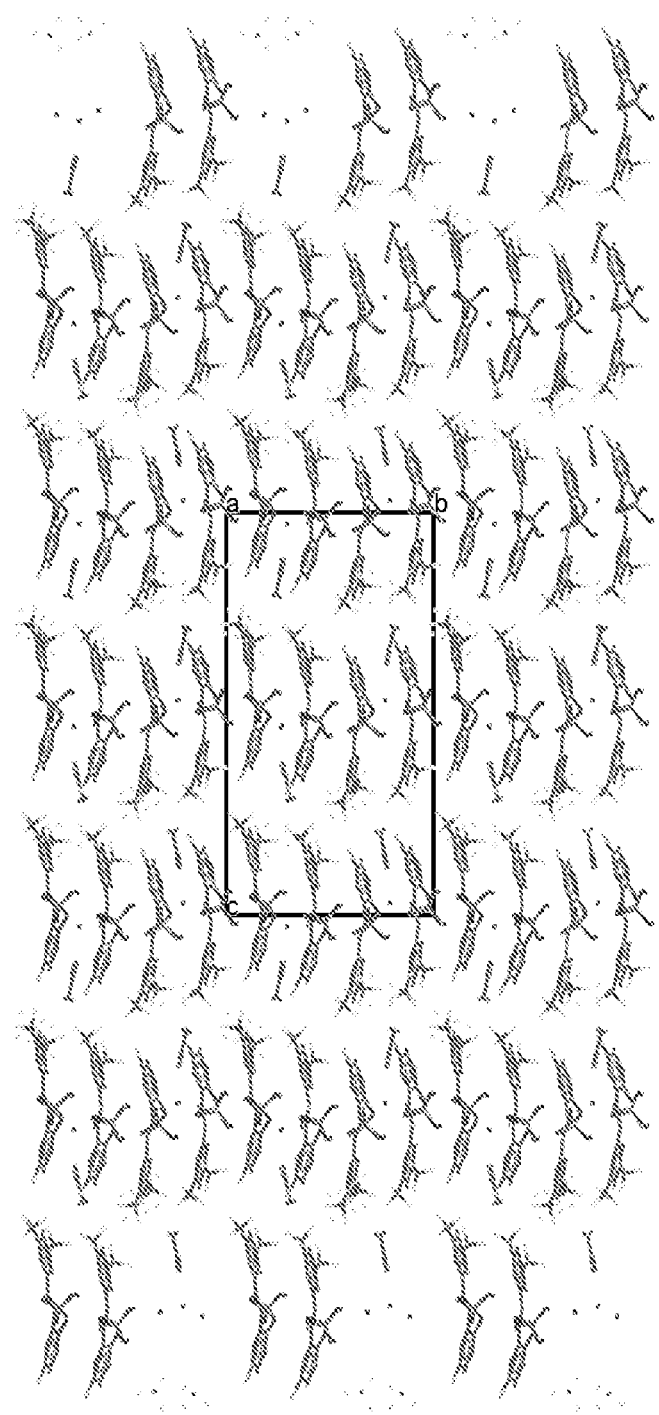
FIG. 15 depicts a packing diagram of hemi-sodium hemi-acetonitrile solvate viewed along the crystallographic a axis.
Figure 16:
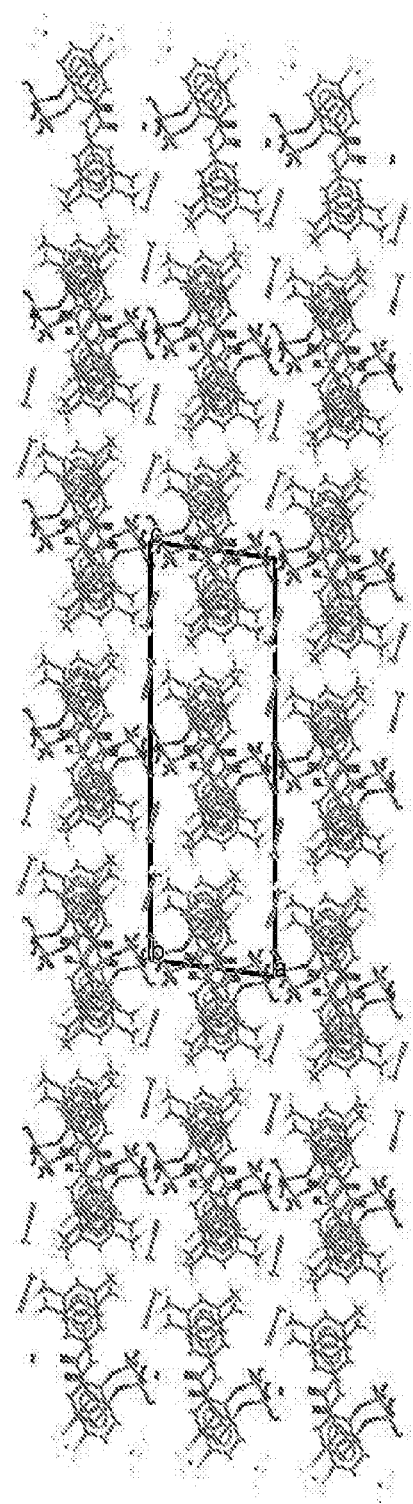
FIG. 16 depicts a packing diagram of hemi-sodium hemi-acetonitrile solvate viewed along the crystallographic b axis.
Figure 17:
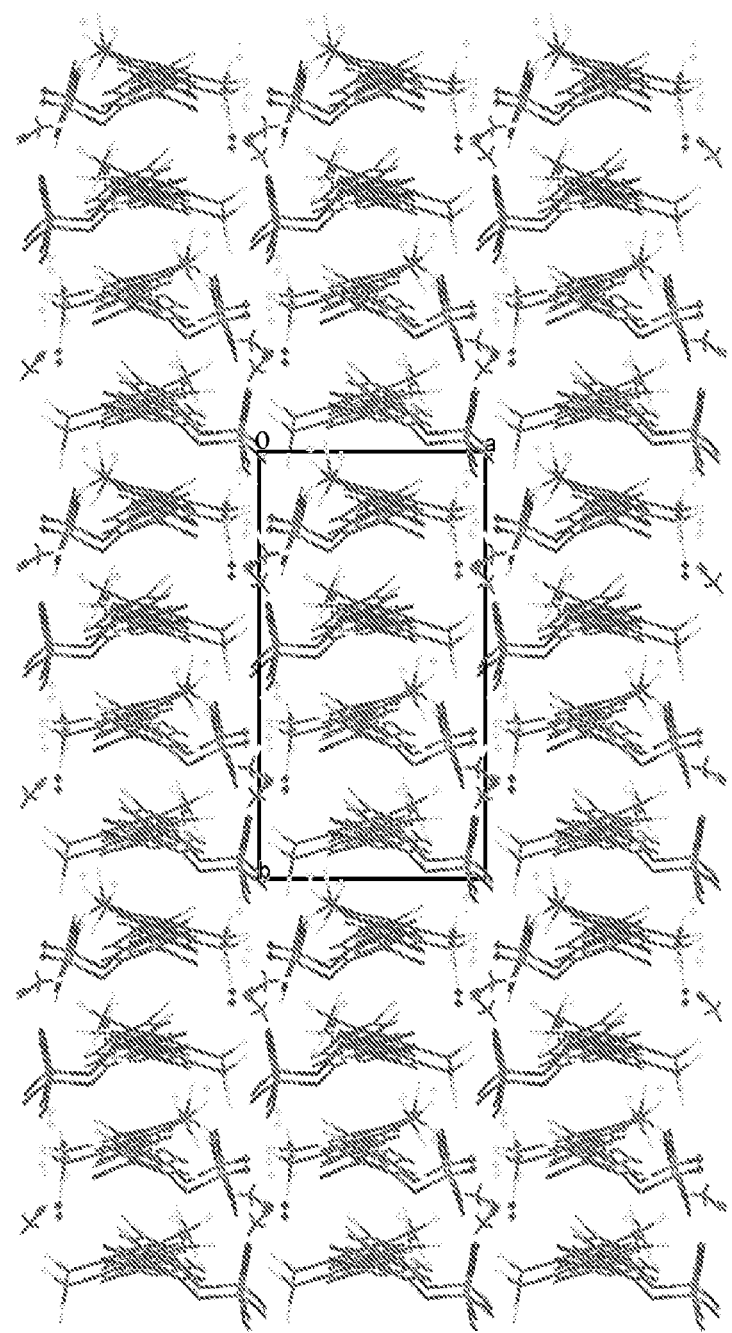
FIG. 17 depicts a packing diagram of hemi-sodium hemi-acetonitrile solvate viewed along the crystallographic c axis.
Figure 18:
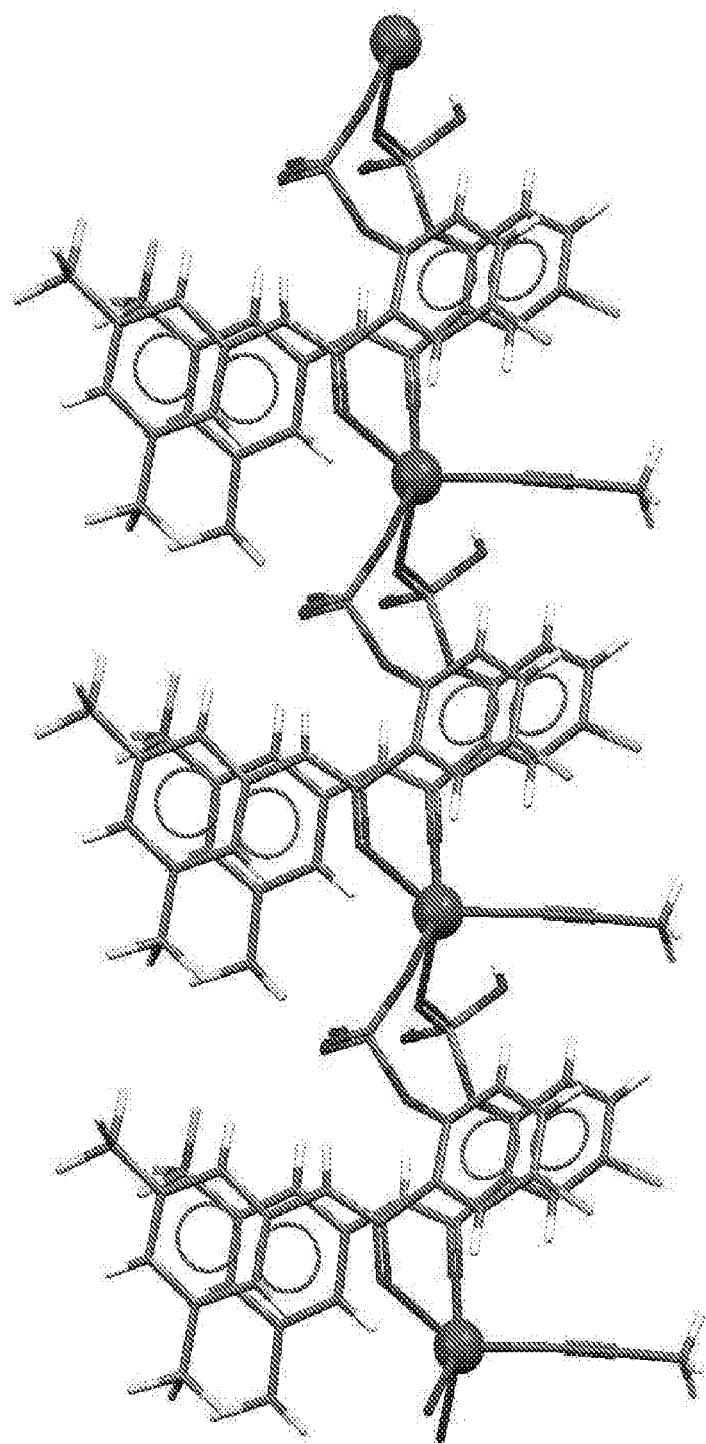
FIG. 18 depicts sodium interactions with Formula I and acetonitrile along the a axis for hemi-sodium hemi-acetonitrile solvate.
Figure 19:
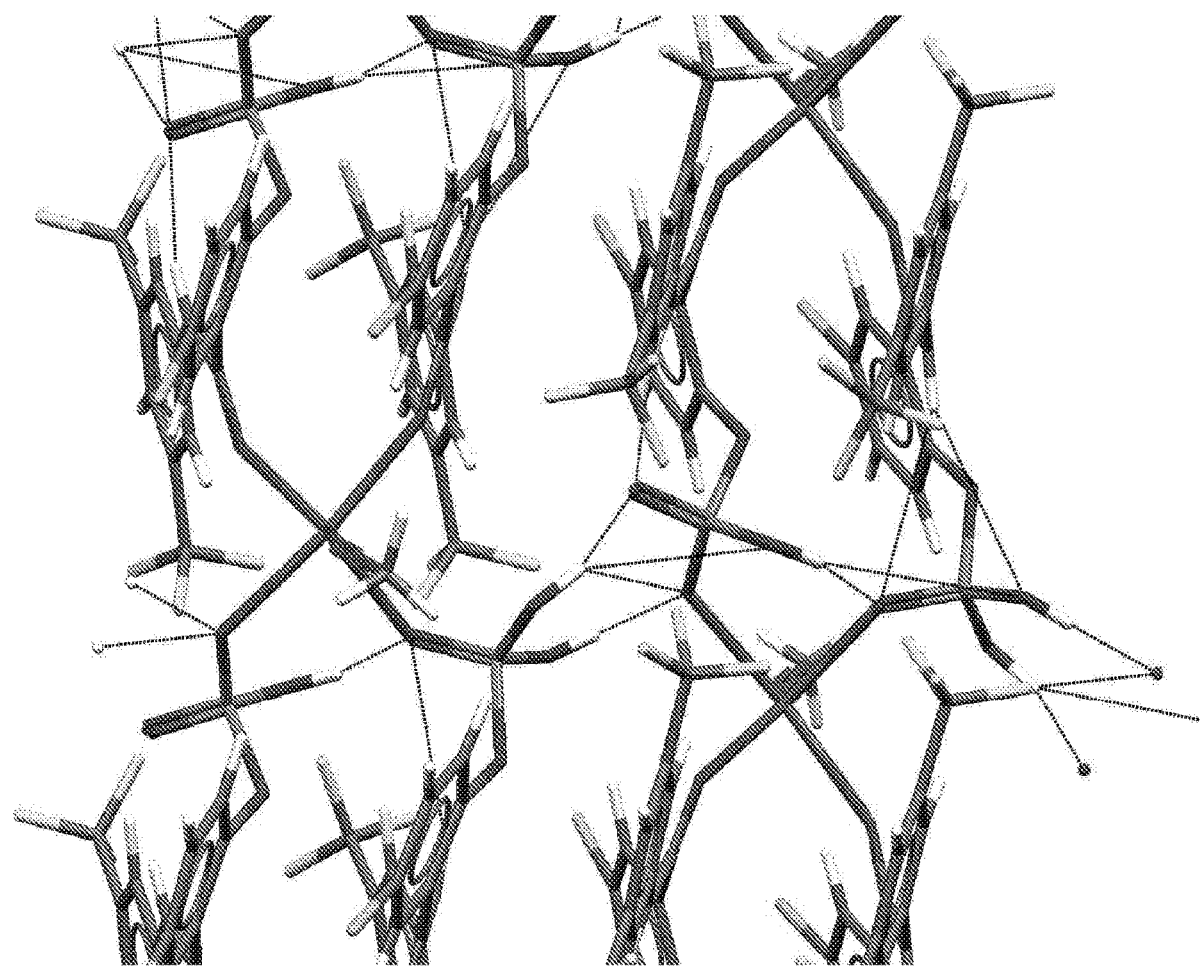
FIG. 19 depicts hydrogen bonding between phosphate groups for hemi-sodium hemi-acetonitrile solvate.

An atomic displacement ellipsoid drawing of the hemi-sodium hemi-acetonitrile solvate is shown in FIG. 13 and atomic labeling is shown in FIG. 14. The asymmetric unit shown in FIG. 13 contains two molecules of Formula I, two mono-deprotonated anions of Formula I, two sodium cations, and two acetonitrile molecules. Packing diagrams viewed along the a, b, and c crystallographic axes are shown in FIGS. 15-17 respectively. The sodium atoms are five coordinate, forming interactions with two phosphate oxygen atoms and two amide oxygen atoms from four different molecules of Formula I, in addition to the acetonitrile nitrogen atom, creating chains along the a axis, shown in FIG. 18. Hydrogen bonding occurs along the b axis between adjacent phosphate groups, as shown in FIG. 19, resulting in a two dimensional network.

Figure 20:
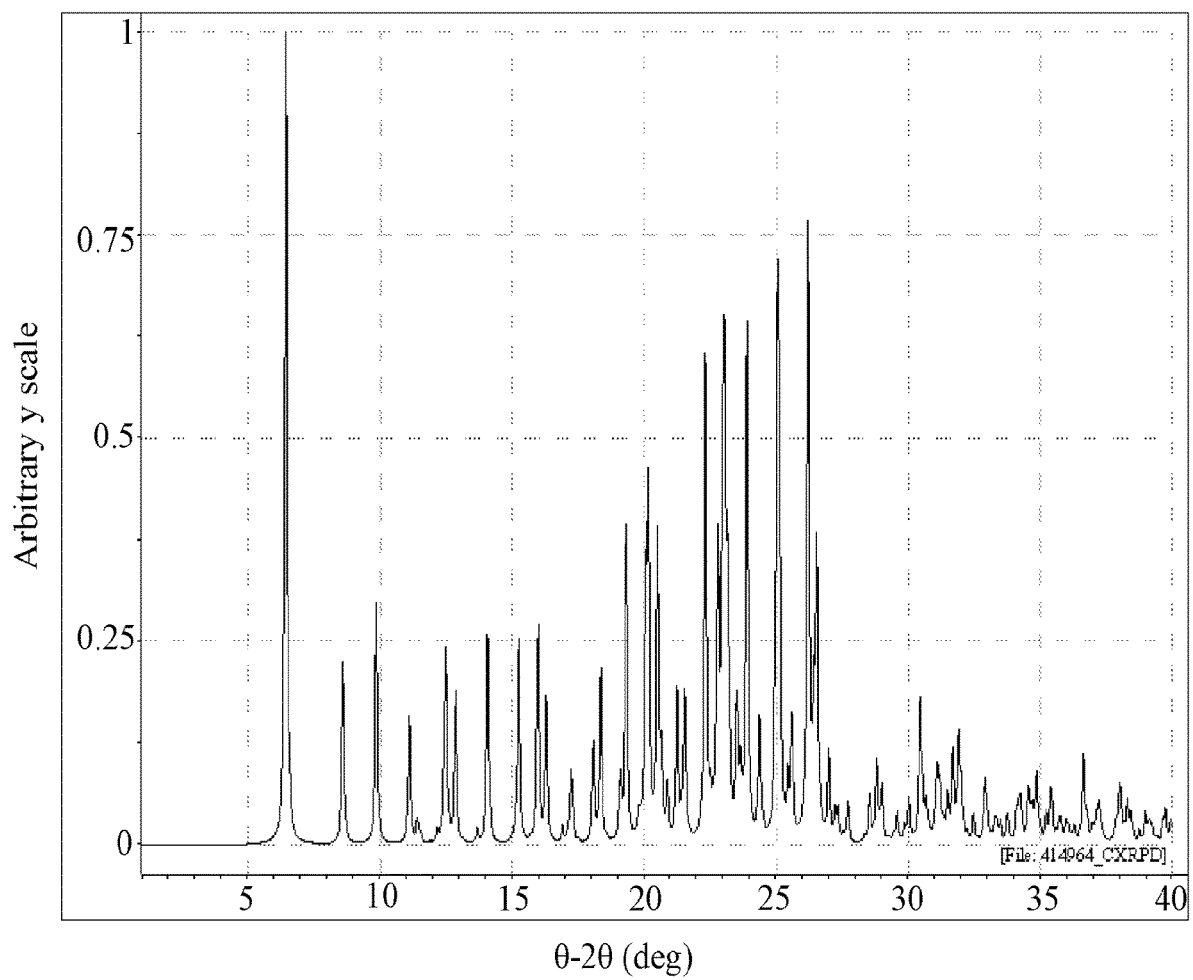
FIG. 20 depicts calculated XRPD pattern of hemi-sodium hemi-acetonitrile solvate.

FIG. 20 shows a calculated XRPD pattern of hemi-sodium hemi-acetonitrile solvate, generated from the single crystal structure.

TABLE 4

Crystal Data and Data Collection Parameters for hemi-sodium hemi-acetonitrile solvate

| | |
|---|---|
| Empirical formula | $C_{32}H_{20}Cl_2F_{12}N_3NaO_{10}P_2$ |
| Formula weight | 990.34 |
| Temperature | 100(2) K |
| Wavelength | 1.54178 Å |
| Crystal system | Monoclinic |
| Space group | P2$_1$ |
| Unit cell dimensions | a = 9.0319(2) Å    α = 90°. |
| | b = 15.4685(4) Å   β = 96.9157(15)°. |
| | c = 27.7447(5) Å   γ = 90°. |
| Volume | 3848.01(15) Å$^3$ |
| Z | 4 |
| Density (calculated) | 1.709 Mg/m$^3$ |
| Absorption coefficient | 3.514 mm$^{-1}$ |
| F (000) | 1984 |
| Crystal size | 0.250 × 0.100 × 0.090 mm$^3$ |
| Theta range for data collection | 1.604 to 72.139°. |
| Index ranges | −11 <= h <= 11, −18 <= k <= 18, −34 <= l <= 34 |
| Reflections collected | 42984 |
| Independent reflections | 13870 [R(int) = 0.0471] |
| Completeness to theta = 67.679° | 97.4% |
| Absorption correction | Semi-empirical from equivalents |
| Max. and min. transmission | 0.743 and 0.538 |
| Refinement method | Full-matrix least-squares on F$^2$ |
| Data/restraints/parameters | 13870/515/1265 |
| Goodness-of-fit on F$^2$ | 1.115 |
| Final R indices [I > 2sigma(I)] | R1 = 0.0509, wR2 = 0.1278 |
| R indices (all data) | R1 = 0.0590, wR2 = 0.1355 |
| Absolute structure parameter | 0.104(19) |
| Extinction coefficient | 0.00106(8) |

Experimental

Preparation

3:8 (v/v) acetonitrile (ACN):toluene solvent mixture is added to 2-{[3,5-bis(trifluoromethyl)phenyl]carbamoyl}-4-chlorophenyl dihydrogen phosphate with sonication. Solution is filtered (0.2 µm nylon). Crystals are grown by partial slow evaporation (vial loosely capped) from solution. Long, thick needles are observed.

Additional experimental details for the synthesis are set forth in this paragraph. 2-{[3,5-bis(trifluoromethyl)phenyl]carbamoyl}-4-chlorophenyl dihydrogen phosphate from Example 2A (28.6 mg) is combined with acetonitrile/toluene 3:8 (v/v, 8 mL) with sonication, resulting in a suspension containing undissolved solids. The suspension is filtered through a 0.2-µm nylon filter, resulting in a clear solution. The solution is loosely capped for slow evaporation at ambient conditions. After partially evaporating over 15 days, the sample is observed to contain a clear liquid phase with a few colorless needles on the bottom.

Data Collection

A colorless rod of $C_{32}H_{20}Cl_2F_{12}N_3NaO_{10}P_2$ [$C_{15}H_9ClF_6NO_5P$, $C_{15}H_8ClF_6NO_5P$, Na, $C_2H_3N$] having approximate dimensions of 0.25×0.10×0.09 mm$^3$, is mounted on a nylon loop in random orientation. Preliminary examination and data collection are performed with Cu Kα radiation (λ=1.54178 Å) on a Rigaku Rapid II diffractometer equipped with confocal optics. Refinements are performed using SHELX2014 (Sheldrick, G. M., *Acta Cryst.*, 2015, C71, 3-8).

Cell constants and an orientation matrix for data collection are obtained from least-squares refinement using the setting angles of 42984 reflections in the range 1°<θ<72°. The space group is determined from the systematic presence of the following conditions: 0k0 k=2n, and from subsequent least-squares refinement to be P2$_1$ (no. 4). The data are collected to a maximum diffraction angle (2θ) of 144.28°, at a temperature of 100 K.

Data Reduction

Frames are integrated with HKL3000 (Otwinowski, Z. et al., *Methods Enzymol.*, 1997, 276, 307). A total of 42984 reflections are collected, of which 13870 are unique. Lorentz and polarization corrections are applied to the data. The linear absorption coefficient is 3.514 mm$^{-1}$ for Cu Kα radiation. An empirical absorption correction using SCALE-PACK (Otwinowski, Z. et al., *Methods Enzymol.*, 1997, 276, 307) is applied. Transmission coefficients range from 0.538 to 0.743. A secondary extinction correction is applied (Glusker, J. et al., Crystal Structure Analysis: A Primer, 2$^{nd}$ ed., Oxford University Press: New York, 1985, page 87). The final coefficient, refined in least-squares, is 0.00106(8) (in absolute units). Intensities of equivalent reflections are averaged. The agreement factor for the averaging is 4.71% based on intensity.

Structure Solution and Refinement

The structure is solved by direct methods using SHELXS-97 (Sheldrick, G. M., *Acta Cryst.*, 2015, C71, 3-8). The remaining atoms are located in succeeding difference Fourier syntheses. Acid hydrogen atoms are refined independently. All other hydrogen atoms are included in the refinement but restrained to ride on the atom to which they are bonded. The structure is refined in full-matrix least-squares by minimizing the function:

$$\Sigma w(|F_o|^2 - |F_c|^2)^2$$

The weight w is defined as:
$1/[\sigma^2(F_o^2) + (0.0493P)^2 + (8.2744P)]$, where $P=(F_o^2+2F_c^2)/3$. Scattering factors are taken from the "International Tables for Crystallography" (International Tables for Crystallograpy, Vol. C, Kluwer Academic Publishers: Dordrecht, The Netherlands, 1992, Tables 4.2.6.8 and 6.1.1.4). Of the 13870 reflections used in the refinements, only the reflections with $F_o^2 > 2\sigma(F_o^2)$ are used in calculating the fit residual, R. A total of 12330 reflections are used in the calculation. The final cycle of refinement includes 1265 variable parameters and converge with unweighted and weighted agreement factors of:

$$R = \Sigma |F_o - F_c|/\Sigma F_o = 0.0509$$

$$R_w = \sqrt{(\Sigma w(F_o^2-F_c^2)^2/\Sigma w(F_o^2)^2)} = 0.1278$$

The standard deviation of an observation of unit weight (goodness of fit) is 1.115. The highest peak in the final difference Fourier has a height of 0.662 e/Å$^3$. The minimum negative peak has a height of −0.452 e/Å$^3$.

Calculated X-Ray Powder Diffraction (XRPD) Pattern

A calculated XRPD pattern is generated for Cu radiation using Mercury (Macrae, C. F. et al., *J. Appl. Cryst.*, 2006, 39, 453-457) and the atomic coordinates, space group, and unit cell parameters from the single crystal structure. Because the single crystal data are collected at low temperatures (100 K), peak shifts may be evident between the pattern calculated from low temperature data and the room temperature experimental powder diffraction pattern, particularly at high diffraction angles.

Atomic Displacement Ellipsoid and Packing Diagrams

The atomic displacement ellipsoid diagram is prepared using Mercury (Macrae, C. F. et al., *J. Appl. Cryst.*, 2006, 39, 453-457). Atoms are represented by 50% probability anisotropic thermal ellipsoids. Packing diagrams and additional figures are also generated with Mercury. Hydrogen bonding is represented as dashed lines.

Example 6—2-{[3,5-bis(trifluoromethyl)phenyl]carbamoyl}-4-chlorophenyl Dihydrogen Phosphate p-Dioxane Solvate (Form I)

2-{[3,5-bis(trifluoromethyl)phenyl]carbamoyl}-4-chlorophenyl dihydrogen phosphate p-dioxane solvate is prepared by fast evaporation from p-dioxane.

Additional experimental details for the synthesis are set forth in this paragraph. 2-{[3,5-bis(trifluoromethyl)phenyl]carbamoyl}-4-chlorophenyl dihydrogen phosphate from Example 2A (37.2 mg) is dissolved in p-dioxane (1 mL) with sonication, resulting in a clear solution. The solution is filtered through a 0.2 μm nylon filter and allowed to evaporate to dryness from an open vial at ambient conditions. Slightly waxy white solids are observed.

$^1$H NMR shows 0.5 moles p-dioxane per mole 2-{[3,5-bis(trifluoromethyl)phenyl]carbamoyl}-4-chlorophenyl dihydrogen phosphate.

Figure 22:
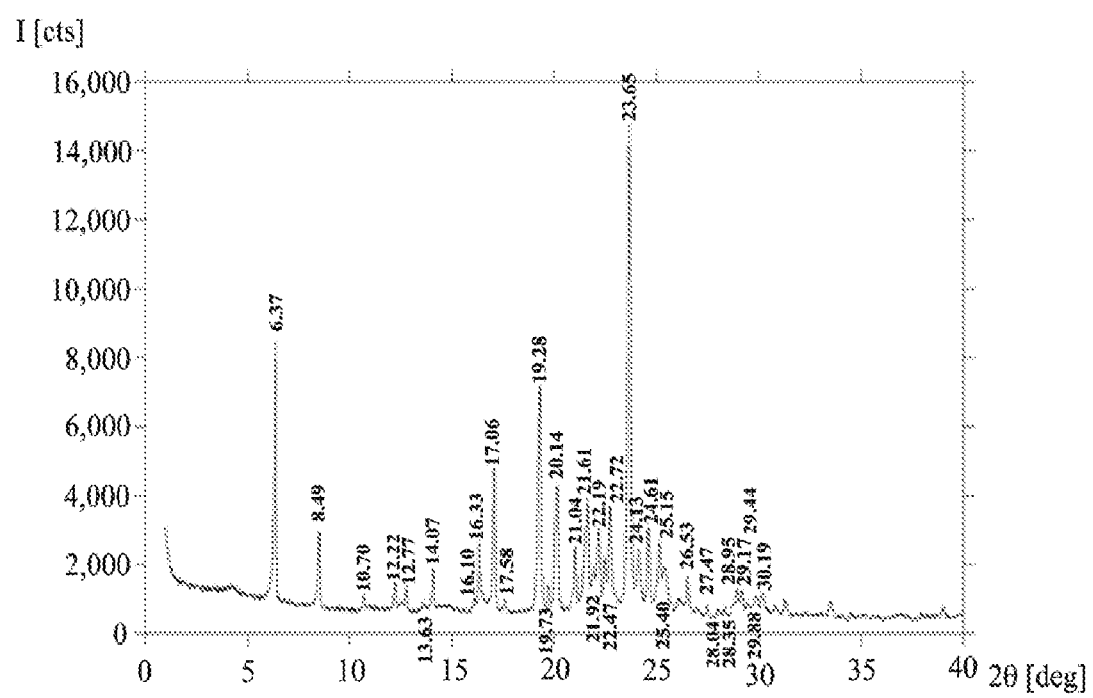
FIG. 22 depicts an XRPD pattern of Form I collected with Cu Kα radiation.

An XRPD pattern of the product (2-{[3,5-bis(trifluoromethyl)phenyl]carbamoyl}-4-chlorophenyl dihydrogen phosphate p-dioxane solvate) is shown in FIG. 22. The XRPD pattern is obtained as described in the general XRPD procedure in Example 1. 2-theta values, d-spacings, and peak intensities for the XRPD pattern shown in FIG. 22 are provided above in Table F in Crystalline Form 3.12. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 721 s, Scan Speed 3.2°/min, Slit: DS: ½°, SS: null, Revolution Time: 1.0 s, Mode: Transmission.

The XRPD pattern in FIG. 22 is successfully indexed, indicating that the sample consists primarily or exclusively of a single crystalline phase. The unit cell volume obtained from the indexing solution is consistent with a hemi-dioxane solvate (can accommodate up to ~0.5 moles p-dioxane).

Example 7—2-{[3,5-bis(trifluoromethyl)phenyl]carbamoyl}-4-chlorophenyl Dihydrogen Phosphate Methanol Solvate (Form L)

2-{[3,5-bis(trifluoromethyl)phenyl]carbamoyl}-4-chlorophenyl dihydrogen phosphate is slow cooled in MeOH/water 26:74 (v/v, a$_w$ 0.89) from 63° C. to room temperature and allowed to stand at room temperature for 5 days. The solution is then kept in the freezer for 4 days. The solution is next allowed to equilibrate to room temperature and vacuum filtered.

Additional experimental details for the synthesis are set forth in this paragraph. A solution of 2-{[3,5-bis(trifluoromethyl)phenyl]carbamoyl}-4-chlorophenyl dihydrogen phosphate from Example 2A (30.0 mg) in MeOH/water 26:74 (v/v, 1.32 mL) is heated with stirring at 63° C., resulting in a slightly hazy solution. The solution is filtered using a pre-warmed syringe and 0.2 μm nylon filter into a warm vial. The solution remains slightly hazy after filtering. The sample is left in a metal heater block on the hot plate, and the heat source is turned off, allowing the solution to slowly cool to ambient temperature without stirring. After standing at ambient temperature for 5 hours, a translucent gelatinous mass and clear liquid phase is observed. The sample placed in the freezer for 4 days. Upon removal from the freezer, a translucent gel is observed. The gel becomes a liquid with white solids in suspension upon equilibration to ambient temperature. The resulting solids are collected by vacuum filtration and air dried on the filter under reduced pressure 1 minute.

$^1$H NMR shows 0.6 moles methanol per mole 2-{[3,5-bis(trifluoromethyl)phenyl]carbamoyl}-4-chlorophenyl dihydrogen phosphate.

Figure 23:
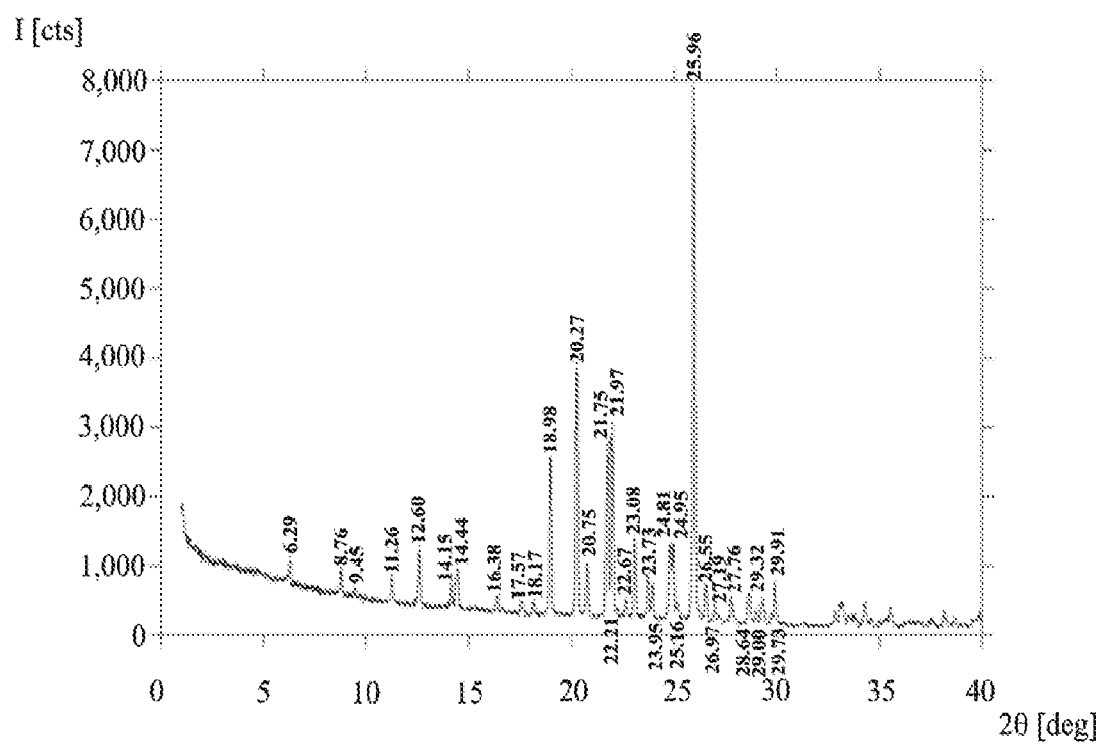
FIG. 23 depicts an XRPD pattern of Form L collected with Cu Kα radiation.

An XRPD pattern of the product (2-{[3,5-bis(trifluoromethyl)phenyl]carbamoyl}-4-chlorophenyl dihydrogen phosphate p-dioxane solvate) is shown in FIG. 23. The XRPD pattern is obtained as described in the general XRPD procedure in Example 1. 2-theta values, d-spacings, and peak intensities for the XRPD pattern shown in FIG. 23 are provided above in Table H in Crystalline Form 4.10. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.01-39.98° 2θ, Step Size: 0.017° 2θ, Collection Time: 718 s, Scan Speed 3.3°/min, Slit: DS: ½°, SS: null, Revolution Time: 1.0 s, Mode: Transmission.

The XRPD pattern in FIG. 23 is successfully indexed, indicating the material consists primarily or exclusively of a single crystalline phase. The unit cell volume obtained from the indexing solution is consistent with up to ~0.5 moles MeOH present.

Figure 29:
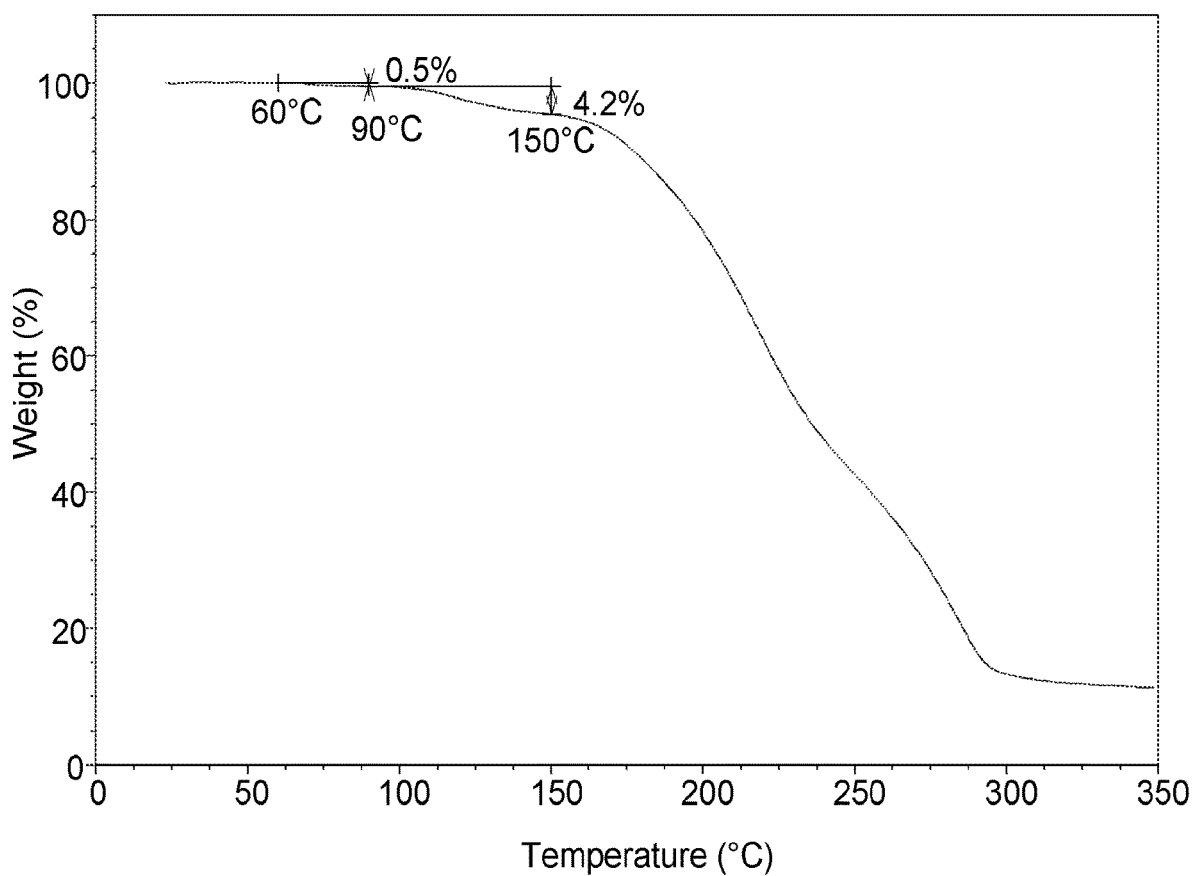
FIG. 29 depicts a TGA thermogram of Form L.
Figure 30:
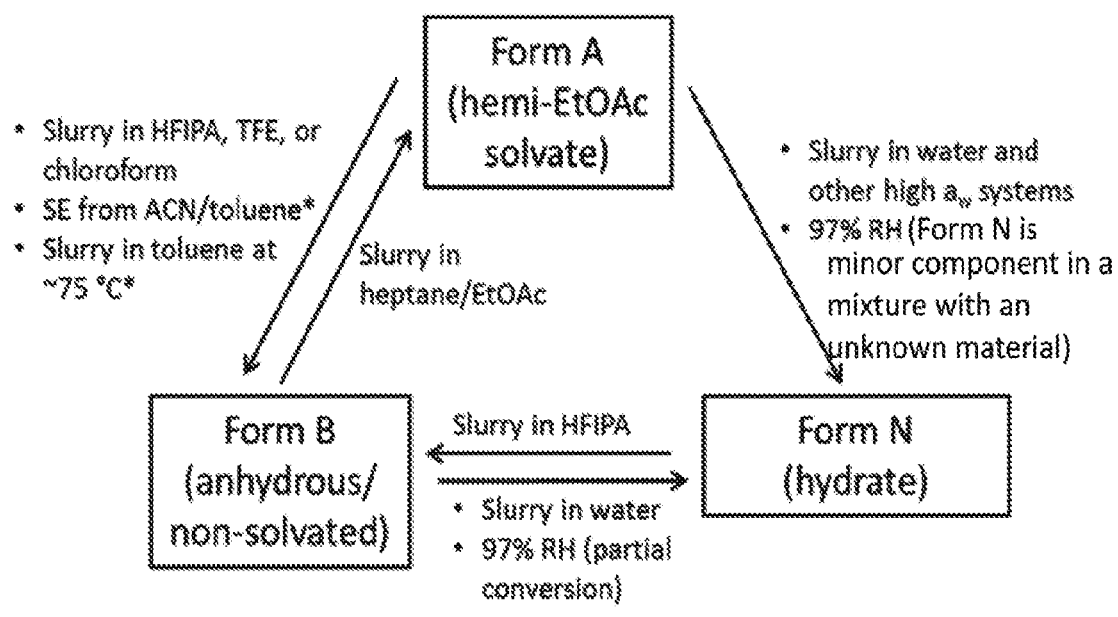
FIG. 30 depicts the interconversion of Forms A, B, and N.

A TGA thermogram of the product (1.2348 mg) is in FIG. 29. Little weight loss is observed up to 90° C. (0.5 weight % loss between 60° C. to 90° C.). Stepwise weight loss of 4.2 weight % is observed between 90° C. and 150° C., likely corresponding with loss of solvent. If MeOH is assumed to be the only volatile, the weight loss corresponds with 0.6 moles MeOH.

Example 8—2-{[3,5-bis(trifluoromethyl)phenyl] carbamoyl}-4-chlorophenyl Dihydrogen Phosphate Hydrate (Form N)

2-{[3,5-bis(trifluoromethyl)phenyl]carbamoyl}-4-chlorophenyl dihydrogen phosphate is slurried in water (pH 5) at room temperature for 5 minutes. Continue to slurry at room temperature for 24 hours. Solution is vacuum filtered. A sub-sample is removed (Part 1), which appears as an off-white paste. The remainder is air dried on the filter for 5 minutes (Part 2). The post-slurry pH of the water is 1.6.

Additional experimental details for the synthesis are set forth in this paragraph. A suspension of 2-{[3,5-bis(trifluoromethyl)phenyl]carbamoyl}-4-chlorophenyl dihydrogen phosphate is prepared using 2-{[3,5-bis(trifluoromethyl) phenyl]carbamoyl}-4-chlorophenyl dihydrogen phosphate from Example 2A (74.6 mg) and water (3 mL). The suspension is left to stir at ambient conditions. After 5 minutes, a thick suspension is observed. The slurry is stirred for 24 hours, and a portion of the resulting solids is isolated by vacuum filtration and collected from the filter while damp (Part 1). Another portion of the resulting solids is isolated by vacuum filtration and air dried on the filter under reduced pressure for 5 minutes (Part 2).

Figure 24:
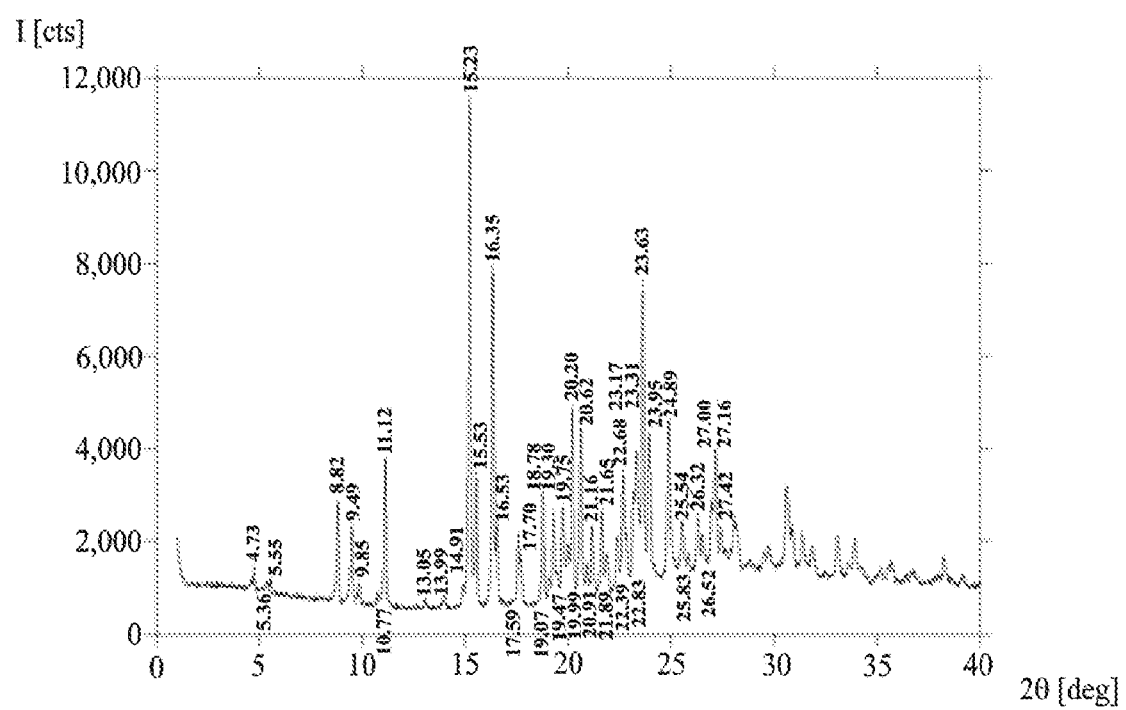
FIG. 24 depicts an XRPD pattern of Form N collected with Cu Kα radiation.
Figure 44:
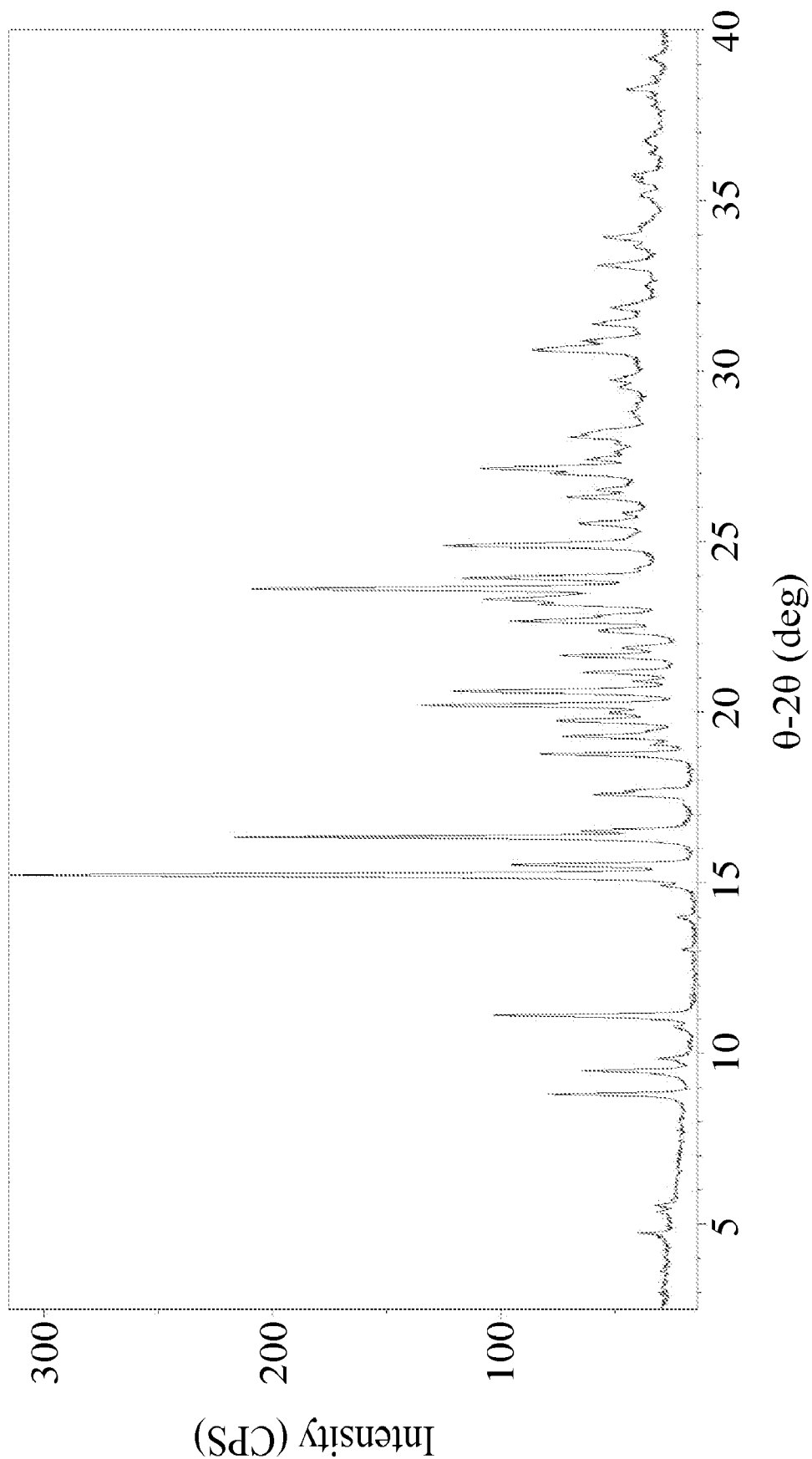
FIG. 44 depicts an XRPD pattern of Form N collected with Cu Kα radiation.

An XRPD pattern of Part 1 is shown in FIG. 24. The XRPD pattern is also shown in FIG. 44. The XRPD pattern is obtained as described in the general XRPD procedure in Example 1. 2-theta values, d-spacings, and peak intensities for the XRPD pattern shown in FIG. 24 are provided above in Table J in Crystalline Form 5.14. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 718 s, Scan Speed 3.3°/min, Slit: DS: ½°, SS: null, Revolution Time: 1.0 s, Mode: Transmission.

The XRPD pattern in FIG. 24 (also shown in FIG. 44) is successfully indexed indicating that the material consists primarily or exclusively of a single crystalline phase. The unit cell volume obtained from the indexing solution can accommodate Formula I with up to ~3 moles of water per mole of Formula I.

Figure 45:
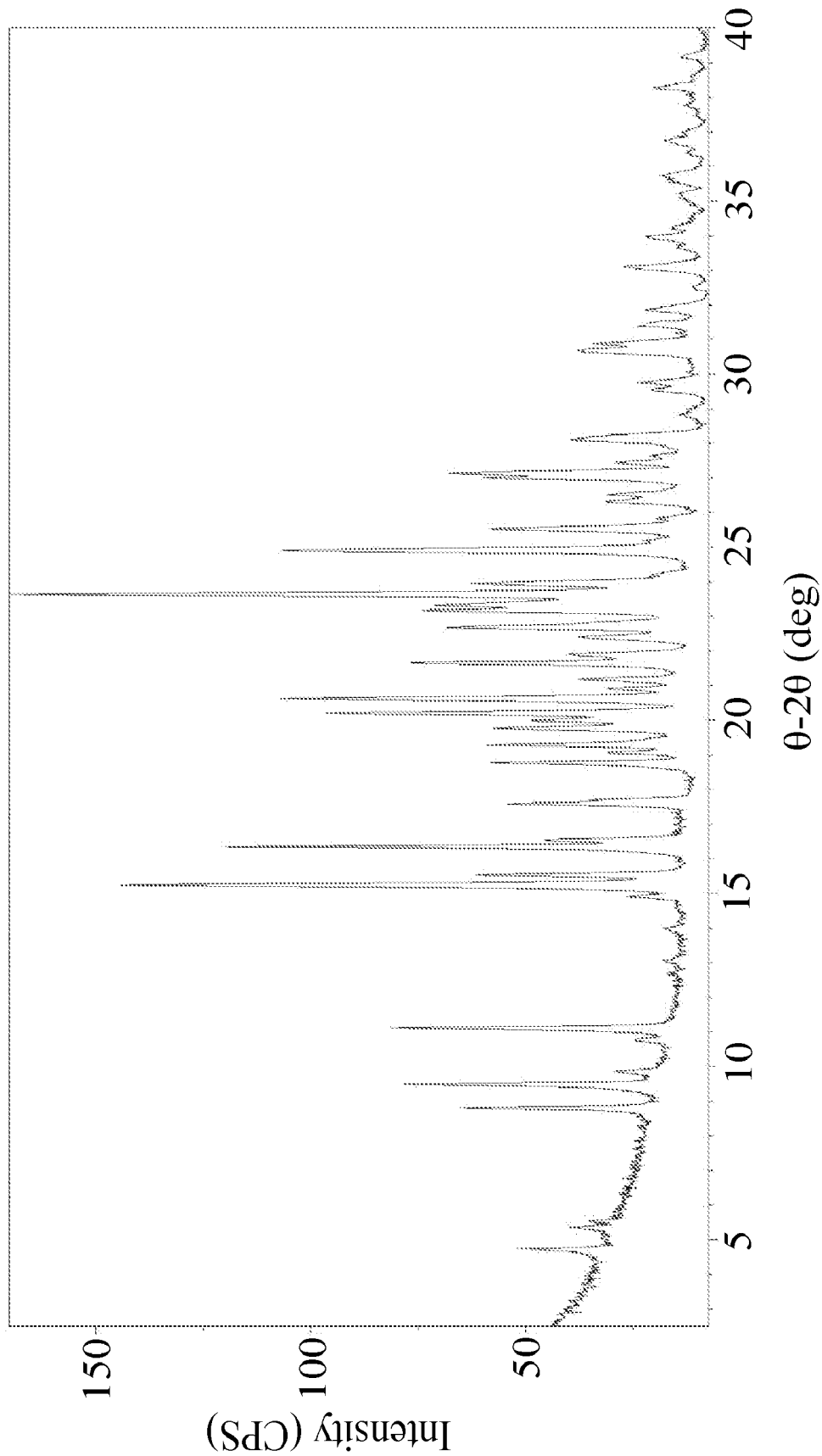
FIG. 45 depicts an XRPD pattern of Form N collected with Cu Kα radiation.

An XRPD pattern of Part 2 shows that it is Form N as well. An XRPD pattern of Part 2 is shown in FIG. 45. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 719 s, Scan Speed 3.3°/min, Slit: DS: ½°, SS: null, Revolution Time: 1.0 s, Mode: Transmission.

Figure 26:
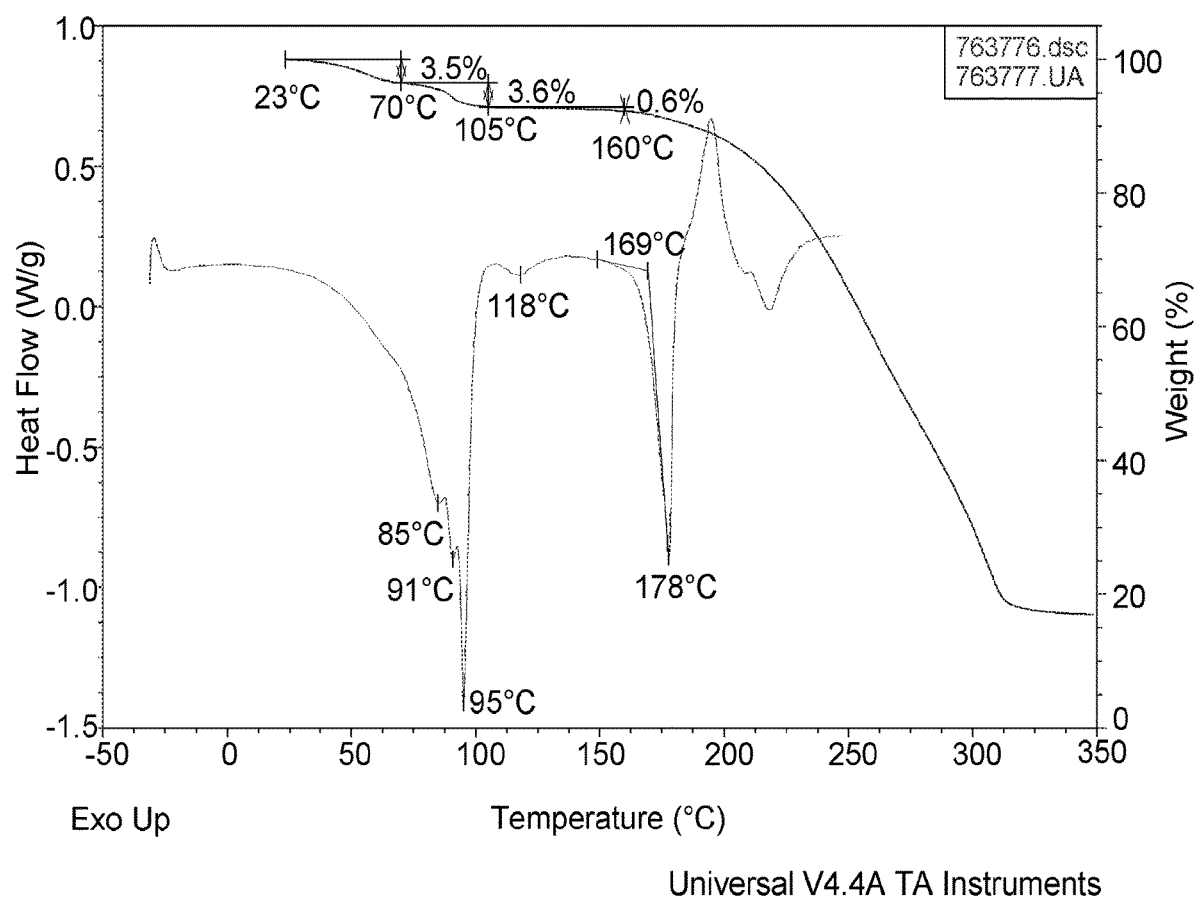
FIG. 26 depicts a DSC and TGA overlay for Form N.

DSC and TGA thermograms of Part 2 are obtained (DSC Parameters: Size: 1.4620 mg, Method: (–30)-250-10, TOC, Instrument: 2920 MDSC V2.6A, TGA: 7.61023 mg). An overlay of the DSC and TGA thermograms is in FIG. 26. The sample exhibits two discrete weight loss steps of 3.5 weight % from 23° C. to 70° C. and 3.6 weight % between 70° C. and 105° C., corresponding with a series of overlapping endotherms at 85° C., 91° C., and 95° C. by DSC, likely indicative of dehydration. If water is assumed to be the only volatile, each weight loss corresponds with 1 mole of water per mole of 2-{[3,5-bis(trifluoromethyl)phenyl]carbamoyl}-4-chlorophenyl dihydrogen phosphate, indicating the sample may be composed of a dihydrate. 0.6 weight % loss is seen between 105° C. to 160° C. in the TGA thermogram. Following dehydration, a small endotherm is observed at 118° C., possibly corresponding with a crystallization event. A relatively sharp endotherm is noted at 178° C. with an onset at 169° C., likely corresponding with concomitant melting and decomposition as evidenced by the steep drop in the TGA thermogram and erratic thermal behaviour by DSC above 175° C. The likely melt onset is at a slightly lower temperature than that for anhydrous/non-solvated Form B (169° C. versus 173° C. for Form B), likely indicating that Form N does not convert to Form B upon dehydration.

Figure 49:
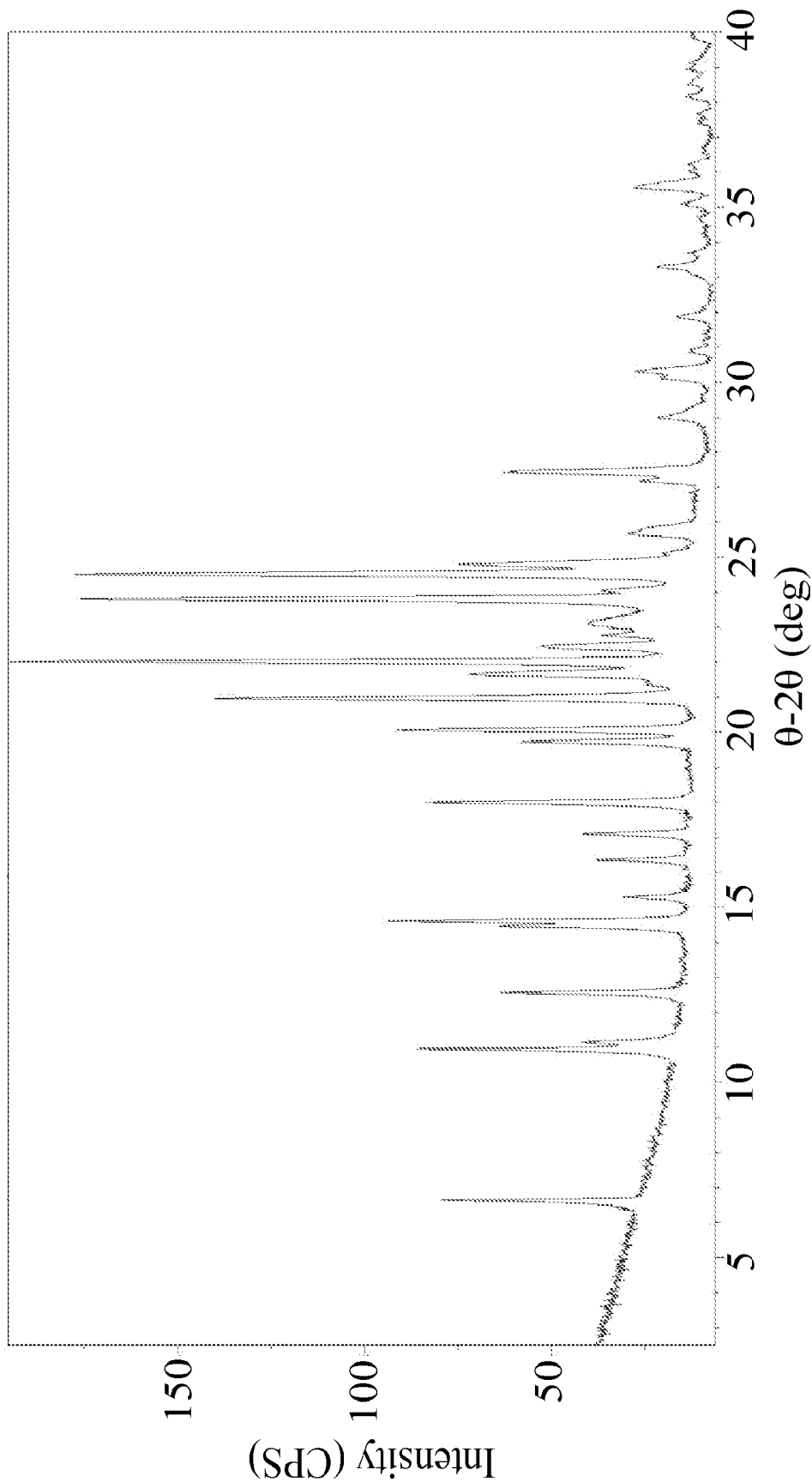
FIG. 49 depicts an XRPD pattern of Form B collected with Cu Kα radiation.

To further confirm the chemical composition of Form N, the material is slurried in hexafluoroisopropanol (HFIPA) for 1 day, which results in conversion to Form B (plus a minor peat at 23° 2θ) by XRPD. An XRPD pattern of the product is shown in FIG. 49. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 718 s, Scan Speed 3.3°/min, Slit: DS: ½°, SS: null, Revolution Time: 1.0 s, Mode: Transmission.

Example 9—2-{[3,5-bis(trifluoromethyl)phenyl] carbamoyl}-4-chlorophenyl Dihydrogen Phosphate Hydrate (Form N)

2-{[3,5-bis(trifluoromethyl)phenyl]carbamoyl}-4-chlorophenyl dihydrogen phosphate is stirred in EtOAc with 1 N HCl and evaporated. The solid is then slurried in water at room temperature for 1 day and vacuum filtered.

Additional experimental details for the synthesis are set forth in this paragraph. A suspension of 2-{[3,5-bis(trifluoromethyl)phenyl]carbamoyl}-4-chlorophenyl dihydrogen phosphate is prepared using 2-{[3,5-bis(trifluoromethyl)phenyl]carbamoyl}-4-chlorophenyl dihydrogen phosphate from Example 2B (127.6 mg) and water (5 mL). The slurry is left to stir at ambient conditions for 1 day, resulting in an opaque white suspension. The resulting solids are isolated by vacuum filtration and air dried on the filter under reduced pressure for 4 minutes.

Figure 46:
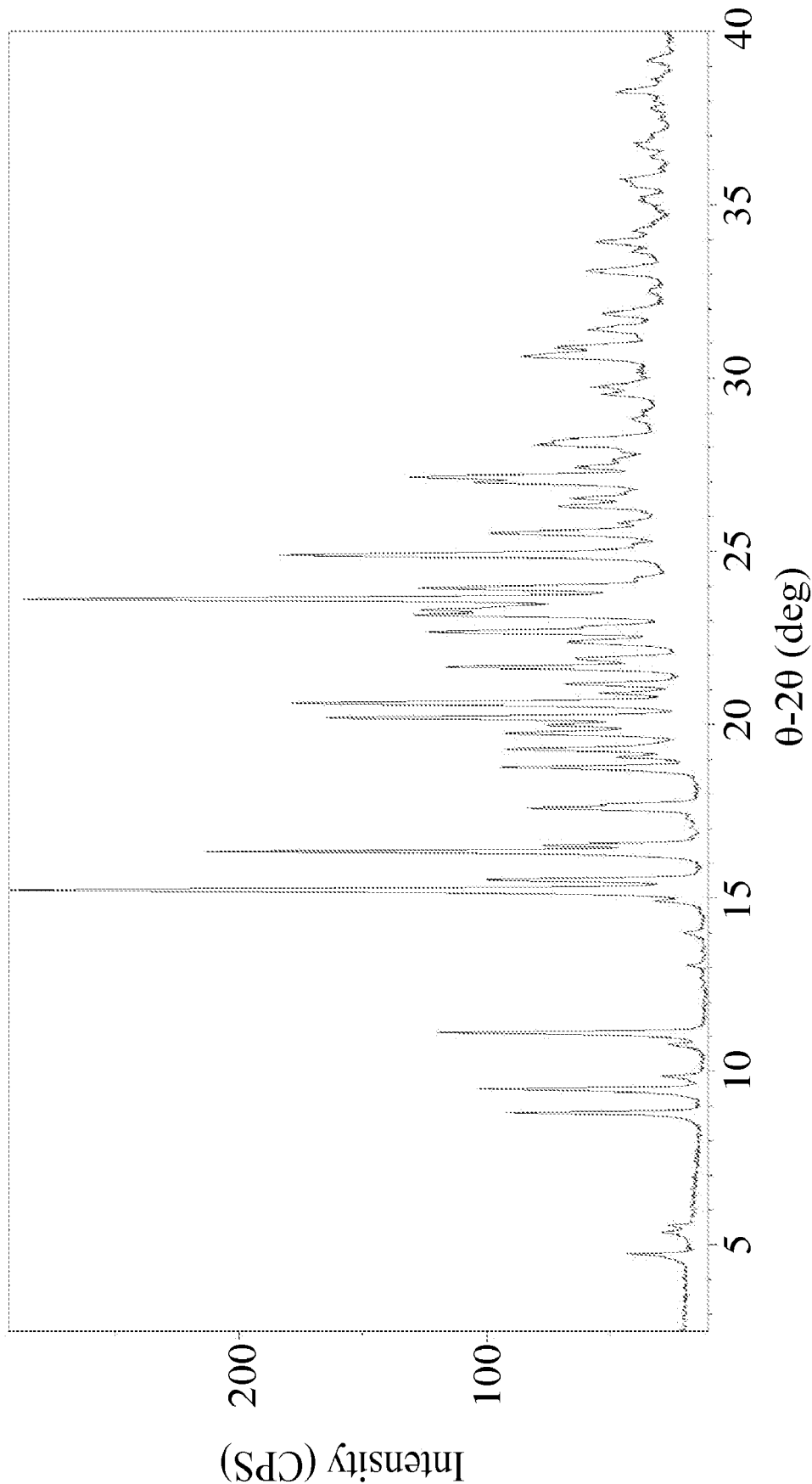
FIG. 46 depicts an XRPD pattern of Form N collected with Cu Kα radiation.

XRPD of the product shows that it is Form N. An XRPD pattern of the product is shown in FIG. 46. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 721 s, Scan Speed 3.2°/min, Slit: DS: ½°, SS: null, Revolution Time: 1.0 s, Mode: Transmission.

Figure 27:
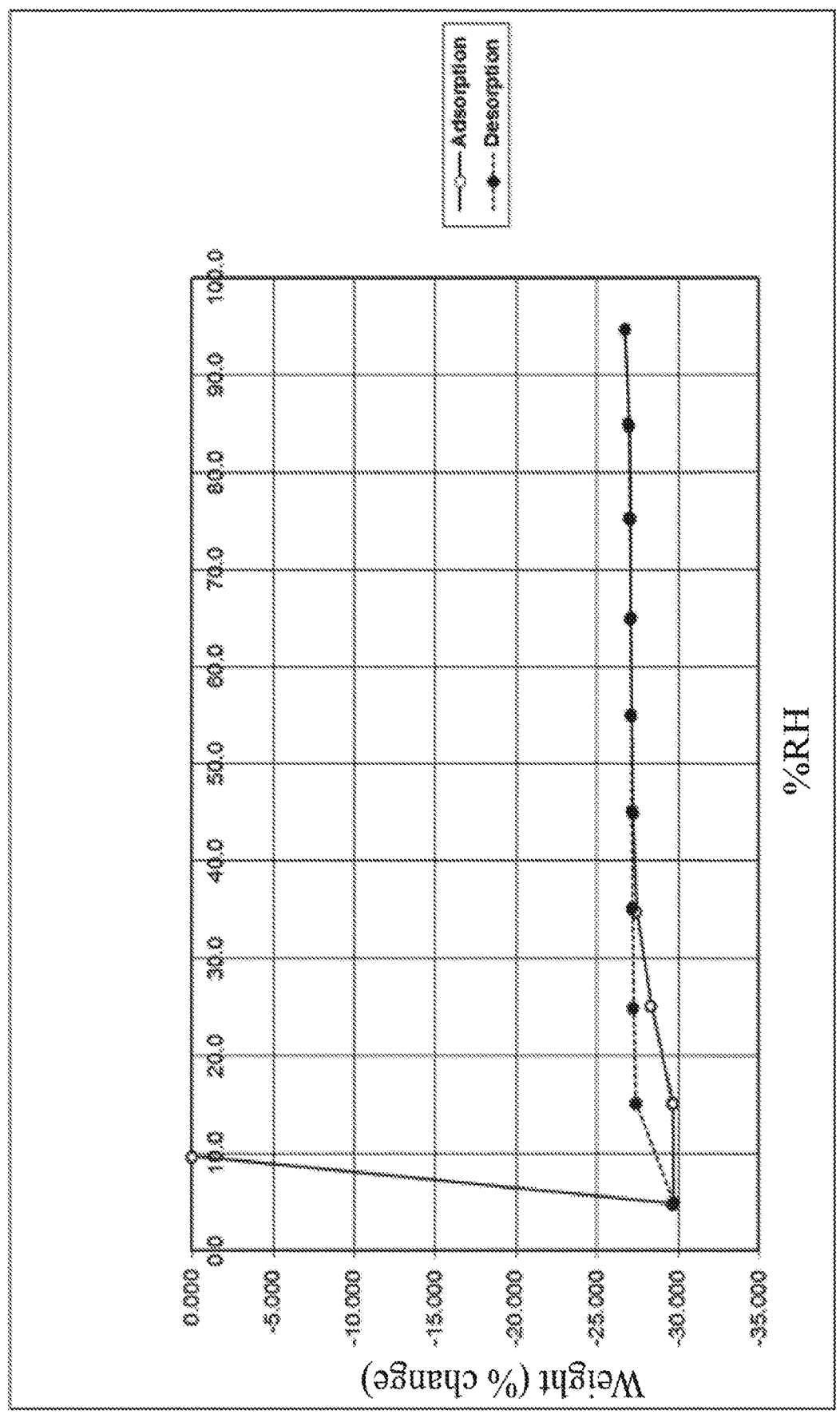
FIG. 27 depicts a DVS isotherm of Form N.
Figure 54:
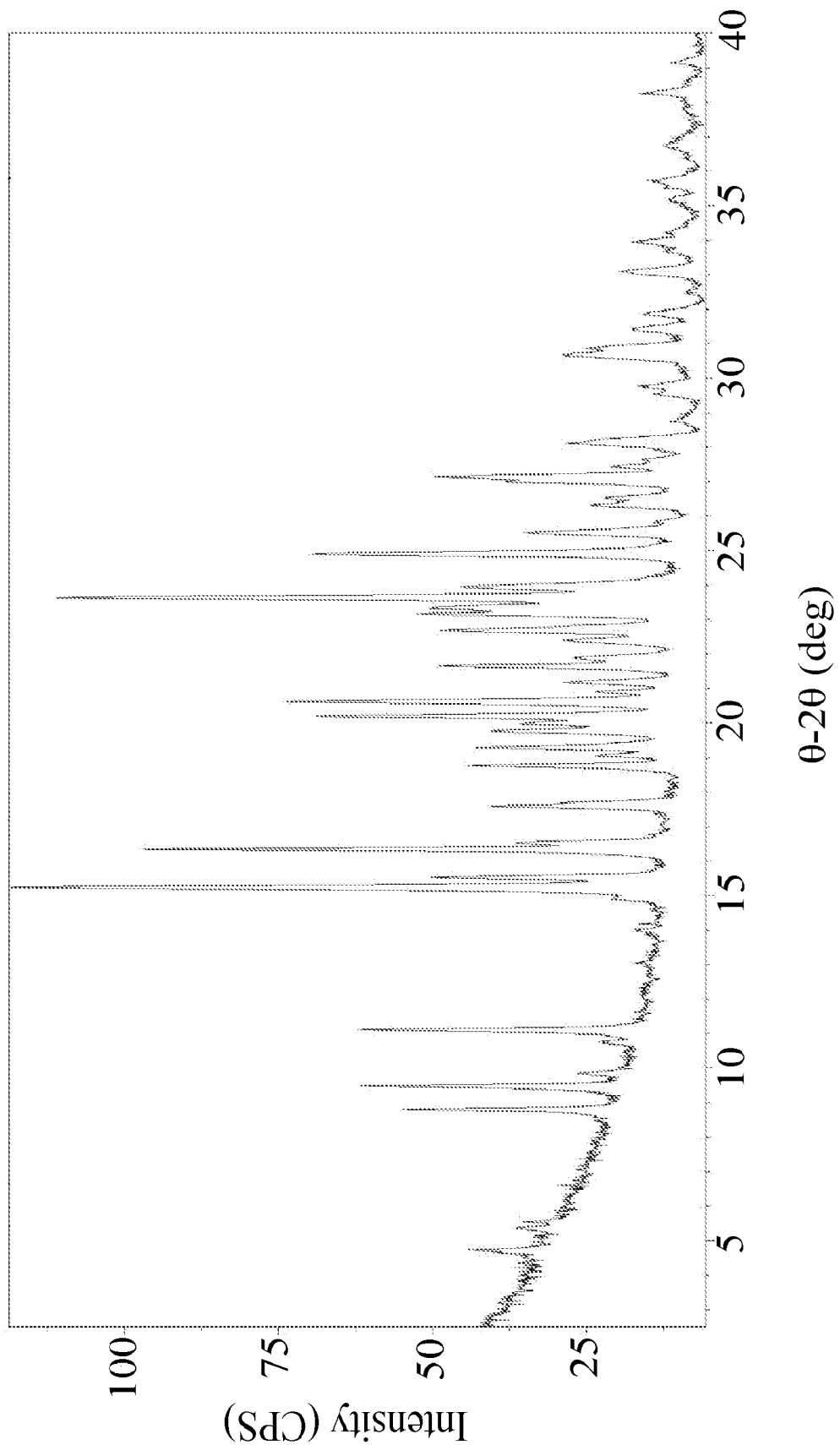
FIG. 54 depicts an XRPD pattern of Form N collected with Cu Kα radiation.

A DVS isotherm of the product is shown in FIG. 27. The product exhibits 30% weight loss upon equilibration to 5% relative humidity, likely indicating loss of residual water. The presence of residual water is consistent with the >100% yield obtained upon preparation of the product. It is unknown whether any potentially unbound water is lost upon this equilibration step as well. Upon increasing the relative humidity from 5% to 95%, the sample gains 3 weight %, indicating significant hygroscopicity. All of this weight is lost upon desorption with slight hysteresis noted between 35% and 5% relative humidity. XRPD of the post-DVS material shows no form change. An XRPD pattern of the post-DVS material is shown in FIG. 54. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 720 s, Scan Speed 3.2°/min, Slit: DS: ½°, SS: null, Revolution Time: 1.0 s, Mode: Transmission.

The product is found to contain 14.2% water by Karl Fischer (KF) analysis, equivalent to 4.2 moles water. A portion of the measured water may be attributable to residual water in the sample. The percent water content by KF is lower than the percent weight loss noted in the DVS experiment at 5% relative humidity, possibly due to partial drying of the sample between analyses and/or preparation for KF analysis.

Example 10—2-{[3,5-bis(trifluoromethyl)phenyl]carbamoyl}-4-chlorophenyl Dihydrogen Phosphate (Form B)

Hexfluoroisopropanol (HFIPA) is added to 2-{[3,5-bis(trifluoromethyl)phenyl]carbamoyl}-4-chlorophenyl dihydrogen phosphate, the solution is refrigerated for 2 months, and vacuum filtered.

Additional experimental details for the synthesis are set forth in this paragraph. 2-{[3,5-bis(trifluoromethyl)phenyl]carbamoyl}-4-chlorophenyl dihydrogen phosphate from Example 2A (29.3 mg) is combined with hexfluoroisopropanol (HFIPA) (0.4 mL) with sonication, resulting in a thick opaque suspension. The sample is stored under refrigeration for 2 months, after which the solids are isolated by vacuum filtration and air dried on the filter under reduced pressure for 0.5-1 minute.

No solvent is detected by $^1$H NMR, indicating a non-solvated material.

Figure 21:
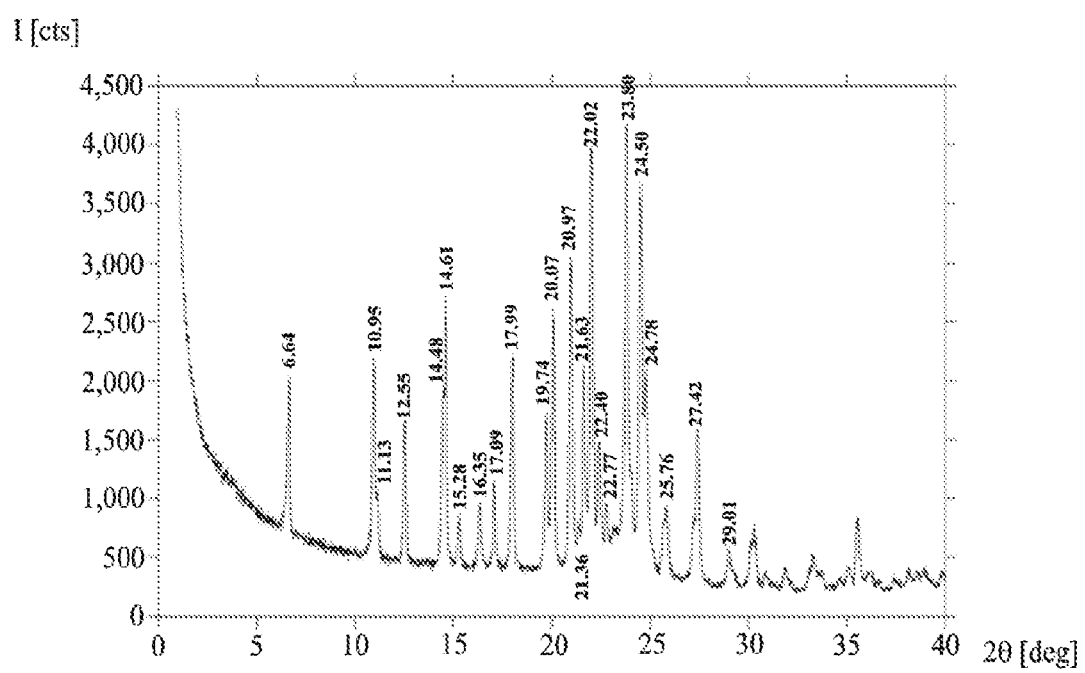
FIG. 21 depicts an XRPD pattern of Form B collected with Cu Kα radiation.
Figure 37:
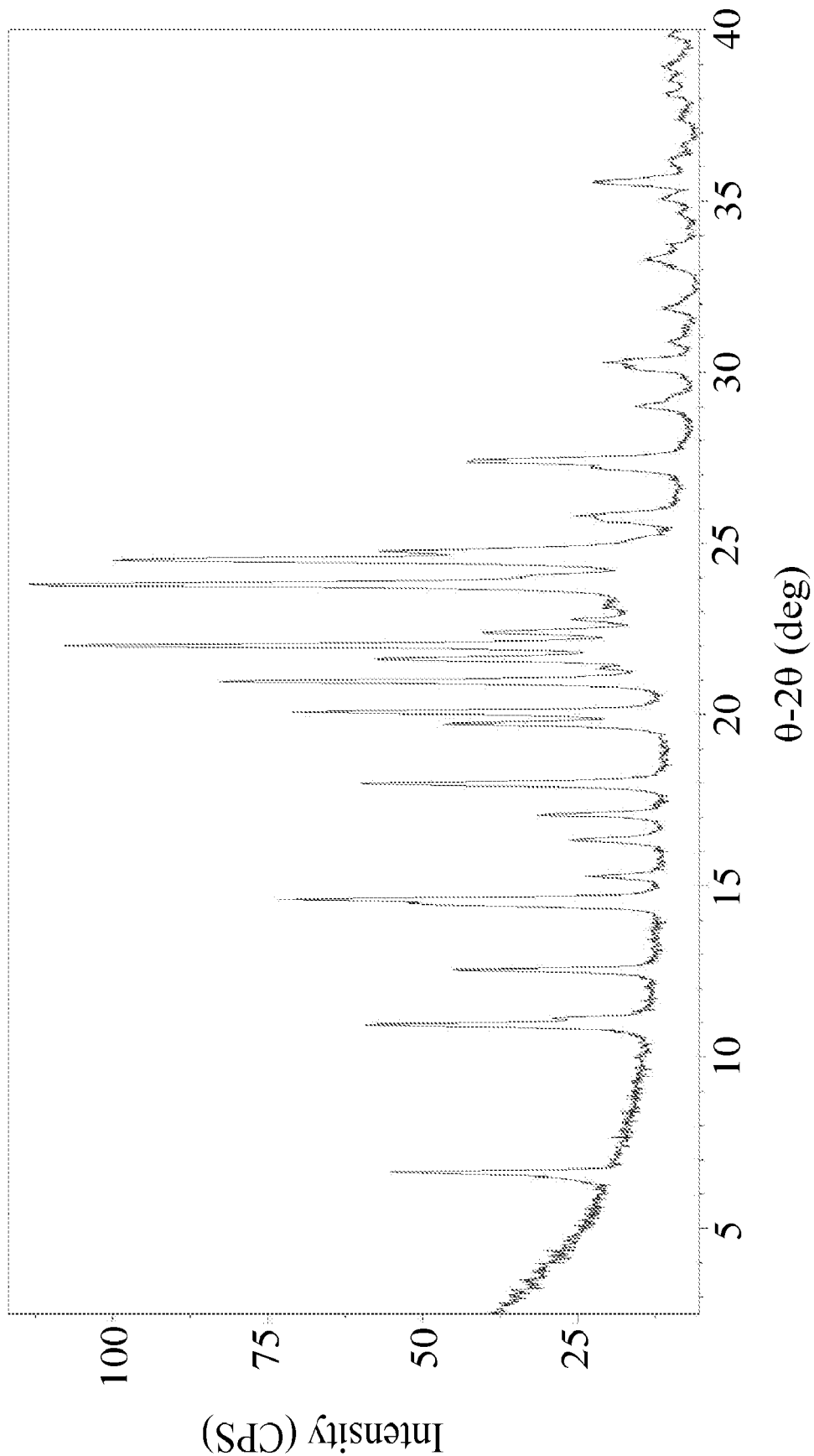
FIG. 37 depicts an XRPD pattern of Form B collected with Cu Kα radiation.

An XRPD pattern of the product is shown in FIG. 21 (Form B+minor peak at ~23° θ). The XRPD pattern is also shown in FIG. 37. The XRPD pattern is obtained as described in the general XRPD procedure in Example 1. 2-theta values, d-spacings, and peak intensities for the XRPD pattern shown in FIG. 21 are provided above in Table D in Crystalline Form 6.11. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.01-39.98° 2θ, Step Size: 0.017° 2θ, Collection Time: 718 s, Scan Speed 3.3°/min, Slit: DS: ½°, SS: null, Revolution Time: 1.0 s, Mode: Transmission.

The XRPD pattern in FIG. 21 (also shown in FIG. 37) is successfully indexed indicating that the sample consists primarily of a single crystalline phase. However, an additional broad peak at ~23° 2θ is present in all XRPD patterns of Form B discussed herein and is inconsistent with the peak positions allowed by the indexing solution, suggesting that samples of Form B contain an additional unknown phase. The unit cell volume obtained from the indexing solution is consistent with anhydrous/non-solvated Formula I.

Figure 40:
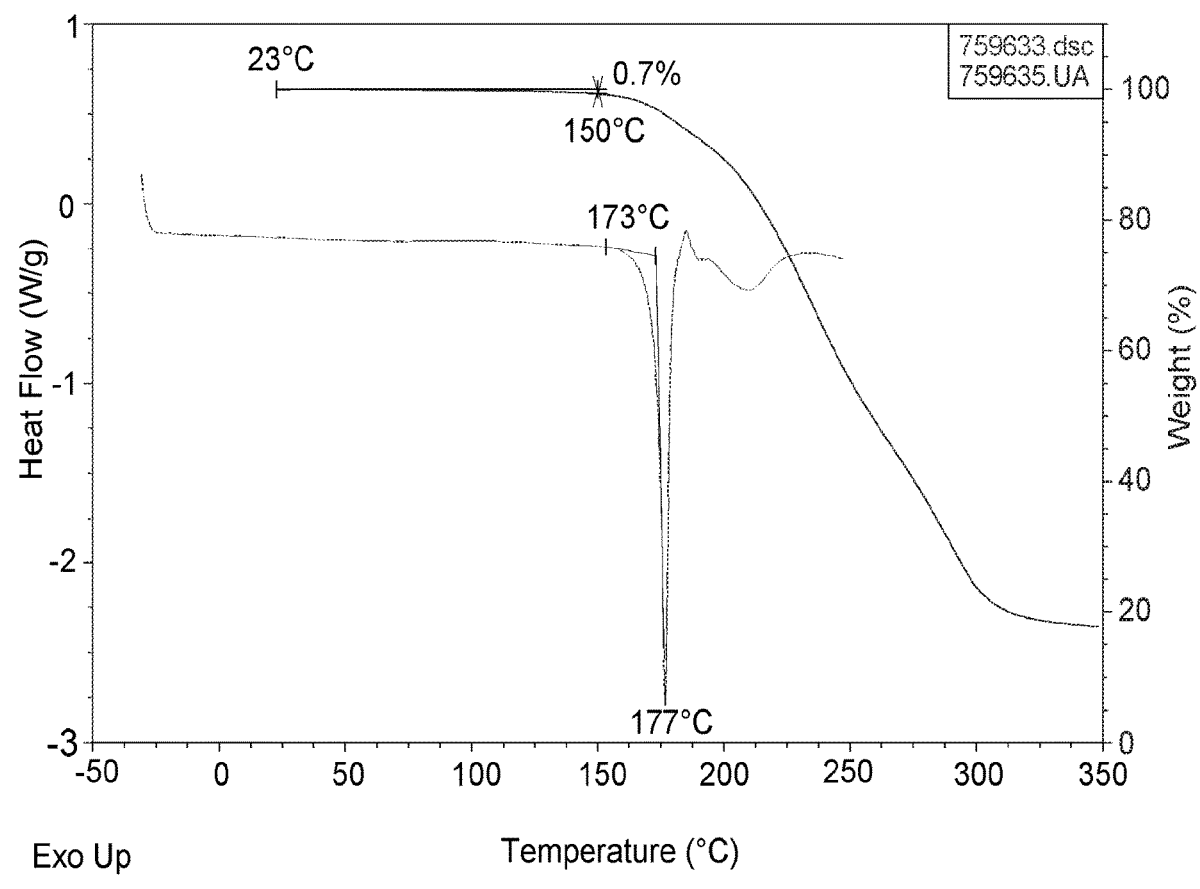
FIG. 40 depicts a DSC and TGA overlay for Form B.

An overlay of DSC and TGA thermograms is shown in FIG. 40 (DSC Parameters: Size: 1.3670 mg, Method: (−30)-250-10, TOC, Instrument: 2920 MDSC V2.6A, TGA: 2.86113 mg). TGA thermogram shows 0.7 weight % loss between 23° C. to 150° C. No broad desolvation endotherms are observed by DSC, consistent with an anhydrous/non-solvated material. DSC thermogram shows a sharp endotherm at 177° C. (onset 173° C.), which likely corresponds with the melt and concurrent decomposition, evidenced by the erratic thermal behavior by DSC and the steep weight loss by TGA above ~150° C.

Example 11—2-{[3,5-bis(trifluoromethyl)phenyl]carbamoyl}-4-chlorophenyl Dihydrogen Phosphate (Form B)

2-{[3,5-bis(trifluoromethyl)phenyl]carbamoyl}-4-chlorophenyl dihydrogen phosphate is stirred in EtOAc with 1 N HCl and evaporated. Acetonitrile is then added to the solid with stirring for a few minutes. MeOH is added with stirring. Toluene is added with stirring (toluene/acetonitrile/MeOH 24:6:1 v/v/v). Partial slow evaporation. Liquid phase is filtered and the solids are discarded. Rotary evaporation at 60-69° C. for 30 minutes. Evaporation under N$_2$ for 5 minutes. Hexafluoroisopropanol (HFIPA) is added to the solids. Slurry at room temperature for 1 day and then vacuum filtered.

Additional experimental details for the synthesis are set forth in this paragraph. 2-{[3,5-bis(trifluoromethyl)phenyl]carbamoyl}-4-chlorophenyl dihydrogen phosphate from Example 2B (86.9 mg) is dissolved in acetonitrile (0.6 mL) with stirring, affording a clear solution. After stirring for a few minutes, precipitation is observed. MeOH (0.1 mL) is added with stirring, yielding a clear solution. Toluene (2.4 mL) is then added with stirring (toluene/acetonitrile/MeOH 24:6:1 v/v/v), and a clear solution is observed. The solution is left to partially evaporate for 1 day from a vial covered with perforated aluminium foil, resulting in a clear liquid phase with a few solids above the solvent line and on the bottom. The liquid phase is filtered through a 0.2-µm nylon filter, yielding a clear solution, and the solids are discarded. The filtered solution is attached to a rotary evaporator equipped with a water bath at 60-69° C. After 30 minutes of attempted evaporation, no significant reduction in volume is observed. The solution is then evaporated under a stream of N$_2$ until no visible liquid remains (5 minutes). The resulting white solids are combined with hexafluoroisopropanol (HFIPA) (2 mL), and undissolved solids are present. The slurry is allowed to stir at ambient temperature for 1 day, resulting in an opaque white suspension. The solids are isolated by vacuum filtration and air dried on the filter under reduced pressure for 2 minutes.

Figure 41:
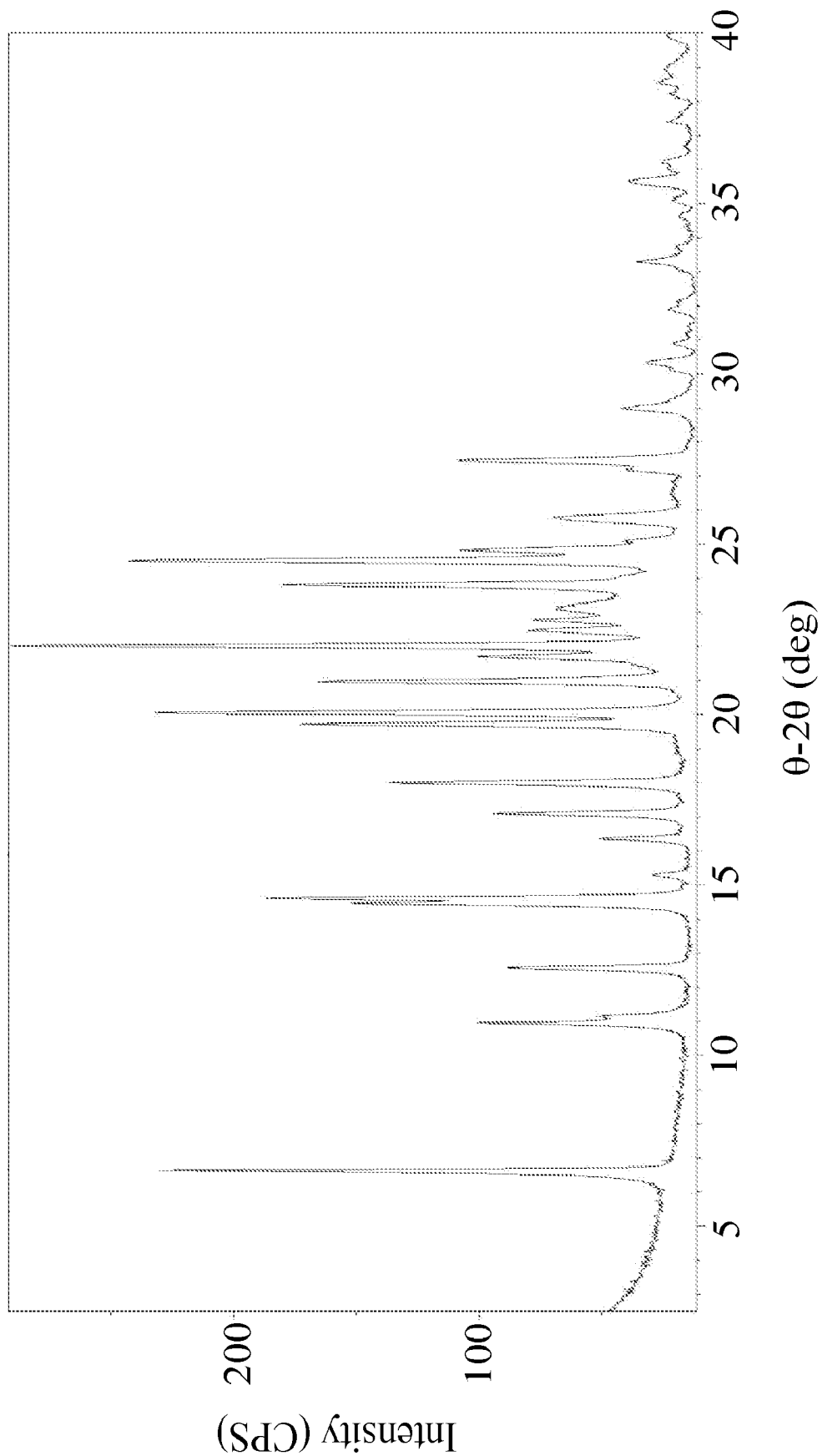
FIG. 41 depicts an XRPD pattern of Form B collected with Cu Kα radiation.

XRPD of the product shows that it is Form B (Form B+peak at 23° 2θ). An XRPD pattern of the product is shown in FIG. 41. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 716 s, Scan Speed 3.3°/min, Slit: DS: ½°, SS: null, Revolution Time: 1.0 s, Mode: Transmission.

The hygroscopicity of Form B is assessed by DVS and stressing at elevated relative humidity (see Example 12 for elevated relative humidity).

Figure 28:
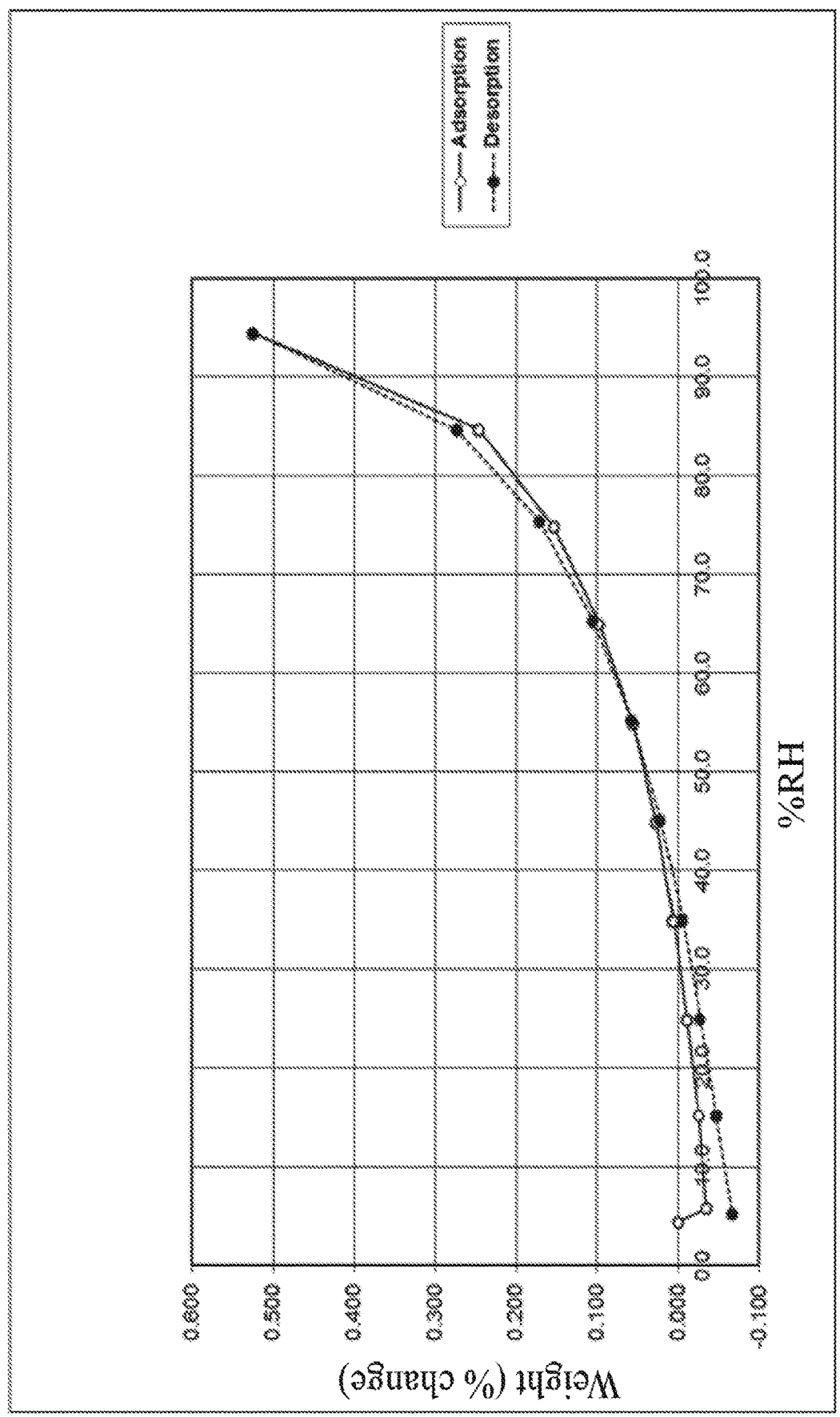
FIG. 28 depicts a DVS isotherm of Form B.
Figure 55:
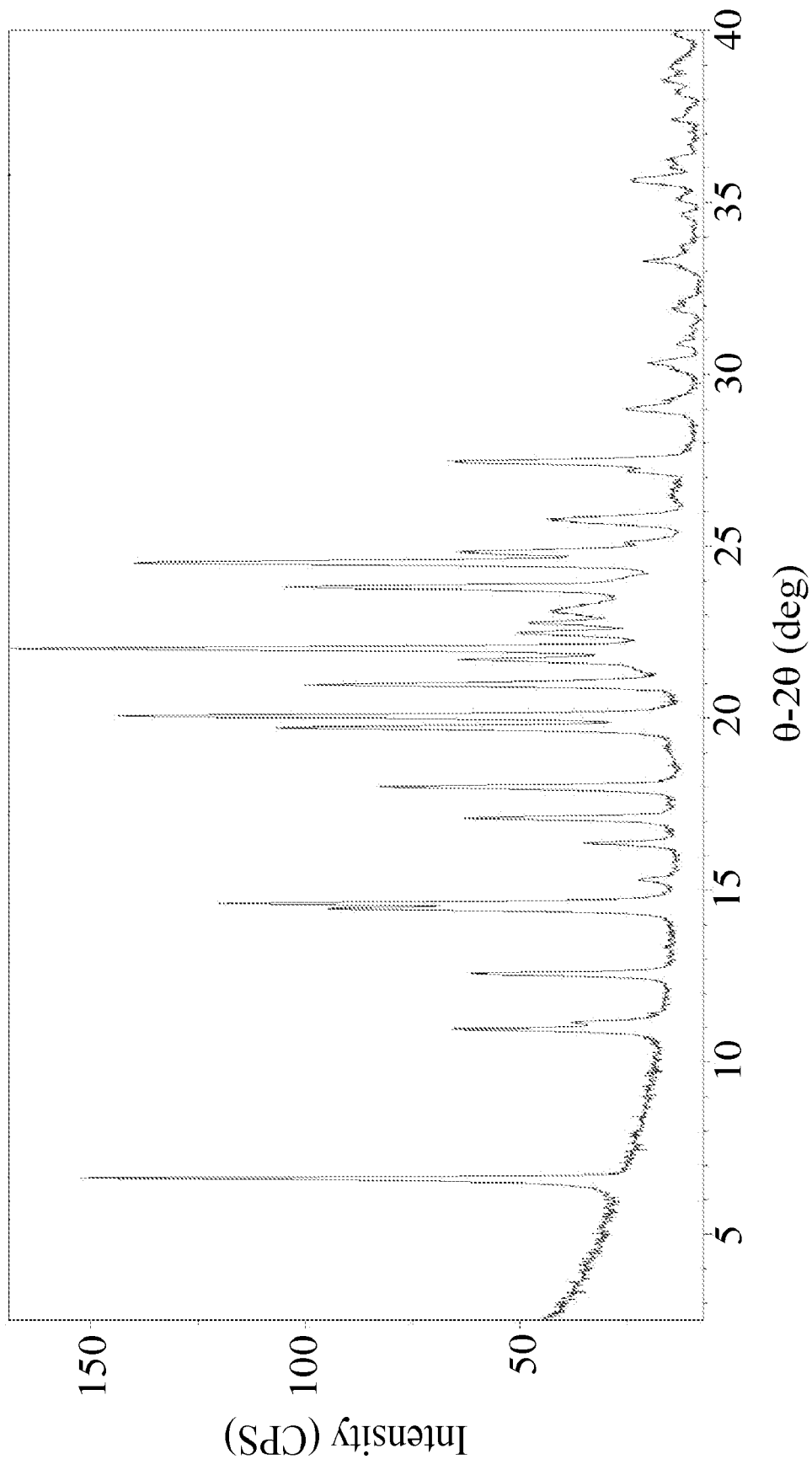
FIG. 55 depicts an XRPD pattern of Form B collected with Cu Kα radiation.

The DVS isotherm for Form B is shown in FIG. 28. The material shows 0.04 weight % loss at 5% relative humidity. The material exhibits relatively low kinetic hygroscopicity, taking up 0.6 weight % water vapour upon sorption from 5% to 95% relative humidity. All of this weight is lost on desorption with little hysteresis noted. XRPD analysis of the post-DVS material indicates no form change. An XRPD pattern of the post-DVS material is shown in FIG. 55. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 719 s, Scan Speed 3.3°/min, Slit: DS: ½°, SS: null, Revolution Time: 1.0 s, Mode: Transmission.

Example 12—Form B to Form N

2-{[3,5-bis(trifluoromethyl)phenyl]carbamoyl}-4-chlorophenyl dihydrogen phosphate and hexafluoroisopropanol (HFIPA) are slurried at room temperature for 4 days and then vacuum filtered.

Figure 42:
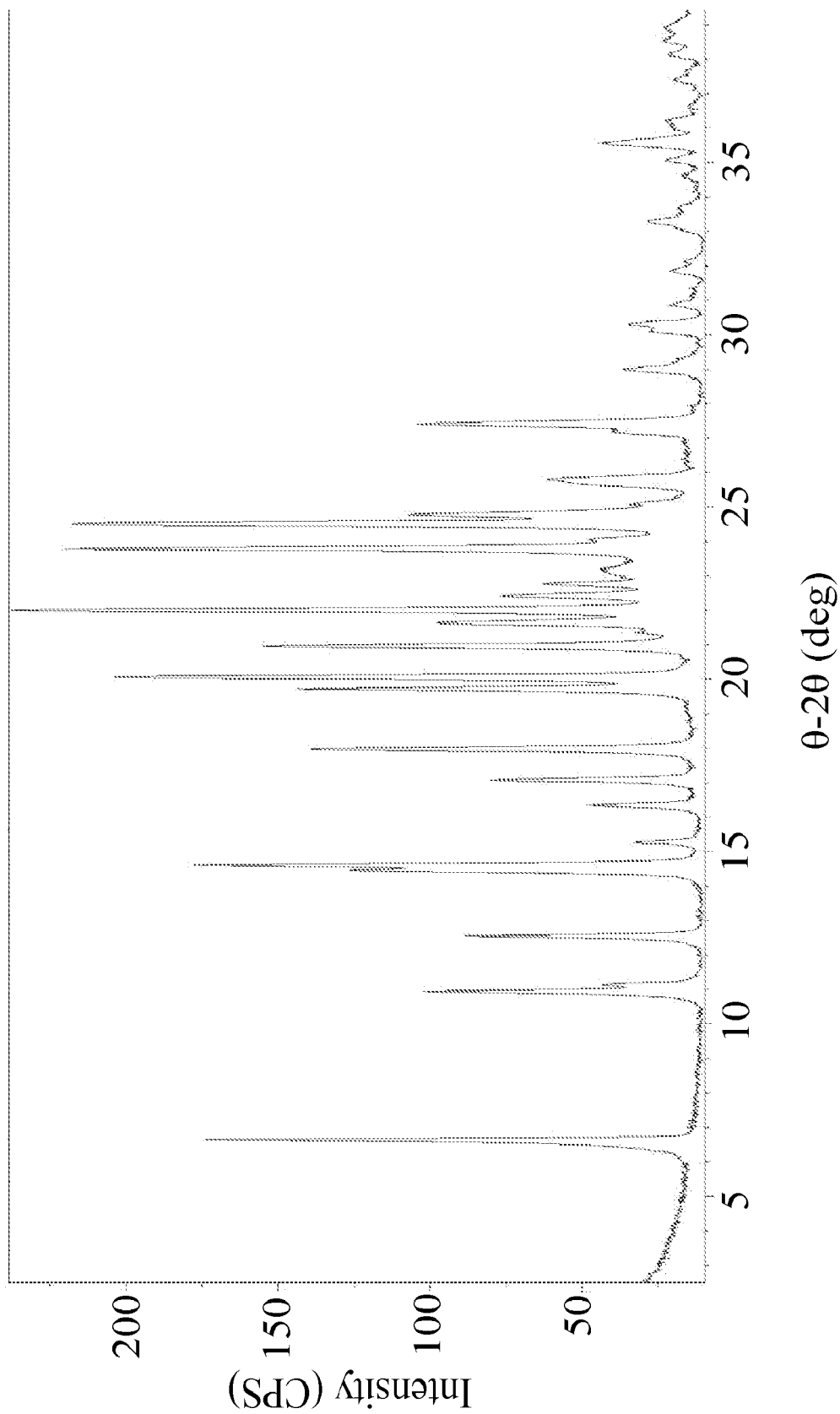
FIG. 42 depicts an XRPD pattern of Form B collected with Cu Kα radiation.

XRPD of the product shows that it is Form B (Form B+minor peak at 23° 2θ). An XRPD pattern of the product is shown in FIG. 42. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.01-39.98° 2θ, Step Size: 0.017° 2θ, Collection Time: 719 s, Scan Speed 3.3°/min, Slit: DS: ½°, SS: null, Revolution Time: 1.0 s, Mode: Transmission.

The product is stressed at 97% relative humidity for 7 days, resulting in partial conversion to Form N. The partial conversion noted after 7 days indicates that Form B would fully convert to hydrated Form N after a longer period of time.

Figure 50:
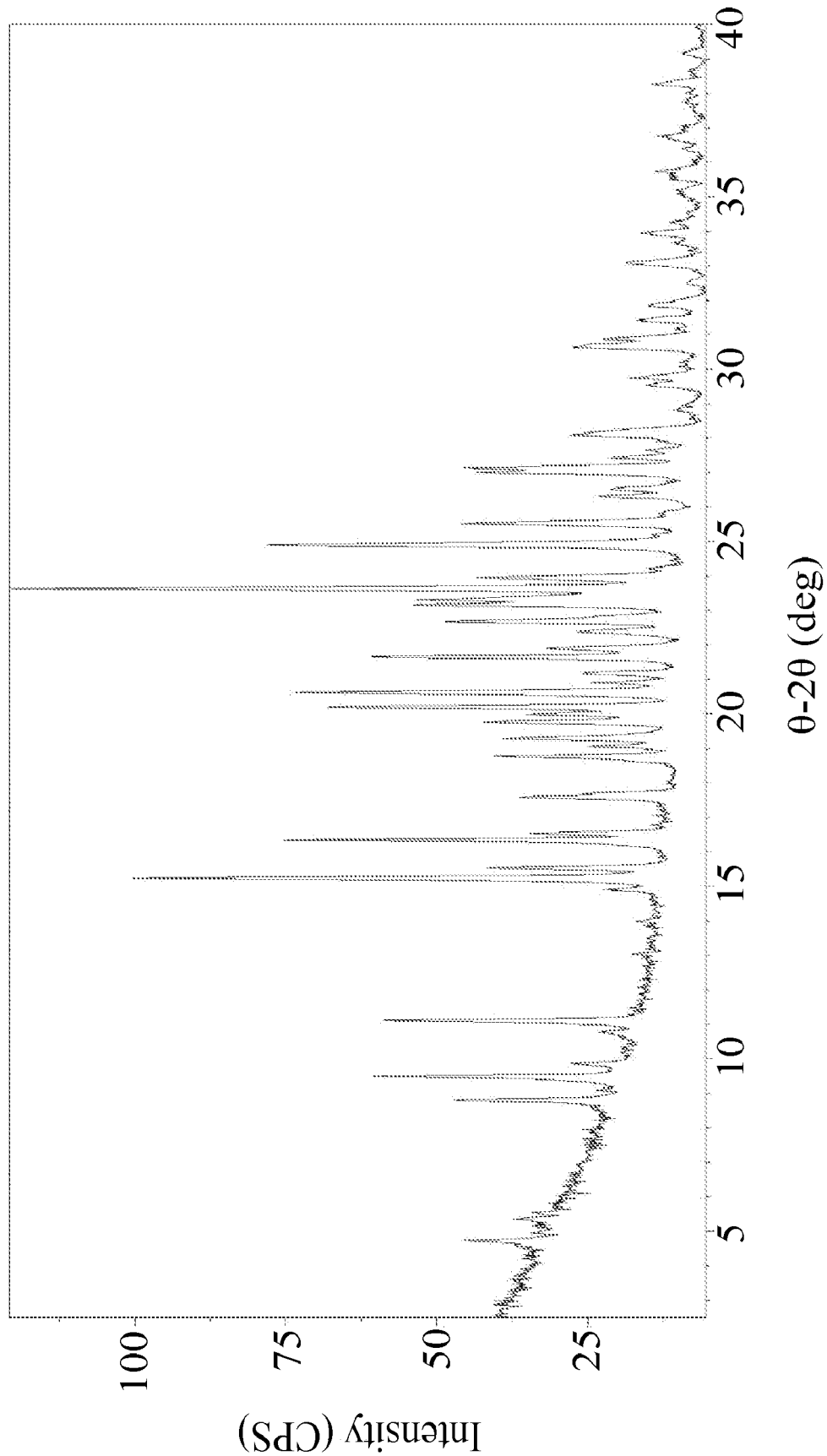
FIG. 50 depicts an XRPD pattern of Form N collected with Cu Kα radiation.

The product converts to Form N upon slurrying with water at room temperature for 7 days and vacuum filtering. An XRPD pattern of the product is shown in FIG. 50. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 715 s, Scan Speed 3.3°/min, Slit: DS: ½°, SS: null, Revolution Time: 1.0 s, Mode: Transmission.

Figure 51:
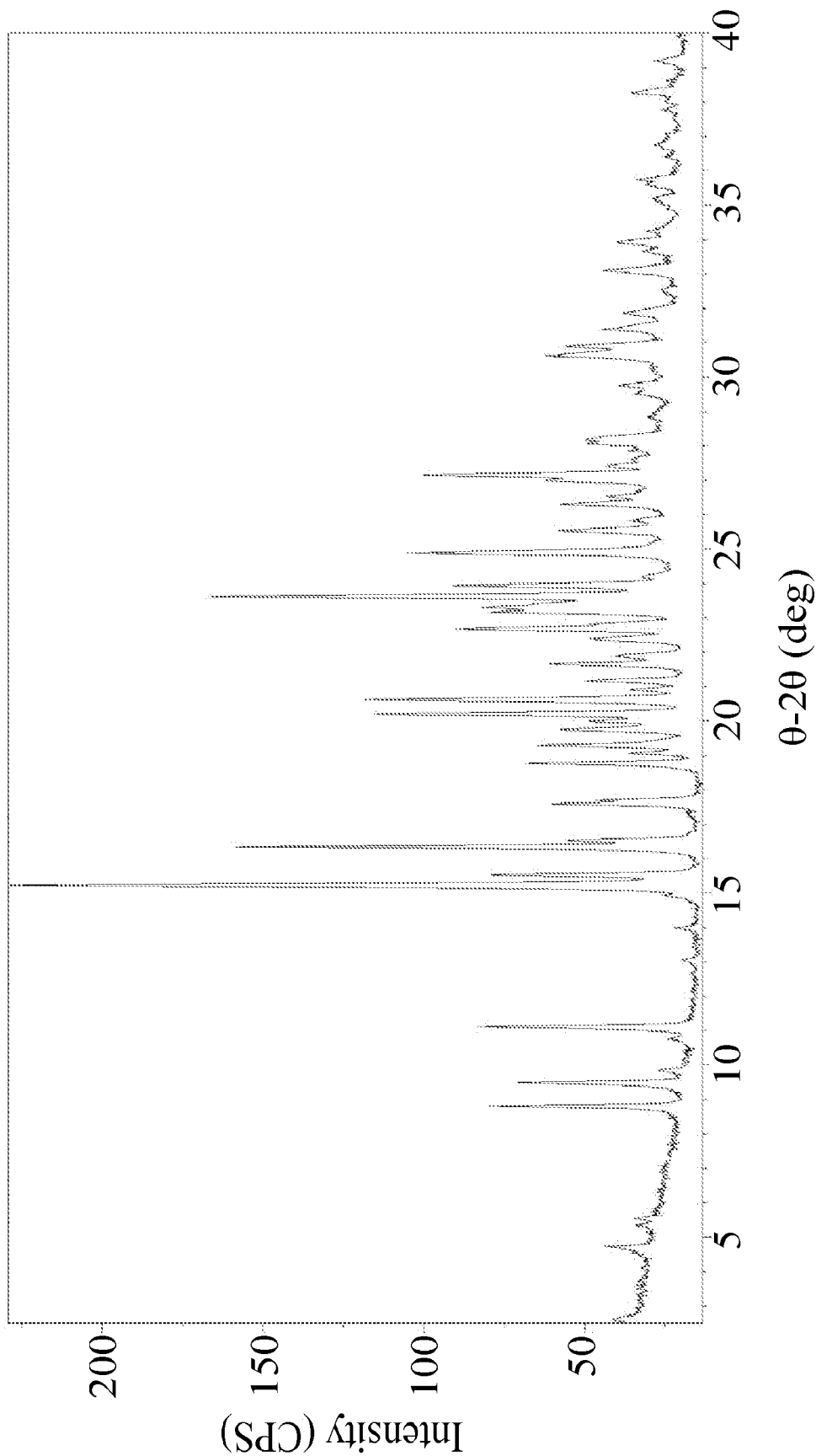
FIG. 51 depicts an XRPD pattern of Form N collected with Cu Kα radiation.

The slurry is repeated for 19 hours to gauge how quickly the conversion occurs and results again in Form N, indicating form conversion within 19 hours (starting material is the product from this example and from Example 21). An XRPD pattern of the product is shown in FIG. 51. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 719 s, Scan Speed 3.3°/min, Slit: DS: ½°, SS: null, Revolution Time: 1.0 s, Mode: Transmission.

Example 13—2-{[3,5-bis(trifluoromethyl)phenyl] carbamoyl}-4-chlorophenyl Dihydrogen Phosphate Step 1—N-(3,5-bis(trifluoromethyl)phenyl)-5-chloro-2-hydroxybenzamide 5-chloro salicylic acid (86.5 g, 501.6 mmol, 1 eq) is dissolved in toluene (1500 mL) under nitrogen atmosphere followed by addition of phosphorus trichloride (22 mL, 250.82 mmol, 0.5 eq) in small portions at room temperature over 15 minutes. Then 3,5-bis-trifluoromethyl-phenylamine (100 g, 436.4 mmol, 0.87 eq) is added to reaction mixture in one lot at room temperature. The reaction mixture is heated to 105±5° C. and stirred for next 16 h at this temperature. After completion of the reaction by TLC (10% ethyl acetate: hexane), the reaction is then cooled to room temperature. The reaction mixture is quenched with a solution of $NaHCO_3$ (50 g) in water (800 mL) and resulting solution is stirred for 15-20 minutes. Both organic and aqueous layers are separated and collected. Upper organic layer is washed with a solution of concentrated HCl (25 mL) in water (400 mL) followed by brine (400 mL) and dried over $Na_2SO_4$. The organic layer is filtered and concentrated under reduced pressure to afford white solid. Heptane (500 mL) is added to the white solid and the resulting suspension is stirred for 30 minutes at room temperature and filtered to afford N-(3,5-bis(trifluoromethyl)phenyl)-5-chloro-2-hydroxybenzamide (150 g) as a white solid. HPLC=99%

Step 2—2-((3,5-bis(trifluoromethyl)phenyl)carbamoyl)-4-chlorophenyl bis(2-(trimethylsilyl)ethyl) phosphate The N-(3,5-bis(trifluoromethyl)phenyl)-5-chloro-2-hydroxybenzamide (145 g, 377.9 mmol, 1 eq) is dissolved in $CH_3CN$ (1450 mL). DMAP (2.77 g, 22.67 mmol, 0.06 eq), N,N-diisopropylethylamine (DIPEA) (97.74 g, 755.98 mmol, 2 eq) and $CCl_4$ (290.7 g, 1889.9 mmol, 5 eq) are added to the above solution in that sequence at room temperature under stirred conditions. The reaction mixture is cooled to 0° C. and a solution of phosphite reagent $((CH_3)_3SiCH_2CH_2O)_2P(O)H)$ (160.7 g, 599.9 mmol, 1.5 eq) in $CH_3CN$ (145 mL) is added drop wise under controlled conditions below 2° C. over period of 30 minutes. The reaction mixture is allowed to warm up to room temperature and stirred for 22 h at room temperature. After completion of the reaction by TLC (10% ethyl acetate:hexane), water (2.175 L) is added to the reaction mixture and the resulting mixture is extracted twice with ethyl acetate (2.175 L and 1.160 L). The combined organic extract is washed with brine (1.450 L), dried over $Na_2SO_4$, and filtered. The filtrate is concentrated under reduce pressure to give the crude material (271 g) which is used as such for next step. HPLC=82.9%

Step 3—Phosphoric Acid mono-[2-(3,5-bis-trifluoromethyl-phenylcarbamoyl)-4-chloro-phenyl] ester Crude 2-((3,5-bis(trifluoromethyl)phenyl)carbamoyl)-4-chlorophenyl bis(2-(trimethylsilyl)ethyl) phosphate (270 g) is added to a mixture of TFA:water (5:1, 2.1 L). The reaction mixture is stirred at room temperature for 3 h. After completion of the reaction by TLC (10% ethyl acetate:hexane), the reaction mixture is poured on a mixture of toluene:water (20:30, 13.5 L) and stirred for 1 h at room temperature. The reaction mixture is filtered and solid is washed with toluene (0.54 L) to afford crude phosphoric acid mono-[2-(3,5-bis-trifluoromethyl-phenylcarbamoyl)-4-chloro-phenyl] ester (160 g) as an off white solid.

Step 4—Purification

Crude solid (160 g, 345.05 mmol, 1 eq) is added to a solution of NaOH (80 g, 2000 mmol, 5.8 eq) in water (4 L) and stirred for 45 minutes at room temperature. The aqueous solution is extracted twice with ethyl acetate (2×1.6 L) to remove impurities. The aqueous solution is then acidified to pH 1 with concentrated HCl (230-250 mL) and extracted twice with ethyl acetate (2×1.6 L). The combined ethyl acetate extract obtained after acidification is dried over sodium sulphate and concentrated under reduce pressure to give 140 g of colorless oil. The oil is dissolved in ethyl acetate (160 mL) and stirred for 30 minute at room temperature. n-Heptane (1.44 L) is added under continuous stirring. The reaction mixture is stirred for 3 h at room temperature and filtered. Solid is washed with n-heptane (80 mL) and dried under vacuum for 30 minutes to afford phosphoric acid mono-[2-(3,5-bis-trifluoromethyl-phenylcarbamoyl)-4-chloro-phenyl] ester (124 g) as off white solid. NMR shows an acetic acid peak. HPLC=98.8%

Step 5—Repurification

Off white solid (124 g) is dissolved in ethyl acetate (124 mL) and stirred for 30 minutes at room temperature, n-heptane (1.11 L) is added under continuous stirring. The reaction mixture is stirred for 3 h at room temperature and filtered. The solid is washed with n-heptane (62 mL) and dried under vacuum for 30 minute to afford phosphoric acid mono-[2-(3,5-bis-trifluoromethyl-phenylcarbamoyl)-4-chloro-phenyl] ester (103 g) as a white solid.

Example 14—2-{[3,5-bis(trifluoromethyl)phenyl]carbamoyl}-4-chlorophenyl Dihydrogen Phosphate Hydrate (Form N)

Step 1—N-(3,5-bis(trifluoromethyl)phenyl)-5-chloro-2-hydroxybenzamide 5-chloro salicylic acid (86.5 g, 501.6 mmol, 1 eq) is dissolved in toluene (1500 mL) under nitrogen atmosphere followed by addition of phosphorus trichloride (22 mL, 250.82 mmol, 0.5 eq) in small portions at room temperature over 15 minutes. Then 3,5-bis-trifluoromethyl-phenylamine (100 g, 436.4 mmol, 0.87 eq) is added to the reaction mixture in one lot at room temperature. The reaction mixture is heated to 105±5° C. and stirred for the next 16 h at this temperature. Progress of reaction is monitored by TLC (mobile phase 10% ethyl acetate in hexane). After completion of the reaction by TLC (10% ethyl acetate:hexane), the reaction is then cooled to room temperature. The reaction mixture is quenched with a solution of NaHCO$_3$ (50 g) in water (800 mL) and the resulting solution is stirred for 15-20 minutes. Both organic and aqueous layers are separated and collected. Upper organic layer is washed with a solution of concentrated HCl (25 mL) in water (400 mL) followed by brine (400 mL) and dried over Na$_2$SO$_4$. The organic layer is filtered and concentrated under reduced pressure to afford a white solid. Heptane (500 mL) is added to the white solid and the resulting suspension is stirred for 30 minutes at room temperature and filtered to afford N-(3,5-bis(trifluoromethyl)phenyl)-5-chloro-2-hydroxybenzamide (150 g) as a white solid. HPLC=99%

Step 2—2-((3,5-bis(trifluoromethyl)phenyl)carbamoyl)-4-chlorophenyl bis(2-(trimethylsilyl)ethyl) phosphate Preparation of bis (2-(trimethylsilyl)ethyl) hydrogen Phosphite Reagent To a cooled solution of trimethylsilyl ethanol (400 g, 3.382 mol, 3.0 eq) in DCM (7.0 L) is added triethyl amine (228 g, 2.255 mol, 2.0 eq) at 0° C. under nitrogen atmosphere. PCl$_3$ (154.8 g, 1.127 mol, 1.0 eq) is then added slowly in small portions at 0 to 10° C. over 45 minutes. The reaction mixture is stirred for 1 h at 0° C. The reaction mixture is allowed to come to room temperature. DM water (2.0 L) is added to the reaction mixture and stirred for 1 h at room temperature. The lower organic layer is separated and upper aqueous layer is extracted with DCM (1.6 L). The combined organic extract is washed with DM water (2.0 L) and dried over Na$_2$SO$_4$. The organic layer is concentrated under vacuum at 45° C. and degassed for 30 minutes at 4° C. to afford crude phosphite reagent (450.0 g) as a light brown oil and stored at 0 to 5° C.

Preparation of 2-((3,5-bis(trifluoromethyl)phenyl)carbamoyl)-4-chlorophenyl bis(2-(trimethylsilyl)ethyl) phosphate N-(3,5-bis(trifluoromethyl)phenyl)-5-chloro-2-hydroxybenzamide (150 g, 391 mmol, 1 eq) is dissolved in CH$_3$CN (1500 mL). DMAP (2.86 g, 23.46 mmol, 0.06 eq), DIPEA (101.07 g, 782 mmol, 2 eq) and CCl$_4$ (300 g, 1955 mmol, 5 eq) are added to the above solution in that sequence at room temperature under stirred conditions. The reaction mixture is cooled to 0° C. and a solution of the phosphite reagent {(((CH$_3$)$_3$SiCH$_2$CH$_2$O)$_2$P(O)H)} (166 g, 586.5 mmol, 1.5 eq) in CH$_3$CN (150 mL) is added drop wise under controlled conditions below 2° C. over period of 30 minutes. The reaction mixture is allowed to warm up to room temperature and stirred for 22 h at room temperature. Progress of the reaction is monitored by TLC (mobile phase 10% ethyl acetate in hexane). After completion of the reaction by TLC (10% ethyl acetate:hexane), water (2.25 L) is added to the reaction mixture and the resulting mixture is extracted twice with ethyl acetate (2.25 L and 1.2 L). The combined organic extract is washed with brine (1.5 L), dried over Na$_2$SO$_4$, and filtered. The filtrate is concentrated under reduced pressure to give the crude material (285 g), which is used as such for next step.

Step 3—Phosphoric Acid mono-[2-(3,5-bis-trifluoromethyl-phenylcarbamoyl)-4-chloro-phenyl] ester Crude 2-((3,5-bis(trifluoromethyl)phenyl)carbamoyl)-4-chlorophenyl bis(2-(trimethylsilyl)ethyl) phosphate (285 g) is added to a mixture of TFA:water (5:1, 2.2 L). The reaction mixture is stirred at room temperature for 3 h. Progress of the reaction is monitored by TLC (mobile phase 10% ethyl acetate in hexane). After completion of the reaction by TLC (10% ethyl acetate:hexane), the reaction mixture is then poured to a mixture of toluene:water (20:30, 14.25 L) and stirred for 1 h at room temperature. The reaction mixture is filtered and the solid is washed with toluene (0.57 L) to afford crude phosphoric acid mono-[2-(3,5-bis-trifluoromethyl-phenylcarbamoyl)-4-chloro-phenyl] ester (212 g) as an off-white wet solid.

Wet solid (212 g) is divided in two equal parts.

First wet half part (106 g) is dried at room temperature for 14 h to afford dry solid as an off white solid (88 g). HPLC=96.0%

Second wet half part (106 g) is dissolved in ethyl acetate (212 mL) and heated up to 50° C. to dissolve solid completely, then cooled to room temperature and n-heptane is added under stirred conditions. The suspension is stirred for 3 h at room temperature and filtered and precipitate is washed with n-heptane (55 mL) to afford wet solid 98 g, which is dried at room temperature for 9 h to afford 78 g as an off white solid. HPLC=99.1%

Some extra peaks are still present in NMR.

Step 4(i)—Purification

Crude solid (25 g from first half part in step 3+25 g from second half part in step 3, 50 g total, 107.82 mmol, 1 eq) is added to a solution of NaOH (25 g, 625 mmol, 5.8 eq) in water (1.25 L) and stirred for 45 minutes at room temperature. The aqueous solution is extracted twice with ethyl acetate (2×0.5 L) to remove impurities. The aqueous solution is then acidified to pH 1 with concentrated HCl (70-80 mL) and extracted twice with ethyl acetate (2×0.5 L). The combined ethyl acetate extract obtained after acidification is dried over sodium sulphate and concentrated under reduced pressure to give 41 g of a colorless oil. The oil is dissolved in ethyl acetate (50 mL) and stirred for 30 minutes at room temperature. n-Heptane (0.450 L) is added under continuous stirring. The reaction mixture is stirred for 3 h at room temperature and filtered. Solid is washed with n-heptane (25 mL) and dried under vacuum for 30 minutes to afford product phosphoric acid mono-[2-(3,5-bis-trifluoromethyl-phenylcarbamoyl)-4-chloro-phenyl] ester (25 g) as an off white solid. HPLC=96.7%

Step 4(ii)—Purification of Remaining Quantity from Step 3 (110 g)

Crude solid (60 g from first half part in step 3+50 g from second half part in step 3, 110 g total, 237.22 mmol, 1 eq) is added to a solution of NaOH (55 g, 1375 mmol, 5.8 eq) in water (1.75 L) and stirred for 45 minute at room temperature. The aqueous solution is washed twice with ethyl acetate (2×1.1 L) to remove impurities. The aqueous solution is then acidified to pH 1 with concentrated HCl (160-180 mL) and extracted twice with ethyl acetate (2×1.1 L). The combined ethyl acetate extract obtained after acidification is dried over sodium sulphate and concentrated under reduce pressure to give 105 g of colorless oil. The oil is dissolved in ethyl acetate (110 mL) and stirred for 30 minutes at room temperature. n-Heptane (0.990 L) is added under continuous stirring. The reaction mixture is stirred for 3 h at room temperature and filtered. Solid is washed with n-heptane (55 mL) and dried under vacuum for 30 minutes to afford phosphoric acid mono-[2-(3,5-bis-trifluoromethyl-phenylcarbamoyl)-4-chloro-phenyl] ester crop-1 (65 g) and precipitate again appears in filtrate which is filtered to afford crop-2 (11 g) as a white solid. NMR shows an acetic acid peak. HPLC=95.8%

Step 5—Repurification

Off white solid (crop-1 and crop-2) (76 g) is dissolved in ethyl acetate (76 mL) and heated up to 50° C. to dissolve solid completely and stirred for 30 minutes at room temperature, n-heptane (684 mL) is added under continuous stirring. The reaction mixture is stirred for 3 h at room temperature and filtered. The solid is washed with n-heptane (38 mL) and dried under vacuum for 30 minutes to afford pure product phosphoric acid mono-[2-(3,5-bis-trifluoromethyl-phenylcarbamoyl)-4-chloro-phenyl] ester repurified crop-1 (35 g) and precipitate again appears in filtrate which is filtered to afford repurified crop-2 (30 g) as a white solid. Repurified crop-1 HPLC=97.6%, Repurified crop-2 HPLC=99.5%

Step 6—Water Treatment

Off white solid repurified crop-1 (7 g out of 35 g) is suspended in DM water (140 mL) and suspension is stirred for 2 h at room temperature and filtered and solid is washed with DM water (35 mL) and dried under vacuum for 1 h to afford phosphoric acid mono-[2-(3,5-bis-trifluoromethyl-phenylcarbamoyl)-4-chloro-phenyl] ester (6 g) as a white solid without ethyl acetate. HPLC=99.5%

Figure 52:
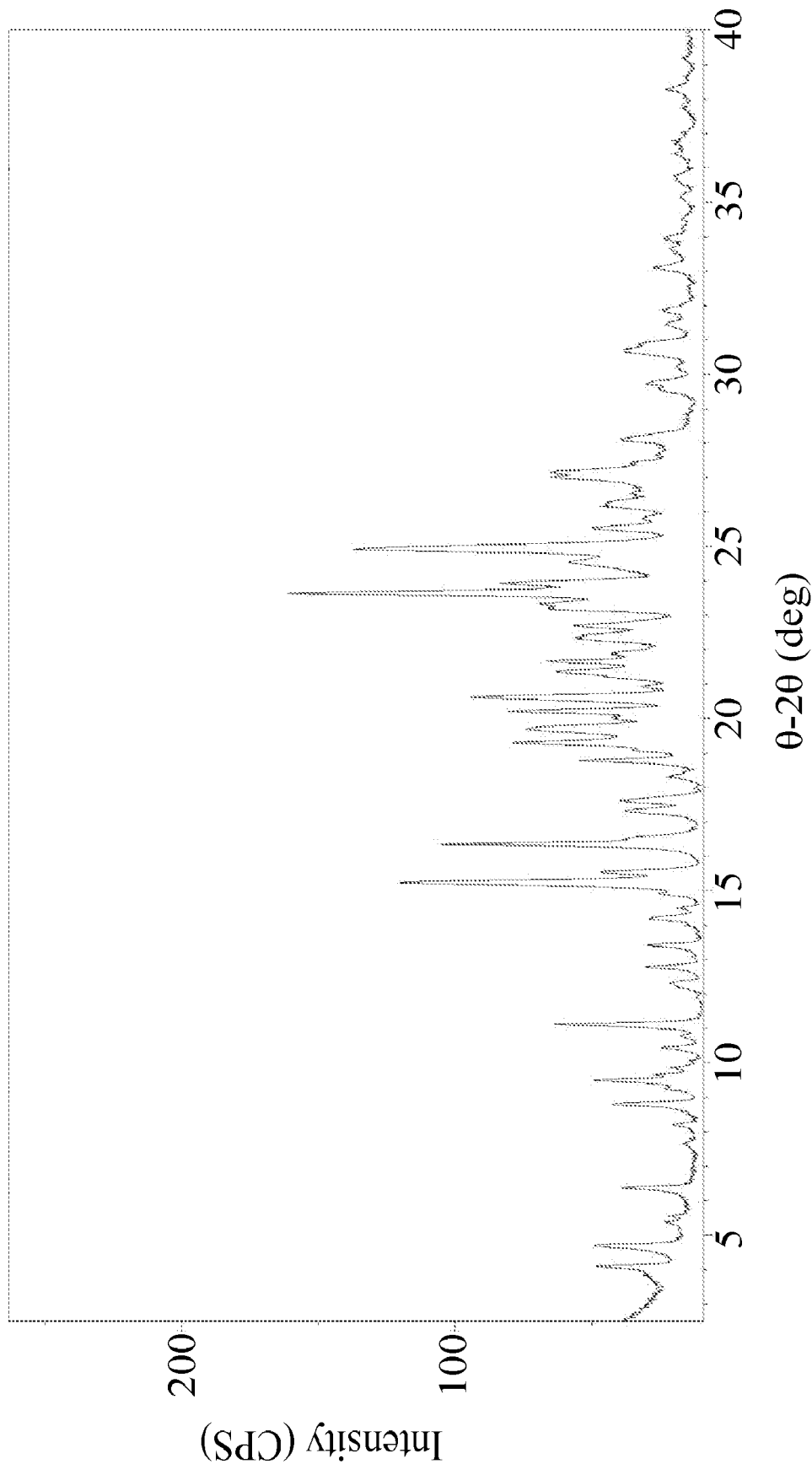
FIG. 52 depicts an XRPD pattern of Form N collected with Cu Kα radiation.

An XRPD pattern of the product is shown in FIG. 52 (Form N plus an unknown material). The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 719 s, Scan Speed 3.3°/min, Slit: DS: ½°, SS: null, Revolution Time: 1.0 s, Mode: Transmission.

A TGA thermogram of the product (3.3710 mg) is obtained. The sample exhibits two discrete weight loss steps of 3.7% weight loss between 29° C. to 70° C. and 3.7% weight loss between 70° C. and 105° C. 1.3% weight loss is seen between 105° C. to 160° C. in the TGA thermogram.

Example 15

2.5 to 5 equivalents of tris(hydroxymethyl)aminomethane is added to crystalline 2-{[3,5-bis(trifluoromethyl)phenyl]carbamoyl}-4-chlorophenyl dihydrogen phosphate (e.g., any of Crystalline Form 1 et seq., Crystalline Form 2 et seq., Crystalline Form 3 et seq., Crystalline Form 4 et seq., Crystalline Form 5 et seq., Crystalline Form 6 et seq.).

Water is added to the mixture and the solution is stirred or sonicated. Yields 10 mg/ml to 20 mg/ml solutions stable for at least 24 hrs.

HPLC conditions for assaying the stability of compositions formed from crystalline 2-{[3,5-bis(trifluoromethyl)phenyl]carbamoyl}-4-chlorophenyl dihydrogen phosphate and a base, e.g., tris(hydroxymethyl)aminomethane are as follows:

Hplc condition c18 SB Agilent 4.6×125 mm column 3 or 5 u

At 1.5 ml per min 10% to 100% acetonitrile with 2 g ammonium acetate per 4 L of water Using waters 2695 hplc running millennium 32 software No baseline subtraction

Example 16—2-{[3,5-bis(trifluoromethyl)phenyl]carbamoyl}-4-chlorophenyl Dihydrogen Phosphate Ethyl Acetate Solvate (Form A)

Step 1—N-(3,5-bis-trifluoromethylphenyl)-5-chloro-2-hydroxybenzamide

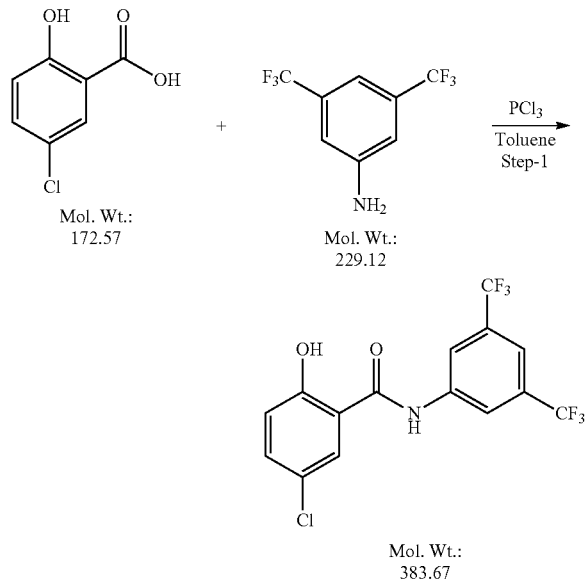

5-chloro salicylic acid (21.9 g, 126.9 mmol, 1.0 eq) is dissolved in toluene (375.0 mL) under nitrogen atmosphere followed by addition of phosphorus trichloride (5.5 mL, 63.45 mmol, 0.5 eq) in small portions at room temperature over 15 minutes. 3,5-bis-trifluoromethyl-phenylamine (25.0 g, 110.4 mmol, and 0.87 eq) is then added to the reaction mixture in one lot at room temperature. The reaction mixture is heated to 105±5° C. and stirred for next 16.0 h at this temperature. Progress of the reaction is monitored by TLC (mobile phase 10% ethyl acetate in hexane). After completion of reaction, the reaction is cooled to room temperature. The reaction mixture is poured to silica gel (0.5 kg) column and column is eluted with (1.5 L) ethyl acetate to give white solid after evaporation of solvent. The solid thus obtained is suspended in n-heptane (150.0 mL) and stirred for 1.0 h at room temperature. The suspension is filtered through buckner funnel to obtain N-(3,5-bis-trifluoromethylphenyl)-5-chloro-2-hydroxybenzamide (31.0 g) as white solid. HPLC=98.9%

Step 2—2-((3, 5-bis (trifluoromethyl)phenyl)carbamoyl)-4-chlorophenyl bis (2-(trimethylsilyl)ethyl) phosphate

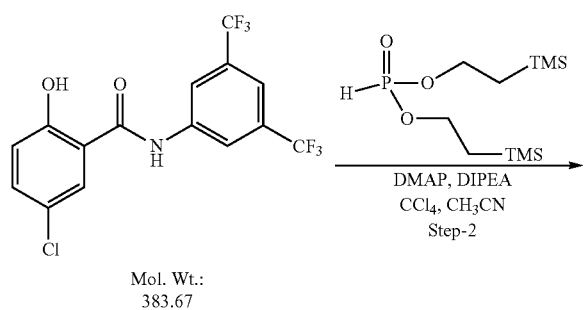

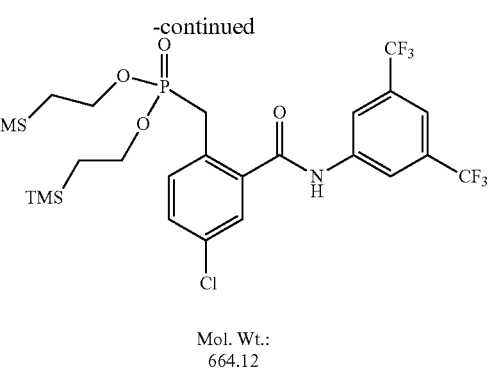

Preparation of bis (2-(trimethylsilyl)ethyl) hydrogen Phosphite Reagent

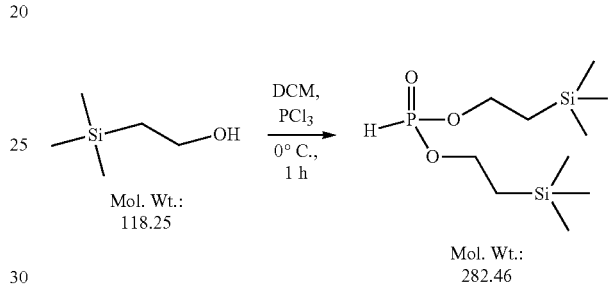

To a cooled solution of trimethylsilyl ethanol (50.0 g, 422.8 mmol, 3.0 eq) in DCM (0.875 L) is added triethyl amine (28.5 g, 281.8 mmol, 2.0 eq) at 0° C. under nitrogen atmosphere. $PCl_3$ (19.3 g, 281.07 mmol, 1.0 eq) is then added slowly in small portions at 0 to 10° C. over 45 minutes. The reaction mixture is stirred for 1.0 h at 0° C. The reaction mixture is allowed to come at room temperature. DM water (0.25 L) is added to the reaction mixture and stirred for 1.0 h at room temperature and layers are separated. The aqueous layer is extracted with DCM (0.25 L). The combined organic extract is washed with DM water (0.25 L) and dried over $Na_2SO_4$. The organic layer is concentrated under vacuum at 45° C. and degassed for 30 minutes at 45° C. to afford crude phosphite reagent (45.0 g) as a light brown oil and stored at 0 to 5° C.

Preparation of 2-((3, 5-bis (trifluoromethyl)phenyl) carbamoyl)-4-chlorophenyl bis (2-(trimethylsilyl) ethyl) phosphate N-(3,5-bis(trifluoromethyl) phenyl)-5-chloro-2-hydroxybenzamide (30.0 g, 78.19 mmol, 1.0 eq) is dissolved in $CH_3CN$ (300.0 mL). DMAP (0.57 g, 4.69 mmol, 0.06 eq), DIPEA (27.2 mL, 156.38 mmol, 2.0 eq) and $CCl_4$ (60.1 g, 390.96 mmol, 5.0 eq) are added to the above solution in the sequence at room temperature with stirring. The reaction mixture is cooled to 0° C. and a solution of phosphite reagent (33.10 g, 117.28 mmol, 1.5 eq) in $CH_3CN$ (30.0 mL) is added drop wise under controlled conditions below 2° C. over a period of 15 minutes. The reaction mixture is allowed to warm up to room temperature and stirred for 22.0 h at room temperature. Progress of the reaction is monitored by TLC (mobile phase 10% ethyl acetate in hexane). After completion of the reaction, the reaction mixture is diluted with ethyl acetate (1.0 L) and water (1.0 L) and layers are separated. The aqueous layer is extracted twice with ethyl acetate (2×0.5 L). The combined organic extract is washed with brine (0.5 L), dried over Na$_2$SO$_4$ and filtered. The filtrate is concentrated under reduced pressure to give the crude material (56.0 g) which is used as such for next step.

Step 3—Phosphoric Acid mono-[2-(3,5-bis-trifluoromethylphenylcarbamoyl)-4-chlorophenyl]ester

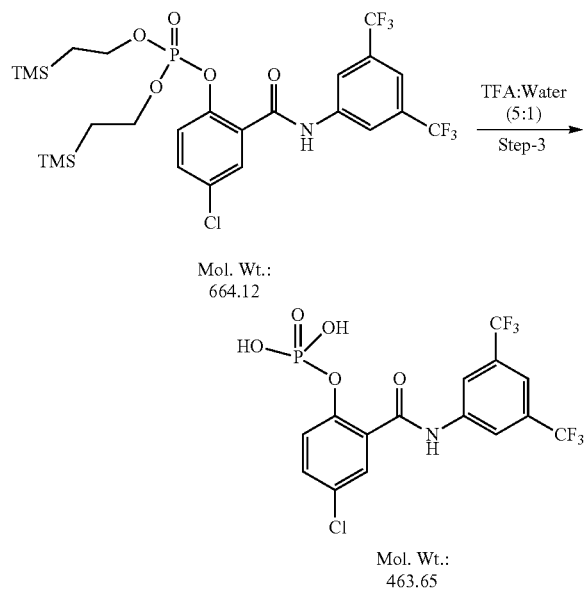

Mol. Wt.: 664.12

Mol. Wt.: 463.65

Crude 2-((3,5-bis(trifluoromethyl)phenyl)carbamoyl)-4-chlorophenyl bis (2-(trimethylsilyl) ethyl) phosphate (55.0 g, 82.81 mmol, 1.0 eq) is added to a mixture of TFA: water (5:1, 428.0 mL). The reaction mixture is stirred at room temperature for 3.0 h. Progress of reaction is monitored by TLC (mobile phase 10% ethyl acetate in hexane). The reaction mixture is concentrated under vacuum below 70° C. to remove volatile solvents. Residue is added to a solution of NaOH (18.0 g, 450.0 mmol, and 5.4 eq) in water (0.55 L) and stirred for 15 minutes at room temperature. The aqueous solution is washed twice with ethyl acetate (2×0.55 L) to remove impurities. The aqueous solution is then acidified to pH 1 with concentrated HCl (35.0 mL) and extracted twice with ethyl acetate (2×0.825 L). The combined ethyl acetate extract obtained after acidification is dried over Na$_2$SO$_4$ and concentrated under reduced pressure to give 35.0 g of colorless oil. The oil crude is dissolved in ethyl acetate (35.0 mL) and n-heptane (175.0 mL) is added with stirring. The reaction mixture is stirred for 3.0 h at room temperature and filtered. Solid is washed with n-heptane (55.0 mL) and dried over vacuum for 30 minutes to afford phosphoric acid mono-[2-(3, 5-bis-trifluoromethylphenylcarbamoyl)-4-chlorophenyl] ester (12.0 g) as off white solid. HPLC=97.7%

Figure 38:
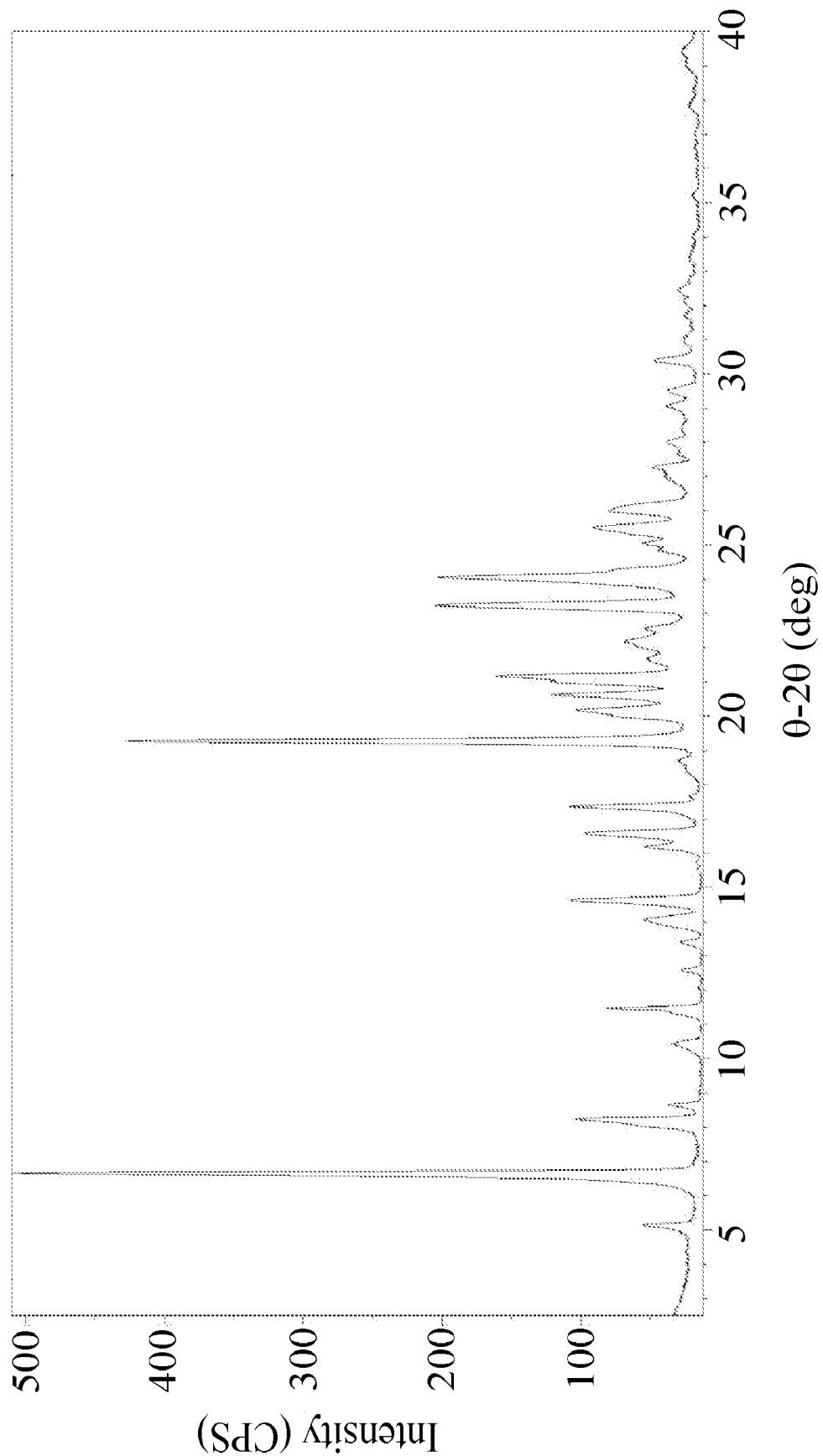
FIG. 38 depicts an XRPD pattern of Form A collected with Cu Kα radiation.

An XRPD pattern of the product is shown in FIG. 38 (Form A). The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 720 s, Scan Speed 3.2°/min, Slit: DS: ½°, SS: null, Revolution Time: 1.0 s, Mode: Transmission.

Example 17—2-{[3,5-bis(trifluoromethyl)phenyl] carbamoyl}-4-chlorophenyl Dihydrogen Phosphate Ethyl Acetate Solvate (Form A+Minor Peaks)

Step 1—N-(3,5-bis-trifluoromethylphenyl)-5-chloro-2-hydroxybenzamide 5-chloro salicylic acid (21.9 g, 126.9 mmol, 1.0 eq) is dissolved in toluene (375.0 mL) under nitrogen atmosphere followed by addition of phosphorus trichloride (5.5 mL, 63.45 mmol, 0.5 eq) in small portions at room temperature over 15 minutes. 3,5-Bis-trifluoromethyl-phenylamine (25.0 g, 110.4 mmol, and 0.87 eq) is then added to the reaction mixture in one lot at room temperature. The reaction mixture is heated to 105±5° C. and stirred for next 16.0 h at this temperature. Progress of the reaction is monitored by TLC (mobile phase 10% ethyl acetate in hexane). After completion of the reaction, the reaction is cooled to room temperature. The reaction mixture is poured to silica gel (0.5 kg) column and column is eluted with (1.5 L) ethyl acetate to give white solid after evaporation of solvent. The solid thus obtained is suspended in n-heptane (150.0 mL) and stirred for 1.0 h at room temperature. The suspension is filtered through buchner funnel to obtain N-(3,5-bis-trifluoromethylphenyl)-5-chloro-2-hydroxybenzamide (31.0 g) as a white solid. HPLC=98.9%

Step 2—2-((3,5-bis(trifluoromethyl)phenyl)carbamoyl)-4-chlorophenyl bis(2-(trimethylsilyl)ethyl) phosphate Preparation of bis (2-(trimethylsilyl) ethyl) hydrogen Phosphite Reagent To a cooled solution of trimethylsilyl ethanol (50.0 g, 422.8 mmol, 3.0 eq) in DCM (0.875 L) is added triethyl amine (28.5 g, 281.8 mmol, 2.0 eq) at 0° C. under nitrogen atmosphere. PCl$_3$ (19.3 g, 281.07 mmol, 1.0 eq) is then added slowly in small portions at 0 to 10° C. over 45 minutes. The reaction mixture is stirred for 1.0 h at 0° C. The reaction mixture is allowed to come at room temperature. DM water (0.25 L) is added to the reaction mixture and stirred for 1.0 h at room temperature and layers are separated. The aqueous layer is extracted with DCM (0.25 L). The combined organic extract is washed with DM water (0.25 L) and dried over Na$_2$SO$_4$. The organic layer is concentrated under vacuum at 45° C. and degassed for 30 minutes at 45° C. to afford crude phosphite reagent (44.0 g) as a light brown oil and stored at 0 to 5° C.

Preparation of 2-((3,5-bis(trifluoromethyl)phenyl) carbamoyl)-4-chlorophenyl bis(2-(trimethylsilyl) ethyl) phosphate N-(3,5-bis(trifluoromethyl)phenyl)-5-chloro-2-hydroxybenzamide (30.0 g, 78.19 mmol, 1.0 eq) is dissolved in CH$_3$CN (300.0 mL). DMAP (0.57 g, 4.69 mmol, 0.06 eq), DIPEA (27.2 mL, 156.38 mmol, 2.0 eq) and CCl$_4$ (60.1 g, 390.96 mmol, 5.0 eq) are added to the above solution in sequence at room temperature with stirring. The reaction mixture is cooled to 0° C. and a solution of phosphite reagent (33.10 g, 117.28 mmol, 1.5 eq) in CH$_3$CN (30.0 mL) is added drop wise under controlled conditions below 2° C. over a period of 15 minutes. The reaction mixture is allowed to warm up to room temperature and stirred for 22.0 h at room temperature. Progress of the reaction is monitored by TLC (mobile phase 10% ethyl acetate in hexane). After completion of the reaction, the reaction mixture is diluted with ethyl acetate (1.0 L) and water (1.0 L), layers are separated. The aqueous layer is extracted twice with ethyl acetate (2×0.5 L). The combined organic extract is washed with brine (0.5 L), dried over $Na_2SO_4$ and filtered. The filtrate is concentrated under reduced pressure to give the crude material (56.0 g) which is used as such for next step.

Step 3—Phosphoric Acid mono-[2-(3, 5-bis-trifluoromethylphenylcarbamoyl)-4-chlorophenyl] ester Crude 2-((3,5-bis(trifluoromethyl)phenyl)carbamoyl)-4-chlorophenyl bis (2-(trimethylsilyl) ethyl) phosphate (55.0 g, 82.81 mmol, 1.0 eq) is added to a mixture of TFA: water (5:1, 428.0 mL). The reaction mixture is stirred at room temperature for 3.0 h. Progress of the reaction is monitored by TLC (mobile phase 10% ethyl acetate in hexane). After completion of the reaction by TLC, the reaction mixture is concentrated under vacuum below 70° C. to remove volatile solvents. Residue is added to a solution of NaOH (18.0 g, 450.0 mmol, and 5.4 eq) in water (0.55 L) and stirred for 15 minutes at room temperature. The aqueous solution is washed twice with ethyl acetate (2×0.55 L) to remove impurities. The aqueous solution is then acidified to pH 1 with concentrated HCl (35.0 mL) and extracted twice with ethyl acetate (2×0.825 L). The combined ethyl acetate extract obtained after acidification is dried over $Na_2SO_4$ and concentrated under reduced pressure to give 38.0 g of colorless oil. The oil crude is dissolved in ethyl acetate (15.0 mL) and n-heptane (175.0 mL) is added with stirring. The reaction mixture is stirred for 3.0 h at room temperature and filtered. Solid is washed with n-heptane (35.0 mL) and dried over vacuum for 30 minutes to afford phosphoric acid mono-[2-(3,5-bis-trifluoromethylphenylcarbamoyl)-4-chlorophenyl] ester (12.4 g) as an off white solid. HPLC=96.4%

Figure 39:
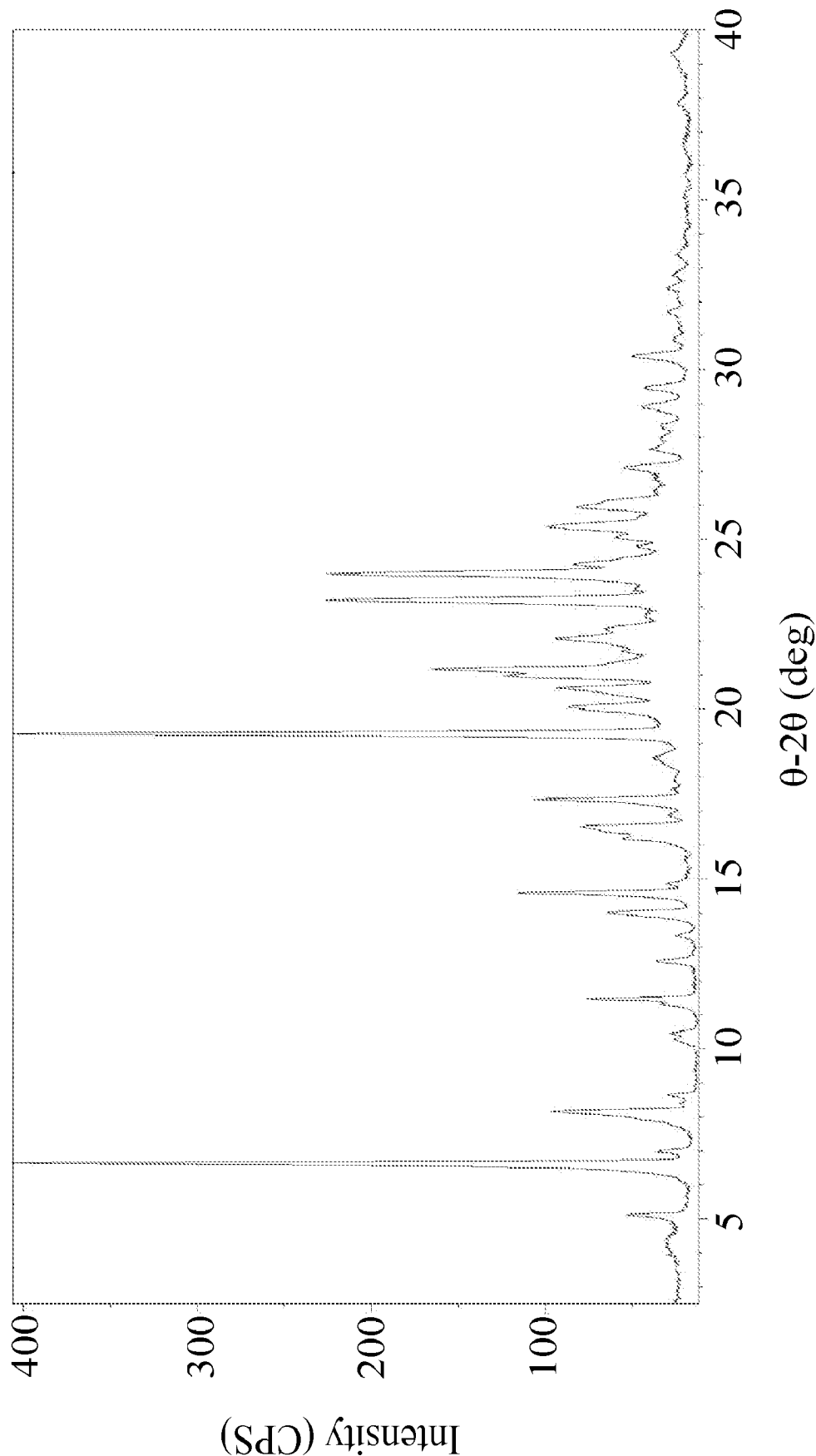
FIG. 39 depicts an XRPD pattern of Form A (plus an unknown minor component) collected with Cu Kα radiation.

An XRPD pattern of the product is shown in FIG. 39 (Form A plus unknown minor component). The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 721 s, Scan Speed 3.2°/min, Slit: DS: ½°, SS: null, Revolution Time: 1.0 s, Mode: Transmission.

Example 18—2-{[3,5-bis(trifluoromethyl)phenyl] carbamoyl}-4-chlorophenyl Dihydrogen Phosphate Hydrate (Form N)

2-{[3,5-bis(trifluoromethyl)phenyl]carbamoyl}-4-chlorophenyl dihydrogen phosphate (165.0 g, 0.355 mol, 1.0 eq) is added to a solution of NaOH (82.5 g, 2.062 mol, 5.8 eq) in water (4.12 L) and stirred for 45 minutes at room temperature. The aqueous solution is washed twice with ethyl acetate (2×1.65 L) to remove impurities. The combined organic is extracted with water (0.82 L). The combined aqueous layer is acidified to pH 1 with concentrated HCl (230.0-250.0 mL) and extracted twice with ethyl acetate (2×1.65 L). The combined ethyl acetate extract obtained after acidification is dried over $Na_2SO_4$ and concentrated under reduced pressure to give 140.0 g of colorless oil. The oil is dissolved in ethyl acetate (165.0 mL) and stirred for 30 minutes at room temperature. n-Heptane (1.48 L) is added with stirring. The mixture is stirred for 3.0 h at room temperature and filtered. Solid is washed with n-heptane (82.0 mL) and dried over vacuum for 30 minutes to afford phosphoric acid mono-[2-(3,5-bis-trifluoromethylphenylcarbamoyl)-4-chlorophenyl] ester (118.0 g) as an off white solid. HPLC=95.0%

The off white solid (108.0 g) is dissolved in water (2.36 L). The mixture is stirred for 3.0 h at room temperature and filtered. The solid is washed with water (0.590 L) and dried over vacuum for 1.0 h to afford pure wet product. The wet solid is dried at room temperature for 3 days and 17 h to obtain dry product (95.0 g) as an off white solid. HPLC=99.4%

The off white solid (95.0 g) is stirred with toluene (0.95 L) for 30 minutes and filtered. Solid is washed with toluene (95.0 mL) to afford phosphoric acid mono-[2-(3, 5-bis-trifluoromethylphenylcarbamoyl)-4-chlorophenyl] ester (90.0 g) as a white solid. HPLC=99.4%

Figure 48:
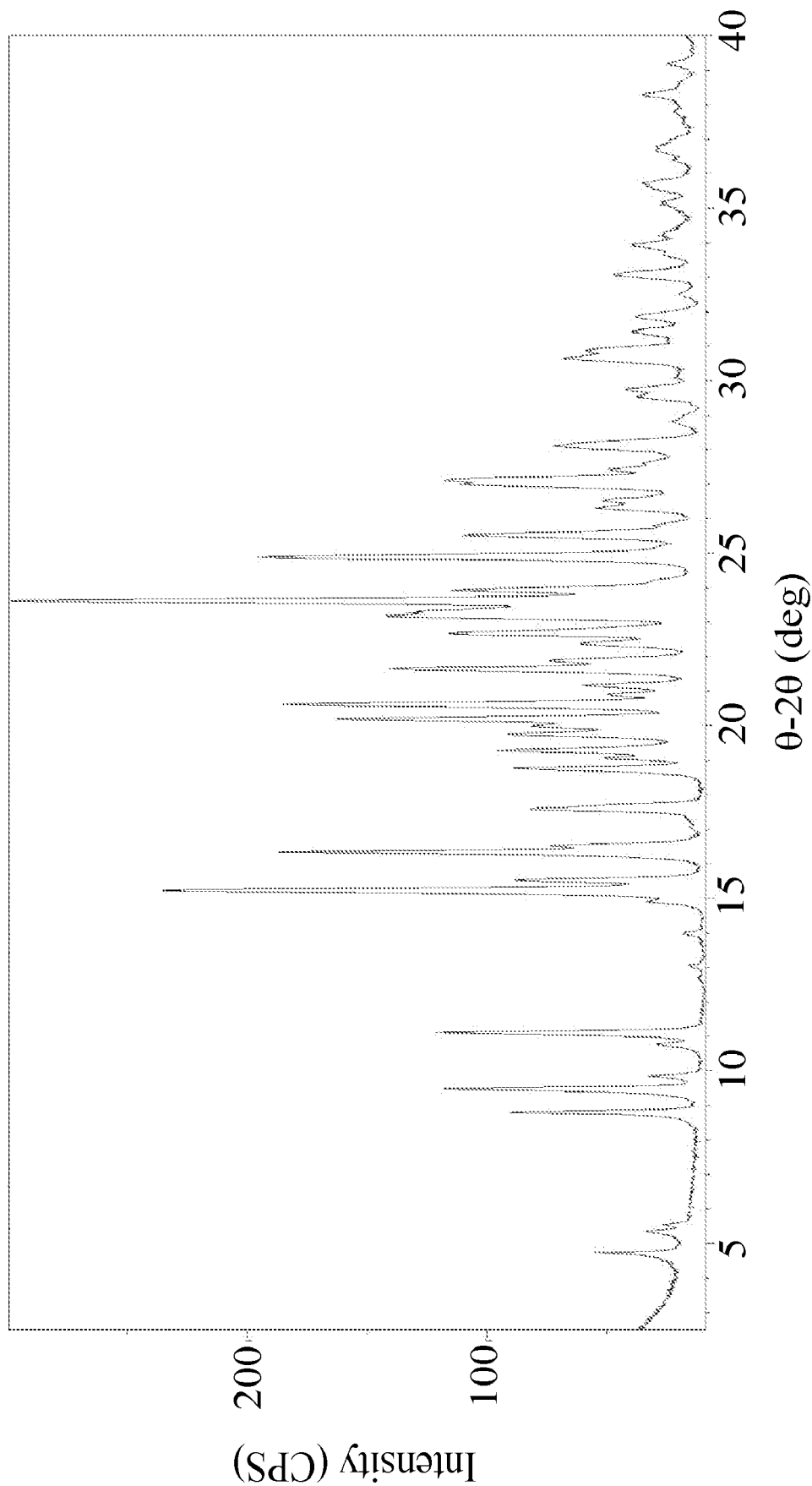
FIG. 48 depicts an XRPD pattern of Form N collected with Cu Kα radiation.

An XRPD pattern of the product is shown in FIG. 48 (Form N). The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 721 s, Scan Speed 3.2°/min, Slit: DS: ½°, SS: null, Revolution Time: 1.0 s, Mode: Transmission.

Example 19—2-{[3,5-bis(trifluoromethyl)phenyl] carbamoyl}-4-chlorophenyl Dihydrogen Phosphate (Form B)

Figure 43:
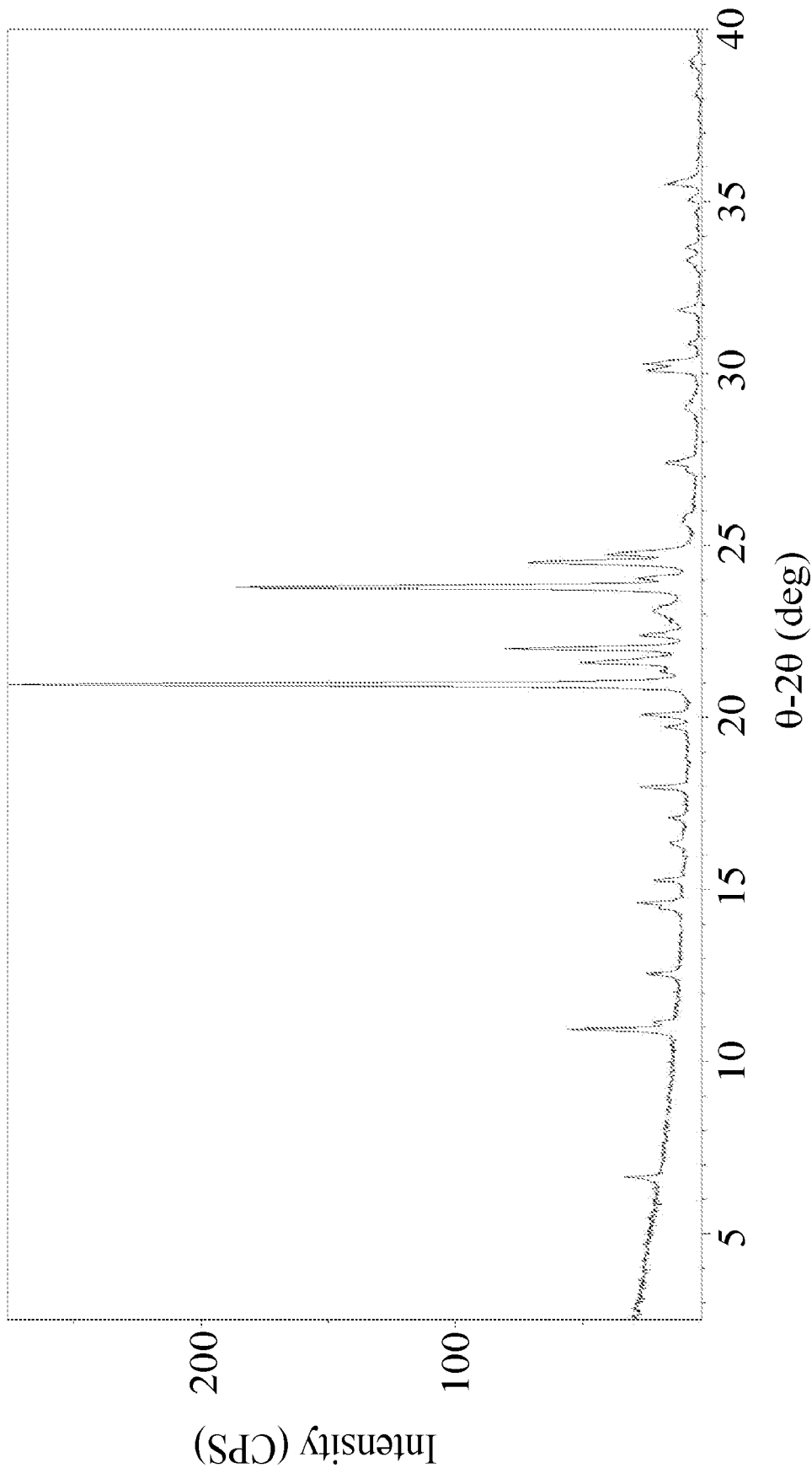
FIG. 43 depicts an XRPD pattern of Form B collected with Cu Kα radiation.

A concentrated solution of 2-{[3,5-bis(trifluoromethyl) phenyl]carbamoyl}-4-chlorophenyl dihydrogen phosphate from Example 2A in 2,2,2-trifluoroethanol (TFE) is slow cooled, after being capped, from 73° C. to room temperature and left to stand at room temperature for 3 days. The solution is stored at room temperature for 29 days and then vacuum filtered. XRPD of the product shows that it is Form B (Form B+minor peak at ~23° 2θ, PO). An XRPD pattern of the product is shown in FIG. 43. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.01-39.98° 2θ, Step Size: 0.017° 2θ, Collection Time: 718 s, Scan Speed 3.3°/min, Slit: DS: ½°, SS: null, Revolution Time: 1.0 s, Mode: Transmission.

Example 20—2-{[3,5-bis(trifluoromethyl)phenyl] carbamoyl}-4-chlorophenyl Dihydrogen Phosphate Hydrate (Form N)

Figure 57:
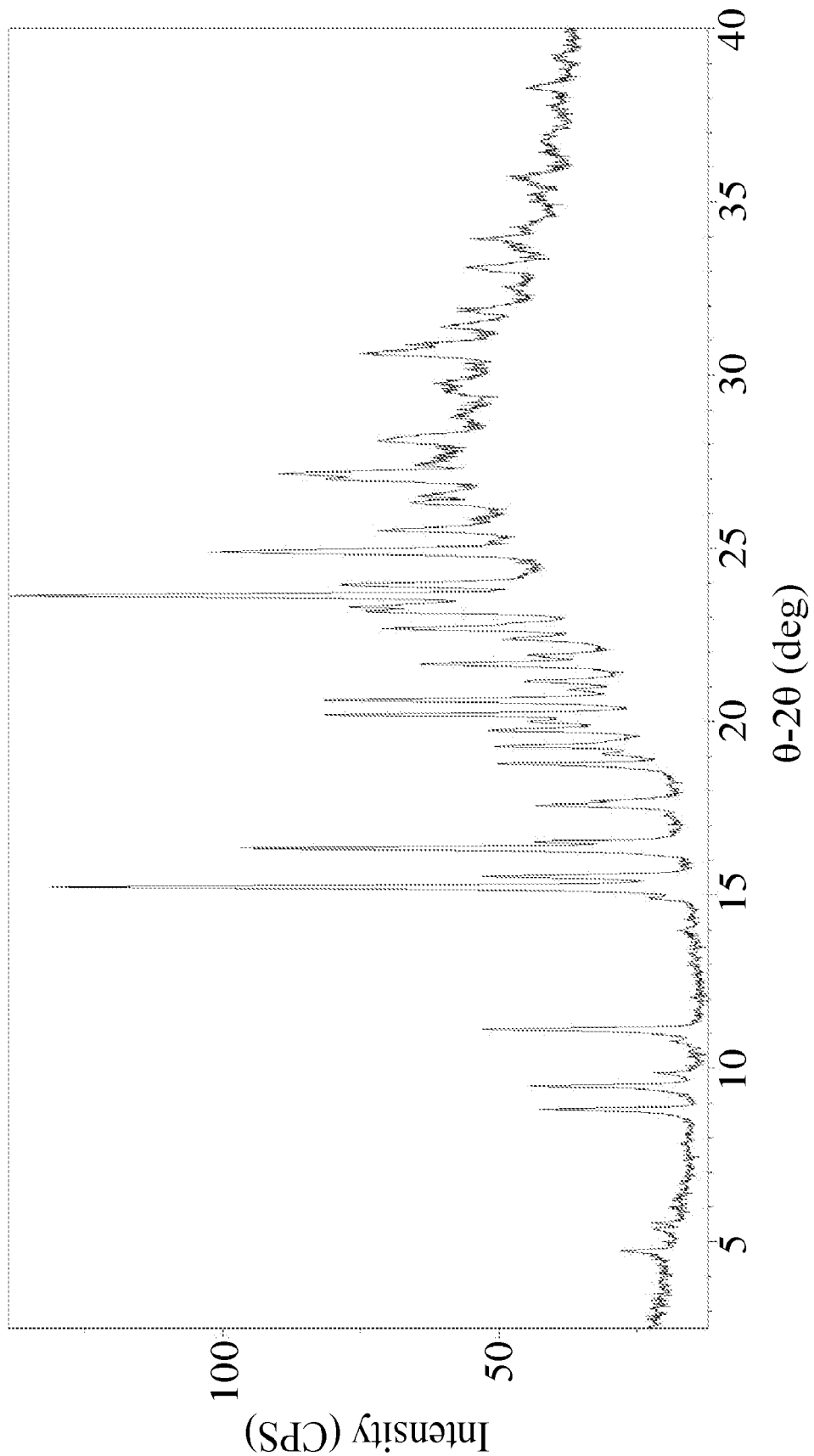
FIG. 57 depicts an XRPD pattern of Form N collected with Cu Kα radiation.

A saturated solution is prepared by adding 3 mL water to 75 mg of 2-{[3,5-bis(trifluoromethyl)phenyl]carbamoyl}-4-chlorophenyl dihydrogen phosphate from Example 2A. Samples are stirred (500 rpm) at ambient conditions for 24 hours. At the end of 24 hours, samples are centrifuged (13000 rpm for 5 min) and the supernatant is filtered through 0.45 μm PVDF filters. An XRPD pattern of the solid from the centrifuged sample, showing the solid is Form N, is in FIG. 57. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.98° 2θ, Step Size: 0.017° 2θ, Collection Time: 720 s, Scan Speed 3.2°/min, Slit: DS: ½°, SS: null, Revolution Time: 1.0 s, Mode: Transmission

Example 21—2-{[3,5-bis(trifluoromethyl)phenyl] carbamoyl}-4-chlorophenyl Dihydrogen Phosphate (Form B)

Figure 53:
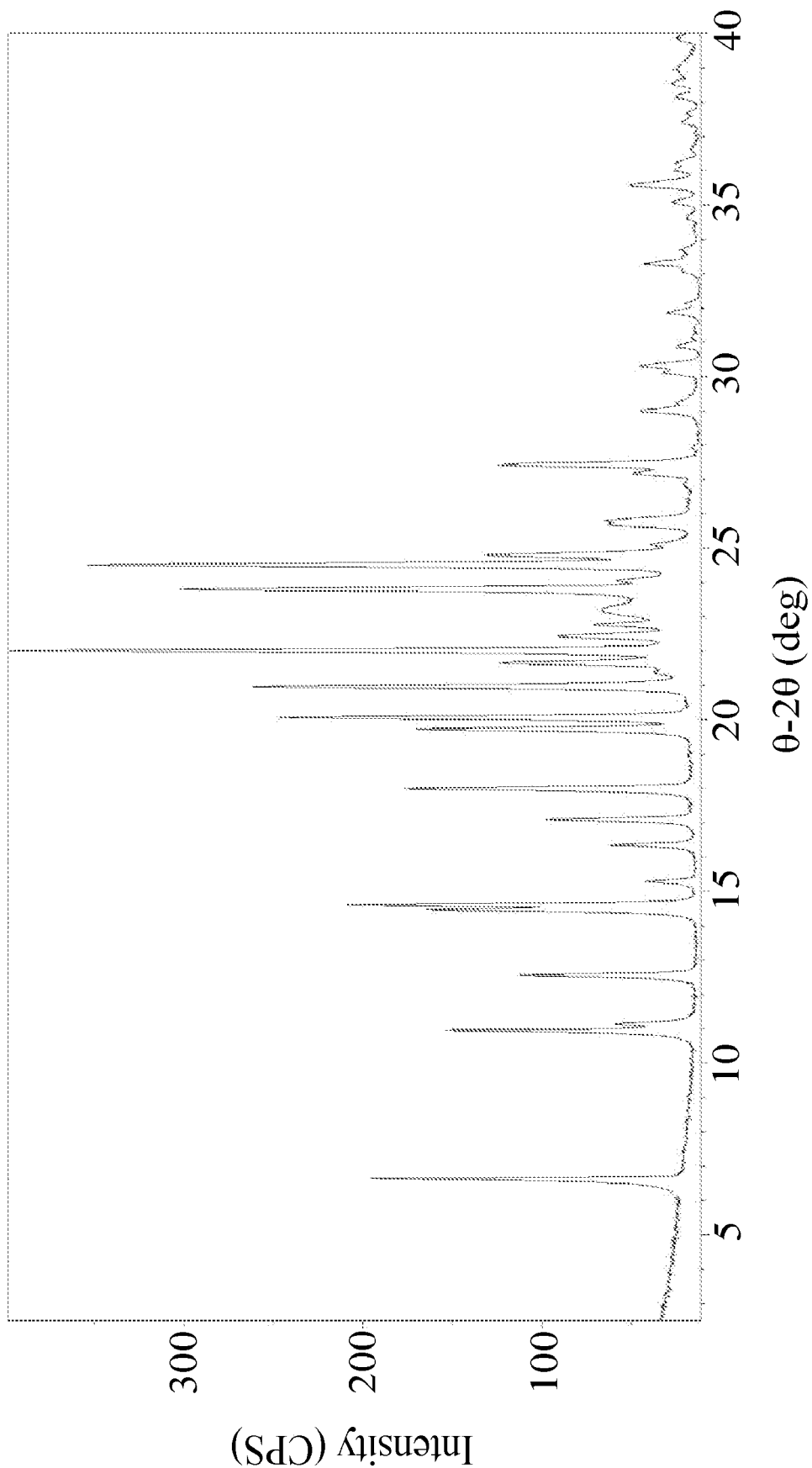
FIG. 53 depicts an XRPD pattern of Form B collected with Cu Kα radiation.

2-{[3,5-bis(trifluoromethyl)phenyl]carbamoyl}-4-chlorophenyl dihydrogen phosphate from Example 2B is slurried in hexafluoroisopropanol (HFIPA) for 4 days and then vacuum filtered. XRPD of the product shows that it is Form B (Form B+minor peak at ~23° 2θ, PO). An XRPD pattern of the product is shown in FIG. 53. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 719 s, Scan Speed 3.3°/min, Slit: DS: ½°, SS: null, Revolution Time: 1.0 s, Mode: Transmission

Figure 47:
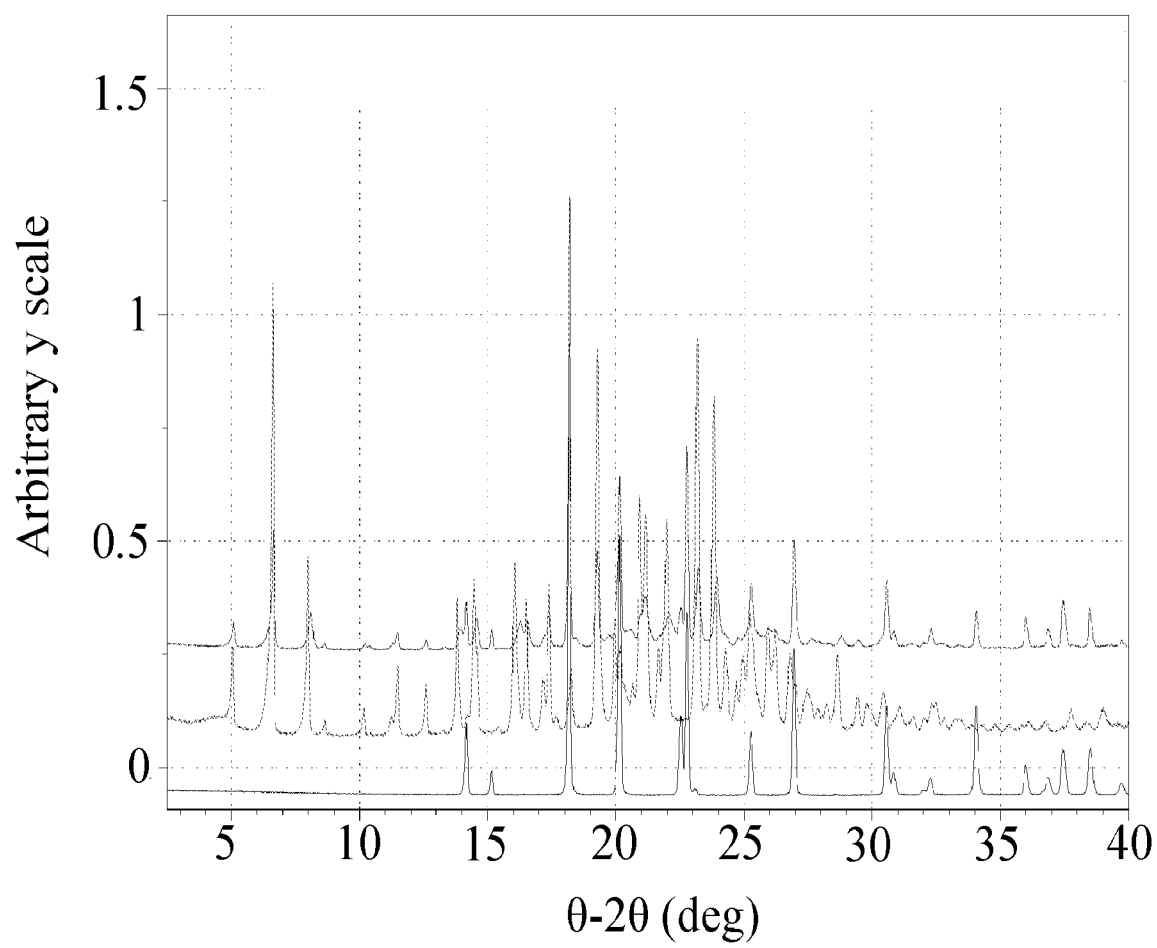
FIG. 47 depicts XRPD patterns of Form A+tris base, Form A, and tris base. Top XRPD pattern is Form A milled with tris base. Middle XRPD pattern is Form A from Example 2A. Bottom XRPD pattern is tris base.
Figure 56:
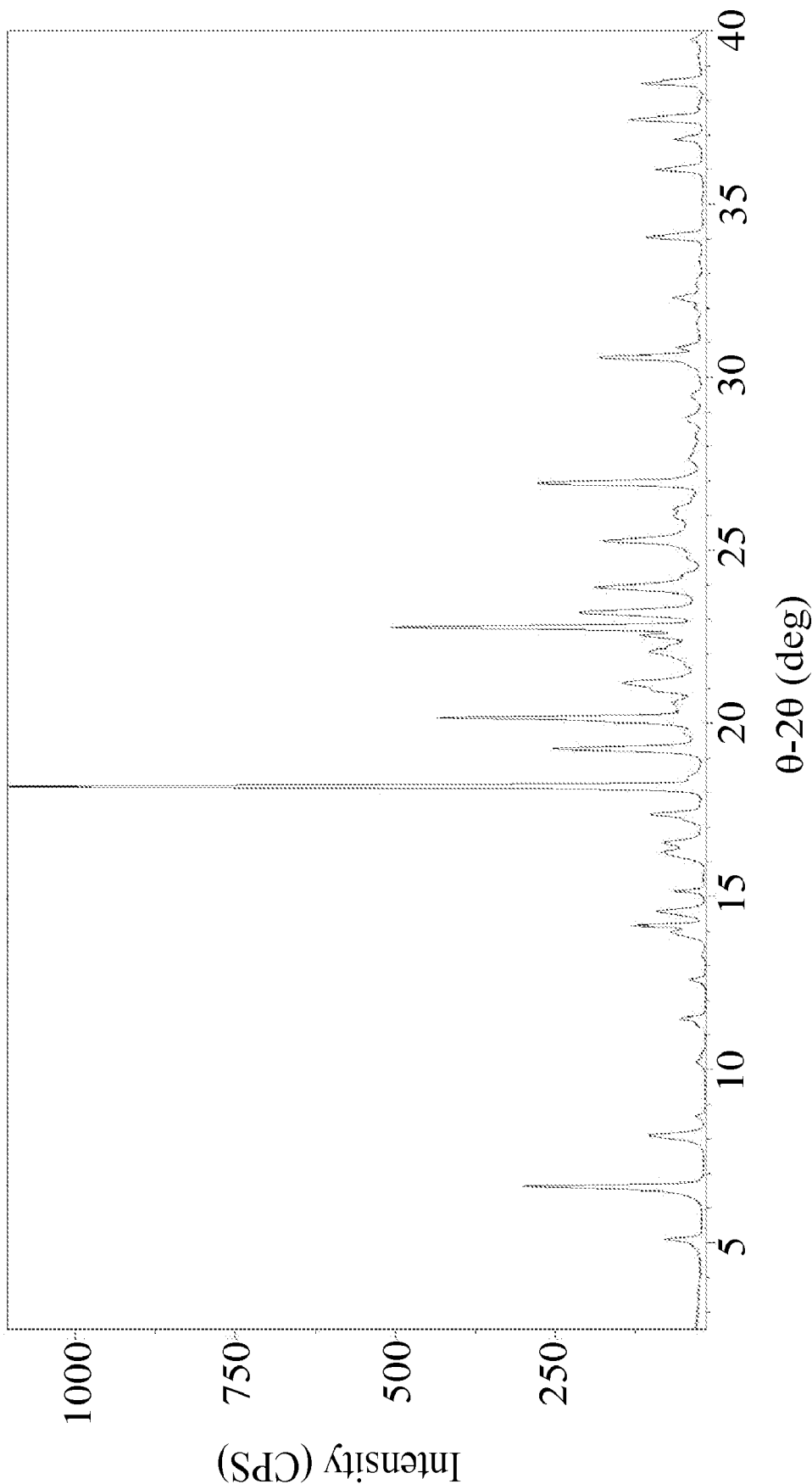
FIG. 56 depicts an XRPD pattern of Form A+tris base.

Example 22—2-{[3,5-bis(trifluoromethyl)phenyl] carbamoyl}-4-chlorophenyl Dihydrogen Phosphate Ethyl Acetate Solvate (Form A) Milled with Tris Base 2-{[3,5-bis(trifluoromethyl)phenyl]carbamoyl}-4-chlorophenyl dihydrogen phosphate is milled with tris base. The top XRPD pattern in FIG. 47 depicts Form A milled with tris base. The XRPD is also shown in FIG. 56. The XRPD pattern is consistent with a physical mixture of Form A and tris base, indicating that no form change occurs upon formulation. The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 717 s, Scan Speed 3.3°/min, Slit: DS: ½°, SS: null, Revolution Time: 1.0 s, Mode: Transmission

Example 23—Attempts to Dry Form A

Several attempts to dry Form A are tried. Rigorous conditions are initially selected due to the high temperature range at which the TGA weight loss is observed (above 90° C.). Drying under vacuum at 80° C. for 1 day results in brown solids stuck to the vial. Gravimetric weight loss of 30% is calculated, and the resulting solids do not appear to be crystalline by optical microscopy.

A drying attempt under milder conditions is attempted. The experiment begins by drying under vacuum at ambient temperature. No significant weight change is measured gravimetrically, so the temperature is gently increased and the weight is monitored. Minor weight loss is noted after 6 hours at 63-65° C., so the sample is held in the vacuum oven at this temperature for 1 day, resulting in 11% gravimetric weight loss. The resulting light brown solids are stuck to the vial and do not appear to be crystalline by optical microscopy. These experiments indicate that vacuum drying Form A at elevated temperature tends to cause decomposition and collapse of the crystalline structure.

Example 24—Form A

Figure 58:
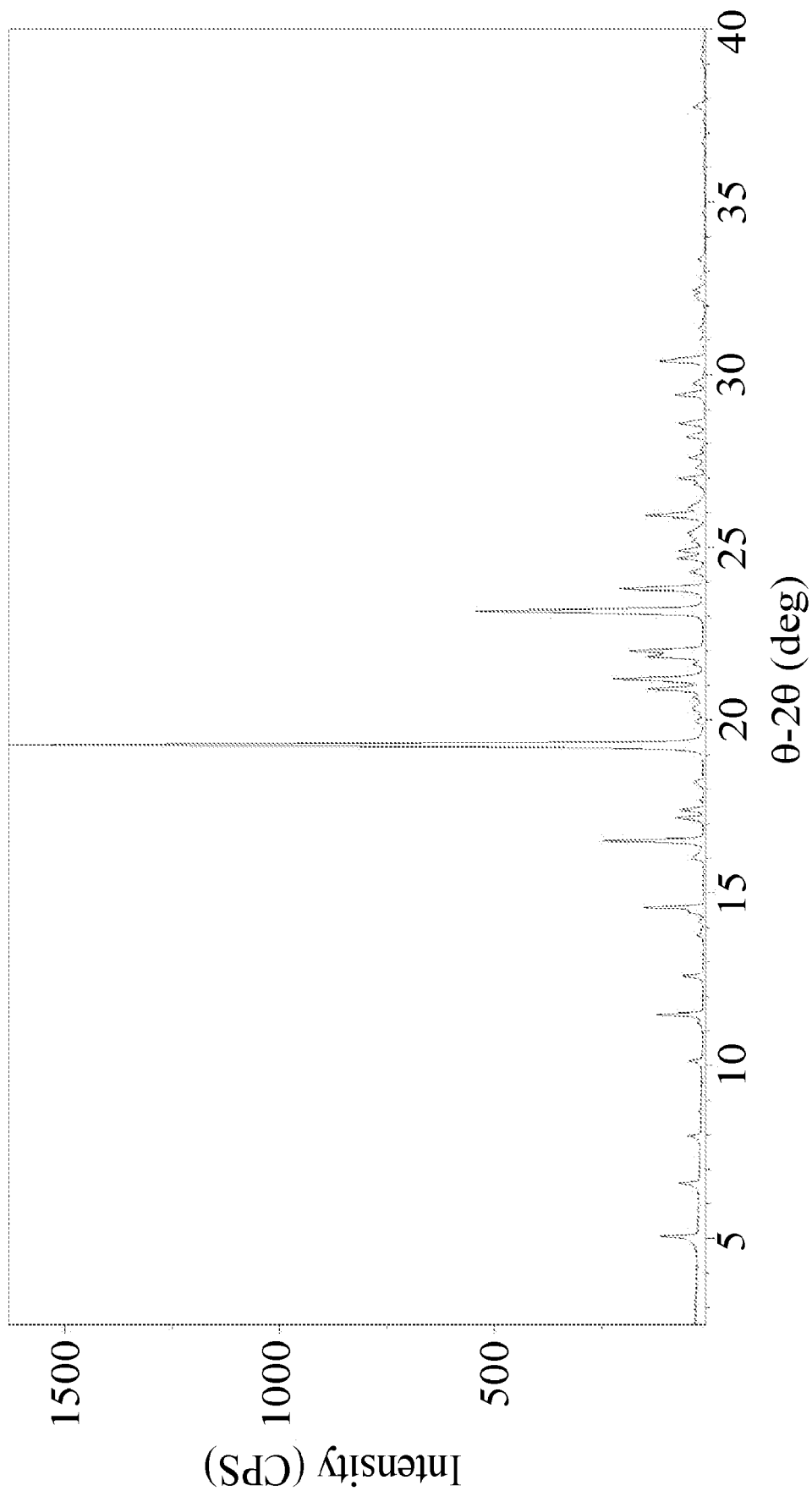
FIG. 58 depicts an XRPD pattern of Form A collected with Cu Kα radiation.

2-{[3,5-bis(trifluoromethyl)phenyl]carbamoyl}-4-chlorophenyl dihydrogen phosphate from Example 2B is crash cooled from a solution of heptane/EtOAc (80:20, v/v) at 75° C. to freezer and is then allowed to stand in the freezer for 3 hours. The liquid phase is decanted and solids are briefly dried under N$_2$. An XRPD pattern of the product is shown in FIG. 58 (Form A, PO). The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 718 s, Scan Speed 3.3°/min, Slit: DS: ½°, SS: null, Revolution Time: 1.0 s, Mode: Transmission.

Figure 59:
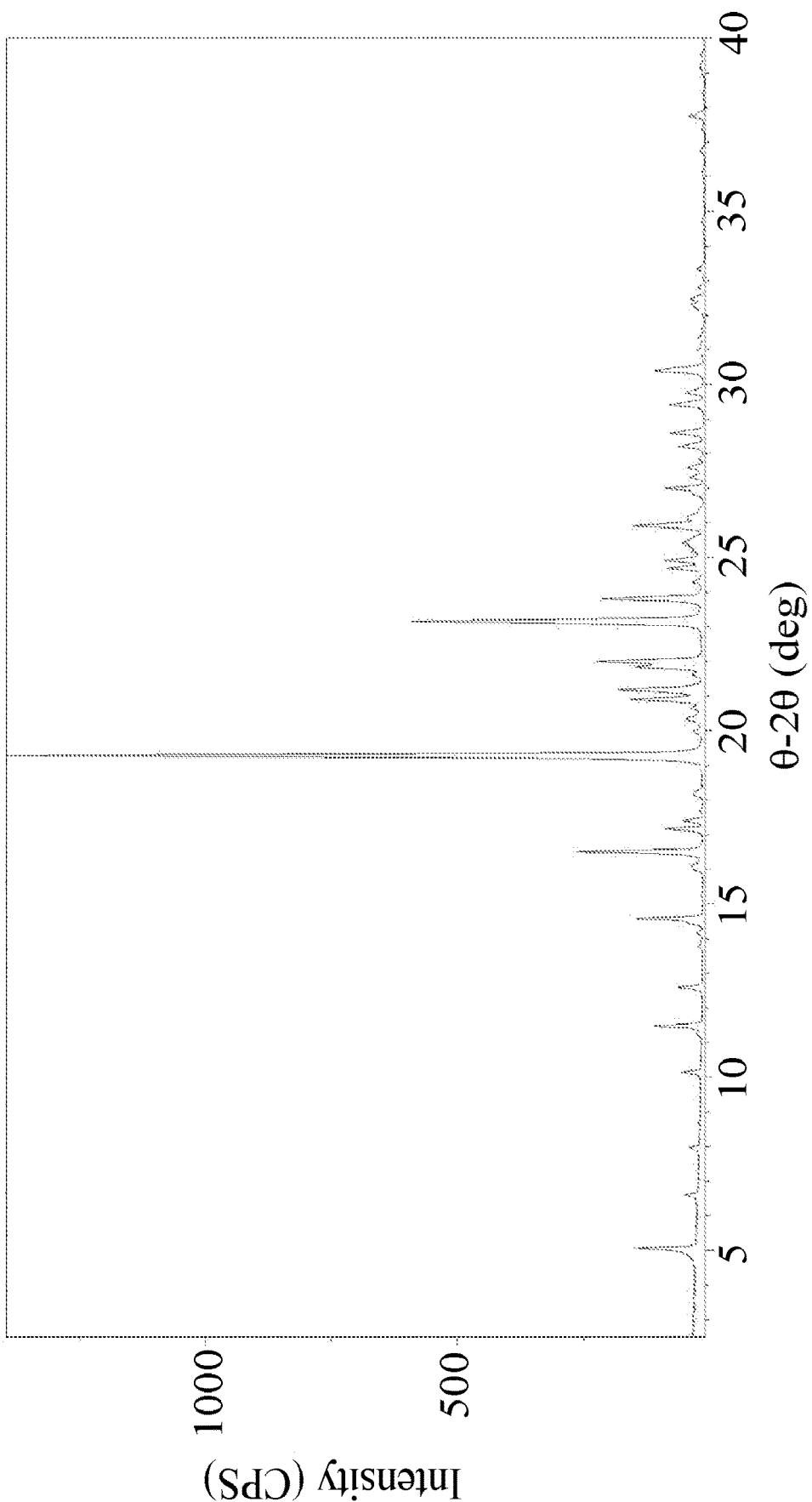
FIG. 59 depicts an XRPD pattern of Form A collected with Cu Kα radiation.

2-{[3,5-bis(trifluoromethyl)phenyl]carbamoyl}-4-chlorophenyl dihydrogen phosphate from Example 2B is fast cooled from a solution of heptane/EtOAc (80:20, v/v) at 75° C. to room temperature and is then allowed to stand at room temperature for 3 hours. The liquid phase is decanted and solids are briefly dried under N$_2$. An XRPD pattern of the product is shown in FIG. 59 (Form A, PO). The XRPD pattern is obtained as described in the general XRPD procedure in Example 1. Data acquisition parameters for the XRPD are: Panalytical X-Pert Pro MPD PW3040 Pro, X-ray Tube: Cu(1.54059 Å), Voltage: 45 kV, Amperage: 40 mA, Scan Range: 1.00-39.99° 2θ, Step Size: 0.017° 2θ, Collection Time: 718 s, Scan Speed 3.3°/min, Slit: DS: ½°, SS: null, Revolution Time: 1.0 s, Mode: Transmission.

The invention claimed is:

1. A hydrate of 2-{[3,5-bis(trifluoromethyl)phenyl]carbamoyl}-4-chlorophenyl dihydrogen phosphate

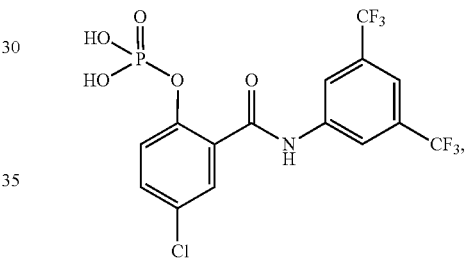

wherein the hydrate exhibits an XRPD pattern comprising at least five 2-theta (°) values selected from the group consisting of 8.8, 9.5, 11.1, 15.2, 15.5, 16.4, 20.2, 20.6, 23.6, 24.0, 24.9, and 27.2, wherein the XRPD is measured using an incident beam of Cu Kα radiation of wavelength 1.54059 Å.

2. A hydrate of 2-{[3,5-bis(trifluoromethyl)phenyl]carbamoyl}-4-chlorophenyl dihydrogen phosphate

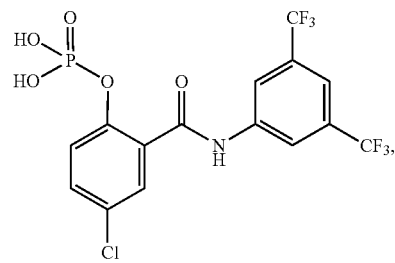 [SMILES: O=C(Nc1cc(C(F)(F)F)cc(C(F)(F)F)c1)c1cc(Cl)ccc1OP(=O)(O)O]

wherein the hydrate exhibits at least one of an XRPD pattern comprising at least five 2-theta (°) values selected from the group consisting of 4.7, 5.4, 5.6, 8.8, 9.5, 9.9, 10.8, 11.1, 13.1, 14.0, 14.9, 15.2, 15.5, 16.4, 16.5, 17.6, 17.7, 18.8, 19.1, 19.3, 19.5, 19.8, 20.0, 20.2, 20.6, 20.9, 21.2, 21.7, 21.9, 22.4, 22.7, 22.8, 23.2, 23.3, 23.6, 24.0, 24.9, 25.5, 25.8, 26.3, 26.5, 27.0, 27.2, and 27.4, wherein the XRPD is measured using an incident beam of Cu Kα radiation, or an XRPD pattern comprising at least five d-spacing (Å) values selected from the group consisting of 18.7, 16.5, 15.9, 10.0, 9.3, 9.0, 8.2, 8.0, 6.8, 6.3, 5.9, 5.8, 5.7, 5.4, 5.0, 4.7, 4.6, 4.5, 4.4, 4.3, 4.2, 4.1, 4.0, 3.9, 3.8, 3.7, 3.6, 3.5, 3.4, and 3.3.

3. The hydrate of claim 2, wherein the hydrate exhibits an XRPD pattern comprising at least twelve d-spacing (Å) values selected from the group consisting of 18.7, 16.5, 15.9, 10.0, 9.3, 9.0, 8.2, 8.0, 6.8, 6.3, 5.9, 5.8, 5.7, 5.4, 5.0, 4.7, 4.6, 4.5, 4.4, 4.3, 4.2, 4.1, 4.0, 3.9, 3.8, 3.7, 3.6, 3.5, 3.4, and 3.3.

4. The hydrate of claim 2, wherein the hydrate exhibits at least one of an XRPD pattern comprising 2-theta (°) values of 8.8±0.2, 9.5±0.2, 11.1±0.2, 15.2±0.2, 15.5±0.2, 16.4±0.2, 20.2±0.2, 20.6±0.2, 23.6±0.2, 24.0±0.2, 24.9±0.2, and 27.2±0.2, wherein the XRPD is measured using an incident beam of Cu Kα radiation of wavelength 1.54059 Å, or an XRPD pattern comprising d-spacing (Å) values of 10.0, 9.3, 8.0, 5.8, 5.7, 5.4, 4.4, 4.3, 3.8, 3.7, 3.6, and 3.3.

5. The hydrate of claim 1, wherein the hydrate exhibits an XRPD substantially as shown in FIG. 24, 45, 46, 48, 50, 51, 54, or 57, wherein the XRPD is measured using radiation of wavelength 1.54059 Å.

6. The hydrate of claim 1, wherein the hydrate exhibits 14% water by Karl Fischer analysis.

7. A non-solvate non-hydrate crystalline form of 2-{[3,5-bis(trifluoromethyl)phenyl]carbamoyl}-4-chlorophenyl dihydrogen phosphate

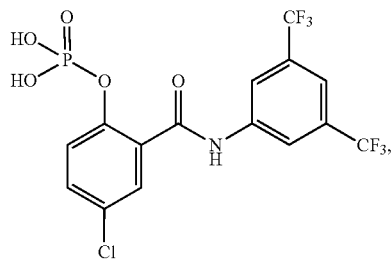

wherein the non-solvate non-hydrate crystalline form exhibits an XRPD pattern comprising at least five 2-theta (°) values selected from the group consisting of 6.6, 11.0, 12.6, 14.5, 14.6, 18.0, 19.7, 20.1, 21.0, 21.6, 22.0, 22.4, 23.8, 24.5, 24.8, and 27.4, wherein the XRPD is measured using an incident beam of Cu Kα radiation of wavelength 1.54059 Å.

8. A non-solvate non-hydrate crystalline form of 2-{[3,5-bis(trifluoromethyl)phenyl]carbamoyl}-4-chlorophenyl dihydrogen phosphate

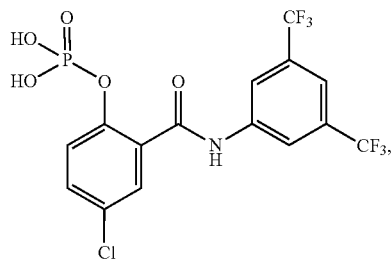

wherein the non-solvate non-hydrate crystalline form exhibits at least one of an XRPD pattern comprising at least five 2-theta (°) values selected from the group consisting of 6.6, 11.0, 11.1, 12.6, 14.5, 14.6, 15.3, 16.4, 17.1, 18.0, 19.7, 20.1, 21.0, 21.4, 21.6, 22.0, 22.4, 22.8, 23.8, 24.5, 24.8, 25.8, 27.4, and 29.0, wherein the XRPD is measured using an incident beam of Cu Kα radiation, or an XRPD pattern comprising at least five d-spacing (Å) values selected from the group consisting of 13.3, 8.1, 7.9, 7.0, 6.1, 5.8, 5.4, 5.2, 4.9, 4.5, 4.4, 4.2, 4.1, 4.0, 3.9, 3.7, 3.6, 3.5, 3.3, and 3.1.

9. The non-solvate non-hydrate crystalline form of claim 8, wherein the non-solvate non-hydrate crystalline form exhibits an XRPD pattern comprising at least sixteen d-spacing (Å) values selected from the group consisting of 13.3, 8.1, 7.9, 7.0, 6.1, 5.8, 5.4, 5.2, 4.9, 4.5, 4.4, 4.2, 4.1, 4.0, 3.9, 3.7, 3.6, 3.5, 3.3, and 3.1.

10. The non-solvate non-hydrate crystalline form of claim 8, wherein the non-solvate non-hydrate crystalline form exhibits at least one of an XRPD pattern comprising 2-theta (°) values of 6.6±0.2, 11.0±0.2, 12.6±0.2, 14.5±0.2, 14.6±0.2, 18.0±0.2, 19.7±0.2, 20.1±0.2, 21.0±0.2, 21.6±0.2, 22.0±0.2, 22.4±0.2, 23.8±0.2, 24.5±0.2, 24.8±0.2, and 27.4±0.2, wherein the XRPD is measured using an incident beam of Cu Kα radiation of wavelength 1.54059 Å, or an XRPD pattern comprising d-spacing (Å) values of 13.3, 8.1, 7.0, 6.1, 4.9, 4.5, 4.4, 4.2, 4.1, 4.0, 3.7, 3.6, and 3.3.

11. The non-solvate non-hydrate crystalline form of claim 7, wherein the non-solvate non-hydrate crystalline form exhibits an XRPD substantially as shown in FIG. 21, 41, 42, 43, 49, 53, or 55, wherein the XRPD is measured using radiation of wavelength 1.54059 Å.

12. A pharmaceutical composition comprising the hydrate of claim 4.

13. A pharmaceutical composition comprising the non-solvate non-hydrate crystalline form of claim 10.

14. A process for preparing a pharmaceutical composition comprising a mono- or di-anion of 2-{[3,5-bis(trifluoromethyl)phenyl]carbamoyl}-4-chlorophenyl dihydrogen phosphate, wherein the process comprises admixing the hydrate of claim 4 and a pharmaceutically acceptable liquid.

15. A process for preparing a pharmaceutical composition comprising a mono- or di-anion of 2-{[3,5-bis(trifluoromethyl)phenyl]carbamoyl}-4-chlorophenyl dihydrogen phosphate, wherein the process comprises admixing the non-solvate non-hydrate crystalline form of claim 10 and a pharmaceutically acceptable liquid.

16. A method of treating or controlling edema in a human in need thereof, wherein the method comprises administering the hydrate of claim 4 to the human.

17. A method of treating or controlling edema in a human in need thereof, wherein the method comprises administering the non-solvate non-hydrate crystalline form of claim 10 to the human.

18. The process of claim 14, wherein the pharmaceutically acceptable liquid is an aqueous solution comprising a base.

19. The process of claim 18, wherein the base is an amine and/or a salt thereof.

20. The process of claim 14, wherein the pharmaceutical composition is for injection.

21. The process of claim 15, wherein the pharmaceutically acceptable liquid is an aqueous solution comprising a base.

22. The process of claim 14, wherein the process comprises admixing the hydrate and a base prior to admixture with the pharmaceutically acceptable liquid.

23. The process of claim 19, wherein the base is tris (hydroxymethyl)aminomethane and/or a salt thereof, meglumine, and/or diethanolamine.

24. The process of claim 22, wherein the base is an amine and/or a salt thereof.

25. The process of claim 24, wherein the base is tris (hydroxymethyl)aminomethane and/or a salt thereof, meglumine, and/or diethanolamine.

26. The hydrate of claim 2, wherein the hydrate exhibits an XRPD pattern comprising at least ten 2-theta (°) values selected from the group consisting of 4.73±0.20, 5.36±0.20, 5.55±0.20, 8.82±0.20, 9.49±0.20, 9.85±0.20, 10.77±0.20, 11.12±0.20, 13.05±0.20, 13.99±0.20, 14.91±0.20, 15.23±0.20, 15.53±0.20, 16.35±0.20, 16.53±0.20, 17.59±0.20, 17.70±0.20, 18.78±0.20, 19.07±0.20, 19.30±0.20, 19.47±0.20, 19.75±0.20, 19.99±0.20, 20.20±0.20, 20.62±0.20, 20.91±0.20, 21.16±0.20, 21.65±0.20, 21.89±0.20, 22.39±0.20, 22.68±0.20, 22.83±0.20, 23.17±0.20, 23.31±0.20, 23.63±0.20, 23.95±0.20, 24.89±0.20, 25.54±0.20, 25.83±0.20, 26.32±0.20, 26.52±0.20, 27.00±0.20, 27.16±0.20, and 27.42±0.20, wherein the XRPD is measured using an incident beam of Cu Kα radiation of wavelength 1.54059 Å.

27. The hydrate of claim 2, wherein the hydrate exhibits an XRPD pattern comprising 2-theta (°) values of 4.73±0.20, 5.36±0.20, 5.55±0.20, 8.82±0.20, 9.49±0.20, 9.85±0.20, 10.77±0.20, 11.12±0.20, 13.05±0.20, 13.99±0.20, 14.91±0.20, 15.23±0.20, 15.53±0.20, 16.35±0.20, 16.53±0.20, 17.59±0.20, 17.70±0.20, 18.78±0.20, 19.07±0.20, 19.30±0.20, 19.47±0.20, 19.75±0.20, 19.99±0.20, 20.20±0.20, 20.62±0.20, 20.91±0.20, 21.16±0.20, 21.65±0.20, 21.89±0.20, 22.39±0.20, 22.68±0.20, 22.83±0.20, 23.17±0.20, 23.31±0.20, 23.63±0.20, 23.95±0.20, 24.89±0.20, 25.54±0.20, 25.83±0.20, 26.32±0.20, 26.52±0.20, 27.00±0.20, 27.16±0.20, and 27.42±0.20, wherein the XRPD is measured using an incident beam of Cu Kα radiation of wavelength 1.54059 Å.

28. The hydrate of claim 1, wherein the hydrate exhibits an XRPD substantially as shown in FIG. 24, wherein the XRPD is measured using radiation of wavelength 1.54059 Å.

29. The non-solvate non-hydrate crystalline form of claim 8, wherein the non-solvate non-hydrate crystalline form exhibits an XRPD pattern comprising at least ten 2-theta (°) values selected from the group consisting of 6.64±0.20, 10.95±0.20, 11.13±0.20, 12.55±0.20, 14.48±0.20, 14.61±0.20, 15.28±0.20, 16.35±0.20, 17.09±0.20, 17.99±0.20, 19.74±0.20, 20.07±0.20, 20.97±0.20, 21.36±0.20, 21.63±0.20, 22.02±0.20, 22.40±0.20, 22.77±0.20, 23.80±0.20, 24.50±0.20, 24.78±0.20, 25.76±0.20, 27.42±0.20, and 29.01±0.20, wherein the XRPD is measured using an incident beam of Cu Kα radiation of wavelength 1.54059 Å.

30. The non-solvate non-hydrate crystalline form of claim 8, wherein the non-solvate non-hydrate crystalline form exhibits an XRPD pattern comprising 2-theta (°) values of 6.64±0.20, 10.95±0.20, 11.13±0.20, 12.55±0.20, 14.48±0.20, 14.61±0.20, 15.28±0.20, 16.35±0.20, 17.09±0.20, 17.99±0.20, 19.74±0.20, 20.07±0.20, 20.97±0.20, 21.36±0.20, 21.63±0.20, 22.02±0.20, 22.40±0.20, 22.77±0.20, 23.80±0.20, 24.50±0.20, 24.78±0.20, 25.76±0.20, 27.42±0.20, and 29.01±0.20, wherein the XRPD is measured using an incident beam of Cu Kα radiation of wavelength 1.54059 Å.

* * * * *